(12) United States Patent
Zhang

(10) Patent No.: US 11,999,767 B2
(45) Date of Patent: *Jun. 4, 2024

(54) TARGET RECOGNITION MOTIFS AND USES THEREOF

(71) Applicants: The Broad Institute, Inc., Cambridge, MA (US); Massachusetts Institute of Technology, Cambridge, MA (US)

(72) Inventor: Feng Zhang, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/133,141

(22) Filed: Dec. 23, 2020

(65) Prior Publication Data

US 2021/0115094 A1    Apr. 22, 2021

Related U.S. Application Data

(62) Division of application No. 16/374,670, filed on Apr. 3, 2019, now Pat. No. 10,968,257.

(60) Provisional application No. 62/652,278, filed on Apr. 3, 2018.

(51) Int. Cl.
    *C07K 14/24*     (2006.01)
    *C12N 15/10*     (2006.01)
    *C12N 15/86*     (2006.01)

(52) U.S. Cl.
    CPC .......... *C07K 14/24* (2013.01); *C12N 15/1086* (2013.01); *C12N 15/86* (2013.01)

(58) Field of Classification Search
    CPC ..... C07K 14/24; C12N 15/86; C12N 15/1086
    See application file for complete search history.

(56) References Cited

U.S. PATENT DOCUMENTS

| | | |
|---|---|---|
| 4,769,061 A | 9/1988 | Comai |
| 4,810,648 A | 3/1989 | Stalker |
| 4,873,316 A | 10/1989 | Meade et al. |
| 4,940,835 A | 7/1990 | Shah et al. |
| 4,975,374 A | 12/1990 | Goodman et al. |
| 5,266,317 A | 11/1993 | Tomalski et al. |
| 5,273,894 A | 12/1993 | Strauch et al. |
| 5,276,268 A | 1/1994 | Strauch et al. |
| 5,494,813 A | 2/1996 | Hepher et al. |
| 5,543,158 A | 8/1996 | Gref et al. |
| 5,561,236 A | 10/1996 | Leemans et al. |
| 5,563,055 A | 10/1996 | Townsend et al. |
| 5,580,859 A | 12/1996 | Felgner et al. |
| 5,589,466 A | 12/1996 | Felgner et al. |
| 5,593,972 A | 1/1997 | Weiner et al. |
| 5,637,489 A | 6/1997 | Strauch et al. |
| 5,646,024 A | 7/1997 | Leemans et al. |
| 5,648,477 A | 7/1997 | Leemans et al. |
| 5,712,107 A | 1/1998 | Nichols |
| 5,739,082 A | 4/1998 | Donn |
| 5,789,156 A | 8/1998 | Bujard et al. |
| 5,814,618 A | 9/1998 | Bujard et al. |
| 5,824,790 A | 10/1998 | Keeling et al. |
| 5,846,946 A | 12/1998 | Huebner et al. |
| 5,855,913 A | 1/1999 | Hanes et al. |
| 5,908,810 A | 6/1999 | Donn |
| 5,908,975 A | 6/1999 | Caimi et al. |
| 5,985,309 A | 11/1999 | Edwards et al. |
| 6,007,845 A | 12/1999 | Domb et al. |
| 6,013,861 A | 1/2000 | Bird et al. |
| 6,248,876 B1 | 6/2001 | Barry et al. |
| 6,284,479 B1 | 9/2001 | Nichols |
| 6,603,061 B1 | 8/2003 | Armstrong et al. |
| 6,734,341 B2 | 5/2004 | Singletary et al. |
| 6,750,059 B1 | 6/2004 | Blakesley et al. |
| 6,768,044 B1 | 7/2004 | Boudec et al. |
| 7,112,665 B1 | 9/2006 | Leemans et al. |
| 7,259,015 B2 | 8/2007 | Kingsman et al. |
| 7,303,910 B2 | 12/2007 | Bebbington et al. |
| 7,351,585 B2 | 4/2008 | Mitrophanous et al. |
| 7,776,321 B2 | 8/2010 | Cascalho et al. |
| 7,868,149 B2 | 1/2011 | Boukharov et al. |
| 8,044,019 B2 | 10/2011 | Uno et al. |
| 8,071,082 B2 | 12/2011 | Zugates et al. |
| 8,372,951 B2 | 2/2013 | Chang et al. |
| 8,404,658 B2 | 3/2013 | Hajjar et al. |
| 8,454,972 B2 | 6/2013 | Nabel et al. |
| 8,575,305 B2 | 11/2013 | Gait et al. |

(Continued)

FOREIGN PATENT DOCUMENTS

| | | |
|---|---|---|
| EP | 0 242 246 A1 | 10/1987 |
| EP | 0 264 166 A1 | 4/1988 |

(Continued)

OTHER PUBLICATIONS

Kwak et al., 2015, Complete genome sequence of *Photorhabdus temperate* subsp. *thracensis* 39-8T, an entomopathogenic bacterium for the improved commercial bioinsecticide, Journal of Biotechnology, 214: 115-116.*

Ffrench-Constant et al., 2014, Photorhabdus Toxins, Advances in Insect Physiology, 47: 343-388.*

Ullah et al., 2014, Identification and Characterization of the Insecticidal Toxin "Makes Caterpillars Floppy" in *Photorhabdus temperate* M1021 Using a Cosmid Library, Toxins, 6: 2024-2040.*

Brown et al., 2006, Txp40, a Ubiquitous Insecticidal Toxin Protein from *Xenorhabdus* and *Photorhabdus* Bacteria, Applied and Environmental Microbiology, 72(2): 1653-1662.*

Ffrench-Constant et al., 2007, Insecticidal toxins from *Photorhabdus* bacteria and their potential use in agriculture, Toxicon, 49: 436-451.*

(Continued)

*Primary Examiner* — Amber D Steele

(74) *Attorney, Agent, or Firm* — F. Brent Nix, Esq.; Johnson, Marcou, Isaacs & Nix, LLC

(57) ABSTRACT

The disclosure provides novel programmable targeting sequences and applications thereof. The targeting sequences can be engineered for binding to proteins, polypeptides, and other macromolecules.

7 Claims, 6 Drawing Sheets

Specification includes a Sequence Listing.

(56) References Cited

U.S. PATENT DOCUMENTS

| | | | |
|---|---|---|---|
| 8,614,194 B1 | 12/2013 | Chen et al. | |
| 8,709,843 B2 | 4/2014 | Shakuda | |
| 2002/0031826 A1 | 3/2002 | Nichols | |
| 2003/0087817 A1 | 5/2003 | Cox et al. | |
| 2003/0207806 A1* | 11/2003 | Ensign | C07K 14/24 514/4.5 |
| 2004/0013648 A1 | 1/2004 | Kingsman et al. | |
| 2004/0171156 A1 | 9/2004 | Hartley et al. | |
| 2004/0242517 A1 | 12/2004 | Cascalho et al. | |
| 2005/0019923 A1 | 1/2005 | Uchegbu et al. | |
| 2006/0168683 A1* | 7/2006 | Hey | C07K 14/24 530/370 |
| 2006/0281180 A1 | 12/2006 | Radcliffe et al. | |
| 2007/0025970 A1 | 2/2007 | Kingsman et al. | |
| 2007/0054961 A1 | 3/2007 | Maden et al. | |
| 2007/0266453 A1 | 11/2007 | Anderson et al. | |
| 2008/0267903 A1 | 10/2008 | Uchegbu et al. | |
| 2009/0007284 A1 | 1/2009 | Radcliffe et al. | |
| 2009/0017543 A1 | 1/2009 | Wilkes et al. | |
| 2009/0018016 A1 | 1/2009 | Duck et al. | |
| 2009/0100536 A1 | 4/2009 | Adams et al. | |
| 2009/0111106 A1 | 4/2009 | Mitrophanous et al. | |
| 2009/0144850 A1 | 6/2009 | Van Winkle et al. | |
| 2010/0317109 A1 | 12/2010 | Maden et al. | |
| 2011/0023139 A1 | 1/2011 | Weinstein et al. | |
| 2011/0027239 A1 | 2/2011 | Paek e al. | |
| 2011/0117189 A1 | 5/2011 | Mazzone et al. | |
| 2011/0195123 A1 | 8/2011 | Shemi | |
| 2011/0293571 A1 | 12/2011 | Widdowson et al. | |
| 2011/0293703 A1 | 12/2011 | Mahon et al. | |
| 2012/0251560 A1 | 10/2012 | Dahlman et al. | |
| 2012/0251618 A1 | 10/2012 | Schrum et al. | |
| 2012/0295960 A1 | 11/2012 | Palfi et al. | |
| 2013/0185823 A1 | 7/2013 | Kuang et al. | |
| 2013/0244279 A1 | 9/2013 | de Fougerolles et al. | |
| 2013/0245107 A1 | 9/2013 | de Fougerolles et al. | |
| 2013/0252281 A1 | 9/2013 | de Fougerolles et al. | |
| 2013/0302401 A1 | 11/2013 | Ma et al. | |
| 2015/0071903 A1 | 3/2015 | Liu et al. | |
| 2015/0118216 A1 | 4/2015 | Liu et al. | |
| 2015/0140070 A1 | 5/2015 | Heartlein et al. | |
| 2016/0082126 A1 | 3/2016 | Xu et al. | |
| 2016/0129120 A1 | 5/2016 | Xu et al. | |
| 2016/0200779 A1 | 7/2016 | Liu et al. | |
| 2016/0244761 A1 | 8/2016 | Payne et al. | |
| 2016/0257951 A1 | 9/2016 | Koizumi et al. | |
| 2017/0029844 A1* | 2/2017 | Ball | A01N 37/46 |
| 2019/0300581 A1 | 10/2019 | Zhang | |
| 2019/0300870 A1 | 10/2019 | Zhang | |

FOREIGN PATENT DOCUMENTS

| | | |
|---|---|---|
| EP | 0 333 033 a1 | 9/1989 |
| EP | 0 571 427 A1 | 12/1993 |
| EP | 0 663 956 A1 | 7/1995 |
| EP | 0 719 338 A1 | 7/1996 |
| EP | 0 728 213 A1 | 8/1996 |
| EP | 1 887 079 A1 | 2/2008 |
| EP | 1 950 303 A1 | 7/2008 |
| EP | 1 999 263 A1 | 12/2008 |
| EP | 2 099 905 A1 | 9/2009 |
| EP | 2 099 915 A1 | 9/2009 |
| JP | 2006-304779 A | 11/2006 |
| WO | 93/01294 A1 | 1/1993 |
| WO | 93/02197 A1 | 2/1993 |
| WO | 93/06487 A1 | 4/1993 |
| WO | 93/19181 A1 | 9/1993 |
| WO | 94/04693 A2 | 3/1994 |
| WO | 94/09144 A1 | 4/1994 |
| WO | 94/11520 A2 | 5/1994 |
| WO | 95/04826 A1 | 2/1995 |
| WO | 95/26407 A1 | 10/1995 |
| WO | 95/31553 A1 | 11/1995 |
| WO | 95/35026 A1 | 12/1995 |
| WO | 96/01904 A1 | 1/1996 |
| WO | 96/15248 A1 | 5/1996 |
| WO | 96/19581 A1 | 6/1996 |
| WO | 96/21023 A1 | 7/1996 |
| WO | 96/27674 A1 | 9/1996 |
| WO | 96/30517 A1 | 10/1996 |
| WO | 96/34968 A2 | 11/1996 |
| WO | 96/38567 A2 | 12/1996 |
| WO | 97/11188 A1 | 3/1997 |
| WO | 97/20936 A1 | 6/1997 |
| WO | 97/26362 A1 | 7/1997 |
| WO | 97/32985 A1 | 9/1997 |
| WO | 97/42328 A1 | 11/1997 |
| WO | 97/44472 A1 | 11/1997 |
| WO | 97/45545 A1 | 12/1997 |
| WO | 97/47806 A1 | 12/1997 |
| WO | 97/47807 A1 | 12/1997 |
| WO | 97/47808 A1 | 12/1997 |
| WO | 98/20145 A2 | 5/1998 |
| WO | 98/22604 A1 | 5/1998 |
| WO | 98/27212 A1 | 6/1998 |
| WO | 98/32326 A2 | 7/1998 |
| WO | 98/39460 A1 | 9/1998 |
| WO | 98/40503 A1 | 9/1998 |
| WO | 99/12950 A2 | 3/1999 |
| WO | 99/24585 A1 | 5/1999 |
| WO | 99/24586 A1 | 5/1999 |
| WO | 99/24593 A1 | 5/1999 |
| WO | 99/53072 A1 | 10/1999 |
| WO | 99/58654 A2 | 11/1999 |
| WO | 99/58688 A2 | 11/1999 |
| WO | 99/58690 A2 | 11/1999 |
| WO | 99/66050 A1 | 12/1999 |
| WO | 00/04173 A1 | 1/2000 |
| WO | 00/08175 A2 | 2/2000 |
| WO | 00/08184 A1 | 2/2000 |
| WO | 00/08185 A1 | 2/2000 |
| WO | 00/11192 A2 | 3/2000 |
| WO | 00/14249 A1 | 3/2000 |
| WO | 00/22140 A1 | 4/2000 |
| WO | 00/28052 A2 | 5/2000 |
| WO | 00/47727 A2 | 8/2000 |
| WO | 00/73422 A1 | 12/2000 |
| WO | 00/77229 A2 | 12/2000 |
| WO | 01/12782 A2 | 2/2001 |
| WO | 01/12826 A2 | 2/2001 |
| WO | 01/14569 A2 | 3/2001 |
| WO | 01/19975 A2 | 3/2001 |
| WO | 01/98509 A2 | 12/2001 |
| WO | 02/034923 A2 | 5/2002 |
| WO | 02/46387 A2 | 6/2002 |
| WO | 02/79410 A2 | 10/2002 |
| WO | 02/083911 A1 | 10/2002 |
| WO | 02/101059 A2 | 12/2002 |
| WO | 03/33540 A2 | 4/2003 |
| WO | 03/071860 A2 | 9/2003 |
| WO | 2004/056999 A1 | 7/2004 |
| WO | 2004/078983 A2 | 9/2004 |
| WO | 2004/090140 A2 | 10/2004 |
| WO | 2005/002359 A2 | 1/2005 |
| WO | 2005/012515 A2 | 2/2005 |
| WO | 2005/012529 A2 | 2/2005 |
| WO | 2005/030941 A1 | 4/2005 |
| WO | 2005/030942 A1 | 4/2005 |
| WO | 2005/095617 A2 | 10/2005 |
| WO | 2005/095618 A2 | 10/2005 |
| WO | 2005/095619 A2 | 10/2005 |
| WO | 2005/095632 A2 | 10/2005 |
| WO | 2005/105152 A2 | 11/2005 |
| WO | 2005/107437 A2 | 11/2005 |
| WO | 2005/123927 A1 | 12/2005 |
| WO | 2006/018319 A1 | 2/2006 |
| WO | 2006/032538 A1 | 3/2006 |
| WO | 2006/045633 A1 | 5/2006 |
| WO | 2006/063862 A1 | 6/2006 |
| WO | 2006/069782 A2 | 7/2006 |
| WO | 2006/072603 A2 | 7/2006 |
| WO | 2006/103107 A1 | 10/2006 |
| WO | 2006/108702 A1 | 10/2006 |

(56) References Cited

FOREIGN PATENT DOCUMENTS

| | | | |
|---|---|---|---|
| WO | 2006/133827 | A2 | 12/2006 |
| WO | 2007/009823 | A1 | 1/2007 |
| WO | 2007/039314 | A2 | 4/2007 |
| WO | 2007/039315 | A1 | 4/2007 |
| WO | 2007/039316 | A1 | 4/2007 |
| WO | 2007/107326 | A1 | 9/2007 |
| WO | 2007/121947 | A1 | 11/2007 |
| WO | 2008/042156 | A1 | 4/2008 |
| WO | 2008/042973 | A2 | 4/2008 |
| WO | 2008/064289 | A2 | 5/2008 |
| WO | 2009/144079 | A1 | 12/2009 |
| WO | 2010/061186 | A2 | 6/2010 |
| WO | 2011/028929 | A3 | 10/2011 |
| WO | 2012/135025 | A2 | 10/2012 |
| WO | 2013/046247 | A1 | 4/2013 |
| WO | 2013/093648 | A2 | 6/2013 |
| WO | 2013/122472 | A1 | 8/2013 |
| WO | 2013/126794 | A1 | 8/2013 |
| WO | 2014/186348 | A2 | 11/2014 |
| WO | 2014/186366 | A1 | 11/2014 |
| WO | 2015/082080 | A1 | 6/2015 |
| WO | 2015/089419 | A2 | 6/2015 |
| WO | 2015/138510 | A1 | 9/2015 |
| WO | 2016/027264 | A1 | 2/2016 |

OTHER PUBLICATIONS

Hinchliffe et al., 2010, Insecticidal Toxins from the *Photorhabdus* and *Xenorhabdus* Bacteria, The Open Toxinology Journal, 3: 83-100.*

Dowling, 2016, Identifying Anti-host Effectors in *Photorhabdus*, Current Topics in Microbiology and Immunology, 402: 25-38.*

Chen, et al., "Predicting Peptide-Mediated Interactions on a Genome-Wide Scale", PLOS Computational Biology, vol. 11, No. 5, May 4, 2015, 13 pages.

Dey, et al., "Toward a "Structural BLAST": Using Structural Relationships to Infer Function", Protein Science, vol. 22, No. 4, Apr. 2013, 359-366.

Zhang, et al., "Structure-Based Prediction of Protein-Protein Interactions on a Genome-Wide Scale", Nature, vol. 490, Oct. 25, 2012, 556-560.

Hirayama et al., 2009, Significant Deviations in the Configurations of Homologous Tandem Repeats in Prokaryotic Genomes, Genomics Proteomics Bioinformatics, 7(4): 163-17 4.

Zhang et al., 2012, Polymorphic toxin systems: Comprehensive characterization of trafficking modes, processing, mechanisms of action, immunity and ecology using comparative genomics, Biology Direct, 7: 18 (76 pages).

* cited by examiner

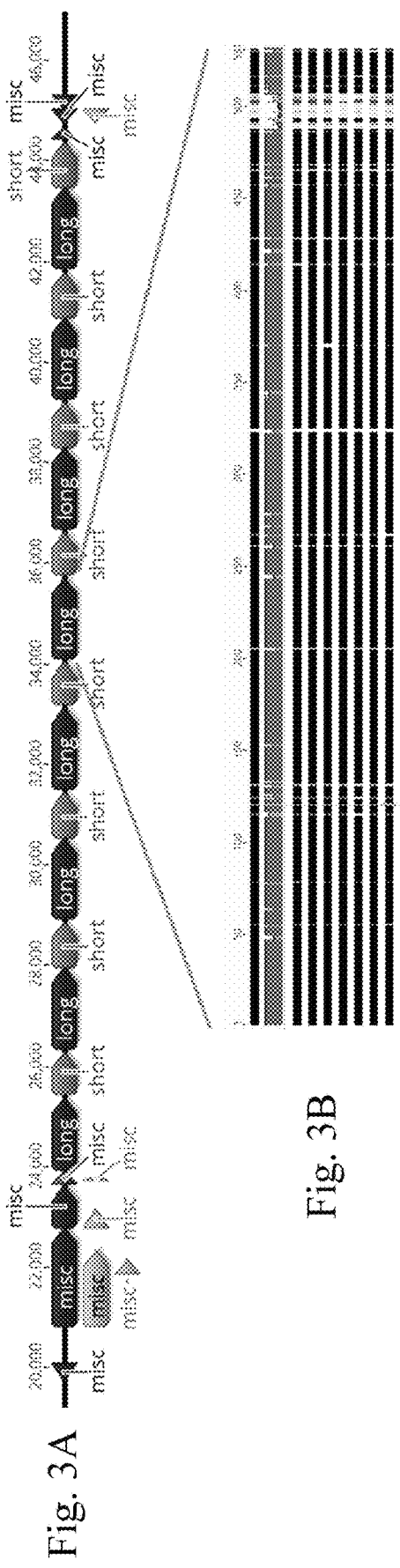
Fig. 3A
Fig. 3B
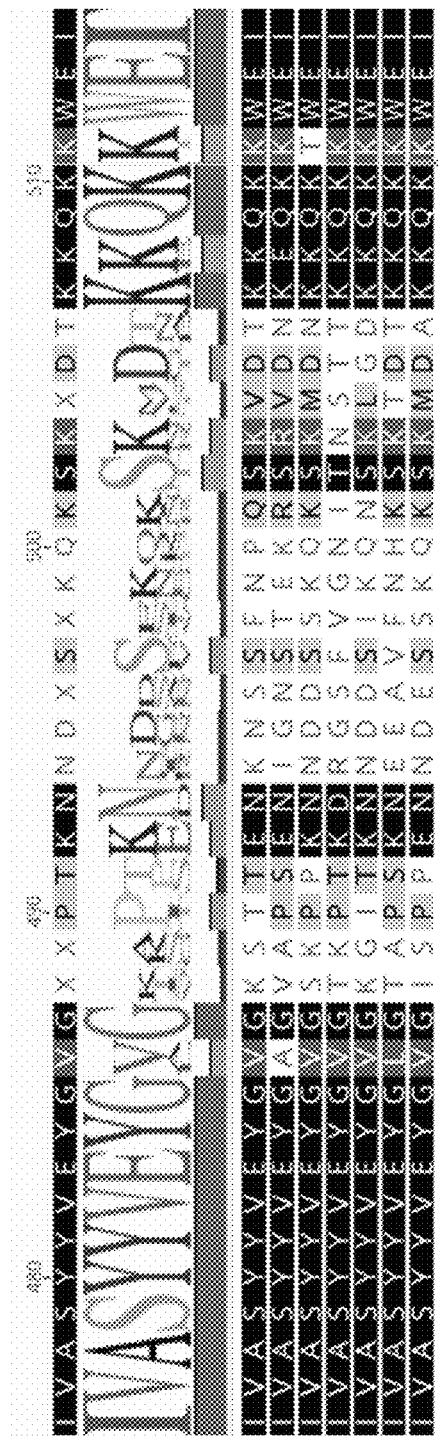
Fig. 3C

```
WP_036843789.1    AADMKADRQKK---------------------SMVKIKKKWKWIIADPLKVSESPLRINLIGEK
WP_105395755.1    DVDAKKENGEKS-------------------IIKITEKWKWVIADPLKASESPLRINLIGEE
OCA54061.1        DVDVGKEDGEKS-------------------LIQVKEKWKWVIADPLKANESPLRINLMGEE
WP_046397830.1    DVDVGKEDGEKS-------------------LIQVKEKWKWVIADPLKANESPLRINLMGEE
WP_036807456.1    DVDVGKEDGEKS-------------------LIQVKEKWKWVIADPLKANESPLRINLMGEE
WP_088373187.1    DVDIKKKNKKMDS------------------TKNLFKVKKKWVIADPLKASESPLRINLIGEE
WP_011146190.1    AVDARRNSSRNS-------------------IIEVRKKWKWVIADPLKASESPLRINLIGEE
WP_040152449.1    AVDIKKKNKKMDS------------------TKNLFKVKKKWVIADPLKASESPLRINLIGKE
WP_036775722.1    ----------------------------------------------------------------
WP_012776453.1    EADIEADGKE--N------------------SI--AKVKKKWVIADPLKASESPLRISLLGEQ
WP_065822736.1    DADVETENEK--K------------------SI--AKIKKKWVIADPLKASESPLRINLLGEE
WP_054478414.1    TADTKKEENR--K------------------SI--VKVKKKWVIADPLKASESPLRINLLGEE
WP_036775012.1    TADTKKEKDR--K------------------SI--AKVKKKWVIADPLKASESPLRINLLGEE
WP_012776450.1    SADAEIGRKK--K------------------ASKKAKNKWTWVIADPLKASESPLRINVLGKE
WP_036773254.1    TADAEIGRKK--K------------------ATKKVKNKWKWVIADPLKASESPLRINLLGKE
WP_036773878.1    EVKAGYIQKESKSVSN------TKGRSKNSGINLIKAD-VMICDK-DEFGPFYFIDFK----
WP_041382200.1    GYAVQVGKTDKKKGKP-GIGNKTATSKKSEETKLKNEKWTIYPALSKKESTWRWSLD----
WP_036773948.1    GYAVQVGKTDKKKVKP-GIGNKTTTSKKSEEAKLKNEKWTIYPALSKKESTWRWSLD----
WP_065822477.1    GYAVQVGKTDKKKVKP-GIGNKTTTSKKSEEAKLKNEKWTIYPALSKKESTWRWSLD----
WP_051691048.1    AYGARVGEVDNINSENKKLGNSK-STAMRNLQDEIEKEKWVLQEPLSKEKSTYRVSFG----
WP_036849041.1    EYGVGVAPSENNGKSI---------GSGSNVDNKKQKKWEIYPKLPKEKSTYKLRLSQ--
WP_046976479.1    EYGVGTKPTKDRGSFV---------GNITNSTTRKQKKWEIYPKLPKEKSTYKLRLAQ--
WP_046976480.1    EYGVGSKPPKNNDDSS---------KQKSKMDNKKQKTWEIYPKLPKEKSTYKLRLSQ--
WP_046976473.1    EYGVGISPPENNDESS---------KQKSKMDAKKQKKWEIYPKLPKEKSTYKLRLSQ--
WP_046976475.1    EYGLGTAPSKNEEAVF---------NHKSKTDTKKQKKWEIYPKLPKEKSTYKLRLTQ--
WP_046976482.1    EYGAGVAPSENIGNST---------EKRSRVDNKEQKKWEIYPKLPKEKSTYKLRLSQ--
WP_082111283.1    EYGVGVAPFDNNGKSI---------RSGSNVDNKKQKKWEIYPKLPKEKSTYKLRLSQ--
AKH65533.1        EYGVGVAPFDNNGKSI---------RSGSNVDNKKQKKWEIYPKLPKEKSTYKLRLSQ--
WP_046976484.1    EYGVGKSTTENKNSSF---------NPQSKVDTKKQKKWEIYPKLPKEKSTYKLRLSQ--
WP_046976477.1    EYGVGKGITKNNDDSI---------KQNSKLGDKKQKKWEIYLKLPKEKSTYKLRLSQ--
WP_088371923.1    EYGAGIAPPKSNRDSA---------KQKDGKDNKKQKKWEIYPKLPKEKSTYKLRLS---
PQQ32646.1        DYGVGVAPSENKEDSF---------SK--RSSNKKRKKWEIYPKLSKEKSTYKLRLSQ--
PQQ36817.1        DYGVGVAPSENKEDSF---------SK--RSSNKKRKKWEIYPKLSKEKSTYKLRLSQ--
WP_054478108.1    EFGMGLVPSENNGKSI---------IKGSKVDNKKQKKWEIYPKLPKEKSTYKLRLSE--
WP_054478110.1    EFGMGIAPPKSNSDSA---------KQKDGKDSKTQKKWEIYPKLPKEKSTYKLRLS---
WP_015834765.1    EFGVGVAPSENKEDSF---------SQ--KSGNKKREKWEVYPKLPKEKSTYKLRLS---
WP_015834769.1    EFGVGLVPSENNGKSI---------IKGSKVDNKKQKKWEIYPRLPKEKSTYKLRLSE--
WP_015834771.1    EFGAGVSPSENSNESS---------KQNSKRDDKKQKKWEIYPKLSKEKSTYKLRLS---
```

Fig. 6

SEQUENCE LISTING

```
<160> NUMBER OF SEQ ID NOS: 174

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = 1-7 amino acid residues comprising at
      least one hydrophobic amino acid residue, at least one charged
      amino acid residue, and/or at least one polar amino acid residue
<220> FEATURE:
<221> NAME/KEY: MISC_FEATURE
<222> LOCATION: (2)..(2)
<223> OTHER INFORMATION: Xaa = Glu or Lys
<220> FEATURE:
<221> NAME/KEY: MISC_FEATURE
<222> LOCATION: (3)..(3)
<223> OTHER INFORMATION: Xaa = Asn or Asp
<220> FEATURE:
<221> NAME/KEY: MISC_FEATURE
<222> LOCATION: (4)..(4)
<223> OTHER INFORMATION: Xaa = 0 to 12 polar, hydrophobic, and/or
      charged amino acid residues
<220> FEATURE:
<221> NAME/KEY: MISC_FEATURE
<222> LOCATION: (5)..(5)
<223> OTHER INFORMATION: Xaa = Ser or Thr
<220> FEATURE:
<221> NAME/KEY: MISC_FEATURE
<222> LOCATION: (6)..(6)
<223> OTHER INFORMATION: Xaa = 1 to 7 amino acid residues comprising a
      polar amino acid residue, a hydrophobic amino acid residue and/or
``` a charged amino acid residue

<400> SEQUENCE: 1

Xaa Xaa Xaa Xaa Xaa Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = 1-7 amino acid residues comprising at
      least one polar amino acid residue and one hydrophobic amino acid
      residue
<220> FEATURE:
<221> NAME/KEY: MISC_FEATURE
<222> LOCATION: (2)..(2)
<223> OTHER INFORMATION: Xaa = Glu or Lys
<220> FEATURE:
<221> NAME/KEY: MISC_FEATURE
<222> LOCATION: (3)..(3)
<223> OTHER INFORMATION: Xaa = Asn or Asp
<220> FEATURE:
<221> NAME/KEY: MISC_FEATURE
<222> LOCATION: (4)..(4)
<223> OTHER INFORMATION: Xaa = 0 to 12 polar, hydrophobic, and/or
      charged amino acid residues
<220> FEATURE:
<221> NAME/KEY: MISC_FEATURE
<222> LOCATION: (5)..(5)
<223> OTHER INFORMATION: Xaa = Ser or Thr
<220> FEATURE:
<221> NAME/KEY: MISC_FEATURE
<222> LOCATION: (6)..(6)
<223> OTHER INFORMATION: Xaa = 1 to 7 amino acid residues comprising a
      polar amino acid residue, a hydrophobic amino acid residue and/or
      a charged amino acid residue

<400> SEQUENCE: 2

Xaa Xaa Xaa Xaa Xaa Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = 1-4 amino acid residues comprising at
      least one hydrophobic residue and/or one polar residue
<220> FEATURE:
<221> NAME/KEY: MISC_FEATURE
<222> LOCATION: (2)..(2)
<223> OTHER INFORMATION: Xaa = Glu or Lys
<220> FEATURE:
<221> NAME/KEY: MISC_FEATURE
<222> LOCATION: (3)..(3)
<223> OTHER INFORMATION: Xaa = Asn or Asp
<220> FEATURE:
<221> NAME/KEY: MISC_FEATURE
<222> LOCATION: (4)..(4)
<223> OTHER INFORMATION: Xaa = 1 to 8 polar and/or charged amino acid
      residues
<220> FEATURE:
<221> NAME/KEY: MISC_FEATURE
<222> LOCATION: (5)..(5)
<223> OTHER INFORMATION: Xaa = Ser or Thr
<220> FEATURE:

```
<221> NAME/KEY: MISC_FEATURE
<222> LOCATION: (6)..(6)
<223> OTHER INFORMATION: Xaa = 1 to 5 hydrophobic and/or charged amino
      acid residues

<400> SEQUENCE: 3

Xaa Xaa Xaa Xaa Xaa Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc
<222> LOCATION: (1)..(1)
<223> OTHER INFORMATION: Xaa = 1-7 amino acid residues comprising a
      charged residue
<220> FEATURE:
<221> NAME/KEY: misc
<222> LOCATION: (2)..(2)
<223> OTHER INFORMATION: Xaa = Glu or Lys
<220> FEATURE:
<221> NAME/KEY: misc
<222> LOCATION: (3)..(3)
<223> OTHER INFORMATION: Xaa = Asn or Asp
<220> FEATURE:
<221> NAME/KEY: misc
<222> LOCATION: (4)..(4)
<223> OTHER INFORMATION: Xaa = 0 to 12 polar, hydrophobic, and/or
      charged amino acid residues
<220> FEATURE:
<221> NAME/KEY: misc
<222> LOCATION: (5)..(5)
<223> OTHER INFORMATION: Xaa = Ser or Thr
<220> FEATURE:
<221> NAME/KEY: misc
<222> LOCATION: (6)..(6)
<223> OTHER INFORMATION: Xaa = 1 to 7 amino acids comprising a charged
      residue and/or a polar residue

<400> SEQUENCE: 4

Xaa Xaa Xaa Xaa Xaa Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = a proline or a threonine or an isoleucine
      (P/T/I), or a proline, a serine, or a threonine (P/S/T)
<220> FEATURE:
<221> NAME/KEY: MISC_FEATURE
<222> LOCATION: (2)..(2)
<223> OTHER INFORMATION: Xaa = Glu or Lys
<220> FEATURE:
<221> NAME/KEY: MISC_FEATURE
<222> LOCATION: (3)..(3)
<223> OTHER INFORMATION: Xaa = Asn or Asp
<220> FEATURE:
<221> NAME/KEY: MISC_FEATURE
<222> LOCATION: (4)..(4)
<223> OTHER INFORMATION: Xaa = a serine, a phenylalanine, or a valine
      (S/F/V), a asparagine or a glutamine (N/Q), or an arginine or a
      lysine (R/K)
<220> FEATURE:
<221> NAME/KEY: MISC_FEATURE
<222> LOCATION: (5)..(5)
```

```
<223> OTHER INFORMATION: Xaa = Ser or Thr
<220> FEATURE:
<221> NAME/KEY: MISC_FEATURE
<222> LOCATION: (6)..(6)
<223> OTHER INFORMATION: Xaa = a lysine, an arginine, or an asparagine
      (K/R/N), or an aspartic acid, a threonine, or a glycine (D/T/G)

<400> SEQUENCE: 5

Xaa Xaa Xaa Xaa Xaa Xaa
1               5

<210> SEQ ID NO 6
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (13)..(14)
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = any amino acid
<220> FEATURE:
<221> NAME/KEY: MISC_FEATURE
<222> LOCATION: (29)..(29)
<223> OTHER INFORMATION: Xaa = any amino acid

<400> SEQUENCE: 6

Ile Val Ala Ser Tyr Tyr Val Glu Tyr Gly Val Gly Xaa Xaa Pro Thr
1               5                   10                  15

Lys Asn Asn Asp Xaa Ser Xaa Lys Gln Lys Ser Lys Xaa Asp Thr Lys
            20                  25                  30

Lys Gln Lys Lys Trp Glu Ile
        35

<210> SEQ ID NO 7
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 7

Ile Val Ala Ser Tyr Tyr Val Glu Tyr Gly Val Gly Lys Ser Thr Thr
1               5                   10                  15

Glu Asn Lys Asn Ser Ser Phe Asn Pro Gln Ser Lys Val Asp Thr Lys
            20                  25                  30

Lys Gln Lys Lys Trp Glu Ile
        35

<210> SEQ ID NO 8
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 8

Ile Val Ala Ser Tyr Tyr Val Glu Tyr Gly Ala Gly Val Ala Pro Ser
1               5                   10                  15
```

```
Glu Asn Ile Gly Asn Ser Thr Glu Lys Arg Ser Arg Val Asp Asn Lys
                20                  25                  30

Glu Gln Lys Lys Trp Glu Ile
        35

<210> SEQ ID NO 9
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 9

Ile Val Ala Ser Tyr Tyr Val Glu Tyr Gly Val Gly Ser Lys Pro Pro
1               5                   10                  15

Lys Asn Asn Asp Asp Ser Ser Lys Gln Lys Ser Lys Met Asp Asn Lys
                20                  25                  30

Lys Gln Lys Thr Trp Glu Ile
        35

<210> SEQ ID NO 10
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 10

Ile Val Ala Ser Tyr Tyr Val Glu Tyr Gly Val Gly Thr Lys Pro Thr
1               5                   10                  15

Lys Asp Arg Gly Ser Phe Val Gly Asn Ile Thr Asn Ser Thr Thr Lys
                20                  25                  30

Lys Gln Lys Lys Trp Glu Ile
        35

<210> SEQ ID NO 11
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 11

Ile Val Ala Ser Tyr Tyr Val Glu Tyr Gly Val Gly Lys Gly Ile Thr
1               5                   10                  15

Lys Asn Asn Asp Asp Ser Ile Lys Gln Asn Ser Lys Leu Gly Asp Lys
                20                  25                  30

Lys Gln Lys Lys Trp Glu Ile
        35

<210> SEQ ID NO 12
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 12

Ile Val Ala Ser Tyr Tyr Val Glu Tyr Gly Leu Gly Thr Ala Pro Ser
1               5                   10                  15

Lys Asn Glu Glu Ala Val Phe Asn His Lys Ser Lys Thr Asp Thr Lys
                20                  25                  30
```

Lys Gln Lys Lys Trp Glu Ile
        35

<210> SEQ ID NO 13
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 13

Ile Val Ala Ser Tyr Tyr Val Glu Tyr Gly Val Gly Ile Ser Pro Pro
1               5                   10                  15

Glu Asn Asn Asp Glu Ser Ser Lys Gln Lys Ser Lys Met Asp Ala Lys
            20                  25                  30

Lys Gln Lys Lys Trp Glu Ile
        35

<210> SEQ ID NO 14
<211> LENGTH: 94
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (76)..(76)
<223> OTHER INFORMATION: Y = thymine/uracil or cytosine

<400> SEQUENCE: 14
tattgaagcg aagggtgtt ttgaactgga taagcaggat aacgggttat atctggtatt    60
tttccatgag gggatygttg ccagttatta tgtg                               94

<210> SEQ ID NO 15
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 15

Ile Glu Ala Glu Gly Cys Phe Glu Leu Asp Lys Gln Asp Asn Gly Leu
1               5                   10                  15

Tyr Leu Val Phe Phe His Glu Gly Ile Val Ala Ser Tyr Tyr Val
            20                  25                  30

<210> SEQ ID NO 16
<211> LENGTH: 93
<212> TYPE: DNA
<213> ORGANISM: Artificial Sequence
<220> FEATURE:
<223> OTHER INFORMATION: Synthetic Oligonucleotide

<400> SEQUENCE: 16
tattgaagcg aagggtgtt ttgaactgga taagcaggat aaaggattat gtctggtgtt    60
tttccatgag gggattgttg ccagttatta tgt                                93

<210> SEQ ID NO 17
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 17

```
Ile Glu Ala Glu Gly Cys Phe Glu Leu Asp Lys Gln Asp Lys Gly Leu
1               5                   10                  15

Cys Leu Val Phe Phe His Glu Gly Ile Val Ala Ser Tyr Tyr Val
            20                  25                  30
```

<210> SEQ ID NO 18
<211> LENGTH: 94
<212> TYPE: DNA
<213> ORGANISM: Artificial Sequence
<220> FEATURE:
<223> OTHER INFORMATION: Synthetic Oligonucleotide

<400> SEQUENCE: 18

```
tattgaagcg aaggggggt tttgaactgg ataagcagga taacgggtta tatctggtat    60
ttttccatga ggggatcgtt gccagttatt atgt                              94
```

<210> SEQ ID NO 19
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 19

```
Ile Glu Ala Glu Gly Gly Phe Glu Leu Asp Lys Gln Asp Asn Gly Leu
1               5                   10                  15

Tyr Leu Val Phe Phe His Glu Gly Ile Val Ala Ser Tyr Tyr Val
            20                  25                  30
```

<210> SEQ ID NO 20
<211> LENGTH: 93
<212> TYPE: DNA
<213> ORGANISM: Artificial Sequence
<220> FEATURE:
<223> OTHER INFORMATION: Synthetic Oligonucleotide

<400> SEQUENCE: 20

```
tattgaagcg aagggtgtt ttgaactgga taagcaggat aaaggattat gtctggtgtt    60
tttccatgag gggatcgttg ccagttatta tgt                               93
```

<210> SEQ ID NO 21
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 21

```
Ile Glu Ala Glu Gly Cys Phe Glu Leu Asp Lys Gln Asp Lys Gly Leu
1               5                   10                  15

Cys Leu Val Phe Phe His Glu Gly Ile Val Ala Ser Tyr Tyr Val
            20                  25                  30
```

<210> SEQ ID NO 22
<211> LENGTH: 93
<212> TYPE: DNA
<213> ORGANISM: Artificial Sequence
<220> FEATURE:
<223> OTHER INFORMATION: Synthetic Oligonucleotide

<400> SEQUENCE: 22

```
tattgaagcg aagggtgct ttgagctgaa taagcaggat aacgggttat atctggtatt    60
```

```
tttccatgag gggattgttg ccagttatta tgt                                    93
```

<210> SEQ ID NO 23
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 23

```
Ile Glu Ala Glu Gly Cys Phe Glu Leu Asn Lys Gln Asp Asn Gly Leu
1               5                   10                  15
Tyr Leu Val Phe Phe His Glu Gly Ile Val Ala Ser Tyr Tyr Val
            20                  25                  30
```

<210> SEQ ID NO 24
<211> LENGTH: 93
<212> TYPE: DNA
<213> ORGANISM: Artificial Sequence
<220> FEATURE:
<223> OTHER INFORMATION: Synthetic Oligonucleotide

<400> SEQUENCE: 24

```
tattgaagcg gaaggctgct ttgagctgaa taagcaggat aacgggttat atctggtatt      60
tttccatgag gggattgttg ccagttatta tgt                                    93
```

<210> SEQ ID NO 25
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 25

```
Ile Glu Ala Glu Gly Cys Phe Glu Leu Asn Lys Gln Asp Asn Gly Leu
1               5                   10                  15
Tyr Leu Val Phe Phe His Glu Gly Ile Val Ala Ser Tyr Tyr Val
            20                  25                  30
```

<210> SEQ ID NO 26
<211> LENGTH: 93
<212> TYPE: DNA
<213> ORGANISM: Artificial Sequence
<220> FEATURE:
<223> OTHER INFORMATION: Synthetic Oligonucleotide

<400> SEQUENCE: 26

```
tattgaagcg gaagggtgtt ttgaactgga taagcaggat aacgggttat atctggtatt      60
tttccatgag gggatcgttg ccagttatta tgt                                    93
```

<210> SEQ ID NO 27
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 27

```
Ile Glu Ala Glu Gly Cys Phe Glu Leu Asp Lys Gln Asp Asn Gly Leu
1               5                   10                  15
Tyr Leu Val Phe Phe His Glu Gly Ile Val Ala Ser Tyr Tyr Val
            20                  25                  30
```

<210> SEQ ID NO 28
<211> LENGTH: 93
<212> TYPE: DNA
<213> ORGANISM: Artificial Sequence
<220> FEATURE:
<223> OTHER INFORMATION: Synthetic Oligonucleotide

<400> SEQUENCE: 28
tattgaagcg aagggtgtt ttgaactgga taagcaggat aaaggattat gtctggtgtt    60
ttttcatgag gggatcgttg ccagttatta tgt                                93

<210> SEQ ID NO 29
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 29

Ile Glu Ala Glu Gly Cys Phe Glu Leu Asp Lys Gln Asp Lys Gly Leu
1               5                   10                  15

Cys Leu Val Phe Phe His Glu Gly Ile Val Ala Ser Tyr Tyr Val
            20                  25                  30

<210> SEQ ID NO 30
<211> LENGTH: 93
<212> TYPE: DNA
<213> ORGANISM: Artificial Sequence
<220> FEATURE:
<223> OTHER INFORMATION: Synthetic Oligonucleotide

<400> SEQUENCE: 30
tattgaagcg aagggtgct ttgagctgaa taagcaggat aacgggttat atctggtatt    60
tttccatgag gggattgttg ccagttatta tgt                                93

<210> SEQ ID NO 31
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 31

Ile Glu Ala Glu Gly Cys Phe Glu Leu Asn Lys Gln Asp Asn Gly Leu
1               5                   10                  15

Tyr Leu Val Phe Phe His Glu Gly Ile Val Ala Ser Tyr Tyr Val
            20                  25                  30

<210> SEQ ID NO 32
<211> LENGTH: 82
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (29)..(29)
<223> OTHER INFORMATION: k = guanine or thymine/uracil
<220> FEATURE:
<221> NAME/KEY: misc_feature
<222> LOCATION: (33)..(33)
<223> OTHER INFORMATION: w = adenine or thymine/uracil
<220> FEATURE:
<221> NAME/KEY: misc_feature
<222> LOCATION: (36)..(36)
<223> OTHER INFORMATION: r = guanine or adenine
<220> FEATURE:

```
<221> NAME/KEY: misc_feature
<222> LOCATION: (48)..(48)
<223> OTHER INFORMATION: r = guanine or adenine
<220> FEATURE:
<221> NAME/KEY: misc_feature
<222> LOCATION: (72)..(72)
<223> OTHER INFORMATION: r = guanine or adenine
<220> FEATURE:
<221> NAME/KEY: misc_feature
<222> LOCATION: (79)..(79)
<223> OTHER INFORMATION: m = adenine or cytosine

<400> SEQUENCE: 32
attatgtgga gtatggggtg ggaattgckc cawctraaaa taatgatrat tcttttaaac    60
aaaaaagcaa artggatamt aa                                             82

<210> SEQ ID NO 33
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (12)..(12)
<223> OTHER INFORMATION: Xaa = Thr; or Ser and Lys; or Glu
<220> FEATURE:
<221> NAME/KEY: MISC_FEATURE
<222> LOCATION: (16)..(16)
<223> OTHER INFORMATION: Xaa = Asn or Asp
<220> FEATURE:
<221> NAME/KEY: MISC_FEATURE
<222> LOCATION: (25)..(25)
<223> OTHER INFORMATION: Xaa = Met or Valine
<220> FEATURE:
<221> NAME/KEY: MISC_FEATURE
<222> LOCATION: (27)..(27)
<223> OTHER INFORMATION: Xaa = Asb or Thr

<400> SEQUENCE: 33

Tyr Tyr Val Glu Tyr Gly Val Gly Ile Ala Pro Xaa Asn Asn Asp Xaa
1               5                   10                  15

Ser Phe Lys Trp Gln Lys Ser Lys Xaa Asp Xaa Lys
            20                  25

<210> SEQ ID NO 34
<211> LENGTH: 83
<212> TYPE: DNA
<213> ORGANISM: Artificial Sequence
<220> FEATURE:
<223> OTHER INFORMATION: Synthetic Oligonucleotide

<400> SEQUENCE: 34
tattatgtgg agtatggggt gggagttgcg ccatttgata taatggtaa gtctatcaga    60 tcaggaagca atgtggataa caa                                           83

<210> SEQ ID NO 35
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 35

Tyr Tyr Val Glu Tyr Gly Val Gly Val Ala Pro Phe Asp Asn Asn Gly
1               5                   10                  15

Lys Ser Ile Arg Ser Gly Ser Asn Val Asp Asn Lys
            20                  25
```

```
<210> SEQ ID NO 36
<211> LENGTH: 83
<212> TYPE: DNA
<213> ORGANISM: Artificial Sequence
<220> FEATURE:
<223> OTHER INFORMATION: Synthetic Oligonucleotide

<400> SEQUENCE: 36
tattatgtgg agtatggggt ggggaaaagt acaactgaaa ataaaaatag tagctttaat    60
ccacagagca aagtagatac caa                                            83

<210> SEQ ID NO 37
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 37

Tyr Tyr Val Glu Tyr Gly Val Gly Lys Ser Thr Thr Glu Asn Lys Asn
1               5                   10                  15

Ser Ser Phe Asn Pro Gln Ser Lys Val Asp Thr Lys
            20                  25

<210> SEQ ID NO 38
<211> LENGTH: 83
<212> TYPE: DNA
<213> ORGANISM: Artificial Sequence
<220> FEATURE:
<223> OTHER INFORMATION: Synthetic Oligonucleotide

<400> SEQUENCE: 38
tattatgtgg agtatggggc aggagtcgcg ccatctgaaa atatcggcaa ctctactgag    60
aaaagaagtc gggtggataa taa                                            83

<210> SEQ ID NO 39
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 39

Tyr Tyr Val Glu Tyr Gly Ala Gly Val Ala Pro Ser Glu Asn Ile Gly
1               5                   10                  15

Asn Ser Thr Glu Lys Arg Ser Arg Val Asp Asn Lys
            20                  25

<210> SEQ ID NO 40
<211> LENGTH: 83
<212> TYPE: DNA
<213> ORGANISM: Artificial Sequence
<220> FEATURE:
<223> OTHER INFORMATION: Synthetic Peptide

<400> SEQUENCE: 40
tattatgtgg agtatggggt ggggagtaag ccacctaaaa ataatgatga ttcctccaaa    60
caaaagagca aatggataa taa                                             83

<210> SEQ ID NO 41
<211> LENGTH: 28
<212> TYPE: PRT
```

```
<213> ORGANISM: Artificial Sequence
<220> FEATURE:
<223> OTHER INFORMATION: Synthetic Peptide

<400> SEQUENCE: 41

Tyr Tyr Val Glu Tyr Gly Val Gly Ser Lys Pro Pro Lys Asn Asn Asp
1               5                   10                  15

Asp Ser Ser Lys Gln Lys Ser Lys Met Asp Asn Lys
            20                  25

<210> SEQ ID NO 42
<211> LENGTH: 83
<212> TYPE: DNA
<213> ORGANISM: Artificial Sequence
<220> FEATURE:
<223> OTHER INFORMATION: Synthetic Oligonucleotide

<400> SEQUENCE: 42
tattatgtgg agtatgggt gggaacaaaa ccaactaaag atagaggtag ttttgttgga     60
aatataacca attcgaccac caa                                           83

<210> SEQ ID NO 43
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 43

Tyr Tyr Val Glu Tyr Gly Val Gly Thr Lys Pro Thr Lys Asp Arg Gly
1               5                   10                  15

Ser Phe Val Gly Asn Ile Thr Asn Ser Thr Thr Lys
            20                  25

<210> SEQ ID NO 44
<211> LENGTH: 83
<212> TYPE: DNA
<213> ORGANISM: Artificial Sequence
<220> FEATURE:
<223> OTHER INFORMATION: Synthetic Oligonucleotide

<400> SEQUENCE: 44
tattatgtgg agtatgggt ggggaaaggt ataactaaaa ataatgatga ttctatcaag     60
caaaatagca aattaggtga taa                                           83

<210> SEQ ID NO 45
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 45

Tyr Tyr Val Glu Tyr Gly Val Gly Lys Gly Ile Thr Lys Asn Asn Asp
1               5                   10                  15

Asp Ser Ile Lys Gln Asn Ser Lys Leu Gly Asp Lys
            20                  25

<210> SEQ ID NO 46
<211> LENGTH: 83
<212> TYPE: DNA
<213> ORGANISM: Artificial Sequence
<220> FEATURE:
<223> OTHER INFORMATION: Synthetic Oligonucleotide
```

```
<400> SEQUENCE: 46
tattatgtgg agtatgggtt aggaactgct ccatctaaaa atgaagaagc tgttttaat      60 cataaaagca aaacagatac aaa                                              83

<210> SEQ ID NO 47
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 47

Tyr Tyr Val Glu Tyr Gly Leu Gly Thr Ala Pro Ser Lys Asn Glu Glu
1               5                   10                  15

Ala Val Phe Asn His Lys Ser Lys Thr Asp Thr Lys
            20                  25

<210> SEQ ID NO 48
<211> LENGTH: 83
<212> TYPE: DNA
<213> ORGANISM: Artificial Sequence
<220> FEATURE:
<223> OTHER INFORMATION: Synthetic Oligonucleotide

<400> SEQUENCE: 48
tattatgtgg agtatggggt aggaatttca ccacctgaaa ataatgatga atcctctaaa      60
caaaagagca aaatggatgc taa                                              83

<210> SEQ ID NO 49
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 49

Tyr Tyr Val Glu Tyr Gly Val Gly Ile Ser Pro Pro Glu Asn Asn Asp
1               5                   10                  15

Glu Ser Ser Lys Gln Lys Ser Lys Met Asp Ala Lys
            20                  25

<210> SEQ ID NO 50
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 50
taagaaacaa aaaaatggg agatatatcc gaaactgccg aaagaaaagt cgacatacaa       60
actgaggtta tcgcaat                                                     77

<210> SEQ ID NO 51
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 51

Lys Lys Gln Lys Lys Trp Glu Ile Tyr Pro Lys Leu Pro Lys Glu Lys
1               5                   10                  15
```

```
Ser Thr Tyr Lys Leu Arg Leu Ser Gln
            20                  25

<210> SEQ ID NO 52
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 52
aagaaacaaa aaaaatggga aatatatccg aagttgccaa agaaaagtc aacatacaaa    60 ctgaggctat cgcaat                                                   76

<210> SEQ ID NO 53
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 53

Lys Lys Gln Lys Lys Trp Glu Ile Tyr Pro Lys Leu Pro Lys Glu Lys
1               5                   10                  15

Ser Thr Tyr Lys Leu Arg Leu Ser Gln
            20                  25

<210> SEQ ID NO 54
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 54
aagaagcaaa aaaaatggga aatatatcca aaactgccaa agaaaagtc gacatataaa    60 ctgaggttat cgcaat                                                   76

<210> SEQ ID NO 55
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 55

Lys Lys Gln Lys Lys Trp Glu Ile Tyr Pro Lys Leu Pro Lys Glu Lys
1               5                   10                  15

Ser Thr Tyr Lys Leu Arg Leu Ser Gln
            20                  25

<210> SEQ ID NO 56
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 56
aaagaacaaa aaaaatggga gatatatccg aagttgccga agaaaagtc gacatacaaa    60 ctgaggttat cgcaat                                                   76
```

<210> SEQ ID NO 57
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 57

Lys Glu Gln Lys Lys Trp Glu Ile Tyr Pro Lys Leu Pro Lys Glu Lys
1               5                   10                  15

Ser Thr Tyr Lys Leu Arg Leu Ser Gln
            20                  25

<210> SEQ ID NO 58
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 58
taagaaacaa aaaacatggg agatatatcc aaaactgccg aaggaaaaat cgacatacaa      60
attgaggtta tcgcaat                                                    77

<210> SEQ ID NO 59
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 59

Lys Lys Gln Lys Thr Trp Glu Ile Tyr Pro Lys Leu Pro Lys Glu Lys
1               5                   10                  15

Ser Thr Tyr Lys Leu Arg Leu Ser Gln
            20                  25

<210> SEQ ID NO 60
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 60
aagaagcaaa aaaatggga gatatacccg aaactaccga agaaaaatc gacgtacaaa       60 ctgaggttag cgcaat                                                    76

<210> SEQ ID NO 61
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 61

Lys Lys Gln Lys Lys Trp Glu Ile Tyr Pro Lys Leu Pro Lys Glu
1               5                   10                  15

Lys Ser Thr Tyr Lys Leu Arg Leu Ala Gln
            20                  25

<210> SEQ ID NO 62
<211> LENGTH: 77
<212> TYPE: DNA

```
<213> ORGANISM: Artificial Sequence
<220> FEATURE:
<223> OTHER INFORMATION: Synthetic Oligonucleotide

<400> SEQUENCE: 62
taagaaacaa aaaaaatggg agatatatct aaaactgccg aaggaaaaat cgacatacaa    60
attgaggtta tcgcaat                                                   77

<210> SEQ ID NO 63
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 63

Lys Lys Gln Lys Lys Trp Glu Ile Tyr Leu Lys Leu Pro Lys Glu Lys
1               5                   10                  15

Ser Thr Tyr Lys Leu Arg Leu Ser Gln
            20                  25

<210> SEQ ID NO 64
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 64
aagaaacaaa aaaatggga gatatatccg aaactaccaa agaaaagtc gacatacaaa      60 ctgaggttaa cgcaat                                                    76

<210> SEQ ID NO 65
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 65

Lys Lys Gln Lys Lys Trp Glu Ile Tyr Pro Lys Leu Pro Lys Glu Lys
1               5                   10                  15

Ser Thr Tyr Lys Leu Arg Leu Thr Gln
            20                  25

<210> SEQ ID NO 66
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 66
aagaaacaaa aaaatggga atatatccg aagttgccga agaaaagtc gacatataaa       60 ttgaggttat cgcaat                                                    76

<210> SEQ ID NO 67
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 67
```

-continued

```
Lys Lys Gln Lys Lys Trp Glu Ile Tyr Pro Lys Leu Pro Glu Lys
1               5                   10                  15

Ser Thr Tyr Lys Leu Arg Leu Ser Gln
            20                  25

<210> SEQ ID NO 68
<211> LENGTH: 43
<212> TYPE: PRT
<213> ORGANISM: Photorhabdus species

<400> SEQUENCE: 68

Ala Ala Asp Met Lys Ala Asp Arg Gln Lys Lys Ser Met Val Lys Ile
1               5                   10                  15

Lys Lys Lys Trp Lys Trp Ile Ile Ala Asp Pro Leu Lys Val Ser Glu
            20                  25                  30

Ser Pro Leu Arg Ile Asn Leu Ile Gly Glu Lys
            35                  40

<210> SEQ ID NO 69
<211> LENGTH: 43
<212> TYPE: PRT
<213> ORGANISM: Photorhabdus species

<400> SEQUENCE: 69

Asp Val Asp Ala Lys Lys Glu Asn Gly Glu Lys Ser Ile Ile Lys Ile
1               5                   10                  15

Thr Glu Lys Trp Lys Trp Val Ile Ala Asp Pro Leu Lys Ala Ser Glu
            20                  25                  30

Ser Pro Leu Arg Ile Asn Leu Ile Gly Glu Glu
            35                  40

<210> SEQ ID NO 70
<211> LENGTH: 43
<212> TYPE: PRT
<213> ORGANISM: Photorhabdus species

<400> SEQUENCE: 70

Asp Val Asp Val Gly Lys Glu Asp Gly Glu Lys Ser Leu Ile Gln Val
1               5                   10                  15

Lys Glu Lys Trp Lys Trp Val Ile Ala Asp Pro Leu Lys Ala Asn Glu
            20                  25                  30

Ser Pro Leu Arg Ile Asn Leu Met Gly Glu Glu
            35                  40

<210> SEQ ID NO 71
<211> LENGTH: 43
<212> TYPE: PRT
<213> ORGANISM: Photorhabdus species

<400> SEQUENCE: 71

Asp Val Asp Val Gly Lys Glu Asp Gly Glu Lys Ser Leu Ile Gln Val
1               5                   10                  15

Lys Glu Lys Trp Lys Trp Val Ile Ala Asp Pro Leu Lys Ala Asn Glu
            20                  25                  30

Ser Pro Leu Arg Ile Asn Leu Met Gly Glu Glu
            35                  40

<210> SEQ ID NO 72
<211> LENGTH: 43
<212> TYPE: PRT
```

<213> ORGANISM: Photorhabdus species

<400> SEQUENCE: 72

Asp Val Asp Val Gly Lys Glu Asp Gly Glu Lys Ser Leu Ile Gln Val
1               5                   10                  15
Lys Glu Lys Trp Lys Trp Val Ile Ala Asp Pro Leu Lys Ala Asn Glu
            20                  25                  30
Ser Pro Leu Arg Ile Asn Leu Met Gly Glu Glu
        35                  40

<210> SEQ ID NO 73
<211> LENGTH: 45
<212> TYPE: PRT
<213> ORGANISM: Photorhabdus species

<400> SEQUENCE: 73

Asp Val Asp Ile Lys Lys Lys Asn Lys Lys Met Asp Ser Thr Lys Asn
1               5                   10                  15
Leu Phe Lys Val Lys Lys Lys Trp Val Ile Ala Asp Pro Leu Lys Ala
            20                  25                  30
Ser Glu Ser Pro Leu Arg Ile Asn Leu Ile Gly Glu Glu
        35                  40                  45

<210> SEQ ID NO 74
<211> LENGTH: 43
<212> TYPE: PRT
<213> ORGANISM: Photorhabdus species

<400> SEQUENCE: 74

Ala Val Asp Ala Arg Arg Asn Ser Ser Arg Asn Ser Ile Ile Glu Val
1               5                   10                  15
Lys Lys Lys Trp Lys Trp Val Ile Ala Asp Pro Leu Lys Ala Ser Glu
            20                  25                  30
Ser Pro Leu Arg Ile Asn Leu Ile Gly Glu Glu
        35                  40

<210> SEQ ID NO 75
<211> LENGTH: 45
<212> TYPE: PRT
<213> ORGANISM: Photorhabdus species

<400> SEQUENCE: 75

Ala Val Asp Ile Lys Lys Lys Asn Lys Lys Met Asp Ser Thr Lys Asn
1               5                   10                  15
Leu Phe Lys Val Lys Lys Lys Trp Val Ile Ala Asp Pro Leu Lys Ala
            20                  25                  30
Ser Glu Ser Pro Leu Arg Ile Asn Leu Ile Gly Lys Glu
        35                  40                  45

<210> SEQ ID NO 76
<211> LENGTH: 41
<212> TYPE: PRT
<213> ORGANISM: Photorhabdus species

<400> SEQUENCE: 76

Glu Ala Asp Ile Glu Ala Asp Gly Lys Glu Asn Ser Ile Ala Lys Val
1               5                   10                  15
Lys Lys Lys Trp Val Ile Ala Asp Pro Leu Lys Ala Ser Glu Ser Pro
            20                  25                  30
Leu Arg Ile Ser Leu Leu Gly Glu Gln

<210> SEQ ID NO 77
<211> LENGTH: 41
<212> TYPE: PRT
<213> ORGANISM: Photorhabdus species

<400> SEQUENCE: 77

Asp Ala Asp Val Glu Thr Glu Asn Glu Lys Lys Ser Ile Ala Lys Ile
1               5                   10                  15

Lys Lys Lys Trp Val Ile Ala Asp Pro Leu Lys Ala Ser Glu Ser Pro
            20                  25                  30

Leu Arg Ile Asn Leu Leu Gly Glu Glu
        35                  40

<210> SEQ ID NO 78
<211> LENGTH: 41
<212> TYPE: PRT
<213> ORGANISM: Photorhabdus species

<400> SEQUENCE: 78

Thr Ala Asp Thr Lys Lys Glu Glu Asn Arg Lys Ser Ile Val Lys Val
1               5                   10                  15

Lys Lys Lys Trp Val Ile Ala Asp Pro Leu Lys Ala Ser Glu Ser Pro
            20                  25                  30

Leu Arg Ile Asn Leu Leu Gly Glu Glu
        35                  40

<210> SEQ ID NO 79
<211> LENGTH: 41
<212> TYPE: PRT
<213> ORGANISM: Photorhabdus species

<400> SEQUENCE: 79

Thr Ala Asp Thr Lys Lys Glu Lys Asp Arg Lys Ser Ile Ala Lys Val
1               5                   10                  15

Lys Lys Lys Trp Val Ile Ala Asp Pro Leu Lys Ala Ser Glu Ser Pro
            20                  25                  30

Leu Arg Ile Asn Leu Leu Gly Glu Glu
        35                  40

<210> SEQ ID NO 80
<211> LENGTH: 43
<212> TYPE: PRT
<213> ORGANISM: Photorhabdus species

<400> SEQUENCE: 80

Ser Ala Asp Ala Glu Ile Gly Arg Lys Lys Ala Ser Lys Lys Ala
1               5                   10                  15

Lys Asn Lys Trp Thr Trp Val Ile Ala Asp Pro Leu Lys Ala Ser Glu
            20                  25                  30

Ser Pro Leu Arg Ile Asn Val Leu Gly Lys Glu
        35                  40

<210> SEQ ID NO 81
<211> LENGTH: 43
<212> TYPE: PRT
<213> ORGANISM: Photorhabdus species

<400> SEQUENCE: 81

Thr Ala Asp Ala Glu Ile Gly Arg Lys Lys Lys Ala Thr Lys Lys Val

-continued

```
                1               5                   10                  15
Lys Asn Lys Trp Lys Trp Val Ile Ala Asp Pro Leu Lys Ala Ser Glu
                20                  25                  30

Ser Pro Leu Arg Ile Asn Leu Leu Gly Lys Glu
            35                  40
```

<210> SEQ ID NO 82
<211> LENGTH: 50
<212> TYPE: PRT
<213> ORGANISM: Photorhabdus species

<400> SEQUENCE: 82

```
Glu Val Lys Ala Gly Tyr Ile Gln Lys Glu Ser Lys Ser Val Ser Asn
1               5                   10                  15

Thr Lys Gly Arg Ser Lys Asn Ser Gly Ile Asn Leu Ile Lys Ala Asp
                20                  25                  30

Val Met Ile Cys Asp Lys Asp Glu Phe Gly Pro Phe Tyr Phe Ile Asp
                35                  40                  45

Phe Lys
    50
```

<210> SEQ ID NO 83
<211> LENGTH: 56
<212> TYPE: PRT
<213> ORGANISM: Photorhabdus species

<400> SEQUENCE: 83

```
Gly Tyr Ala Val Gln Val Gly Lys Thr Asp Lys Lys Gly Lys Pro
1               5                   10                  15

Gly Ile Gly Asn Lys Thr Ala Thr Ser Lys Lys Ser Glu Glu Thr Lys
                20                  25                  30

Leu Lys Asn Glu Lys Trp Thr Ile Tyr Pro Ala Leu Ser Lys Lys Glu
            35                  40                  45

Ser Thr Trp Arg Trp Ser Leu Asp
    50                  55
```

<210> SEQ ID NO 84
<211> LENGTH: 56
<212> TYPE: PRT
<213> ORGANISM: Photorhabdus species

<400> SEQUENCE: 84

```
Gly Tyr Ala Val Gln Val Gly Lys Thr Asp Lys Lys Lys Val Lys Pro
1               5                   10                  15

Gly Ile Gly Asn Lys Thr Thr Thr Ser Lys Lys Ser Glu Glu Ala Lys
                20                  25                  30

Leu Lys Asn Glu Lys Trp Thr Ile Tyr Pro Ala Leu Ser Lys Lys Glu
            35                  40                  45

Ser Thr Trp Arg Trp Ser Leu Asp
    50                  55
```

<210> SEQ ID NO 85
<211> LENGTH: 56
<212> TYPE: PRT
<213> ORGANISM: Photorhabdus species

<400> SEQUENCE: 85

```
Gly Tyr Ala Val Gln Val Gly Lys Thr Asp Lys Lys Val Lys Pro
1               5                   10                  15
```

```
Gly Ile Gly Asn Lys Thr Thr Thr Ser Lys Lys Ser Glu Ala Lys
            20                  25                  30

Leu Lys Asn Glu Lys Trp Thr Ile Tyr Pro Ala Leu Ser Lys Lys Glu
            35                  40                  45

Ser Thr Trp Arg Trp Ser Leu Asp
        50                  55

<210> SEQ ID NO 86
<211> LENGTH: 56
<212> TYPE: PRT
<213> ORGANISM: Photorhabdus species

<400> SEQUENCE: 86

Ala Tyr Gly Ala Arg Val Gly Glu Val Asp Asn Ile Asn Ser Glu Asn
1               5                   10                  15

Lys Lys Leu Gly Asn Ser Lys Ser Thr Ala Met Arg Asn Leu Gln Asp
            20                  25                  30

Glu Ile Glu Lys Glu Trp Val Leu Gln Glu Pro Leu Ser Lys Glu Lys
            35                  40                  45

Ser Thr Tyr Arg Val Ser Phe Gly
        50                  55

<210> SEQ ID NO 87
<211> LENGTH: 49
<212> TYPE: PRT
<213> ORGANISM: Photorhabdus species

<400> SEQUENCE: 87

Glu Tyr Gly Val Gly Val Ala Pro Ser Glu Asn Asn Gly Lys Ser Ile
1               5                   10                  15

Gly Ser Gly Ser Asn Val Asp Asn Lys Lys Gln Lys Lys Trp Glu Ile
            20                  25                  30

Tyr Pro Lys Leu Pro Lys Glu Lys Ser Thr Tyr Lys Leu Arg Leu Ser
            35                  40                  45

Gln

<210> SEQ ID NO 88
<211> LENGTH: 49
<212> TYPE: PRT
<213> ORGANISM: Photorhabdus species

<400> SEQUENCE: 88

Glu Tyr Gly Val Gly Thr Lys Pro Thr Lys Asp Arg Gly Ser Phe Val
1               5                   10                  15

Gly Asn Ile Thr Asn Ser Thr Thr Lys Lys Gln Lys Lys Trp Glu Ile
            20                  25                  30

Tyr Pro Lys Leu Pro Lys Glu Lys Ser Thr Tyr Lys Leu Arg Leu Ala
            35                  40                  45

Gln

<210> SEQ ID NO 89
<211> LENGTH: 49
<212> TYPE: PRT
<213> ORGANISM: Photorhabdus species

<400> SEQUENCE: 89

Glu Tyr Gly Val Gly Ser Lys Pro Pro Lys Asn Asn Asp Asp Ser Ser
1               5                   10                  15

Lys Gln Lys Ser Lys Met Asp Asn Lys Lys Gln Lys Thr Trp Glu Ile
```

-continued

```
                20                  25                  30

Tyr Pro Lys Leu Pro Lys Glu Lys Ser Thr Tyr Lys Leu Arg Leu Ser
            35                  40                  45

Gln

<210> SEQ ID NO 90
<211> LENGTH: 49
<212> TYPE: PRT
<213> ORGANISM: Photorhabdus species

<400> SEQUENCE: 90

Glu Tyr Gly Val Gly Ile Ser Pro Pro Glu Asn Asn Asp Glu Ser Ser
1               5                   10                  15

Lys Gln Lys Ser Lys Met Asp Ala Lys Lys Gln Lys Lys Trp Glu Ile
            20                  25                  30

Tyr Pro Lys Leu Pro Lys Glu Lys Ser Thr Tyr Lys Leu Arg Leu Ser
            35                  40                  45

Gln

<210> SEQ ID NO 91
<211> LENGTH: 49
<212> TYPE: PRT
<213> ORGANISM: Photorhabdus species

<400> SEQUENCE: 91

Glu Tyr Gly Leu Gly Thr Ala Pro Ser Lys Asn Glu Glu Ala Val Phe
1               5                   10                  15

Asn His Lys Ser Lys Thr Asp Thr Lys Lys Gln Lys Lys Trp Glu Ile
            20                  25                  30

Tyr Pro Lys Leu Pro Lys Glu Lys Ser Thr Tyr Lys Leu Arg Leu Thr
            35                  40                  45

Gln

<210> SEQ ID NO 92
<211> LENGTH: 49
<212> TYPE: PRT
<213> ORGANISM: Photorhabdus species

<400> SEQUENCE: 92

Glu Tyr Gly Ala Gly Val Ala Pro Ser Glu Asn Ile Gly Asn Ser Thr
1               5                   10                  15

Glu Lys Arg Ser Arg Val Asp Asn Lys Glu Gln Lys Lys Trp Glu Ile
            20                  25                  30

Tyr Pro Lys Leu Pro Lys Glu Lys Ser Thr Tyr Lys Leu Arg Leu Ser
            35                  40                  45

Gln

<210> SEQ ID NO 93
<211> LENGTH: 49
<212> TYPE: PRT
<213> ORGANISM: Photorhabdus species

<400> SEQUENCE: 93

Glu Tyr Gly Val Gly Val Ala Pro Phe Asp Asn Asn Gly Lys Ser Ile
1               5                   10                  15

Arg Ser Gly Ser Asn Val Asp Asn Lys Lys Gln Lys Lys Trp Glu Ile
            20                  25                  30

Tyr Pro Lys Leu Pro Lys Glu Lys Ser Thr Tyr Lys Leu Arg Leu Ser
```

Gln

<210> SEQ ID NO 94
<211> LENGTH: 49
<212> TYPE: PRT
<213> ORGANISM: Photorhabdus species

<400> SEQUENCE: 94

Glu Tyr Gly Val Gly Val Ala Pro Phe Asp Asn Asn Gly Lys Ser Ile
1               5                   10                  15

Arg Ser Gly Ser Asn Val Asp Asn Lys Lys Gln Lys Lys Trp Glu Ile
            20                  25                  30

Tyr Pro Lys Leu Pro Lys Glu Lys Ser Thr Tyr Lys Leu Arg Leu Ser
        35                  40                  45

Gln

<210> SEQ ID NO 95
<211> LENGTH: 49
<212> TYPE: PRT
<213> ORGANISM: Photorhabdus species

<400> SEQUENCE: 95

Glu Tyr Gly Val Gly Lys Ser Thr Thr Glu Asn Lys Asn Ser Ser Phe
1               5                   10                  15

Asn Pro Gln Ser Lys Val Asp Thr Lys Gln Lys Lys Trp Glu Ile
            20                  25                  30

Tyr Pro Lys Leu Pro Lys Glu Lys Ser Thr Tyr Lys Leu Arg Leu Ser
        35                  40                  45

Gln

<210> SEQ ID NO 96
<211> LENGTH: 49
<212> TYPE: PRT
<213> ORGANISM: Photorhabdus species

<400> SEQUENCE: 96

Glu Tyr Gly Val Gly Lys Gly Ile Thr Lys Asn Asn Asp Asp Ser Ile
1               5                   10                  15

Lys Gln Asn Ser Lys Leu Gly Asp Lys Lys Gln Lys Lys Trp Glu Ile
            20                  25                  30

Tyr Leu Lys Leu Pro Lys Glu Lys Ser Thr Tyr Lys Leu Arg Leu Ser
        35                  40                  45

Gln

<210> SEQ ID NO 97
<211> LENGTH: 48
<212> TYPE: PRT
<213> ORGANISM: Photorhabdus species

<400> SEQUENCE: 97

Glu Tyr Gly Ala Gly Ile Ala Pro Pro Lys Ser Asn Arg Asp Ser Ala
1               5                   10                  15

Lys Gln Lys Asp Gly Lys Asp Asn Lys Lys Gln Lys Lys Trp Glu Ile
            20                  25                  30

Tyr Pro Lys Leu Pro Lys Glu Lys Ser Thr Tyr Lys Leu Arg Leu Ser
        35                  40                  45

-continued

```
<210> SEQ ID NO 98
<211> LENGTH: 47
<212> TYPE: PRT
<213> ORGANISM: Photorhabdus species

<400> SEQUENCE: 98

Asp Tyr Gly Val Gly Val Ala Pro Ser Glu Asn Lys Glu Asp Ser Phe
1               5                   10                  15

Ser Lys Arg Ser Ser Asn Lys Lys Arg Lys Lys Trp Glu Ile Tyr Pro
            20                  25                  30

Lys Leu Ser Lys Glu Lys Ser Thr Tyr Lys Leu Arg Leu Ser Gln
        35                  40                  45

<210> SEQ ID NO 99
<211> LENGTH: 47
<212> TYPE: PRT
<213> ORGANISM: Photorhabdus species

<400> SEQUENCE: 99

Asp Tyr Gly Val Gly Val Ala Pro Ser Glu Asn Lys Glu Asp Ser Phe
1               5                   10                  15

Ser Lys Arg Ser Ser Asn Lys Lys Arg Lys Lys Trp Glu Ile Tyr Pro
            20                  25                  30

Lys Leu Ser Lys Glu Lys Ser Thr Tyr Lys Leu Arg Leu Ser Gln
        35                  40                  45

<210> SEQ ID NO 100
<211> LENGTH: 49
<212> TYPE: PRT
<213> ORGANISM: Photorhabdus species

<400> SEQUENCE: 100

Glu Phe Gly Met Gly Leu Val Pro Ser Glu Asn Asn Gly Lys Ser Ile
1               5                   10                  15

Ile Lys Gly Ser Lys Val Asp Asn Lys Lys Gln Lys Lys Trp Glu Ile
            20                  25                  30

Tyr Pro Lys Leu Pro Lys Glu Lys Ser Thr Tyr Lys Leu Arg Leu Ser
        35                  40                  45

Glu

<210> SEQ ID NO 101
<211> LENGTH: 48
<212> TYPE: PRT
<213> ORGANISM: Photorhabdus species

<400> SEQUENCE: 101

Glu Phe Gly Met Gly Ile Ala Pro Pro Lys Ser Asn Ser Asp Ser Ala
1               5                   10                  15

Lys Gln Lys Asp Gly Lys Asp Ser Lys Thr Gln Lys Lys Trp Glu Ile
            20                  25                  30

Tyr Pro Lys Leu Pro Lys Glu Lys Ser Thr Tyr Lys Leu Arg Leu Ser
        35                  40                  45

<210> SEQ ID NO 102
<211> LENGTH: 46
<212> TYPE: PRT
<213> ORGANISM: Photorhabdus species

<400> SEQUENCE: 102

Glu Phe Gly Val Gly Val Ala Pro Ser Glu Asn Lys Glu Asp Ser Phe
1               5                   10                  15
```

-continued

```
Ser Gln Lys Ser Gly Asn Lys Lys Arg Glu Lys Trp Glu Val Tyr Pro
                20                  25                  30

Lys Leu Pro Lys Glu Lys Ser Thr Tyr Lys Leu Arg Leu Ser
            35                  40                  45

<210> SEQ ID NO 103
<211> LENGTH: 49
<212> TYPE: PRT
<213> ORGANISM: Photorhabdus species

<400> SEQUENCE: 103

Glu Phe Gly Val Gly Leu Val Pro Ser Glu Asn Asn Gly Lys Ser Ile
1               5                   10                  15

Ile Lys Gly Ser Lys Val Asp Asn Lys Gln Lys Lys Trp Glu Ile
                20                  25                  30

Tyr Pro Arg Leu Pro Lys Glu Lys Ser Thr Tyr Lys Leu Arg Leu Ser
            35                  40                  45

Glu

<210> SEQ ID NO 104
<211> LENGTH: 48
<212> TYPE: PRT
<213> ORGANISM: Photorhabdus species

<400> SEQUENCE: 104

Glu Phe Gly Ala Gly Val Ser Pro Ser Glu Asn Ser Asn Glu Ser Ser
1               5                   10                  15

Lys Gln Asn Ser Lys Arg Asp Asp Lys Lys Gln Lys Lys Trp Glu Ile
                20                  25                  30

Tyr Pro Lys Leu Ser Lys Glu Lys Ser Thr Tyr Lys Leu Arg Leu Ser
            35                  40                  45

<210> SEQ ID NO 105
<211> LENGTH: 7
<212> TYPE: PRT
<213> ORGANISM: SV40 virus

<400> SEQUENCE: 105

Pro Lys Lys Lys Arg Lys Val
1               5

<210> SEQ ID NO 106
<211> LENGTH: 16
<212> TYPE: PRT
<213> ORGANISM: Homo sapiens

<400> SEQUENCE: 106

Lys Arg Pro Ala Ala Thr Lys Lys Ala Gly Gln Ala Lys Lys Lys Lys
1               5                   10                  15

<210> SEQ ID NO 107
<211> LENGTH: 9
<212> TYPE: PRT
<213> ORGANISM: Homo sapiens

<400> SEQUENCE: 107

Pro Ala Ala Lys Arg Val Lys Leu Asp
1               5

<210> SEQ ID NO 108
<211> LENGTH: 11
```

```
<212> TYPE: PRT
<213> ORGANISM: Homo sapiens

<400> SEQUENCE: 108

Arg Gln Arg Arg Asn Glu Leu Lys Arg Ser Pro
1               5                   10

<210> SEQ ID NO 109
<211> LENGTH: 38
<212> TYPE: PRT
<213> ORGANISM: Homo sapiens

<400> SEQUENCE: 109

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 110
<211> LENGTH: 42
<212> TYPE: PRT
<213> ORGANISM: Homo sapiens

<400> SEQUENCE: 110

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 111
<211> LENGTH: 8
<212> TYPE: PRT
<213> ORGANISM: Homo sapiens

<400> SEQUENCE: 111

Val Ser Arg Lys Arg Pro Arg Pro
1               5

<210> SEQ ID NO 112
<211> LENGTH: 8
<212> TYPE: PRT
<213> ORGANISM: Homo sapiens

<400> SEQUENCE: 112

Pro Pro Lys Lys Ala Arg Glu Asp
1               5

<210> SEQ ID NO 113
<211> LENGTH: 8
<212> TYPE: PRT
<213> ORGANISM: Homo sapiens

<400> SEQUENCE: 113

Pro Gln Pro Lys Lys Lys Pro Leu
1               5

<210> SEQ ID NO 114
<211> LENGTH: 12
<212> TYPE: PRT
```

<213> ORGANISM: Mus musculus

<400> SEQUENCE: 114

Ser Ala Leu Ile Lys Lys Lys Lys Met Ala Pro
1               5                   10

<210> SEQ ID NO 115
<211> LENGTH: 5
<212> TYPE: PRT
<213> ORGANISM: Influenza virus

<400> SEQUENCE: 115

Asp Arg Leu Arg Arg
1               5

<210> SEQ ID NO 116
<211> LENGTH: 7
<212> TYPE: PRT
<213> ORGANISM: Influenza virus

<400> SEQUENCE: 116

Pro Lys Gln Lys Lys Arg Lys
1               5

<210> SEQ ID NO 117
<211> LENGTH: 10
<212> TYPE: PRT
<213> ORGANISM: Hepatitis virus

<400> SEQUENCE: 117

Arg Lys Leu Lys Lys Ile Lys Lys Leu
1               5                   10

<210> SEQ ID NO 118
<211> LENGTH: 10
<212> TYPE: PRT
<213> ORGANISM: Mus musculus

<400> SEQUENCE: 118

Arg Glu Lys Lys Lys Phe Leu Lys Arg Arg
1               5                   10

<210> SEQ ID NO 119
<211> LENGTH: 20
<212> TYPE: PRT
<213> ORGANISM: Homo sapiens

<400> SEQUENCE: 119

Lys Arg Lys Gly Asp Glu Val Asp Gly Val Asp Glu Val Ala Lys Lys
1               5                   10                  15

Lys Ser Lys Lys
            20

<210> SEQ ID NO 120
<211> LENGTH: 17
<212> TYPE: PRT
<213> ORGANISM: Homo sapiens

<400> SEQUENCE: 120

Arg Lys Cys Leu Gln Ala Gly Met Asn Leu Glu Ala Arg Lys Thr Lys
1               5                   10                  15

Lys

-continued

```
<210> SEQ ID NO 121
<211> LENGTH: 11
<212> TYPE: PRT
<213> ORGANISM: Homo sapiens

<400> SEQUENCE: 121

Leu Tyr Pro Glu Arg Leu Arg Arg Ile Leu Thr
1               5                   10

<210> SEQ ID NO 122
<211> LENGTH: 33
<212> TYPE: PRT
<213> ORGANISM: Homo sapiens

<400> SEQUENCE: 122

Cys Thr Gly Thr Ala Cys Cys Thr Gly Ala Gly Cys Gly Gly Cys
1               5                   10                  15

Thr Gly Cys Gly Gly Cys Gly Gly Ala Thr Cys Cys Thr Gly Ala Cys
            20                  25                  30

Cys

<210> SEQ ID NO 123
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 123

Gly Gly Gly Gly Ser Gly Gly Gly Gly Ser Gly Gly Gly Gly Ser
1               5                   10                  15

<210> SEQ ID NO 124
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 124

Gly Gly Gly Gly Ser
1               5

<210> SEQ ID NO 125
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 125

Gly Gly Gly Gly Ser Gly Gly Gly Gly Ser
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 126

Glu Asn Leu Tyr Phe Gln Gly
1               5
```

-continued

```
<210> SEQ ID NO 127
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 127

Gly Pro Leu Gly Ile Ala Gly Gln
1               5

<210> SEQ ID NO 128
<211> LENGTH: 505
<212> TYPE: PRT
<213> ORGANISM: Photorhabdus asymbiotica

<400> SEQUENCE: 128

Met Asp Thr Val Val Gly Val Asn Ala Gly Lys Ala Cys Ala Thr Cys
1               5                   10                  15

Asp Val Pro Pro Ser Cys Thr His Arg Tyr Met Leu Thr Asp Asp Cys
                20                  25                  30

Asn Ile Tyr Ile Asn Phe Pro Ser Ile Ser Lys Met Phe Glu Val Val
            35                  40                  45

Ser Ile Ile Ser Glu Lys Lys Ser His Thr Phe Met Ser Ser Phe Thr
    50                  55                  60

Pro Thr Asn Cys Ile Asn Asn Lys Glu Asn Cys Pro Thr Thr Tyr Ile
65                  70                  75                  80

Phe Arg Lys Gly Gly Thr Glu Asn Ile Glu Leu Thr Pro Lys Asn Pro
                85                  90                  95

Lys Lys Ser Tyr Thr Ile Thr Asn Asp Gln Ala Lys Leu Pro Ile Phe
            100                 105                 110

Thr Thr Pro Trp Glu Trp Leu Lys Glu Phe Phe Ala Arg Asp Val Asn
        115                 120                 125

Glu Ile Asp Lys Val Thr Tyr Tyr Ser Gln Thr Val Asp Cys Ser Gly
130                 135                 140

Leu Val Gln Lys Thr Gln Thr Asp Val Tyr Pro Lys Tyr Ile Leu Ser
145                 150                 155                 160

Gly Glu Leu Lys Ile Asp Val Lys His Ala Ala His Ser Thr Phe Lys
                165                 170                 175

Ala Lys Arg Ser Asp Tyr Asn Lys Asp Gln Phe Glu Gln Leu Lys Asn
            180                 185                 190

Glu Leu Gly Lys Thr Lys Trp Ser Glu Ile Gly Arg Tyr Val His Glu
        195                 200                 205

Lys Glu Tyr Thr Ala Thr Gly Lys Thr Glu Phe Gln Leu Phe Asp Lys
210                 215                 220

Lys Asn Asn Ser Asn Phe Thr Ile Phe Glu Gly Lys Lys Asn Ile Trp
225                 230                 235                 240

Lys Asp Lys Lys Ser Leu Val Glu Lys Val Lys Asp Ala Val Glu Lys
                245                 250                 255

Ala Gly Thr Arg Ile Leu Ala Asn Lys Gly Gly Met Ala Gly Ile Lys
            260                 265                 270

Glu Ile Asn Leu Leu Gly Pro Ser Val Glu Ile Ser Gly Asn Lys Glu
        275                 280                 285

Leu Lys Ile Ile Asp Ser Ile Pro Ser Phe Glu Tyr Asn Cys Lys Leu
290                 295                 300

Lys Leu Ala Pro Leu Leu Gly Leu Glu Val Arg Leu Asp Ile Ile Asn
305                 310                 315                 320
```

Val Leu Ile Ala Ile Leu Gly Ser Pro Val Ala Gly Lys Lys Trp His
            325                 330                 335

Asp Leu Arg Lys Leu Met Glu Glu Gln Lys Asp Lys Met Asp Glu Thr
            340                 345                 350

Ile Lys Asn Gly Lys Thr Thr Gly Tyr Thr Leu Phe Tyr Ile Asp Phe
            355                 360                 365

Ile Ile Ser Gly Glu Ile Leu Asn Gly Gly Val Thr Ile Thr Lys Lys
            370                 375                 380

Asn Asn His Val Lys Leu Ile Gly Glu Ile Glu Asn Lys Leu Pro Leu
385                 390                 395                 400

Glu Leu Lys Ala Gly Phe Glu Ala Gly Phe Arg Val Leu Tyr Val Lys
            405                 410                 415

Gly Ile Leu Thr Thr Thr Gly Gly Lys Thr Ala Leu Ser Ala Gly
            420                 425                 430

Leu Lys Cys Asp Asp Ser Gly Leu Gly Ile Tyr Phe Ser His Glu Gly
            435                 440                 445

Ile Lys Ala Tyr Phe Glu Val Glu Val Lys Ala Gly Tyr Ile Gln Lys
            450                 455                 460

Glu Ser Lys Ser Val Ser Asn Thr Lys Gly Arg Ser Lys Asn Ser Gly
465                 470                 475                 480

Ile Asn Leu Ile Lys Ala Asp Val Met Ile Cys Asp Lys Asp Glu Phe
            485                 490                 495

Gly Pro Phe Tyr Phe Ile Asp Phe Lys
            500                 505

<210> SEQ ID NO 129
<211> LENGTH: 536
<212> TYPE: PRT
<213> ORGANISM: Photorhabdus temperata

<400> SEQUENCE: 129

Met Thr Glu His Thr Ile Ser Pro Arg Ala Gly Val Ala Cys Met Thr
1               5                   10                  15

Cys Asn Asn Pro Asp Pro Cys Ile Tyr Lys Ile Ser Val Thr Phe Gly
            20                  25                  30

Gln His Thr Gln Val Trp Pro Glu Lys Pro Ala Ile Lys Met Asp Leu
        35                  40                  45

Ile Asp His Gly Lys Gly Gln Lys Gly Thr Ile His Ile Glu Asp Lys
    50                  55                  60

Cys His Asn Ala Pro Lys His His Ala Val Leu Thr Gly Gly Gln Lys
65                  70                  75                  80

Glu Ala Thr Ile Ala Phe Asn Thr Pro Gln Ala Val Thr Leu Phe Tyr
            85                  90                  95

Lys Asp Lys Ser Glu Asp Thr Glu Ile Glu Asn Gly Leu Gln Ser Val
            100                 105                 110

Trp Ser Tyr Leu Ser Asn Leu Ala Asn Pro Thr Asp Met Tyr Ser Asp
        115                 120                 125

Pro Arg Tyr Tyr Gln Leu Ile Ala Gln Gly Cys Ile Ser Ala Gln Lys
    130                 135                 140

Tyr Ala Thr Met Ala Val Tyr Pro Ser Val Ser Phe Met Val Ser Val
145                 150                 155                 160

Gly Phe Ser Phe Asp Phe Ser His Gly Gln Arg Ser Met Lys Glu Arg
            165                 170                 175

Arg Asp Glu Gln Ala Lys Ala Arg Asn Thr Met Glu Asn Val Lys Pro

```
                180             185             190
Lys Asn Gly Asn Lys Leu Arg Ala Gly Trp Thr Val Asn Thr Asp Glu
            195                 200                 205

Phe Tyr Ile Ser Arg Glu Thr Ala Leu His Val Glu Tyr Ala Leu Thr
    210                 215                 220

Val Gln Asp Ile Asp Tyr Ser Ala Lys Phe Ala Glu Val Asn Lys Val
225                 230                 235                 240

Arg Lys Thr Arg Gln Ser Leu Asp Ala Ile Lys Arg Val Glu Lys Leu
                245                 250                 255

Leu Gly Tyr Thr Gln Lys Tyr Leu Val Pro Ala Pro Asp Ser Asn Gly
            260                 265                 270

Lys Gly Thr Arg Asn Tyr Leu Leu Phe Asp Leu Asn Ile Thr Pro Ile
        275                 280                 285

Asn Ile Gly Leu Ala Tyr Ala Tyr Asp Arg Thr Thr Ser Val Asp Asp
    290                 295                 300

Ser Ser His Phe Leu Gly Phe Ser Ala Ala Pro Phe Met Gly Met Ser
305                 310                 315                 320

Ala Lys Leu Asp Leu Ile Gln Leu Gly Ala Ala Tyr Cys Lys Ile Glu
                325                 330                 335

Ser Ile Ala Ala Lys Phe Arg Lys Ala Leu Ala Arg Arg Asn Ala Lys
            340                 345                 350

Asp Glu Asn Tyr Leu Glu Leu Glu Cys Cys Ile Ile Leu Thr Cys Asn
        355                 360                 365

Leu Ser Phe Gln Leu Gly Ala Ala Tyr Lys Gln Lys Gln Trp Thr Phe
    370                 375                 380

Asp Val Gly Asp Lys Asn Asp Leu Lys Leu Gly Leu Ala Gly Lys Ile
385                 390                 395                 400

Asn Ala Ala Phe Lys Thr His Ile Met Ile Met Glu Ile Ala Met Ser
                405                 410                 415

Ala Gly Gly Val Ile Lys Thr Ala Ala Gly Phe Lys Leu Asp Gln His
            420                 425                 430

Asp Gly Gly Ile Asp Leu Ala Gly Tyr His Asp Gly Ile Val Ala Glu
        435                 440                 445

Ile Glu Val Ala Ala Asp Met Lys Ala Asp Arg Gln Lys Lys Ser Met
    450                 455                 460

Val Lys Ile Lys Lys Trp Lys Trp Ile Ile Ala Asp Pro Leu Lys
465                 470                 475                 480

Val Ser Glu Ser Pro Leu Arg Ile Asn Leu Ile Gly Glu Lys Arg Pro
                485                 490                 495

Val Val Gln Pro Glu Ile Val Pro Gly Ala Glu Thr Ala Ser Trp Glu
            500                 505                 510

Met Asn Tyr Asp Pro Asn Ser Lys Pro Lys Leu Asp Lys Ile Pro Phe
        515                 520                 525

Ile Asn Ala Gly Phe Pro Arg Met
    530                 535

<210> SEQ ID NO 130
<211> LENGTH: 535
<212> TYPE: PRT
<213> ORGANISM: Photorhabdus luminescens

<400> SEQUENCE: 130

Met Ala Glu Gln Thr Ile Ser His Arg Ala Gly Val Ala Cys Met Thr
1               5                   10                  15
```

```
Cys Asp Asn Pro Asp Pro Cys Ile Tyr Lys Ile Ser Val Thr Phe Gly
             20                  25                  30

Gln Asn Thr Gln Ile Trp Pro Glu Lys Pro Ala Ile Lys Met Ser Leu
         35                  40                  45

Ile Asp His Gly Lys Gly Gln Lys Gly Thr Ile Gln Ile Glu Thr Lys
     50                  55                  60

Cys Asn Asn Ala Ala Lys His His Ala Val Leu Thr Gly Gly Gln Lys
 65                  70                  75                  80

Glu Lys Thr Leu Glu Phe Asn Ala Pro Gln Glu Val Thr Leu Phe Tyr
                 85                  90                  95

Lys Asp Gln Leu Ala Asp Ala Glu Ile Glu Ser Asp Leu Glu Ser Val
            100                 105                 110

Trp Phe Tyr Leu Ser Asn Leu Ala Asn Pro Thr Asp Ile Tyr Ser Glu
            115                 120                 125

Pro Arg Tyr Tyr Lys Leu Ile Thr Gln Gly Cys Leu Asp Ser Gln Gln
        130                 135                 140

Tyr Ala Thr Ile Ala Val Tyr Pro Ser Val Ser Phe Met Val Ser Val
145                 150                 155                 160

Gly Leu Ser Phe Asp Phe Ser His Gly Glu Arg Thr Val Lys Glu Arg
                165                 170                 175

Arg Asp Glu Gln Lys Lys Ala Arg Gln Ala Met Glu Asn Val Lys Pro
            180                 185                 190

Lys Asn Gly Asn Lys Leu Arg Ser Gly Trp Thr Thr His Thr Asp Pro
        195                 200                 205

Phe Tyr Leu Thr Arg Gln Thr Ala Ile Asn Val Glu Tyr Ala Leu Thr
    210                 215                 220

Val Gln Asp Met Asp Tyr Ser Ala Lys Phe Ala Glu Ile Asn Lys Val
225                 230                 235                 240

Arg Lys Asn Leu Pro Asn Leu Glu Ala Ile Asn Arg Val Glu Lys Leu
                245                 250                 255

Leu Gly Tyr Thr Lys Glu Tyr Leu Ala Pro Asp Pro Asp Ser Lys Gly
            260                 265                 270

Thr Arg Ser Tyr Gln Leu Leu Glu Leu Lys Val Asp Pro Ile Asn Ile
        275                 280                 285

Gly Leu Ala Tyr Ala Tyr Asp Arg Thr Thr Ser Met Asp Asp Arg Thr
    290                 295                 300

His Phe Leu Gly Phe Ser Ala Ala Pro Phe Leu Gly Met Thr Ala Lys
305                 310                 315                 320

Leu Asp Leu Ile Gln Met Gly Ala Ala Tyr Cys Lys Ile Glu Arg Val
                325                 330                 335

Ala Ala Lys Phe Arg Glu Ala Val Ala Arg Arg Asn Ser Asn Asp Lys
            340                 345                 350

Asn Tyr Leu Asp Leu Glu Cys Cys Ile Ile Leu Thr Cys Asn Leu Ser
        355                 360                 365

Phe Gln Leu Gly Ala Ala Tyr Lys Gln Lys Gln Trp Thr Phe Asp Ala
    370                 375                 380

Gly Asn Lys Asn Asp Leu Lys Leu Ser Leu Glu Gly Lys Met Asn Val
385                 390                 395                 400

Ala Phe Lys Thr His Ile Met Ile Met Glu Val Ala Met Gly Ala Gly
                405                 410                 415

Val Ala Val Lys Thr Ala Ala Gly Phe Glu Leu Asp Gln His Asp Lys
            420                 425                 430

Gly Ile Asp Leu Ala Gly Tyr His Asn Gly Ile Val Ala Glu Phe Ala
```

```
            435                 440                 445
Val Asp Val Asp Ile Lys Lys Asn Lys Met Asp Ser Thr Lys
450                 455                 460

Asn Leu Phe Lys Val Lys Lys Trp Val Ile Ala Asp Pro Leu Lys
465                 470                 475                 480

Ala Ser Glu Ser Pro Leu Arg Ile Asn Leu Ile Gly Glu Arg Ser
                485                 490                 495

Val Val Arg Pro Glu Ile Val Pro Gly Ala Glu Thr Ala Ser Trp Glu
                500                 505                 510

Met Gly Tyr Asp Pro Asn Phe Lys Pro Lys Met Asp Asn Leu Pro Phe
                515                 520                 525

Ile Thr Gly Phe Pro Arg Met
530                 535
```

<210> SEQ ID NO 131
<211> LENGTH: 533
<212> TYPE: PRT
<213> ORGANISM: Photorhabdus luminescens

<400> SEQUENCE: 131

```
Met Ala Glu Gln Thr Ile Ser Ser Arg Ala Gly Val Ala Cys Met Thr
1               5                   10                  15

Cys Asp Asn Pro Asp Pro Cys Ile Tyr Lys Ile Ser Val Thr Phe Gly
                20                  25                  30

Gln Asn Thr Gln Val Trp Pro Glu Lys Pro Ala Ile Lys Met Ser Leu
            35                  40                  45

Ile Asp His Gly Lys Gly Gln Lys Gly Thr Ile Gln Ile Glu Gly Lys
        50                  55                  60

Cys Asn Asn Thr Val Lys His His Ala Val Leu Thr Gly Gly Gln Lys
65                  70                  75                  80

Glu Lys Thr Leu Glu Phe Asn Ala Pro Gln Glu Val Thr Leu Phe Tyr
                85                  90                  95

Lys Asp Gln Leu Lys Asp Ala Glu Ile Glu Ser Asp Leu Asp Ser Val
                100                 105                 110

Trp Phe Tyr Leu Ser Asn Leu Ala Asn Pro Thr Asp Met Tyr Ser Glu
            115                 120                 125

Pro Arg Tyr Tyr Lys Leu Ile Thr Gln Gly Cys Leu Asp Ser Arg Gln
        130                 135                 140

Tyr Ala Thr Ile Ala Val Tyr Pro Ser Val Ser Phe Met Val Ser Val
145                 150                 155                 160

Gly Leu Ser Phe Asp Phe Ser His Gly Glu Arg Ser Val Lys Glu Arg
                165                 170                 175

Arg Asp Glu Gln Lys Lys Ala Arg Gln Ala Met Glu Asn Val Lys Pro
            180                 185                 190

Lys Asn Gly Asn Lys Leu Arg Ser Gly Trp Thr Thr His Thr Asp Pro
        195                 200                 205

Phe Tyr Leu Thr Arg Gln Thr Ala Ile Asn Val Glu Tyr Ala Leu Thr
    210                 215                 220

Val Gln Asp Met Asp Tyr Ser Ala Lys Phe Ala Glu Val Asn Gln Val
225                 230                 235                 240

Arg Lys Thr Leu Pro Asn Leu Glu Ala Ile Asn Arg Val Glu Lys Leu
                245                 250                 255

Leu Gly Tyr Thr Lys Glu Tyr Leu Ala Pro Asp Pro Asp Ser Lys Gly
            260                 265                 270
```

```
Thr Arg Ser Tyr Gln Leu Leu Glu Leu Lys Val Asp Pro Ile Asn Ile
            275                 280                 285

Gly Leu Ala Tyr Ala Tyr Gly Arg Thr Thr Ser Met Asp Asp Arg Thr
        290                 295                 300

His Phe Leu Gly Phe Ser Ala Ala Pro Phe Met Gly Met Thr Ala Lys
305                 310                 315                 320

Leu Asp Leu Ile Gln Met Gly Ala Ala Tyr Cys Lys Ile Lys Lys Val
                325                 330                 335

Val Ala Lys Phe Arg Glu Ala Leu Ala Arg Arg Asn Ser Asn Asp Lys
            340                 345                 350

Asn Tyr Leu Asp Leu Glu Cys Cys Leu Ile Leu Thr Cys Asn Leu Ser
        355                 360                 365

Phe Gln Leu Gly Ala Ala Tyr Lys Gln Lys Gln Trp Thr Phe Asp Ala
    370                 375                 380

Gly Asn Lys Asn Asp Leu Lys Leu Ser Leu Glu Gly Lys Val Asn Val
385                 390                 395                 400

Ala Phe Lys Thr His Ile Met Ile Met Glu Val Ala Met Gly Ala Gly
                405                 410                 415

Val Ala Val Lys Thr Ala Ala Gly Phe Glu Leu Asp Gln His Asp Lys
            420                 425                 430

Gly Ile Asp Leu Ala Gly Tyr His Asn Gly Ile Val Ala Glu Ile Gln
        435                 440                 445

Val Ala Val Asp Ala Arg Arg Asn Ser Ser Arg Asn Ser Ile Ile Glu
    450                 455                 460

Val Lys Lys Lys Trp Lys Trp Val Ile Ala Asp Pro Leu Lys Ala Ser
465                 470                 475                 480

Glu Ser Pro Leu Arg Ile Asn Leu Ile Gly Glu Arg Pro Ile Asn
                485                 490                 495

Arg Pro Glu Ile Val Pro Gly Ala Glu Thr Ala Ser Trp Glu Met Gly
            500                 505                 510

Tyr Asp Pro Asn Phe Lys Pro Lys Met Asp Asn Ile Pro Phe Ile Thr
        515                 520                 525

Gly Leu Pro Gly Met
    530

<210> SEQ ID NO 132
<211> LENGTH: 535
<212> TYPE: PRT
<213> ORGANISM: Photorhabdus luminescens

<400> SEQUENCE: 132

Met Ala Glu Gln Thr Ile Ser Ser Arg Ala Gly Val Ala Cys Met Thr
1               5                   10                  15

Cys Asp Asn Pro Asp Pro Cys Ile Tyr Lys Ile Ser Val Thr Phe Gly
            20                  25                  30

Gln Asn Thr Gln Val Trp Pro Glu Lys Pro Val Ile Lys Met Gly Leu
        35                  40                  45

Ile Asp Asp Gly Lys Gly Gln Lys Gly Thr Ile Gln Ile Glu Gly Lys
    50                  55                  60

Cys Asn Asn Val Asp Lys His His Ala Val Leu Thr Gly Gly Gln Lys
65                  70                  75                  80

Glu Lys Thr Leu Glu Phe Asn Ala Pro Gln Glu Val Thr Leu Phe Tyr
                85                  90                  95

Lys Asp Gln Leu Lys Asp Ala Glu Ile Glu Ser Asp Leu Glu Ser Val
            100                 105                 110
```

-continued

Trp Phe Tyr Leu Ser Asn Leu Ala Asn Pro Thr Asp Met Tyr Ser Glu
            115                 120                 125

Pro Arg Tyr Tyr Lys Leu Ile Thr Gln Gly Cys Leu Asp Asn Gln Gln
130                 135                 140

Tyr Ala Thr Ile Ala Val Tyr Pro Ser Val Ser Phe Met Val Ser Val
145                 150                 155                 160

Gly Leu Ser Phe Asp Phe Ser His Gly Glu Arg Ser Val Lys Glu Arg
            165                 170                 175

Arg Asp Glu Gln Lys Lys Ala Arg Gln Ala Met Glu Asn Val Lys Pro
            180                 185                 190

Lys Asn Gly Asn Lys Leu Arg Ser Gly Trp Thr Thr His Thr Asp Pro
            195                 200                 205

Phe Tyr Leu Thr Arg Gln Thr Ala Ile Asn Val Glu Tyr Ala Leu Thr
            210                 215                 220

Val Gln Asp Met Asp Tyr Ser Ala Lys Phe Ala Glu Val Asn Gln Val
225                 230                 235                 240

Arg Lys Thr Leu Pro Asn Leu Glu Ala Ile Asn Arg Val Glu Lys Leu
                245                 250                 255

Leu Gly Tyr Thr Lys Glu Tyr Leu Ala Pro Asp Pro Asp Ser Lys Gly
            260                 265                 270

Thr Arg Ser Tyr Gln Leu Leu Glu Leu Lys Val Asp Pro Ile Asn Ile
            275                 280                 285

Gly Leu Ala Tyr Ala Tyr Asp Arg Thr Thr Ser Met Asp Asp Arg Thr
290                 295                 300

His Phe Leu Gly Phe Ser Ala Ala Pro Phe Met Gly Met Thr Ala Lys
305                 310                 315                 320

Leu Asp Leu Ile Gln Met Gly Ala Ala Tyr Cys Lys Ile Glu Lys Val
                325                 330                 335

Ala Ala Lys Phe Arg Glu Ala Leu Ala Arg Arg Asn Ser Asn Asp Lys
            340                 345                 350

Asn Tyr Leu Asp Leu Glu Cys Cys Ile Ile Leu Thr Cys Asn Leu Ser
            355                 360                 365

Phe Gln Leu Gly Ala Ala Tyr Lys Gln Lys Gln Trp Thr Phe Asp Ala
            370                 375                 380

Gly Asn Lys Asn Asp Leu Lys Leu Ser Leu Glu Gly Lys Val Asn Val
385                 390                 395                 400

Ala Phe Lys Thr His Ile Met Ile Val Glu Val Ala Ile Gly Val Gly
                405                 410                 415

Gly Ala Ile Lys Thr Ala Ala Gly Phe Glu Leu Asp Gln His Asp Lys
            420                 425                 430

Gly Ile Asp Leu Ala Gly Tyr His Asn Gly Ile Val Ala Glu Phe Glu
            435                 440                 445

Val Ala Val Asp Ile Lys Lys Lys Asn Lys Lys Met Asp Ser Thr Lys
450                 455                 460

Asn Leu Phe Lys Val Lys Lys Lys Trp Val Ile Ala Asp Pro Leu Lys
465                 470                 475                 480

Ala Ser Glu Ser Pro Leu Arg Ile Asn Leu Ile Gly Lys Glu Arg Ser
                485                 490                 495

Val Val Arg Pro Glu Ile Val Pro Gly Ala Glu Thr Ala Ser Trp Glu
            500                 505                 510

Met Gly Tyr Asp Pro Asn Phe Lys Pro Lys Met Asp Asn Leu Pro Phe
            515                 520                 525

```
Ile Thr Gly Phe Pro Arg Met
    530                 535

<210> SEQ ID NO 133
<211> LENGTH: 424
<212> TYPE: PRT
<213> ORGANISM: Photorhabdus luminescens

<400> SEQUENCE: 133

Met Val Glu Gln Thr Ile Ser Ser Arg Ala Gly Val Ala Cys Met Thr
1               5                   10                  15

Cys Asp Asn Pro Asp Pro Cys Ile Tyr Lys Ile Ser Val Thr Phe Gly
            20                  25                  30

Gln Asn Thr Gln Val Trp Pro Glu Lys Pro Val Ile Lys Met Gly Leu
        35                  40                  45

Ile Asp Asp Gly Lys Gly Gln Lys Gly Met Ile Gln Ile Glu Gly Lys
    50                  55                  60

Cys Asn Asn Ala Asp Lys His His Ala Val Leu Thr Gly Gly Gln Lys
65                  70                  75                  80

Glu Lys Thr Leu Glu Phe Asn Ala Pro Gln Glu Val Thr Leu Phe Tyr
                85                  90                  95

Lys Asp Gln Leu Lys Asp Ala Glu Ile Glu Ser Asp Leu Glu Ser Val
            100                 105                 110

Trp Phe Tyr Leu Ser Asn Leu Ala Asn Pro Thr Asp Met Tyr Ser Glu
        115                 120                 125

Pro Arg Tyr Tyr Lys Leu Ile Thr Gln Gly Cys Leu Asp Ser Gln Gln
    130                 135                 140

Tyr Ala Thr Ile Ala Val Tyr Pro Ser Val Ser Phe Met Val Ser Val
145                 150                 155                 160

Gly Leu Ser Phe Asp Phe Ser His Gly Glu Arg Ser Val Lys Glu Arg
                165                 170                 175

Arg Asp Glu Gln Lys Lys Ala Arg Gln Ala Met Glu Asn Val Lys Pro
            180                 185                 190

Lys Asn Gly Asn Lys Leu Arg Ser Gly Trp Thr Thr His Thr Asp Pro
        195                 200                 205

Phe Tyr Leu Thr Arg Gln Thr Ala Ile Asn Val Glu Tyr Ala Leu Thr
    210                 215                 220

Val Gln Asp Met Asp Tyr Ser Ala Lys Phe Ala Glu Val Asn Lys Val
225                 230                 235                 240

Arg Lys Thr Leu Pro Asn Leu Glu Ala Ile Asn Arg Val Glu Lys Leu
                245                 250                 255

Leu Gly Tyr Thr Lys Glu Tyr Leu Ala Pro Asp Pro Asp Ser Lys Gly
            260                 265                 270

Thr Arg Ser Tyr Gln Leu Leu Glu Leu Lys Val Asp Pro Ile Asn Ile
        275                 280                 285

Gly Leu Ala Tyr Ala Tyr Asp Arg Thr Thr Ser Met Asp Asp Arg Thr
    290                 295                 300

His Phe Leu Gly Phe Ser Ala Ala Pro Phe Leu Gly Met Thr Ala Lys
305                 310                 315                 320

Leu Asp Leu Ile Gln Met Gly Ala Ala Tyr Cys Lys Ile Glu Lys Val
                325                 330                 335

Ala Ala Lys Phe Arg Lys Ala Leu Ala Arg Arg Asn Ser Asn Asp Lys
            340                 345                 350

Asn Tyr Leu Asp Leu Glu Cys Cys Ile Ile Leu Thr Cys Asn Leu Ser
        355                 360                 365
```

```
Phe Gln Leu Gly Ala Ala Tyr Lys Gln Lys Gln Trp Thr Phe Asp Ala
        370                 375                 380

Gly Asn Lys Asn Asp Leu Lys Leu Ser Leu Glu Gly Lys Val Asn Val
385                 390                 395                 400

Ala Phe Lys Thr His Ile Met Ile Val Glu Val Ala Ile Gly Val Gly
                405                 410                 415

Gly Ala Ile Lys Thr Ala Ala Gly
            420

<210> SEQ ID NO 134
<211> LENGTH: 533
<212> TYPE: PRT
<213> ORGANISM: Photorhabdus luminescens

<400> SEQUENCE: 134

Met Ala Glu Gln Thr Ile Ser Ser Arg Ala Gly Val Ala Cys Met Thr
1               5                   10                  15

Cys Asp Asn Pro Asp Pro Cys Ile Tyr Lys Ile Ser Val Thr Phe Gly
            20                  25                  30

Gln Asn Thr Gln Val Trp Pro Glu Lys Pro Val Ile Lys Met Gly Leu
        35                  40                  45

Ile Asp Asp Gly Lys Gly Gln Lys Gly Thr Ile Gln Ile Glu Gly Lys
50                  55                  60

Cys Asn Asn Ala Asp Lys His His Ala Val Leu Thr Gly Gly Gln Lys
65                  70                  75                  80

Glu Lys Thr Leu Glu Phe Asn Ala Pro Gln Glu Val Thr Leu Phe Tyr
                85                  90                  95

Lys Asp Gln Leu Lys Asp Ala Glu Ile Glu Ser Asp Leu Glu Ser Val
            100                 105                 110

Trp Phe Tyr Leu Ser Asn Leu Ala Asn Pro Thr Asp Met Tyr Ser Glu
        115                 120                 125

Pro Arg Tyr Tyr Lys Leu Ile Thr Gln Gly Cys Leu Asp Asn Gln Gln
130                 135                 140

Tyr Ala Thr Ile Ala Val Tyr Pro Ser Val Ser Phe Met Val Ser Val
145                 150                 155                 160

Gly Leu Ser Phe Asp Phe Ser His Gly Glu Arg Ser Val Lys Glu Arg
                165                 170                 175

Arg Asp Glu Gln Lys Lys Ala Arg Leu Ala Met Glu Asn Val Lys Pro
            180                 185                 190

Lys Asn Gly Asn Lys Leu Arg Ser Gly Trp Thr Thr His Thr Asp Pro
        195                 200                 205

Phe Tyr Leu Thr Arg Gln Thr Ala Ile Asn Val Glu Tyr Ala Leu Thr
210                 215                 220

Val Gln Asp Met Asp Tyr Ser Ala Lys Phe Ala Glu Val Asn Lys Val
225                 230                 235                 240

Arg Lys Thr Leu Pro Asn Leu Glu Ala Ile Asn Arg Val Glu Lys Leu
                245                 250                 255

Leu Gly Tyr Thr Lys Glu Tyr Leu Ala Pro Asp Pro Asp Ser Lys Gly
            260                 265                 270

Thr Arg Ser Tyr Gln Leu Leu Glu Leu Lys Val Asp Pro Ile Asn Ile
        275                 280                 285

Gly Leu Ala Tyr Ala Tyr Asp Arg Thr Thr Ser Met Asp Asp Arg Thr
290                 295                 300

His Phe Leu Gly Phe Ser Ala Ala Pro Phe Met Gly Met Thr Ala Lys
```

```
                 305                 310                 315                 320
Leu Asp Leu Ile Gln Met Gly Ala Ala Tyr Cys Lys Ile Lys Ser Val
                325                 330                 335

Ala Ala Lys Phe Arg Glu Ala Leu Ala Arg Arg Asn Ser Asn Asp Lys
            340                 345                 350

Asn Tyr Leu Asp Leu Glu Cys Cys Leu Ile Leu Ala Cys Asn Leu Ser
        355                 360                 365

Phe Gln Leu Gly Ala Ala Tyr Lys Gln Lys Gln Trp Thr Phe Asp Ala
    370                 375                 380

Gly Asp Lys Asn Asp Leu Lys Leu Ser Leu Glu Gly Lys Met Asn Val
385                 390                 395                 400

Ala Phe Lys Thr His Ile Met Ile Met Glu Ala Ala Met Gly Val Gly
                405                 410                 415

Val Ala Val Lys Thr Ala Ala Gly Phe Glu Leu Asp Gln His Asp Lys
            420                 425                 430

Gly Ile Asp Leu Ala Gly Tyr His Asn Gly Ile Val Ala Glu Phe Glu
        435                 440                 445

Val Asp Val Asp Ala Lys Lys Glu Asn Gly Glu Lys Ser Ile Ile Lys
    450                 455                 460

Ile Thr Glu Lys Trp Lys Trp Val Ile Ala Asp Pro Leu Lys Ala Ser
465                 470                 475                 480

Glu Ser Pro Leu Arg Ile Asn Leu Ile Gly Glu Arg Pro Ile Thr
                485                 490                 495

Arg Pro Glu Ile Val Pro Gly Ala Glu Thr Thr Ser Trp Glu Met Gly
            500                 505                 510

Tyr Asp Pro Asn Phe Lys Pro Lys Met Asp Asn Ile Pro Phe Ile Thr
        515                 520                 525

Gly Leu Pro Gly Met
    530

<210> SEQ ID NO 135
<211> LENGTH: 774
<212> TYPE: PRT
<213> ORGANISM: Photorhabdus luminescens
<220> FEATURE:
<221> NAME/KEY: misc_feature
<222> LOCATION: (346)..(349)
<223> OTHER INFORMATION: Xaa can be any naturally occurring amino acid

<400> SEQUENCE: 135

Met Ala Glu Gln Thr Ile Ser Ser Arg Ala Gly Val Ala Cys Met Thr
1               5                   10                  15

Cys Asp Asn Pro Asp Pro Cys Ile Tyr Lys Ile Ser Val Thr Phe Gly
            20                  25                  30

Arg Asn Thr Gln Val Trp Pro Glu Lys Pro Val Ile Lys Met Ser Leu
        35                  40                  45

Ile Asp Asn Gly Lys Gly Gln Lys Gly Thr Ile Gln Ile Glu Gly Lys
    50                  55                  60

Cys Asn Asn Thr Ala Lys His His Ala Val Leu Thr Gly Gly Gln Lys
65                  70                  75                  80

Glu Lys Thr Leu Glu Phe Asn Ala Pro Gln Glu Val Thr Leu Phe Tyr
                85                  90                  95

Lys Asp Gln Leu Gln Asp Ala Glu Ile Glu Ser Asp Leu Glu Ser Val
            100                 105                 110

Trp Phe Tyr Leu Ser Asn Leu Ala Asn Pro Thr Asp Met Tyr Ser Glu
        115                 120                 125
```

```
Pro Arg Tyr Tyr Lys Leu Ile Thr Gln Gly Cys Leu Glu Ser Arg Gln
    130                 135                 140

Tyr Ala Thr Ile Ala Val Tyr Pro Ser Val Ser Phe Met Val Ser Val
145                 150                 155                 160

Gly Leu Ser Phe Asp Phe Ser His Gly Glu Arg Ser Val Lys Glu Arg
                165                 170                 175

Arg Asp Glu Gln Lys Lys Ala Arg Leu Ala Met Glu Asn Val Lys Pro
            180                 185                 190

Lys Asn Gly Asn Lys Leu Arg Ser Gly Trp Thr Thr His Thr Asp Pro
        195                 200                 205

Phe Tyr Leu Thr Arg Gln Thr Ala Ile Asn Val Glu Tyr Ala Leu Thr
    210                 215                 220

Val Gln Asp Met Asp Tyr Ser Ala Lys Phe Ala Glu Val Asn Lys Val
225                 230                 235                 240

Arg Lys Thr Leu Pro Asn Leu Glu Ala Ile Asn Arg Val Glu Lys Leu
                245                 250                 255

Leu Gly Tyr Thr Lys Glu Tyr Leu Ala Pro Asp Pro Asp Ser Lys Gly
            260                 265                 270

Thr Arg Ser Tyr Gln Leu Leu Glu Leu Lys Val Asp Leu Ile Asn Ile
        275                 280                 285

Gly Leu Ala Tyr Ala Tyr Asp Arg Thr Thr Ser Met Asp Asp Arg Thr
    290                 295                 300

His Phe Leu Gly Phe Ser Ala Ala Pro Phe Met Gly Met Thr Ala Lys
305                 310                 315                 320

Leu Asp Leu Ile Gln Met Gly Ala Ala Tyr Cys Lys Ile Glu Lys Val
                325                 330                 335

Ala Ala Lys Phe Arg Lys Ala Leu Ala Xaa Xaa Xaa Xaa Leu Glu Ser
            340                 345                 350

Val Trp Phe Tyr Leu Ser Asn Leu Ala Asn Pro Thr Asp Met Tyr Ser
        355                 360                 365

Glu Pro Arg Tyr Tyr Lys Leu Ile Thr Gln Gly Cys Leu Glu Ser Arg
    370                 375                 380

Gln Tyr Ala Thr Ile Ala Val Tyr Pro Ser Val Ser Phe Met Val Ser
385                 390                 395                 400

Ala Gly Leu Ser Phe Asp Phe Ser His Gly Glu Arg Ser Val Lys Glu
                405                 410                 415

Arg Arg Asp Glu Gln Lys Lys Ala Arg Leu Ala Met Glu Asn Val Lys
            420                 425                 430

Pro Lys Asn Gly Asn Lys Leu Arg Ser Gly Trp Thr Thr His Thr Asp
        435                 440                 445

Pro Phe Tyr Leu Thr Arg Gln Thr Ala Ile Asn Val Glu Tyr Ala Leu
    450                 455                 460

Thr Val Gln Asp Met Asp Tyr Ser Ala Lys Phe Ala Lys Val Asn Lys
465                 470                 475                 480

Val Arg Lys Thr Leu Pro Asn Leu Glu Val Ile Asn Arg Val Glu Lys
                485                 490                 495

Leu Leu Gly Tyr Thr Lys Glu Tyr Leu Ala Pro Asp Pro Asp Ser Lys
            500                 505                 510

Gly Thr Arg Ser Tyr Gln Leu Leu Glu Leu Lys Val Asp Pro Ile Asn
        515                 520                 525

Ile Gly Leu Ala Tyr Ala Tyr Asp Arg Thr Thr Ser Met Asp Asp Arg
    530                 535                 540
```

```
Thr His Phe Leu Gly Phe Ser Ala Ala Pro Phe Gly Met Thr Ala
545                 550                 555                 560

Lys Leu Asp Leu Ile Gln Met Gly Ala Ala Tyr Cys Lys Ile Lys Ser
                565                 570                 575

Val Ala Ala Lys Phe Arg Glu Ala Leu Ala Arg Arg Asn Ser Asn Asp
            580                 585                 590

Lys Asn Tyr Leu Asp Leu Glu Cys Cys Ile Ile Leu Thr Cys Asn Leu
        595                 600                 605

Ser Phe Gln Leu Gly Ala Ala Tyr Lys Gln Lys Trp Thr Phe Asp
    610                 615                 620

Ala Gly Asp Lys Asn Asp Leu Lys Leu Ser Leu Glu Gly Lys Ala Asn
625                 630                 635                 640

Val Ala Phe Lys Thr His Ile Met Ile Met Glu Ala Ala Met Gly Val
                645                 650                 655

Gly Val Ala Val Lys Thr Ala Ala Gly Phe Glu Leu Asp Gln His Asp
                660                 665                 670

Lys Gly Ile Asp Leu Ala Gly Tyr His Asn Gly Ile Val Ala Glu Phe
                675                 680                 685

Glu Val Asp Val Asp Val Gly Lys Glu Asp Gly Glu Lys Ser Leu Ile
690                 695                 700

Gln Val Lys Glu Lys Trp Lys Trp Val Ile Ala Asp Pro Leu Lys Ala
705                 710                 715                 720

Asn Glu Ser Pro Leu Arg Ile Asn Leu Met Gly Glu Glu Arg Ser Val
                725                 730                 735

Val Arg Pro Glu Ile Val Pro Gly Ala Glu Thr Gly Ser Trp Glu Met
            740                 745                 750

Gly Tyr Asp Pro Asn Phe Lys Pro Lys Met Asp Asn Ile Pro Phe Ile
        755                 760                 765

Thr Gly Leu Pro Gly Met
    770

<210> SEQ ID NO 136
<211> LENGTH: 533
<212> TYPE: PRT
<213> ORGANISM: Photorhabdus luminescens

<400> SEQUENCE: 136

Met Ala Glu Gln Thr Ile Ser Ser Arg Ala Gly Val Ala Cys Met Thr
1               5                   10                  15

Cys Asp Asn Pro Asp Pro Cys Ile Tyr Lys Ile Ser Val Thr Phe Gly
                20                  25                  30

Gln Asn Thr Gln Val Trp Pro Glu Lys Pro Val Ile Lys Met Gly Leu
            35                  40                  45

Ile Asp Asp Gly Lys Gly Gln Lys Gly Thr Ile Gln Ile Glu Gly Lys
        50                  55                  60

Cys Asn Asn Ala Asp Lys His His Ala Val Leu Thr Gly Gly Gln Lys
65                  70                  75                  80

Glu Lys Thr Leu Glu Phe Asn Ala Pro Gln Glu Val Thr Leu Phe Tyr
                85                  90                  95

Lys Asp Gln Leu Lys Asp Ala Glu Ile Glu Ser Asp Leu Glu Ser Val
            100                 105                 110

Trp Phe Tyr Leu Ser Asn Leu Ala Asn Pro Thr Asp Met Tyr Ser Glu
        115                 120                 125

Pro Arg Tyr Tyr Lys Leu Ile Thr Gln Gly Cys Leu Asp Asn Gln Gln
    130                 135                 140
```

Tyr Ala Thr Ile Ala Val Tyr Pro Ser Val Ser Phe Met Val Ser Val
145                 150                 155                 160

Gly Leu Ser Phe Asp Phe Ser His Gly Glu Arg Ser Val Lys Glu Arg
            165                 170                 175

Arg Asp Glu Gln Lys Lys Ala Arg Leu Ala Met Glu Asn Val Lys Pro
        180                 185                 190

Lys Asn Gly Asn Lys Leu Arg Ser Gly Trp Thr Thr His Thr Asp Pro
        195                 200                 205

Phe Tyr Leu Thr Arg Gln Thr Ala Ile Asn Val Glu Tyr Ala Leu Thr
    210                 215                 220

Val Gln Asp Met Asp Tyr Ser Ala Lys Phe Ala Glu Val Asn Lys Val
225                 230                 235                 240

Arg Lys Thr Leu Pro Asn Leu Glu Ala Ile Asn Arg Val Glu Lys Leu
            245                 250                 255

Leu Gly Tyr Thr Lys Glu Tyr Leu Ala Pro Asp Pro Asp Ser Lys Gly
            260                 265                 270

Thr Arg Ser Tyr Gln Leu Leu Glu Leu Lys Val Asp Pro Ile Asn Ile
        275                 280                 285

Gly Leu Ala Tyr Ala Tyr Asp Arg Thr Thr Ser Met Asp Asp Arg Thr
290                 295                 300

His Phe Leu Gly Phe Ser Ala Ala Pro Phe Met Gly Met Thr Ala Lys
305                 310                 315                 320

Leu Asp Leu Ile Gln Met Gly Ala Ala Tyr Cys Lys Ile Lys Ser Val
            325                 330                 335

Ala Ala Lys Phe Arg Glu Ala Leu Ala Arg Arg Asn Ser Asn Asp Lys
            340                 345                 350

Asn Tyr Leu Asp Leu Glu Cys Cys Ile Ile Leu Thr Cys Asn Leu Ser
        355                 360                 365

Phe Gln Leu Gly Ala Ala Tyr Lys Gln Lys Gln Trp Thr Phe Asp Ala
    370                 375                 380

Gly Asp Lys Asn Asp Leu Lys Leu Ser Leu Glu Gly Lys Ala Asn Val
385                 390                 395                 400

Ala Phe Lys Thr His Ile Met Ile Met Glu Ala Ala Met Gly Val Gly
            405                 410                 415

Val Ala Val Lys Thr Ala Ala Gly Phe Glu Leu Asp Gln His Asp Lys
            420                 425                 430

Gly Ile Asp Leu Ala Gly Tyr His Asn Gly Ile Val Ala Glu Phe Glu
        435                 440                 445

Val Asp Val Asp Val Gly Lys Glu Asp Gly Glu Lys Ser Leu Ile Gln
450                 455                 460

Val Lys Glu Lys Trp Lys Trp Val Ile Ala Asp Pro Leu Lys Ala Asn
465                 470                 475                 480

Glu Ser Pro Leu Arg Ile Asn Leu Met Gly Glu Glu Arg Ser Val Val
            485                 490                 495

Arg Pro Glu Ile Val Pro Gly Ala Glu Thr Gly Ser Trp Glu Met Gly
            500                 505                 510

Tyr Asp Pro Asn Phe Lys Pro Lys Met Asp Asn Ile Pro Phe Ile Thr
        515                 520                 525

Gly Leu Pro Gly Met
    530

<210> SEQ ID NO 137
<211> LENGTH: 533

```
<212> TYPE: PRT
<213> ORGANISM: Photorhabdus luminescens

<400> SEQUENCE: 137
```

| | | | | | | | | | | | | | | |
|---|---|---|---|---|---|---|---|---|---|---|---|---|---|---|

Met Ala Glu Gln Thr Ile Ser Ser Arg Ala Gly Val Ala Cys Met Thr
1               5                   10                  15

Cys Asp Asn Pro Asp Pro Cys Ile Tyr Lys Ile Ser Val Thr Phe Gly
            20                  25                  30

Gln Asn Thr Gln Val Trp Pro Glu Lys Pro Val Ile Lys Met Gly Leu
        35                  40                  45

Ile Asp Asp Gly Lys Gly Gln Lys Gly Thr Ile Gln Ile Glu Gly Lys
    50                  55                  60

Cys Asn Asn Ala Asp Lys His His Ala Val Leu Thr Gly Gly Gln Lys
65                  70                  75                  80

Glu Lys Thr Leu Glu Phe Asn Ala Pro Gln Glu Val Thr Leu Phe Tyr
                85                  90                  95

Lys Asp Gln Leu Lys Asp Ala Glu Ile Glu Ser Asp Leu Glu Ser Val
            100                 105                 110

Trp Phe Tyr Leu Ser Asn Leu Ala Asn Pro Thr Asp Met Tyr Ser Glu
        115                 120                 125

Pro Arg Tyr Tyr Lys Leu Ile Thr Gln Gly Cys Leu Asp Asn Gln Gln
    130                 135                 140

Tyr Ala Lys Ile Ala Val Tyr Pro Ser Val Ser Phe Met Val Ser Val
145                 150                 155                 160

Gly Leu Ser Phe Asp Phe Ser His Gly Glu Arg Ser Val Lys Glu Arg
                165                 170                 175

Arg Asp Glu Gln Lys Lys Ala Arg Leu Ala Met Glu Asn Val Lys Pro
            180                 185                 190

Lys Asn Gly Asn Lys Leu Arg Ser Gly Trp Thr Thr His Thr Asp Pro
        195                 200                 205

Phe Tyr Leu Thr Arg Gln Thr Ala Ile Asn Val Glu Tyr Ala Leu Thr
    210                 215                 220

Val Gln Asp Met Asp Tyr Ser Ala Lys Phe Ala Glu Val Asn Lys Val
225                 230                 235                 240

Arg Lys Thr Leu Pro Asn Leu Glu Ala Ile Asn Arg Val Glu Lys Leu
                245                 250                 255

Leu Gly Tyr Thr Lys Glu Tyr Leu Ala Pro Asp Pro Asp Ser Lys Gly
            260                 265                 270

Thr Arg Ser Tyr Gln Leu Leu Glu Leu Lys Val Asp Pro Ile Asn Ile
        275                 280                 285

Gly Leu Ala Tyr Ala Tyr Asp Arg Thr Thr Ser Met Asp Asp Arg Thr
    290                 295                 300

His Phe Leu Gly Phe Ser Ala Ala Pro Phe Met Gly Met Thr Ala Lys
305                 310                 315                 320

Leu Asp Leu Ile Gln Met Gly Ala Ala Tyr Cys Lys Ile Lys Ser Val
                325                 330                 335

Ala Ala Lys Phe Arg Glu Ala Leu Ala Arg Arg Asn Ser Asn Asp Lys
            340                 345                 350

Asn Tyr Leu Asp Leu Glu Cys Cys Ile Ile Leu Thr Cys Asn Leu Ser
        355                 360                 365

Phe Gln Leu Gly Ala Ala Tyr Lys Gln Lys Gln Trp Thr Phe Asp Ala
    370                 375                 380

Gly Asp Lys Asn Asp Leu Lys Leu Ser Leu Glu Gly Lys Ala Asn Val
385                 390                 395                 400

```
Ala Phe Lys Thr His Ile Met Ile Met Glu Ala Ala Met Gly Val Gly
            405                 410                 415

Val Ala Val Lys Thr Ala Ala Gly Phe Glu Leu Asp Gln His Asp Lys
            420                 425                 430

Gly Ile Asp Leu Ala Gly Tyr His Asn Gly Ile Val Ala Glu Phe Glu
            435                 440                 445

Val Asp Val Asp Val Gly Lys Glu Asp Gly Glu Lys Ser Leu Ile Gln
450                 455                 460

Val Lys Glu Lys Trp Lys Trp Val Ile Ala Asp Pro Leu Lys Ala Asn
465                 470                 475                 480

Glu Ser Pro Leu Arg Ile Asn Leu Met Gly Glu Arg Ser Val Val
                485                 490                 495

Arg Pro Glu Ile Val Pro Gly Ala Glu Thr Gly Ser Trp Glu Met Gly
            500                 505                 510

Tyr Asp Pro Asn Phe Lys Pro Lys Met Asp Asn Ile Pro Phe Ile Thr
            515                 520                 525

Gly Leu Pro Gly Met
        530

<210> SEQ ID NO 138
<211> LENGTH: 532
<212> TYPE: PRT
<213> ORGANISM: Photorhabdus asymbiotica

<400> SEQUENCE: 138

Met Thr Gln Gln Ser Thr Ser Pro Pro Ala Gly Ala Ala Cys Met Thr
1               5                   10                  15

Cys Asn Asn Pro Asp Pro Cys Leu Cys Glu Ile Ser Val Thr Phe Glu
            20                  25                  30

Lys Lys Thr Gln Val Trp Pro Lys Pro Ser Ile Asn Met Asn Leu
        35                  40                  45

Val Asp Asp Gly Lys Gly Gln Thr Gly Thr Ile Gln Ile Ala Glu Lys
    50                  55                  60

Cys Asp His Thr Lys His Gln Ala Val Leu Leu Gly Gly Pro Lys Glu
65                  70                  75                  80

Lys Thr Leu Lys Phe Asn Thr Pro Glu Lys Val Thr Leu Phe Tyr Lys
                85                  90                  95

Glu His Leu Glu Asp Thr Asp Ile Glu Ser Ser Leu Glu Ser Ile Val
            100                 105                 110

Ser Tyr Leu Ser Asn Ile Ala Asn Pro Ser Asp Met Tyr Lys Ala Pro
        115                 120                 125

Arg Tyr Tyr Lys Leu Val Thr Glu Ala Cys Thr Gly Arg Gln Lys Tyr
    130                 135                 140

Val Thr Ile Ala Val Tyr Pro Ser Val Arg Phe Met Val Ser Val Gly
145                 150                 155                 160

Phe Gly Phe Asp Phe Ser His Gly Glu Arg Pro Ile Lys Glu Arg
                165                 170                 175

Asp Glu Gln Arg Lys Ala Arg Arg Ala Met Glu Asn Val Lys Pro Lys
            180                 185                 190

Asp Gly Asn Lys Leu Arg Gly Gly Trp Thr Val His Thr Asp Lys Phe
        195                 200                 205

Tyr Leu Thr Arg Glu Thr Thr Leu Ser Val Glu Tyr Ala Leu Thr Val
    210                 215                 220

Gln Asp Met Asp Tyr Ser Asn Lys Phe Ala Lys Ala Asn Lys Val Arg
```

```
                225                 230                 235                 240
        Lys Thr Arg Glu Ser Leu Asp Ala Ile Asn Arg Val Glu Lys Leu Leu
                            245                 250                 255

Gly Tyr Thr Lys Lys Tyr Leu Ala Pro Ala Pro Asp Ser Lys Gly Lys
                        260                 265                 270

Gly Thr His Asp Tyr Gln Leu Phe Asp Leu Lys Ile Ala Pro Ile Asn
                        275                 280                 285

Ile Gly Leu Ala Tyr Ala Tyr Asp Arg Thr Ala Ser Val Asp Asp Ser
                    290                 295                 300

Thr His Phe Val Gly Phe Ser Ala Ala Pro Phe Met Gly Met Thr Ala
        305                 310                 315                 320

Lys Leu Asp Leu Ile Gln Met Gly Ala Ala Tyr Cys Lys Ile Asp Thr
                            325                 330                 335

Ile Ala Ala Lys Phe Arg Lys Ala Ile Glu Arg Lys Asn Ala Asn Asp
                        340                 345                 350

Lys Asn Tyr Leu Glu Ile Glu Cys Cys Leu Ile Leu Thr Cys Asn Leu
                    355                 360                 365

Ser Phe Gln Leu Gly Ala Ala Tyr Lys Ser Lys Gln Trp Thr Phe Asp
            370                 375                 380

Ala Gly Asp Lys Asn Asp Leu Lys Leu Ser Leu Glu Gly Lys Ile Asn
        385                 390                 395                 400

Ala Ala Phe Lys Thr Lys Ile Met Ile Met Glu Val Ala Leu Asn Ala
                            405                 410                 415

Lys Gly Ala Val Lys Thr Ala Ala Gly Phe Lys Phe Asp Gln His Asp
                        420                 425                 430

Lys Gly Ile Asp Leu Val Gly Tyr His Asp Gly Ile Thr Ala Glu Ile
                    435                 440                 445

Glu Val Glu Ala Asp Ile Glu Ala Asp Gly Lys Glu Asn Ser Ile Ala
        450                 455                 460

Lys Val Lys Lys Lys Trp Val Ile Ala Asp Pro Leu Lys Ala Ser Glu
        465                 470                 475                 480

Ser Pro Leu Arg Ile Ser Leu Leu Gly Glu Gln Arg Pro Ile Thr Arg
                            485                 490                 495

Pro Glu Thr Val Pro Gly Ala Glu Thr Thr Pro Trp Glu Met Gly Tyr
                        500                 505                 510

Asn Pro Lys Pro Lys Leu Asp Asn Ile Pro Phe Ile Asn Ser Gly Phe
                    515                 520                 525

Pro Gly Met Arg
            530

<210> SEQ ID NO 139
<211> LENGTH: 532
<212> TYPE: PRT
<213> ORGANISM: Photorhabdus asymbiotica

<400> SEQUENCE: 139

Met Thr Lys Gln Arg Ile Ser Pro Pro Ala Gly Ala Ala Cys Met Thr
        1               5                   10                  15

Cys Asn Asn Pro Asp Pro Cys Leu Cys Glu Ile Ser Val Thr Phe Asp
                        20                  25                  30

Lys Lys Thr Gln Val Trp Pro Lys Pro Met Ile Asn Met Asn Leu
                    35                  40                  45

Val Asp Asn Gly Lys Gly Gln Thr Gly Thr Ile Gln Ile Ala Glu Lys
        50                  55                  60
```

```
Cys Asp His Ala Lys His Gln Ala Val Leu Leu Gly Gly Pro Lys Glu
 65                  70                  75                  80

Lys Thr Leu Lys Phe Asn Thr Pro Glu Lys Val Thr Leu Phe Tyr Lys
                 85                  90                  95

Glu His Leu Glu Asp Thr Asp Ile Glu Asn Gly Leu Glu Ser Ile Val
            100                 105                 110

Ser Tyr Leu Ser Asn Ile Ala Asn Pro Thr Asp Met Tyr Lys Ala Pro
        115                 120                 125

Arg Tyr Tyr Lys Leu Val Thr Glu Ala Cys Thr Gly Arg Gln Lys Tyr
    130                 135                 140

Ala Thr Ile Ala Val Tyr Pro Ser Val Ser Phe Met Val Ser Val Gly
145                 150                 155                 160

Phe Gly Phe Asp Phe Ser His Gly Glu Arg Pro Ile Lys Glu Arg Arg
                165                 170                 175

Asp Glu Gln Arg Lys Ala Arg Gln Ala Met Ala Asn Val Lys Pro Lys
            180                 185                 190

Asp Gly Asn Lys Leu Arg Gly Gly Trp Thr Val His Thr Asp Lys Phe
        195                 200                 205

Tyr Leu Thr Arg Glu Thr Ala Leu Asn Val Glu Tyr Ala Leu Thr Val
    210                 215                 220

Gln Asp Met Asp Tyr Ser Asn Lys Phe Ala Lys Thr Asn Lys Val Arg
225                 230                 235                 240

Lys Thr Arg Glu Ser Leu Asp Ala Ile Asn Arg Val Glu Lys Leu Leu
                245                 250                 255

Gly Tyr Thr Lys Lys Tyr Leu Ala Pro Ala Pro Asp Ser Lys Gly Lys
            260                 265                 270

Gly Thr His Asp Tyr Gln Leu Phe Asp Leu Lys Ile Ala Pro Ile Asn
        275                 280                 285

Ile Gly Leu Ala Tyr Ala Tyr Asn Arg Thr Thr Ser Val Ala Asp Ser
    290                 295                 300

Ser His Phe Val Gly Phe Ser Ala Ala Pro Phe Met Gly Met Thr Ala
305                 310                 315                 320

Lys Leu Asp Leu Ile Gln Met Gly Ala Ala Tyr Cys Lys Ile Asp Lys
                325                 330                 335

Ile Ala Ala Lys Phe Arg Lys Ala Ile Glu Arg Lys Asn Ala Asn Asp
            340                 345                 350

Lys Asn Tyr Leu Glu Ile Glu Cys Cys Leu Ile Leu Ala Cys Asn Leu
        355                 360                 365

Ser Phe Gln Leu Gly Ala Ala Tyr Lys Ser Lys Gln Trp Thr Phe Asp
    370                 375                 380

Ala Gly Asn Lys Asn Asp Leu Lys Leu Ser Leu Glu Gly Lys Ile Asn
385                 390                 395                 400

Ala Ala Phe Lys Thr Arg Ile Met Ile Met Glu Val Ala Leu Asn Ala
                405                 410                 415

Lys Gly Ala Val Lys Thr Ala Ala Gly Phe Lys Phe Asp Gln His Asp
            420                 425                 430

Lys Gly Ile Asp Leu Val Gly Tyr His Asp Gly Ile Thr Ala Glu Ile
        435                 440                 445

Glu Leu Asp Ala Asp Val Glu Thr Asn Glu Lys Lys Ser Ile Ala
    450                 455                 460

Lys Ile Lys Lys Lys Trp Val Ile Ala Asp Pro Leu Lys Ala Ser Glu
465                 470                 475                 480

Ser Pro Leu Arg Ile Asn Leu Leu Gly Glu Glu Arg Leu Ile Thr Arg
```

```
                485                 490                 495
Pro Glu Thr Val Leu Gly Ala Glu Thr Ala Pro Trp Glu Met Gly Tyr
            500                 505                 510

Asn Pro Lys Pro Lys Leu Asp Asn Ile Pro Phe Ile Asn Ser Gly Phe
            515                 520                 525

Pro Gly Met Arg
        530

<210> SEQ ID NO 140
<211> LENGTH: 532
<212> TYPE: PRT
<213> ORGANISM: Photorhabdus heterorhabditis

<400> SEQUENCE: 140

Met Thr Gln Gln Arg Thr Ser Pro Pro Ala Gly Ala Ala Cys Met Thr
1               5                   10                  15

Cys Asn Asn Pro Asp Pro Cys Leu Cys Glu Ile Ser Val Thr Phe Asp
                20                  25                  30

Lys Lys Thr Gln Val Trp Pro Lys Pro Met Ile Asn Met Asn Leu
            35                  40                  45

Val Asp Asp Gly Lys Gly Gln Thr Gly Thr Ile His Ile Ala Glu Lys
50                  55                  60

Cys Asp His Ala Lys His Gln Ala Val Leu Leu Gly Gly Pro Lys Glu
65                  70                  75                  80

Lys Thr Leu Lys Phe Asn Thr Pro Glu Lys Val Thr Leu Phe Tyr Lys
                85                  90                  95

Glu His Leu Glu Asp Thr Asp Ile Glu Asn Gly Leu Glu Ser Val Val
            100                 105                 110

Ser Tyr Leu Ser Asn Ile Ala Asn Pro Thr Asp Met Tyr Lys Ala Pro
            115                 120                 125

Arg Tyr Tyr Lys Leu Val Thr Glu Ala Cys Thr Gly Arg Gln Lys Tyr
130                 135                 140

Val Thr Ile Ala Val Tyr Pro Ser Val Ser Phe Met Ile Ser Val Gly
145                 150                 155                 160

Phe Gly Phe Asp Phe Ser His Gly Glu Arg Pro Ile Lys Glu Arg Arg
                165                 170                 175

Asp Glu Gln Arg Lys Ala Arg Gln Ala Met Ala Asn Val Lys Pro Lys
            180                 185                 190

Asp Gly Asn Lys Leu Arg Gly Gly Trp Thr Val His Thr Asp Lys Phe
            195                 200                 205

Tyr Leu Thr Arg Glu Thr Ala Leu Asn Val Glu Tyr Ala Leu Thr Val
            210                 215                 220

Gln Asp Met Asp Tyr Ser Asn Lys Phe Ala Lys Ala Asn Lys Val Arg
225                 230                 235                 240

Lys Thr Arg Glu Ser Leu Asp Ala Ile Asn Arg Val Glu Lys Leu Leu
                245                 250                 255

Gly Tyr Thr Lys Lys Tyr Leu Ala Pro Ala Pro Asp Ser Lys Gly Lys
            260                 265                 270

Gly Thr His Asp Tyr Gln Leu Phe Asp Leu Lys Ile Asp Pro Ile Asn
            275                 280                 285

Ile Gly Leu Ala Tyr Ala Tyr Asn Arg Thr Thr Ser Val Asp Asp Ser
            290                 295                 300

Ser His Phe Val Gly Phe Ser Ala Ala Pro Phe Met Gly Met Thr Ala
305                 310                 315                 320
```

```
Lys Leu Asp Leu Ile Gln Met Gly Ala Ala Tyr Cys Lys Ile Asp Lys
                325                 330                 335

Ile Ala Ala Lys Phe Arg Lys Ala Ile Glu Arg Lys Asn Ala Asn Asp
            340                 345                 350

Lys Asn Tyr Leu Glu Ile Glu Cys Cys Leu Ile Leu Thr Cys Asn Leu
        355                 360                 365

Ser Phe Gln Leu Gly Ala Ala Tyr Lys Ser Lys Gln Trp Thr Phe Asp
    370                 375                 380

Ala Gly Asn Lys Asn Ala Leu Lys Leu Ser Leu Glu Gly Lys Ile Asn
385                 390                 395                 400

Ala Ala Phe Lys Thr Lys Ile Met Ile Met Glu Val Ala Leu Asn Ala
                405                 410                 415

Lys Gly Ala Ile Lys Thr Ala Ala Gly Phe Lys Phe Asp Gln His Asp
            420                 425                 430

Lys Gly Ile Asp Leu Val Gly Tyr His Asp Gly Ile Thr Ala Glu Ile
        435                 440                 445

Glu Val Thr Ala Asp Thr Lys Lys Glu Glu Asn Arg Lys Ser Ile Val
    450                 455                 460

Lys Val Lys Lys Lys Trp Val Ile Ala Asp Pro Leu Lys Ala Ser Glu
465                 470                 475                 480

Ser Pro Leu Arg Ile Asn Leu Leu Gly Glu Glu Gln Leu Ile Thr Arg
                485                 490                 495

Pro Glu Thr Val Pro Gly Ala Glu Ile Ala Pro Trp Glu Met Gly Tyr
            500                 505                 510

Asn Pro Lys Pro Lys Leu Asp Asn Ile Pro Phe Ile Thr Thr Gly Phe
        515                 520                 525

Pro Gly Met Arg
    530

<210> SEQ ID NO 141
<211> LENGTH: 532
<212> TYPE: PRT
<213> ORGANISM: Photorhabdus asymbiotica

<400> SEQUENCE: 141

Met Thr Gln Gln Arg Thr Ser Pro Pro Ala Gly Ala Ala Cys Met Thr
1               5                   10                  15

Cys Asn Asn Pro Asp Pro Cys Leu Cys Glu Ile Ser Val Thr Phe Asp
            20                  25                  30

Lys Lys Thr Gln Val Trp Pro Lys Lys Pro Met Ile Asn Met Asn Leu
        35                  40                  45

Val Asp Asp Gly Lys Gly Gln Thr Gly Thr Ile Gln Ile Ala Glu Lys
    50                  55                  60

Cys Asp His Ala Lys His Gln Ala Val Leu Leu Gly Gly Pro Lys Glu
65                  70                  75                  80

Lys Thr Leu Lys Phe Asn Thr Pro Glu Lys Val Thr Leu Phe Tyr Lys
                85                  90                  95

Glu His Leu Glu Asp Thr Asp Ile Glu Asn Gly Leu Lys Ser Val Val
            100                 105                 110

Ser Tyr Leu Ser Asn Ile Ala Asn Pro Thr Asp Met Tyr Lys Ala Pro
        115                 120                 125

Arg Tyr Tyr Lys Leu Val Thr Glu Ala Cys Thr Gly Arg Gln Lys Tyr
    130                 135                 140

Ala Thr Ile Ala Val Tyr Pro Ser Val Ser Phe Met Val Ser Val Gly
145                 150                 155                 160
```

```
            Phe Gly Phe Asp Phe Ser His Gly Glu Arg Pro Ile Lys Glu Arg Arg
                            165                 170                 175

Asp Glu Gln Arg Lys Ala Arg Gln Ala Met Ala Asn Val Lys Pro Lys
                        180                 185                 190

Asp Gly Asn Lys Leu Arg Gly Gly Trp Thr Val His Thr Asp Lys Phe
                        195                 200                 205

Tyr Leu Thr Arg Glu Thr Ala Leu Asn Val Glu Tyr Ala Leu Thr Val
                        210                 215                 220

Gln Asp Met Asp Tyr Ser Asn Lys Phe Ala Lys Thr Asn Lys Val Arg
            225                 230                 235                 240

Lys Thr Arg Glu Ser Leu Asp Ala Ile Asn Arg Val Glu Lys Leu Leu
                            245                 250                 255

Gly Tyr Thr Lys Lys Tyr Leu Ala Pro Ala Pro Asp Ser Lys Gly Lys
                        260                 265                 270

Gly Thr His Asp Tyr Gln Leu Phe Asp Leu Lys Ile Asp Pro Ile Asn
                        275                 280                 285

Ile Gly Leu Ala Tyr Ala Tyr Asp Arg Thr Ser Ser Val Asp Asp Ser
                        290                 295                 300

Ser His Phe Val Gly Phe Ser Ala Ala Pro Phe Met Gly Met Thr Ala
            305                 310                 315                 320

Lys Leu Asp Leu Ile Gln Met Gly Ala Ala Tyr Cys Lys Ile Asp Lys
                            325                 330                 335

Ile Ala Ala Lys Phe Arg Lys Ala Ile Glu Arg Lys Asn Ala Asn Asp
                        340                 345                 350

Lys Asn Tyr Leu Glu Ile Glu Cys Cys Leu Ile Leu Thr Cys Asn Leu
                        355                 360                 365

Ser Phe Gln Leu Gly Ala Ala Tyr Lys Ser Lys Gln Trp Thr Phe Asp
                        370                 375                 380

Ala Gly Asn Lys Asn Ala Leu Lys Leu Ser Leu Glu Gly Lys Ile Asn
            385                 390                 395                 400

Ala Ala Phe Lys Thr Lys Ile Met Ile Met Glu Val Ala Leu Asn Ala
                            405                 410                 415

Lys Gly Ala Val Lys Thr Ala Ala Gly Phe Lys Phe Asp Gln His Asp
                        420                 425                 430

Lys Gly Ile Asp Leu Val Gly Tyr His Asp Gly Ile Thr Ala Glu Ile
                        435                 440                 445

Glu Val Thr Ala Asp Thr Lys Lys Glu Lys Asp Arg Lys Ser Ile Ala
            450                 455                 460

Lys Val Lys Lys Lys Trp Val Ile Ala Asp Pro Leu Lys Ala Ser Glu
            465                 470                 475                 480

Ser Pro Leu Arg Ile Asn Leu Leu Gly Glu Glu Arg Leu Ile Thr Arg
                            485                 490                 495

Pro Glu Thr Val Pro Gly Ala Glu Thr Thr Pro Trp Glu Met Gly Tyr
                        500                 505                 510

Asn Pro Lys Pro Lys Leu Asp Asn Ile Pro Phe Ile Thr Thr Gly Phe
                        515                 520                 525

Pro Gly Met Arg
                    530

<210> SEQ ID NO 142
<211> LENGTH: 500
<212> TYPE: PRT
<213> ORGANISM: Photorhabdus asymbiotica
```

<400> SEQUENCE: 142

```
Met Thr Lys Gln Arg Ile Ser Pro Pro Ala Gly Ser Ala Cys Met Thr
1               5                   10                  15

Cys Asn Asn Pro Asn Pro Cys Leu Cys Glu Val Ser Val Thr Phe Glu
            20                  25                  30

Lys Lys Thr Gln Val Trp Pro Lys Pro Ser Ile Asn Met Asn Leu
        35                  40                  45

Val Asp Asn Gly Lys Gly Gln Ile Gly Thr Ile Lys Ile Thr Glu Lys
    50                  55                  60

Cys Asp His Ala Lys His Gln Ala Lys Leu His Gly Gly Pro Lys Glu
65              70                  75                  80

Lys Thr Leu Lys Phe Asn Thr Pro Glu Lys Val Thr Leu Phe Tyr Lys
                85                  90                  95

Glu Glu Leu Lys Ser Ile Asp Ile Gln Asn Gly Leu Lys Ser Val Ala
            100                 105                 110

Ser Tyr Leu Ser Asn Ile Ala Asn Pro Thr Asp Met Tyr Lys Ala Pro
        115                 120                 125

Arg Tyr Tyr Lys Leu Glu Ile Lys Ala Cys Thr Gly Ser Arg Lys Tyr
    130                 135                 140

Ala Thr Ile Ala Val Tyr Pro Ser Val Arg Phe Met Val Ser Val Gly
145                 150                 155                 160

Phe Ser Phe Asn Leu Ser Tyr Asp Lys Arg Ser Ile Lys Glu Arg Arg
                165                 170                 175

Asp Glu Gln Ile Lys Ala Arg Gln Ala Met Glu Asn Val Lys Pro Lys
            180                 185                 190

Asn Gly Asn Lys Leu Arg Lys Gly Trp Thr Thr Arg Thr Asp Glu Phe
        195                 200                 205

Ser Leu Thr Arg Glu Thr Lys Leu Lys Val Glu Tyr Ala Leu Thr Val
    210                 215                 220

Gln Asp Lys Asp Tyr Ser Thr Ser Phe Ile Asn Thr Lys Gln Ala Lys
225                 230                 235                 240

Glu Thr Arg Lys Asp Leu Asp Ala Ile Ser Leu Ala Glu Lys Leu Leu
                245                 250                 255

Gly Tyr Thr Lys Lys Tyr Leu Val Pro Ala Pro Gly Ser Lys Gly Lys
            260                 265                 270

Ala Ser Gln Asn Tyr Glu Leu Leu Asn Leu Lys Leu Thr Pro Ser Asn
        275                 280                 285

Ile Gly Leu Ala Tyr Ala Tyr Asp Arg Thr Thr Ser Val Glu Asp Ser
    290                 295                 300

Thr His Phe Val Gly Phe Tyr Ala Ala Pro Leu Met Gly Met Thr Ala
305                 310                 315                 320

Lys Leu Asp Leu Ile Gln Leu Gly Ala Thr Tyr Cys Lys Ile Glu Phe
                325                 330                 335

Leu Ala Ala Lys Phe Arg Gln Ala Leu Glu Arg Lys Asn Ala Asn Asp
            340                 345                 350

Lys Asn Tyr Leu Glu Leu Glu Cys Cys Leu Ile Val Thr Cys Asp Leu
        355                 360                 365

Ser Phe Gln Leu Gly Ala Ala Tyr Lys Ser Lys Gln Trp Thr Phe Asp
    370                 375                 380

Ala Gly Asn Lys Asn Asn Leu Lys Leu Ser Leu Glu Gly Lys Val Ser
385                 390                 395                 400

Ala Ala Phe Lys Gln Lys Ile Leu Ile Val Glu Ile Ala Leu Asn Ala
                405                 410                 415
```

```
Lys Gly Thr Ile Lys Thr Ala Ala Gly Phe Gln Phe Asp Gln His Asn
                420                 425                 430

Lys Gly Ile Asp Leu Val Gly Tyr His Asn Gly Ile Thr Ala Glu Ile
            435                 440                 445

Glu Leu Ser Ala Asp Ala Glu Ile Gly Arg Lys Lys Ala Ser Lys
    450                 455                 460

Lys Ala Lys Asn Lys Trp Thr Trp Val Ile Ala Asp Pro Leu Lys Ala
465                 470                 475                 480

Ser Glu Ser Pro Leu Arg Ile Asn Val Leu Gly Lys Glu Arg Pro Ile
                485                 490                 495

Thr Val Gln Lys
            500

<210> SEQ ID NO 143
<211> LENGTH: 500
<212> TYPE: PRT
<213> ORGANISM: Photorhabdus asymbiotica

<400> SEQUENCE: 143

Met Thr Lys Gln Arg Ile Ser Pro Pro Ala Gly Ala Ala Cys Met Thr
1               5                   10                  15

Cys Asn Asn Pro Asp Pro Cys Leu Tyr Glu Ile Asn Val Thr Phe Asp
                20                  25                  30

Lys Lys Thr Gln Val Trp Pro Lys Ser Ser Ile Asn Met Asn Leu
            35                  40                  45

Val Asp Asn Gly Lys Gly Gln Thr Gly Thr Ile Lys Ile Thr Glu Lys
 50                 55                  60

Cys Asp His Ala Lys His Gln Ala Lys Leu His Gly Gly Thr Lys Glu
65                  70                  75                  80

Lys Ala Leu Lys Phe Asn Thr Pro Glu Lys Val Thr Leu Phe Tyr Lys
                85                  90                  95

Glu Gln Leu Lys Ser Thr Asp Ile Gln Asn Asp Leu Lys Ser Ile Ala
            100                 105                 110

Ser Tyr Leu Ser Asn Ile Ala Asn Pro Thr Asp Met Tyr Lys Ala Pro
        115                 120                 125

Arg Tyr Tyr Lys Leu Glu Ile Gln Ala Cys Thr Asp Arg Arg Lys Tyr
    130                 135                 140

Ala Thr Ile Ala Val Tyr Pro Ser Val Arg Phe Met Val Ser Val Gly
145                 150                 155                 160

Phe Ser Phe Asp Leu Ser Tyr Asp Lys Arg Ser Ile Lys Glu Arg Arg
                165                 170                 175

Asp Glu Gln Arg Lys Ala Arg Leu Ala Met Glu Asn Val Lys Pro Lys
            180                 185                 190

Asn Gly Asn Lys Leu Arg Lys Gly Trp Thr Thr Arg Thr Asp Glu Phe
        195                 200                 205

Ser Leu Thr Arg Glu Thr Lys Leu Lys Val Glu Tyr Ala Leu Thr Val
    210                 215                 220

Gln Asp Lys Asp Tyr Ser Ala Ser Phe Val Asn Thr Lys Gln Thr Lys
225                 230                 235                 240

Glu Thr Arg Arg Asn Leu Asp Ala Ile Ser Leu Ala Glu Lys Leu Leu
                245                 250                 255

Gly Tyr Thr Lys Thr Tyr Leu Val Pro Ala Pro Gly Ser Lys Gly Lys
            260                 265                 270

Thr Pro Gln Asn Tyr Gln Leu Leu Asn Leu Lys Leu Thr Pro Ser Asn
```

```
                275                 280                 285
Ile Gly Leu Ala Tyr Ala Tyr Asp Arg Thr Thr Ser Val Glu Asp Ser
    290                 295                 300

Thr His Phe Ala Gly Phe Tyr Ala Ala Pro Phe Met Ser Met Thr Gly
305                 310                 315                 320

Lys Leu Asp Leu Ile Gln Met Gly Ala Ala Tyr Cys Lys Ile Glu Phe
                325                 330                 335

Leu Ala Ala Lys Phe Arg Gln Ala Leu Glu Arg Lys Asn Ala Asn Asp
            340                 345                 350

Lys Asn Tyr Leu Glu Phe Glu Cys Cys Leu Ile Val Thr Cys Asp Leu
        355                 360                 365

Ser Phe Gln Leu Gly Ala Ala Tyr Lys Ser Lys Gln Trp Thr Phe Asp
    370                 375                 380

Ala Gly Asn Lys Asn Asn Leu Lys Leu Ser Leu Glu Gly Lys Val Ser
385                 390                 395                 400

Ala Ala Phe Lys Gln Asn Ile Phe Ile Val Glu Ile Ala Leu Asn Ala
                405                 410                 415

Lys Gly Thr Ile Lys Thr Ala Ala Gly Phe Gln Phe Asp Gln His Asn
            420                 425                 430

Asn Gly Leu Asp Leu Val Gly Tyr His Asp Gly Met Thr Ala Glu Ile
        435                 440                 445

Glu Leu Thr Ala Asp Ala Glu Ile Gly Arg Lys Lys Ala Thr Lys
    450                 455                 460

Lys Val Lys Asn Lys Trp Lys Trp Val Ile Ala Asp Pro Leu Lys Ala
465                 470                 475                 480

Ser Glu Ser Pro Leu Arg Ile Asn Leu Leu Gly Lys Glu Arg Pro Ala
                485                 490                 495

Ile Val Arg Arg
            500

<210> SEQ ID NO 144
<211> LENGTH: 550
<212> TYPE: PRT
<213> ORGANISM: Photorhabdus asymbiotica

<400> SEQUENCE: 144

Met Ala Lys Ile His Ser Gly Val Ala Gly Ser Ala Cys Gln Thr Cys
1               5                   10                  15

Gly Ile Pro Asp Ser Cys Thr Leu Glu Ala Thr Ile Glu Phe Gly Glu
            20                  25                  30

Gln Lys Gly Val Tyr Arg Gln Glu Ala Phe Asn Lys Lys Phe Ser His
        35                  40                  45

Leu Val Glu Phe Lys Pro Asp Asn Asn Ile Ser Lys Pro Val Lys Leu
    50                  55                  60

Leu Leu Ser Ser Ile Ser Lys Ser Cys Ile Ser Lys Asn Gln Asp Cys
65                  70                  75                  80

Pro Val Gly Tyr Val Phe Asp Glu Asn Gly Arg Val Val Ile Arg Phe
                85                  90                  95

Thr Pro Lys Gln Ser Tyr Glu Gly Ser Leu Arg Tyr Thr Lys Arg Cys
            100                 105                 110

Lys Asn Phe Asp Tyr Ser Glu Arg Asn Pro Ile Thr Leu Leu Ser Ser
        115                 120                 125

Phe Leu Tyr Arg Glu Ala Leu Leu Thr Asp Pro Arg Tyr Asn Gln Ile
    130                 135                 140
```

-continued

```
Tyr Arg Leu Ser Met Ala Glu Cys Asp Asp Lys Pro Phe Ile Pro Val
145                 150                 155                 160

Leu Ser Gln Asp Tyr Met Gly Ile Gly Leu Val Asn Ser Arg Ile Glu
            165                 170                 175

Thr Ile Asn Asn Val Ile Thr Val Gly Lys Arg His Leu Phe Ser Ser
        180                 185                 190

Ser Phe Thr Leu Ile Leu Pro Arg Ser Val Asp Val Asp Ile Lys Ile
    195                 200                 205

Ser Phe Asp Gln Ser Val Gln Ile Gln Ser Asp Glu Lys Arg Lys Glu
210                 215                 220

Leu Met Lys Thr Glu Lys Lys Ser Gly Tyr Lys Pro Asp His Ser
225                 230                 235                 240

Gly Trp Thr Lys Lys Thr Gly Lys Tyr Val Ser Asn Lys Gly Ile Lys
                245                 250                 255

Ile Glu Gly Ser Ile Thr Ala Thr Leu Gly Lys Asp Glu Thr Lys Trp
            260                 265                 270

Ser Arg Glu Leu Glu Gln Lys Phe Lys Glu Gln Thr Asn Lys Ile Lys
        275                 280                 285

Val Leu Ser Asp Ile Asp Arg Gly Ile Gly Lys Ile Asn Tyr Val Leu
    290                 295                 300

Gln Asn Asp Gly Ser Asn Glu Tyr Pro Leu Leu Gly Cys Lys Leu Thr
305                 310                 315                 320

Tyr Pro Val Ile Ser Ile Lys Gly Lys Gly Cys Ile Lys Arg Met Ser
                325                 330                 335

Ser Gln Lys Ile Ile Pro Gln Tyr Glu Phe Glu Val Lys Gly Ser Pro
            340                 345                 350

Leu Phe Gly Phe Lys Ile Thr Leu Asp Leu Leu Gln Ala Phe Ala Ala
        355                 360                 365

Val Tyr Lys Val Asp Thr Val Leu Ala Lys Val Arg Lys Glu Ala Ala
    370                 375                 380

Ala Gln Glu Val Ser Val Lys Gln Asp Gly His Gly Ala Tyr Ala Lys
385                 390                 395                 400

Ala Glu Leu Asn Ile Ile Phe Asp Phe Thr Ile Ile Ala Gly Phe Gly
                405                 410                 415

Phe Lys Thr Asp Glu Thr Gly Glu Trp Gly Tyr Asp Lys Lys Glu Ala
            420                 425                 430

Lys Leu Met Gly Ser Ile Thr Gly Lys Thr Asn Ile Glu Val Gly Val
        435                 440                 445

Gly Phe Trp Gly Phe Ser Gly Tyr Phe Lys Ala Glu Ala Met Ile Lys
    450                 455                 460

Ala Glu Ala Tyr Leu Gly Ile Asp Asp Thr Asp Pro Lys Lys Leu Asp
465                 470                 475                 480

Leu Ile Leu Tyr His Asp Gly Ile Thr Ala Ile Ala Ser Met Gly Tyr
                485                 490                 495

Ala Val Gln Val Gly Lys Thr Asp Lys Lys Val Lys Pro Gly Ile
            500                 505                 510

Gly Asn Lys Thr Thr Thr Ser Lys Lys Ser Glu Glu Ala Lys Leu Lys
        515                 520                 525

Asn Glu Lys Trp Thr Ile Tyr Pro Ala Leu Ser Lys Lys Glu Ser Thr
    530                 535                 540

Trp Arg Trp Ser Leu Asp
545                 550
```

<210> SEQ ID NO 145
<211> LENGTH: 550
<212> TYPE: PRT
<213> ORGANISM: Photorhabdus asymbiotica

<400> SEQUENCE: 145

| Met | Ala | Lys | Ile | His | Ser | Gly | Val | Ala | Gly | Ser | Ala | Cys | Gln | Thr | Cys |
|---|---|---|---|---|---|---|---|---|---|---|---|---|---|---|---|
| 1 | | | | 5 | | | | | 10 | | | | | 15 | |

| Gly | Ile | Pro | Asp | Ser | Cys | Thr | Leu | Glu | Ala | Thr | Ile | Glu | Phe | Gly | Glu |
| | | | 20 | | | | | 25 | | | | | 30 | | |

| Gln | Lys | Gly | Val | Tyr | Arg | Gln | Glu | Ala | Phe | Asn | Lys | Lys | Phe | Ser | His |
| | | | 35 | | | | | 40 | | | | | 45 | | |

| Leu | Val | Glu | Phe | Lys | Pro | Asp | Asn | Asn | Ile | Ser | Lys | Pro | Val | Lys | Leu |
| | 50 | | | | | 55 | | | | | 60 | | | | |

| Leu | Leu | Ser | Ser | Ile | Ser | Lys | Ser | Cys | Ile | Ser | Lys | Asn | Gln | Asp | Cys |
| 65 | | | | | 70 | | | | | 75 | | | | | 80 |

| Pro | Val | Gly | Tyr | Val | Phe | Asp | Glu | Asn | Gly | Arg | Val | Val | Ile | Arg | Phe |
| | | | | 85 | | | | | 90 | | | | | 95 | |

| Thr | Pro | Lys | Gln | Ser | Tyr | Glu | Gly | Ser | Leu | Arg | Tyr | Thr | Lys | Arg | Tyr |
| | | | 100 | | | | | 105 | | | | | 110 | | |

| Lys | Asn | Phe | Asp | Tyr | Ser | Glu | Arg | Asn | Pro | Ile | Thr | Leu | Leu | Ser | Ser |
| | | | 115 | | | | | 120 | | | | | 125 | | |

| Phe | Leu | Tyr | Arg | Glu | Ala | Leu | Leu | Thr | Asp | Pro | Arg | Tyr | Asn | Gln | Ile |
| | 130 | | | | | 135 | | | | | 140 | | | | |

| Tyr | Arg | Leu | Ser | Met | Ala | Glu | Cys | Asp | Asp | Lys | Pro | Phe | Ile | Pro | Val |
| 145 | | | | | 150 | | | | | 155 | | | | | 160 |

| Leu | Ser | Gln | Asp | Tyr | Met | Gly | Ile | Gly | Leu | Val | Asn | Ser | Arg | Ile | Glu |
| | | | | 165 | | | | | 170 | | | | | 175 | |

| Thr | Ile | Asn | Asn | Val | Ile | Thr | Val | Gly | Lys | Arg | His | Leu | Phe | Ser | Ser |
| | | | 180 | | | | | 185 | | | | | 190 | | |

| Ser | Phe | Thr | Leu | Ile | Leu | Pro | Arg | Ser | Val | Asp | Val | Asp | Ile | Lys | Ile |
| | | | 195 | | | | | 200 | | | | | 205 | | |

| Ser | Phe | Asp | Gln | Ser | Val | Gln | Ile | Gln | Ser | Asp | Glu | Lys | Arg | Lys | Glu |
| | 210 | | | | | 215 | | | | | 220 | | | | |

| Leu | Met | Lys | Thr | Glu | Lys | Lys | Lys | Ser | Gly | Tyr | Lys | Pro | Asp | His | Ser |
| 225 | | | | | 230 | | | | | 235 | | | | | 240 |

| Gly | Trp | Thr | Lys | Lys | Thr | Gly | Lys | Tyr | Val | Ser | Asn | Lys | Gly | Ile | Lys |
| | | | | 245 | | | | | 250 | | | | | 255 | |

| Ile | Glu | Gly | Ser | Ile | Thr | Ala | Thr | Leu | Gly | Lys | Asp | Glu | Thr | Lys | Trp |
| | | | 260 | | | | | 265 | | | | | 270 | | |

| Ser | Arg | Glu | Leu | Glu | Gln | Lys | Phe | Lys | Glu | Gln | Thr | Asn | Lys | Ile | Lys |
| | | | 275 | | | | | 280 | | | | | 285 | | |

| Val | Leu | Ser | Asp | Ile | Asp | Arg | Gly | Ile | Gly | Lys | Ile | Asn | Tyr | Val | Leu |
| | 290 | | | | | 295 | | | | | 300 | | | | |

| Gln | Asn | Asp | Gly | Ser | Asn | Glu | Tyr | Pro | Leu | Leu | Gly | Cys | Lys | Leu | Thr |
| 305 | | | | | 310 | | | | | 315 | | | | | 320 |

| Tyr | Pro | Val | Ile | Ser | Ile | Lys | Gly | Lys | Gly | Cys | Ile | Lys | Arg | Met | Ser |
| | | | | 325 | | | | | 330 | | | | | 335 | |

| Ser | Gln | Lys | Ile | Ile | Pro | Gln | Tyr | Glu | Phe | Glu | Val | Lys | Gly | Ser | Pro |
| | | | 340 | | | | | 345 | | | | | 350 | | |

| Leu | Phe | Gly | Phe | Lys | Ile | Thr | Leu | Asp | Leu | Leu | Gln | Ala | Phe | Ala | Ala |
| | | | 355 | | | | | 360 | | | | | 365 | | |

| Val | Tyr | Lys | Val | Asp | Thr | Val | Leu | Ala | Lys | Val | Arg | Lys | Glu | Ala | Ala |
| | 370 | | | | | 375 | | | | | 380 | | | | |

-continued

```
Ala Gln Glu Val Ser Val Lys Gln Asp Gly His Gly Ala Tyr Ala Lys
385                 390                 395                 400

Ala Glu Leu Asn Ile Ile Phe Asp Phe Thr Ile Ile Ala Gly Phe Gly
            405                 410                 415

Phe Lys Thr Asp Glu Thr Gly Glu Trp Gly Tyr Asp Lys Lys Glu Ala
        420                 425                 430

Lys Leu Met Gly Ser Ile Thr Gly Lys Thr Asn Ile Glu Val Gly Val
            435                 440                 445

Gly Phe Trp Gly Phe Ser Gly Tyr Phe Lys Ala Glu Ala Met Ile Lys
450                 455                 460

Ala Glu Ala Tyr Leu Gly Ile Asp Asp Thr Asp Pro Lys Lys Leu Asp
465                 470                 475                 480

Leu Ile Leu Tyr His Asp Gly Ile Thr Ala Ile Ala Ser Met Gly Tyr
                485                 490                 495

Ala Val Gln Val Gly Lys Thr Asp Lys Lys Val Lys Pro Gly Ile
                500                 505                 510

Gly Asn Lys Thr Thr Thr Ser Lys Lys Ser Glu Glu Ala Lys Leu Lys
            515                 520                 525

Asn Glu Lys Trp Thr Ile Tyr Pro Ala Leu Ser Lys Lys Glu Ser Thr
530                 535                 540

Trp Arg Trp Ser Leu Asp
545                 550

<210> SEQ ID NO 146
<211> LENGTH: 550
<212> TYPE: PRT
<213> ORGANISM: Photorhabdus asymbiotica

<400> SEQUENCE: 146

Met Ala Lys Ile His Ser Gly Val Ala Gly Ser Ala Cys Gln Thr Cys
1               5                   10                  15

Gly Ile Pro Asp Ser Cys Thr Leu Glu Ala Thr Ile Glu Phe Gly Glu
            20                  25                  30

Gln Lys Gly Val Tyr Arg Gln Glu Ala Phe Asn Lys Lys Phe Ser His
        35                  40                  45

Leu Val Glu Phe Lys Pro Ala Asn Asn Ile Ser Lys Pro Val Lys Leu
    50                  55                  60

Leu Leu Ser Ser Ile Ser Lys Ser Cys Ile Ser Lys Asn Gln Asp Cys
65                  70                  75                  80

Pro Val Gly Tyr Val Phe Asp Glu Asn Gly Arg Val Val Ile Arg Phe
                85                  90                  95

Thr Pro Lys Gln Ser Tyr Glu Gly Ser Leu Arg Tyr Thr Lys Arg Cys
            100                 105                 110

Lys Asn Phe Asp Tyr Ser Glu Arg Asn Pro Ile Thr Leu Leu Ser Ser
        115                 120                 125

Phe Leu Tyr Arg Glu Ala Leu Leu Thr Asp Pro Arg Tyr Asn Gln Ile
    130                 135                 140

Tyr Arg Leu Ser Met Ala Glu Cys Asp Asp Lys Pro Phe Ile Pro Val
145                 150                 155                 160

Phe Ser Gln Gln Tyr Met Gly Ile Glu Leu Ile Asn Ser Arg Ile Lys
                165                 170                 175

Ala Met Asn Asp Val Ile Thr Val Gly Lys Arg His Leu Phe Ser Ser
            180                 185                 190

Ser Phe Thr Leu Ile Leu Pro Arg Ser Val Asp Val Asp Ile Lys Ile
        195                 200                 205
```

Ser Phe Asp Lys Ser Val Gln Ile Gln Ser Asp Glu Lys Arg Lys Glu
    210                 215                 220

Leu Met Lys Thr Glu Asn Lys Lys Ser Gly Tyr Lys Pro Asp His Ser
225                 230                 235                 240

Gly Trp Thr Lys Thr Gly Lys Tyr Val Ser Asn Lys Gly Ile Lys
                245                 250                 255

Ile Glu Gly Ser Ile Thr Ala Thr Leu Gly Lys Asp Glu Thr Lys Trp
            260                 265                 270

Ser Arg Glu Leu Glu Gln Lys Phe Lys Glu Gln Thr Asn Lys Ile Lys
        275                 280                 285

Val Leu Ser Asp Ile Asp Arg Gly Ile Gly Lys Ile Asn Tyr Val Leu
    290                 295                 300

Gln Asn Gly Gly Ser Asn Glu Tyr Pro Leu Leu Gly Cys Lys Leu Thr
305                 310                 315                 320

Tyr Pro Val Ile Ser Ile Lys Gly Lys Gly Cys Ile Lys Arg Met Pro
                325                 330                 335

Ser Gln Lys Ile Ile Pro Gln Tyr Glu Phe Glu Val Lys Gly Ser Pro
            340                 345                 350

Leu Phe Gly Phe Lys Ile Thr Leu Asp Leu Leu Gln Ala Phe Ala Ala
        355                 360                 365

Val Tyr Lys Val Asp Thr Val Leu Ala Lys Val Arg Lys Glu Ala Ala
    370                 375                 380

Ala Gln Glu Val Ser Val Lys Gln Asp Gly Arg Gly Ala Tyr Ala Lys
385                 390                 395                 400

Ala Glu Leu Asn Ile Ile Phe Asp Phe Thr Ile Ala Gly Phe Gly
                405                 410                 415

Phe Lys Thr Asp Glu Thr Gly Leu Trp Gly Tyr Asp Lys Lys Glu Ala
            420                 425                 430

Lys Leu Val Gly Ser Ile Thr Gly Lys Thr Asn Ile Glu Val Gly Val
        435                 440                 445

Gly Phe Trp Gly Leu Ser Gly Tyr Phe Lys Ala Glu Ala Met Ile Lys
    450                 455                 460

Ala Glu Ala Tyr Leu Gly Ile Asp Asp Thr Asp Pro Lys Lys Leu Asp
465                 470                 475                 480

Phe Ile Leu Tyr His Asp Gly Ile Thr Ala Ile Ala Ser Met Gly Tyr
                485                 490                 495

Ala Val Gln Val Gly Lys Thr Asp Lys Lys Lys Gly Lys Pro Gly Ile
            500                 505                 510

Gly Asn Lys Thr Ala Thr Ser Lys Lys Ser Glu Glu Thr Lys Leu Lys
        515                 520                 525

Asn Glu Lys Trp Thr Ile Tyr Pro Ala Leu Ser Lys Lys Glu Ser Thr
    530                 535                 540

Trp Arg Trp Ser Leu Asp
545                 550

<210> SEQ ID NO 147
<211> LENGTH: 535
<212> TYPE: PRT
<213> ORGANISM: Photorhabdus asymbiotica

<400> SEQUENCE: 147

Met Thr Ser Leu Ala Ala Gly Asn Ala Ile Cys Asp Cys Lys Asn Pro
1               5                   10                  15

Asp Thr Cys Thr His Arg Val Asp Ile Thr Leu Gly Asp Lys Lys Phe

```
            20                  25                  30
Ser Tyr Ile Gln Glu Lys Phe Ser Pro Ala Ile Tyr Met Val Val Glu
        35                  40                  45
Asp Asp Gln Pro Ile Pro Leu Thr Ile Lys Ser Ile Ser Lys Gly Cys
 50                  55                  60
Ala Ser Ser Asn Ser Gln Cys Pro Ile Gly Asp Ile Tyr Asp Asp Asn
 65                  70                  75                  80
Val Phe Gln His Ile Ala Arg Phe Ser Pro Ala Gln Pro Tyr Lys Gly
                85                  90                  95
Lys Ile Thr Tyr Gln Leu Pro Ala Gly Gly Phe Ser Leu Glu Glu Asn
            100                 105                 110
Asn Pro Leu Arg Phe Leu Val Lys Phe Ile Ser Pro Asp Asn Trp Ser
        115                 120                 125
Ala Gly Leu Ala Lys Ser Ser Tyr Phe Ile Arg Val Thr Glu Cys Ala
        130                 135                 140
Gly Glu Pro Phe Val Pro Gln Lys Ile Asn Ile His Asn Glu Ile Lys
145                 150                 155                 160
Asn Ile Phe Val Gly Lys Asn Pro Val Phe Tyr Thr Ala Ile Asn Leu
                165                 170                 175
Val Leu Leu Glu Lys Phe Glu Val Asp Val Phe Gly Leu Lys Gln
            180                 185                 190
Ala Ile Glu Glu Phe Asn Asp Glu Gln Arg Arg Gln Thr Phe Arg Glu
        195                 200                 205
Asn Tyr Pro Asn Arg Ala Arg Pro Gly Ser Arg Tyr Glu Lys Arg Leu
        210                 215                 220
Thr Arg Lys Tyr Thr Thr Pro Tyr Glu Val Thr Asn Thr Leu Thr Ile
225                 230                 235                 240
Thr Gly Lys Ile Ser Ser Thr Arg Gly Lys Glu Thr Arg Lys Trp Ser
                245                 250                 255
Lys Glu Leu Glu Gln Glu Tyr Lys Lys Gly Thr Tyr Lys Leu Ser Leu
            260                 265                 270
Leu Glu Ser Val Gly Asn Ser Val Lys Gln Val Asn Lys Val Leu Ser
        275                 280                 285
Asp Gly Lys Lys Pro Asp Glu Ile Lys Leu Leu Ser Ala Glu Ile Leu
        290                 295                 300
Tyr Pro Val Ile Asn Leu His Gly Glu Gly Ala Leu Cys Gln Ser Ala
305                 310                 315                 320
Thr Asn Gln Leu Tyr Phe Lys Arg Lys Gly Ser Ile Lys Ala Ala Pro
                325                 330                 335
Leu Phe Gly Ile Ala Leu Arg Leu Asp Val Ile Gln Met Phe Ala Asn
            340                 345                 350
Tyr Tyr Lys Leu Asp Met Leu Val Ala Thr Ile Arg Glu His Gly Gln
        355                 360                 365
Glu Arg Glu Gln Glu Val Lys Arg Gly Lys Asp Gly Ala Tyr Leu Gly
        370                 375                 380
Val Lys Leu Asp Leu Ile Val Lys Gly Ser Ile Asp Leu Ser Phe Ser
385                 390                 395                 400
Trp Ala Ser Asp Glu Lys Lys Glu Trp His Phe Glu Pro Gly Ala Leu
                405                 410                 415
Val Lys Gly Ser Leu Ala Ile Gly Ala Glu Thr Asn Ile Arg Gly Gly
            420                 425                 430
Val Arg Tyr Trp Ala Val Glu Gly Tyr Phe Lys Ala Ser Ala Glu Val
        435                 440                 445
```

```
Met Ala Glu Val Cys Val Ala Leu Asp Asn Ser Arg Lys Asp Lys Leu
    450                 455                 460

Asp Leu Val Phe Tyr His Glu Gly Ile Lys Ala Lys Ser Asn Val Ala
465                 470                 475                 480

Tyr Gly Ala Arg Val Gly Glu Val Asp Asn Ile Asn Ser Glu Asn Lys
                485                 490                 495

Lys Leu Gly Asn Ser Lys Ser Thr Ala Met Arg Asn Leu Gln Asp Glu
                500                 505                 510

Ile Glu Lys Glu Trp Val Leu Gln Glu Pro Leu Ser Lys Glu Lys Ser
            515                 520                 525

Thr Tyr Arg Val Ser Phe Gly
    530                 535

<210> SEQ ID NO 148
<211> LENGTH: 531
<212> TYPE: PRT
<213> ORGANISM: Photorhabdus temperata

<400> SEQUENCE: 148

Met Leu Ser Val Asn Met Lys Ser Ala Val Cys Asp Cys Lys Ile Pro
1               5                   10                  15

Asp Pro Cys Ile His Lys Leu Thr Leu Lys Val Gly Lys Arg Val Phe
                20                  25                  30

Ile Tyr Asn Gln Ile Glu Pro Ile Gly Asp Ile Trp Val Asp Glu
            35                  40                  45

Ala Asp Gly Ile Pro Val Thr Ile Ser Leu Val Gly Lys Arg Cys Val
    50                  55                  60

Ser Asp Asn Pro His Cys Pro Lys Ala Ile Phe Tyr Ser Pro Asp Asn
65                  70                  75                  80

Pro Met Phe Gln Phe His Glu Leu Ala Lys Asn Pro Ile Lys Gly Pro
                85                  90                  95

Gly Thr Glu Asp Glu Ile Cys Phe Ser Arg His Thr Ile Pro Val Asp
                100                 105                 110

Pro Ile Glu His Asp Pro Leu Gly Phe Ile Ala Ser Ser Leu Phe Gln
            115                 120                 125

Gln Gly Glu Leu Ser His Leu Pro His Thr Asp Tyr Ile Leu Glu Leu
130                 135                 140

Thr Gln Cys Tyr Gly Gln Pro Phe Val Thr Arg Ser Phe Pro Leu Ala
145                 150                 155                 160

Asp Asn Lys Val Lys Ala Leu Leu Leu Gly Pro Val Asp Ala Leu Tyr
                165                 170                 175

Thr Thr Ile His Val Leu Pro Gln Tyr Glu Trp Thr Leu Asp Met Thr
            180                 185                 190

Ile Gly Ala Glu Gln Ala Val Arg Glu Arg Ser Val Ala Glu Arg Lys
            195                 200                 205

Glu Glu Ala Leu Thr Ala Arg Lys Gln Val Asn Pro Gln Ala Lys Arg
    210                 215                 220

Pro Gly Glu Asn Trp His Lys Arg Thr Ala Gly Tyr Glu Leu Thr Asp
225                 230                 235                 240

Thr Leu Thr Ile Glu Gly Arg Phe Ala Tyr Thr Leu Gly Pro Tyr Ser
                245                 250                 255

Arg Thr Phe Thr His Glu Leu Glu Glu Phe Lys Thr Lys Arg Lys
                260                 265                 270

Lys Leu Gly Leu Val Asn Lys Gly Leu Gln Ala Val Asp Thr Leu Gln
```

```
            275                 280                 285
Lys Leu Phe Ser Ser Glu Gly Ser Gln Glu Ile Lys Leu Leu Glu Met
        290                 295                 300
Glu Ile Gln Thr Pro Glu Ile Lys Leu Ser Gly Gly Ser Lys Leu Val
305                 310                 315                 320
Asn Ala Thr His Gly Asn Glu Ala Tyr Phe Gln Ala Ile Ser Val
                325                 330                 335
Glu Leu Ala Pro Leu Ile Gly Met Lys Leu Arg Leu Asp Leu Ile Gln
            340                 345                 350
Ala Phe Ala Thr Glu Phe Gly Val Glu Lys Leu Ile Ala Leu Ile Arg
            355                 360                 365
Glu Gln Gly Leu Lys Gly Lys Ala Val Asp Glu Gly Arg Asp Gly
        370                 375                 380
Ala Tyr Leu Gly Ala Gln Leu Asp Met Val Leu Glu Gly Ala Leu Asn
385                 390                 395                 400
Leu Ser Phe Lys Tyr Ala Ser Asn Glu Glu Arg Glu Met Glu Phe Gln
                405                 410                 415
Leu Gly Asp Met Val Lys Gly Thr Leu Ala Ile Ser Ala Glu Thr Asn
            420                 425                 430
Ile Gln Ala Gly Phe Lys Tyr Tyr Leu Val Glu Gly Tyr Phe Lys Ala
            435                 440                 445
Gly Ala Asp Ile Glu Ala Glu Gly Cys Phe Glu Leu Asp Lys Gln Asp
450                 455                 460
Asn Gly Leu Tyr Leu Val Phe Phe His Glu Gly Ile Val Ala Ser Tyr
465                 470                 475                 480
Tyr Val Glu Tyr Gly Val Gly Val Ala Pro Ser Glu Asn Asn Gly Lys
                485                 490                 495
Ser Ile Gly Ser Gly Ser Asn Val Asp Asn Lys Lys Gln Lys Lys Trp
            500                 505                 510
Glu Ile Tyr Pro Lys Leu Pro Lys Glu Lys Ser Thr Tyr Lys Leu Arg
            515                 520                 525
Leu Ser Gln
    530

<210> SEQ ID NO 149
<211> LENGTH: 531
<212> TYPE: PRT
<213> ORGANISM: Photorhabdus temperata

<400> SEQUENCE: 149

Met Leu Ser Val Asn Met Lys Ser Ala Val Cys Asp Cys Lys Ile Pro
1               5                   10                  15
Asp Pro Cys Ile His Lys Leu Thr Leu Lys Val Gly Lys Arg Val Phe
            20                  25                  30
Ile Tyr His Gln Ile Glu Pro Ile Gly Asp Ile Trp Val Val Asp Glu
        35                  40                  45
Ser Asp Gly Ile Pro Val Ala Ile Ser Leu Val Gly Lys Arg Cys Ile
    50                  55                  60
Ser Asp Asn Pro Gln Cys Pro Lys Ala Ile Phe Tyr Ser Gln Asp Asn
65              70                  75                  80
Pro Ala Phe Gln Phe His Glu Leu Ala Lys Asn Pro Ile Lys Gly Pro
                85                  90                  95
Gly Thr Glu Asp Lys Ile His Phe Ser Asn His Thr Leu Pro Val Asp
            100                 105                 110
```

```
Pro Ile Ala Ser Asp Pro Leu Gly Phe Ile Glu Ala Ser Val Phe Gln
            115                 120                 125

Pro Gly Glu Leu Ser His Leu Pro His Thr Asp Tyr Ile Leu Glu Leu
        130                 135                 140

Thr Gln Cys Tyr Gly Gln Pro Phe Val Thr Arg Ser Phe Pro Leu Ala
145                 150                 155                 160

Asp Asp Lys Val Lys Ala Leu Leu Gly Pro Val Asp Ala Leu Tyr
                165                 170                 175

Thr Thr Ile His Val Leu Pro Gln Tyr Glu Trp Thr Leu Asp Val Thr
                180                 185                 190

Ile Gly Ala Glu Gln Glu Val Arg Glu Arg Ser Val Val Glu Arg Lys
                195                 200                 205

Ala Glu Ala Leu Glu Glu Arg Lys Lys Ala Asn Pro His Ala Lys Arg
        210                 215                 220

Pro Gly Glu Asn Trp His Lys Arg Thr Ala Gly Tyr Glu Leu Thr Asp
225                 230                 235                 240

Thr Leu Thr Val Asp Gly Ser Phe Ala Tyr Thr Leu Gly Pro Tyr Ser
                245                 250                 255

His Thr Phe Thr Ser Glu Leu Glu Glu Phe Lys Thr Lys Arg Arg
                260                 265                 270

Lys Leu Gly Leu Val Asn Lys Gly Leu Gln Ala Val Asp Thr Leu Gln
        275                 280                 285

Lys Leu Phe Ser Ser Glu Gly Ser Gln Glu Ile Lys Leu Leu Asp Met
        290                 295                 300

Glu Ile Gln Thr Pro Glu Ile Lys Leu Ser Gly Gly Ser Lys Leu Val
305                 310                 315                 320

Asn Ala Ser His Gly Asn Glu Ala Tyr Phe Glu Gln Ala Val Ala Val
                325                 330                 335

Glu Leu Ala Pro Leu Met Gly Ile Lys Leu Arg Leu Asp Leu Ile Gln
                340                 345                 350

Ala Phe Ala Thr Glu Phe Gly Val Glu Lys Leu Ile Ala Leu Ile Arg
                355                 360                 365

Glu Gln Gly Leu Lys Gly Lys Ala Ala Val Asp Asp Gly Arg Asp Gly
        370                 375                 380

Ala Tyr Leu Gly Ala Gln Leu Asp Met Val Leu Glu Gly Ala Leu Asn
385                 390                 395                 400

Leu Ser Phe Lys Tyr Ala Ser Asn Glu Glu Arg Glu Met Gly Phe Gln
                405                 410                 415

Leu Gly Asp Met Val Lys Gly Thr Leu Ala Ile Arg Ala Glu Thr Asn
                420                 425                 430

Ile Gln Ala Gly Phe Lys Tyr Tyr Leu Val Glu Gly Tyr Phe Lys Ala
                435                 440                 445

Gly Ala Asp Ile Glu Ala Glu Gly Gly Phe Glu Leu Asp Lys Gln Asp
        450                 455                 460

Asn Gly Leu Tyr Leu Val Phe Phe His Glu Gly Ile Val Ala Ser Tyr
465                 470                 475                 480

Tyr Val Glu Tyr Gly Val Gly Lys Ser Thr Thr Glu Asn Lys Asn Ser
                485                 490                 495

Ser Phe Asn Pro Gln Ser Lys Val Asp Thr Lys Lys Gln Lys Lys Trp
                500                 505                 510

Glu Ile Tyr Pro Lys Leu Pro Lys Glu Lys Ser Thr Tyr Lys Leu Arg
                515                 520                 525

Leu Ser Gln
```

<210> SEQ ID NO 150
<211> LENGTH: 531
<212> TYPE: PRT
<213> ORGANISM: Photorhabdus temperata

<400> SEQUENCE: 150

Met Leu Ser Val Asn Met Lys Ser Ala Val Cys Asp Cys Lys Ile Pro
1               5                   10                  15

Asp Pro Cys Ile His Lys Leu Thr Leu Lys Val Gly Lys Arg Val Phe
            20                  25                  30

Ile Tyr His Gln Ile Glu Pro Ile Gly Asp Ile Trp Val Val Asp Asp
        35                  40                  45

Ala Asp Gly Ile Pro Val Thr Ile Ser Leu Val Gly Lys Arg Cys Ile
    50                  55                  60

Ser Asp Asn Pro Gln Cys Pro Lys Ala Ile Phe Tyr Ser Pro Asp Asn
65                  70                  75                  80

Pro Ala Phe Gln Phe His Glu Leu Ala Lys Asn Pro Ile Lys Gly Pro
                85                  90                  95

Gly Thr Glu Asp Lys Ile His Phe Ser Asn His Thr Leu Pro Val Asp
            100                 105                 110

Pro Ile Ala Ser Asp Pro Leu Gly Phe Ile Glu Ala Ser Leu Phe Gln
        115                 120                 125

Pro Gly Ala Leu Asn His Leu Pro His Thr Asp Tyr Ile Leu Glu Leu
    130                 135                 140

Thr Gln Cys Tyr Gly Gln Pro Phe Ile Thr Arg Ser Phe Pro Leu Ala
145                 150                 155                 160

Asp Asp Lys Val Lys Ala Leu Leu Gly Pro Val Asp Ala Leu Tyr
                165                 170                 175

Thr Thr Ile His Val Leu Pro Gln Tyr Glu Trp Thr Leu Asp Val Thr
            180                 185                 190

Ile Gly Ala Glu Gln Glu Val Arg Glu Arg Ser Val Ala Glu Arg Lys
        195                 200                 205

Ala Glu Ala Leu Glu Glu Arg Lys Lys Ala Asn Pro His Ala Lys Arg
    210                 215                 220

Pro Gly Glu Asn Trp His Lys Arg Thr Ala Gly Tyr Glu Leu Thr Asp
225                 230                 235                 240

Thr Leu Thr Leu Glu Gly Ser Phe Ala Tyr Thr Leu Gly Pro Tyr Ser
                245                 250                 255

His Thr Phe Thr His Glu Leu Glu Glu Leu Lys Thr Lys Arg Arg
            260                 265                 270

Lys Leu Gly Leu Val Asp Lys Gly Leu Gln Ala Val Asp Thr Leu Gln
        275                 280                 285

Lys Leu Phe Ser Ser Glu Gly Ser Gln Glu Ile Lys Leu Leu Asp Met
    290                 295                 300

Glu Ile Gln Thr Pro Glu Ile Lys Leu Ser Gly Gly Ser Lys Leu Val
305                 310                 315                 320

Asn Ala Ser His Gly Asn Glu Ala Tyr Phe Glu Gln Ala Val Ala Val
                325                 330                 335

Glu Leu Ala Pro Leu Ile Gly Val Lys Leu Arg Leu Asp Leu Ile Gln
            340                 345                 350

Ala Phe Ala Thr Glu Phe Gly Val Glu Lys Leu Ile Ala Leu Ile Arg
        355                 360                 365

-continued

```
Glu Gln Gly Leu Lys Gly Lys Ala Ala Val Asp Asp Gly Arg Asp Gly
    370                 375                 380

Ala Tyr Leu Gly Ala Gln Leu Asp Met Val Leu Glu Gly Ala Leu Asn
385                 390                 395                 400

Leu Ser Phe Lys Tyr Ala Ser Asn Glu Glu Arg Glu Met Glu Phe Gln
                405                 410                 415

Leu Gly Asp Leu Val Arg Gly Thr Leu Ala Ile Arg Ala Glu Thr Asn
            420                 425                 430

Ile Gln Ala Gly Phe Lys Tyr Tyr Leu Val Glu Gly Tyr Phe Lys Ala
                435                 440                 445

Gly Ala Asp Ile Glu Ala Glu Gly Cys Phe Glu Leu Asn Lys Gln Asp
450                 455                 460

Asn Gly Leu Tyr Leu Val Phe Phe His Glu Gly Ile Val Ala Ser Tyr
465                 470                 475                 480

Tyr Val Glu Tyr Gly Val Gly Ile Ser Pro Pro Glu Asn Asn Asp Glu
                485                 490                 495

Ser Ser Lys Gln Lys Ser Lys Met Asp Ala Lys Lys Gln Lys Lys Trp
            500                 505                 510

Glu Ile Tyr Pro Lys Leu Pro Lys Glu Lys Ser Thr Tyr Lys Leu Arg
                515                 520                 525

Leu Ser Gln
    530

<210> SEQ ID NO 151
<211> LENGTH: 531
<212> TYPE: PRT
<213> ORGANISM: Photorhabdus temperata

<400> SEQUENCE: 151

Met Leu Ser Val Asn Met Lys Ser Ala Val Cys Asp Cys Lys Ile Pro
1               5                   10                  15

Asp Pro Cys Ile His Lys Leu Thr Leu Lys Val Gly Lys Arg Val Phe
                20                  25                  30

Ile Tyr His Gln Ile Glu Pro Ile Gly Asp Ile Trp Val Val Asp Glu
            35                  40                  45

Ser Asp Gly Ile Pro Val Ala Ile Ser Leu Val Gly Lys Arg Cys Ile
50                  55                  60

Ser Asp Asn Pro Gln Cys Pro Lys Ala Ile Phe Tyr Ser Pro Asp Asn
65                  70                  75                  80

Pro Ala Phe Gln Phe His Glu Leu Ala Lys Asn Pro Ile Lys Gly Pro
                85                  90                  95

Gly Thr Glu Asp Lys Ile His Phe Ser Asn His Thr Leu Pro Val Asp
            100                 105                 110

Pro Ile Glu Asn Asp Pro Leu Gly Phe Ile Glu Val Ser Leu Phe Gln
        115                 120                 125

Pro Gly Ala Leu Asn His Leu Pro His Thr Asp Tyr Ile Leu Glu Leu
    130                 135                 140

Thr Gln Cys Tyr Gly Gln Pro Phe Ile Thr Arg Ser Phe Pro Leu Ala
145                 150                 155                 160

Asp Asp Lys Val Lys Ala Leu Leu Leu Gly Pro Val Asp Ala Leu Tyr
                165                 170                 175

Thr Thr Ile His Val Leu Pro Gln Tyr Glu Trp Thr Leu Asp Val Thr
            180                 185                 190

Ile Gly Ala Glu Gln Glu Val Arg Glu Arg Ser Val Ala Glu Arg Lys
        195                 200                 205
```

```
Ala Glu Ala Leu Glu Glu Arg Lys Lys Ala Asn Pro His Ala Lys Arg
        210                 215                 220
Pro Gly Glu Asn Trp His Lys Arg Thr Ala Gly Tyr Glu Leu Thr Asp
225                 230                 235                 240
Thr Leu Thr Val Asp Gly Ser Phe Ala Tyr Thr Leu Gly Pro Tyr Ser
                245                 250                 255
His Thr Phe Thr Ser Glu Leu Glu Glu Phe Lys Thr Lys Arg Arg
            260                 265                 270
Lys Leu Gly Leu Val Asp Lys Gly Leu Gln Ala Val Asp Thr Leu Gln
        275                 280                 285
Lys Leu Phe Ser Ser Glu Gly Ser Gln Glu Ile Lys Leu Leu Asp Met
        290                 295                 300
Glu Ile Gln Thr Pro Glu Ile Lys Leu Ser Gly Gly Ser Lys Leu Val
305                 310                 315                 320
Asn Ala Pro Gln Gly Asn Glu Ala Tyr Phe Glu Gln Ala Val Ala Val
                325                 330                 335
Glu Leu Ala Pro Leu Met Gly Ile Lys Leu Arg Leu Asp Leu Ile Gln
            340                 345                 350
Ala Phe Ala Thr Glu Phe Gly Val Glu Lys Leu Ile Ala Leu Ile Arg
        355                 360                 365
Glu Gln Gly Leu Lys Gly Lys Ala Ala Val Asp Asp Gly Arg Asp Gly
        370                 375                 380
Ala Tyr Leu Gly Ala Gln Leu Asp Met Val Leu Glu Gly Ala Leu Asn
385                 390                 395                 400
Leu Ser Phe Lys Tyr Ala Ser Asn Glu Glu Arg Glu Met Glu Phe Gln
                405                 410                 415
Leu Gly Asp Met Val Lys Gly Thr Leu Ala Ile Arg Ala Glu Thr Asn
            420                 425                 430
Ile Gln Ala Gly Phe Lys Tyr Tyr Leu Val Glu Gly Tyr Phe Lys Ala
        435                 440                 445
Gly Ala Asp Ile Glu Ala Glu Gly Cys Phe Glu Leu Asp Lys Gln Asp
450                 455                 460
Asn Gly Leu Tyr Leu Val Phe Phe His Glu Gly Ile Val Ala Ser Tyr
465                 470                 475                 480
Tyr Val Glu Tyr Gly Val Gly Lys Gly Ile Thr Lys Asn Asn Asp Asp
                485                 490                 495
Ser Ile Lys Gln Asn Ser Lys Leu Gly Asp Lys Lys Gln Lys Lys Trp
            500                 505                 510
Glu Ile Tyr Leu Lys Leu Pro Lys Glu Lys Ser Thr Tyr Lys Leu Arg
        515                 520                 525
Leu Ser Gln
    530

<210> SEQ ID NO 152
<211> LENGTH: 531
<212> TYPE: PRT
<213> ORGANISM: Photorhabdus temperata

<400> SEQUENCE: 152

Met Leu Ser Val Asn Met Lys Ser Ala Val Cys Asp Cys Lys Ile Pro
1               5                   10                  15

Asp Pro Cys Ile His Lys Leu Thr Leu Lys Val Gly Lys Arg Val Phe
            20                  25                  30

Ile Tyr His Gln Ile Glu Pro Ile Gly Asp Ile Trp Val Val Asp Glu
```

```
                35                  40                  45
Ser Asp Gly Ile Pro Val Ala Ile Ser Leu Val Gly Lys Arg Cys Val
 50                  55                  60

Ser Asp Asn Pro Gln Cys Pro Lys Ala Ile Phe Tyr Ser Pro Asp Asn
 65                  70                  75                  80

Pro Ala Phe Gln Phe His Glu Leu Ala Lys Asn Pro Ile Lys Gly Pro
                 85                  90                  95

Gly Thr Glu Asp Lys Ile His Phe Ser Asn His Thr Leu Pro Val Asp
                100                 105                 110

Pro Ile Ala Ser Asp Pro Leu Gly Phe Ile Glu Ala Ser Val Phe Gln
                115                 120                 125

Pro Gly Glu Leu Ser His Leu Pro His Thr Asp Tyr Ile Leu Glu Leu
                130                 135                 140

Thr Gln Cys Tyr Gly Gln Pro Phe Val Thr Arg Ser Phe Pro Leu Ala
145                 150                 155                 160

Asp Asp Lys Val Lys Ala Leu Leu Gly Pro Val Asp Ala Leu Tyr
                165                 170                 175

Thr Thr Ile His Val Leu Pro Gln Tyr Glu Trp Thr Leu Asp Val Thr
                180                 185                 190

Ile Gly Ala Glu Gln Glu Val Arg Glu Arg Ser Val Glu Arg Lys
                195                 200                 205

Ala Glu Ala Leu Glu Glu Arg Lys Lys Ala Asn Pro His Ala Lys Arg
210                 215                 220

Pro Gly Glu Asn Trp His Lys Arg Thr Ala Gly Tyr Glu Leu Thr Asp
225                 230                 235                 240

Thr Leu Thr Leu Glu Gly Ser Phe Ala Tyr Thr Leu Gly Pro Tyr Ser
                245                 250                 255

His Thr Phe Thr His Glu Leu Glu Glu Phe Lys Thr Lys Arg Gln
                260                 265                 270

Lys Leu Gly Leu Val Asn Lys Gly Leu Gln Ala Val Asp Thr Leu Gln
                275                 280                 285

Lys Leu Phe Ser Ser Glu Gly Ser Gln Glu Ile Lys Leu Leu Asp Met
                290                 295                 300

Glu Ile Gln Thr Pro Glu Ile Lys Leu Ser Gly Gly Ser Lys Leu Val
305                 310                 315                 320

Asn Ala Pro Gln Gly Asn Glu Ala Tyr Phe Glu Gln Ala Val Ala Val
                325                 330                 335

Glu Leu Ala Pro Leu Met Gly Ile Lys Leu Arg Leu Asp Leu Ile Gln
                340                 345                 350

Ala Phe Ala Thr Glu Phe Gly Val Glu Lys Leu Ile Ala Leu Ile Arg
                355                 360                 365

Glu Gln Gly Leu Lys Gly Lys Ala Ala Val Asp Asp Gly Arg Asp Gly
                370                 375                 380

Ala Tyr Leu Gly Ala Gln Leu Asp Met Val Leu Glu Gly Ala Leu Asn
385                 390                 395                 400

Leu Ser Phe Lys Tyr Ala Ser Asn Glu Glu Arg Glu Met Glu Phe Gln
                405                 410                 415

Leu Gly Asp Leu Val Arg Gly Thr Leu Ala Ile Arg Ala Glu Thr Asn
                420                 425                 430

Ile Gln Ala Gly Phe Lys Tyr Tyr Leu Val Glu Gly Tyr Phe Lys Ala
                435                 440                 445

Gly Ala Asp Ile Glu Ala Glu Gly Cys Phe Glu Leu Asp Lys Gln Asp
450                 455                 460
```

Lys Gly Leu Cys Leu Val Phe Phe His Glu Gly Ile Val Ala Ser Tyr
465                 470                 475                 480

Tyr Val Glu Tyr Gly Leu Gly Thr Ala Pro Ser Lys Asn Glu Glu Ala
                485                 490                 495

Val Phe Asn His Lys Ser Lys Thr Asp Thr Lys Lys Gln Lys Lys Trp
            500                 505                 510

Glu Ile Tyr Pro Lys Leu Pro Lys Glu Lys Ser Thr Tyr Lys Leu Arg
            515                 520                 525

Leu Thr Gln
    530

<210> SEQ ID NO 153
<211> LENGTH: 531
<212> TYPE: PRT
<213> ORGANISM: Photorhabdus temperata

<400> SEQUENCE: 153

Met Leu Ser Val Asn Met Lys Ser Ala Val Cys Asp Cys Lys Ile Pro
1               5                   10                  15

Asp Pro Cys Ile His Lys Leu Thr Leu Lys Val Gly Lys Arg Val Phe
            20                  25                  30

Ile Tyr His Gln Ile Glu Pro Ile Gly Asp Ile Trp Val Val Asp Asp
        35                  40                  45

Ala Asp Gly Ile Pro Val Ala Ile Ser Leu Val Gly Lys Arg Cys Val
    50                  55                  60

Ser Asp Asn Pro Gln Cys Pro Lys Ala Ile Phe Tyr Ser Pro Asp Asn
65                  70                  75                  80

Pro Ala Phe Gln Phe His Glu Leu Ala Lys Asn Pro Ile Lys Gly Pro
                85                  90                  95

Gly Thr Glu Asp Lys Ile His Phe Ser Asn His Thr Leu Pro Val Asp
            100                 105                 110

Pro Ile Ala Ser Asp Pro Leu Gly Phe Ile Glu Ala Ser Val Phe Gln
        115                 120                 125

Pro Gly Glu Leu Ser His Leu Pro His Thr Asp Tyr Ile Leu Glu Leu
    130                 135                 140

Thr Gln Cys Tyr Gly Gln Pro Phe Val Thr Arg Ser Phe Pro Leu Ala
145                 150                 155                 160

Asp Asp Lys Val Lys Ala Leu Leu Leu Gly Pro Val Asp Ala Leu Tyr
                165                 170                 175

Thr Thr Ile His Val Leu Pro Gln Tyr Glu Trp Thr Leu Asp Val Thr
            180                 185                 190

Ile Gly Ala Glu Gln Glu Val Arg Glu Arg Ser Val Ala Glu Arg Lys
        195                 200                 205

Ala Glu Ala Leu Glu Glu Arg Lys Lys Ala Asn Pro His Ala Lys Arg
    210                 215                 220

Pro Gly Glu Asn Trp His Lys Arg Thr Ala Gly Tyr Glu Leu Thr Asp
225                 230                 235                 240

Thr Leu Thr Val Asp Gly Ser Phe Ala Tyr Thr Leu Gly Pro Tyr Ser
                245                 250                 255

His Thr Phe Thr Ser Glu Leu Glu Glu Phe Lys Thr Lys Arg Arg
            260                 265                 270

Lys Leu Gly Leu Val Asn Lys Gly Leu Gln Ala Val Asp Thr Leu Gln
        275                 280                 285

Lys Leu Phe Ser Ser Glu Gly Ser Gln Glu Ile Lys Leu Leu Asp Met

```
                290                 295                 300
Glu Ile Gln Thr Pro Glu Ile Lys Leu Ser Gly Gly Ser Lys Leu Val
305                 310                 315                 320

Asn Ala Pro Gln Gly Asn Glu Ala Tyr Phe Glu Gln Ala Val Ala Val
                325                 330                 335

Glu Leu Ala Pro Leu Met Gly Ile Lys Leu Arg Leu Asp Leu Ile Gln
                340                 345                 350

Ala Phe Ala Thr Glu Phe Gly Val Glu Lys Leu Ile Ala Leu Ile Arg
                355                 360                 365

Glu Gln Gly Leu Lys Gly Lys Ala Ala Val Asp Asp Gly Arg Asp Gly
                370                 375                 380

Ala Tyr Leu Gly Ala Gln Leu Asp Met Val Leu Gly Gly Ala Leu Asn
385                 390                 395                 400

Leu Ser Phe Lys Tyr Ala Ser Asn Glu Glu Arg Glu Met Glu Phe Gln
                405                 410                 415

Leu Gly Asp Met Ile Lys Gly Thr Leu Ala Ile Ser Ala Glu Thr Asn
                420                 425                 430

Ile Gln Ala Gly Phe Lys Tyr Tyr Leu Val Glu Gly Tyr Phe Lys Ala
                435                 440                 445

Gly Ala Asp Ile Glu Ala Glu Gly Cys Phe Glu Leu Asn Lys Gln Asp
450                 455                 460

Asn Gly Leu Tyr Leu Val Phe Phe His Glu Gly Ile Val Ala Ser Tyr
465                 470                 475                 480

Tyr Val Glu Tyr Gly Val Gly Thr Lys Pro Thr Lys Asp Arg Gly Ser
                485                 490                 495

Phe Val Gly Asn Ile Thr Asn Ser Thr Thr Lys Lys Gln Lys Lys Trp
                500                 505                 510

Glu Ile Tyr Pro Lys Leu Pro Lys Glu Lys Ser Thr Tyr Lys Leu Arg
                515                 520                 525

Leu Ala Gln
    530

<210> SEQ ID NO 154
<211> LENGTH: 530
<212> TYPE: PRT
<213> ORGANISM: Photorhabdus temperata

<400> SEQUENCE: 154

Met Leu Ser Val Asn Met Lys Ser Ala Val Cys Asp Cys Lys Ile Pro
1               5                   10                  15

Asp Pro Cys Ile His Lys Leu Thr Leu Lys Val Gly Lys Arg Val Phe
                20                  25                  30

Ile Tyr His Gln Ile Glu Pro Ile Gly Asp Ile Trp Val Val Asp Asp
                35                  40                  45

Ala Asp Gly Ile Pro Val Ala Ile Ser Leu Val Gly Lys Arg Cys Val
50                  55                  60

Ser Asp Asn Pro Gln Cys Pro Lys Ala Ile Phe Tyr Ser Pro Asp Asn
65                  70                  75                  80

Pro Ala Phe Gln Phe His Glu Leu Ala Lys Asn Pro Ile Lys Gly Pro
                85                  90                  95

Gly Thr Glu Asp Lys Ile His Phe Ser Asn His Thr Leu Pro Val Asp
                100                 105                 110

Pro Ile Ala Ser Asp Pro Leu Gly Phe Ile Glu Ser Ser Leu Phe Gln
                115                 120                 125
```

```
Pro Gly Glu Leu Ser His Leu Pro His Thr Asp Tyr Ile Leu Glu Leu
130                 135                 140

Thr Gln Cys Tyr Gly Gln Pro Phe Val Thr Arg Ser Phe Pro Leu Ala
145                 150                 155                 160

Asp Asp Lys Val Lys Ala Leu Leu Gly Pro Val Asp Ala Leu Tyr
                165                 170                 175

Thr Thr Ile His Val Leu Pro Gln Tyr Glu Trp Thr Leu Asp Val Thr
                180                 185                 190

Ile Gly Ala Glu Gln Glu Val Arg Glu Arg Ser Val Thr Glu Arg Lys
                195                 200                 205

Ala Glu Ala Leu Glu Glu Arg Lys Lys Ala Asn Pro His Ala Lys Arg
210                 215                 220

Pro Gly Glu Asn Trp His Lys Arg Thr Ala Gly Tyr Glu Leu Thr Asp
225                 230                 235                 240

Thr Leu Thr Val Asp Gly Ser Phe Ala Tyr Thr Leu Gly Pro Tyr Ser
                245                 250                 255

His Thr Phe Thr Ser Glu Leu Glu Glu Phe Lys Thr Lys Arg Arg
                260                 265                 270

Lys Leu Gly Leu Val Asn Lys Gly Leu Gln Ala Val Asp Thr Leu Gln
                275                 280                 285

Lys Leu Phe Ser Ser Glu Gly Ser Gln Glu Ile Lys Leu Leu Asp Met
                290                 295                 300

Glu Ile Gln Thr Pro Glu Ile Lys Leu Ser Gly Gly Ser Lys Leu Val
305                 310                 315                 320

Asn Ala Pro Gln Gly Asn Glu Ala Tyr Phe Glu Gln Ala Val Ala Val
                325                 330                 335

Glu Leu Ala Pro Leu Met Gly Ile Lys Leu Arg Leu Asp Leu Ile Gln
                340                 345                 350

Ala Phe Ala Thr Glu Phe Gly Val Glu Lys Leu Ile Ala Leu Ile Arg
                355                 360                 365

Glu Gly Leu Lys Gly Lys Ala Ala Val Asp Asp Gly Arg Asp Gly Ala
                370                 375                 380

Tyr Leu Gly Ala Gln Leu Asp Met Val Leu Glu Gly Ala Leu Asn Leu
385                 390                 395                 400

Ser Phe Lys Tyr Ala Ser Asn Glu Arg Glu Met Glu Phe Gln Leu
                405                 410                 415

Gly Asp Met Ile Lys Gly Thr Leu Ala Ile Ser Ala Glu Thr Asn Ile
                420                 425                 430

Gln Ala Gly Phe Lys Tyr Leu Val Glu Gly Tyr Phe Lys Ala Gly
                435                 440                 445

Ala Asp Ile Glu Ala Glu Gly Cys Phe Glu Leu Asn Lys Gln Asp Asn
450                 455                 460

Gly Leu Tyr Leu Val Phe Phe His Glu Gly Ile Val Ala Ser Tyr Tyr
465                 470                 475                 480

Val Glu Tyr Gly Val Gly Ser Lys Pro Pro Lys Asn Asn Asp Asp Ser
                485                 490                 495

Ser Lys Gln Lys Ser Lys Met Asp Asn Lys Gln Lys Thr Trp Glu
                500                 505                 510

Ile Tyr Pro Lys Leu Pro Lys Glu Lys Ser Thr Tyr Lys Leu Arg Leu
                515                 520                 525

Ser Gln
530
```

```
<210> SEQ ID NO 155
<211> LENGTH: 531
<212> TYPE: PRT
<213> ORGANISM: Photorhabdus temperata

<400> SEQUENCE: 155

Met Leu Ser Val Asn Met Lys Ser Ala Val Cys Asp Cys Lys Ile Pro
1               5                   10                  15

Asp Pro Cys Ile His Lys Leu Thr Leu Lys Val Gly Lys Arg Val Phe
            20                  25                  30

Ile Tyr His Gln Ile Glu Pro Ile Gly Asp Ile Trp Val Val Asp Asp
        35                  40                  45

Ala Asp Gly Ile Pro Val Ala Ile Ser Leu Val Gly Lys Arg Cys Val
    50                  55                  60

Ser Asp Asn Pro Gln Cys Pro Lys Ala Ile Phe Tyr Ser Pro Asp Asn
65                  70                  75                  80

Pro Ala Phe Gln Phe His Glu Leu Ala Lys Asn Pro Ile Lys Gly Pro
                85                  90                  95

Gly Thr Glu Asp Lys Ile His Phe Ser Asn His Thr Leu Pro Val Asp
            100                 105                 110

Pro Ile Ala Ser Asp Pro Leu Gly Phe Ile Glu Ser Ser Leu Phe Gln
        115                 120                 125

Pro Gly Glu Leu Ser His Leu Pro His Thr Asp Tyr Ile Leu Glu Leu
    130                 135                 140

Thr Gln Cys Tyr Gly Gln Pro Phe Val Thr Arg Ser Phe Pro Leu Ala
145                 150                 155                 160

Asp Asp Lys Val Lys Ala Leu Leu Leu Gly Pro Val Asp Ala Leu Tyr
                165                 170                 175

Thr Thr Ile His Val Leu Pro Gln Tyr Glu Trp Thr Leu Asp Val Thr
            180                 185                 190

Ile Gly Ala Glu Gln Glu Val Arg Glu Arg Ser Val Ala Glu Arg Lys
        195                 200                 205

Ala Glu Ala Leu Glu Glu Arg Lys Lys Ala Asn Pro His Ala Lys Arg
    210                 215                 220

Pro Gly Glu Asn Trp His Lys Arg Thr Ala Gly Tyr Glu Leu Thr Asp
225                 230                 235                 240

Thr Leu Thr Leu Glu Gly Ser Phe Ala Tyr Thr Leu Gly Pro Tyr Ser
                245                 250                 255

His Thr Phe Thr His Glu Leu Glu Glu Phe Lys Thr Lys Arg Gln
            260                 265                 270

Lys Leu Gly Leu Val Asn Lys Gly Leu Gln Ala Val Asp Thr Leu Gln
        275                 280                 285

Lys Leu Phe Ser Ser Glu Gly Ser Gln Glu Ile Lys Leu Leu Asp Met
    290                 295                 300

Glu Ile Gln Thr Pro Glu Ile Lys Leu Ser Gly Gly Ser Lys Leu Val
305                 310                 315                 320

Asn Ala Ser His Gly Asn Glu Ala Tyr Phe Glu Gln Ala Val Ala Val
                325                 330                 335

Glu Leu Ala Pro Leu Met Gly Ile Lys Leu Arg Leu Asp Leu Ile Gln
            340                 345                 350

Ala Phe Ala Thr Glu Phe Gly Val Glu Lys Leu Ile Ala Leu Ile Arg
        355                 360                 365

Glu Gln Gly Leu Lys Gly Lys Ala Ala Val Asp Asp Gly Arg Asp Gly
    370                 375                 380
```

-continued

```
Ala Tyr Leu Gly Ala Gln Leu Asp Met Val Leu Glu Gly Ala Leu Asn
385                 390                 395                 400

Leu Ser Phe Lys Tyr Ala Ser Asn Glu Glu Arg Glu Met Glu Phe Gln
            405                 410                 415

Leu Gly Asp Met Val Lys Gly Thr Leu Ala Ile Arg Ala Glu Thr Asn
        420                 425                 430

Ile Gln Ala Gly Phe Lys Tyr Tyr Leu Val Glu Gly Tyr Phe Lys Ala
            435                 440                 445

Gly Ala Asp Ile Glu Ala Gly Cys Phe Glu Leu Asp Lys Gln Asp
        450                 455                 460

Lys Gly Leu Cys Leu Val Phe Phe His Glu Gly Ile Val Ala Ser Tyr
465                 470                 475                 480

Tyr Val Glu Tyr Gly Ala Gly Val Ala Pro Ser Glu Asn Ile Gly Asn
                485                 490                 495

Ser Thr Glu Lys Arg Ser Arg Val Asp Asn Lys Glu Gln Lys Lys Trp
                500                 505                 510

Glu Ile Tyr Pro Lys Leu Pro Lys Glu Lys Ser Thr Tyr Lys Leu Arg
            515                 520                 525

Leu Ser Gln
    530

<210> SEQ ID NO 156
<211> LENGTH: 481
<212> TYPE: PRT
<213> ORGANISM: Photorhabdus temperata

<400> SEQUENCE: 156

Met Leu Ser Val Asn Met Lys Ser Ala Val Cys Asp Cys Lys Ile Pro
1               5                   10                  15

Asp Pro Cys Ile His Lys Leu Thr Leu Lys Val Gly Lys Arg Val Phe
            20                  25                  30

Ile Tyr His Gln Ile Glu Pro Ile Gly Asp Ile Trp Val Val Asp Asp
        35                  40                  45

Ala Asp Gly Ile Pro Val Ala Ile Ser Leu Val Gly Lys Arg Cys Val
    50                  55                  60

Ser Asp Asn Pro Gln Cys Pro Lys Ala Ile Phe Tyr Ser Pro Asp Asn
65                  70                  75                  80

Pro Ala Phe Gln Phe His Glu Leu Ala Lys Asn Pro Ile Lys Gly Pro
                85                  90                  95

Gly Thr Glu Asp Lys Ile His Phe Ser Asn His Thr Leu Pro Val Asp
            100                 105                 110

Pro Ile Ala Ser Asp Pro Leu Gly Phe Ile Glu Ser Ser Leu Phe Gln
        115                 120                 125

Pro Gly Glu Leu Ser His Leu Pro His Thr Asp Tyr Ile Leu Glu Leu
    130                 135                 140

Thr Gln Cys Tyr Gly Gln Pro Phe Val Thr Arg Ser Phe Pro Leu Ala
145                 150                 155                 160

Asp Asp Lys Val Lys Ala Leu Leu Gly Pro Val Asp Ala Leu Tyr
                165                 170                 175

Thr Thr Ile His Val Leu Pro Gln Tyr Glu Trp Thr Leu Asp Val Thr
            180                 185                 190

Ile Gly Ala Glu Gln Glu Val Arg Glu Arg Ser Val Thr Glu Arg Lys
        195                 200                 205

Ala Glu Ala Leu Glu Glu Arg Lys Lys Ala Asn Pro His Ala Lys Arg
    210                 215                 220
```

Pro Gly Glu Asn Trp His Lys Arg Thr Ala Gly Tyr Glu Leu Thr Asp
225                 230                 235                 240

Thr Leu Thr Val Asp Gly Ser Phe Ala Tyr Thr Leu Gly Pro Tyr Ser
            245                 250                 255

His Thr Phe Thr Ser Glu Leu Glu Glu Glu Phe Lys Thr Lys Arg Arg
        260                 265                 270

Lys Leu Gly Leu Val Asn Lys Gly Leu Gln Ala Val Ala Val Glu Leu
    275                 280                 285

Ala Pro Leu Met Gly Ile Lys Leu Arg Leu Asp Leu Ile Gln Ala Phe
290                 295                 300

Ala Thr Glu Phe Gly Val Glu Lys Leu Ile Ala Leu Ile Arg Glu Gln
305                 310                 315                 320

Gly Leu Lys Gly Lys Ala Val Asp Asp Gly Arg Asp Gly Ala Tyr
                325                 330                 335

Leu Gly Ala Gln Leu Asp Met Val Leu Glu Gly Ala Leu Asn Leu Ser
            340                 345                 350

Phe Lys Tyr Ala Ser Asn Glu Glu Arg Glu Met Gly Phe Gln Leu Gly
        355                 360                 365

Asp Met Val Lys Gly Thr Leu Ala Ile Arg Ala Glu Thr Asn Ile Gln
    370                 375                 380

Ala Gly Phe Lys Tyr Tyr Leu Val Glu Gly Tyr Phe Lys Ala Gly Ala
385                 390                 395                 400

Asp Ile Glu Ala Glu Gly Cys Phe Glu Leu Asp Lys Gln Asp Lys Gly
                405                 410                 415

Leu Cys Leu Val Phe Phe His Glu Gly Ile Val Ala Ser Tyr Tyr Val
            420                 425                 430

Glu Tyr Gly Val Gly Val Ala Pro Phe Asp Asn Asn Gly Lys Ser Ile
        435                 440                 445

Arg Ser Gly Ser Asn Val Asp Asn Lys Lys Gln Lys Lys Trp Glu Ile
    450                 455                 460

Tyr Pro Lys Leu Pro Lys Glu Lys Ser Thr Tyr Lys Leu Arg Leu Ser
465                 470                 475                 480

Gln

<210> SEQ ID NO 157
<211> LENGTH: 476
<212> TYPE: PRT
<213> ORGANISM: Photorhabdus temperata

<400> SEQUENCE: 157

Met Lys Ser Ala Val Cys Asp Cys Lys Ile Pro Asp Pro Cys Ile His
1               5                   10                  15

Lys Leu Thr Leu Lys Val Gly Lys Arg Val Phe Ile Tyr His Gln Ile
            20                  25                  30

Glu Pro Ile Gly Asp Ile Trp Val Asp Asp Ala Asp Gly Ile Pro
        35                  40                  45

Val Ala Ile Ser Leu Val Gly Lys Arg Cys Val Ser Asp Asn Pro Gln
50                  55                  60

Cys Pro Lys Ala Ile Phe Tyr Ser Pro Asp Asn Pro Ala Phe Gln Phe
65                  70                  75                  80

His Glu Leu Ala Lys Asn Pro Ile Lys Gly Pro Gly Thr Glu Asp Lys
                85                  90                  95

Ile His Phe Ser Asn His Thr Leu Pro Val Asp Pro Ile Ala Ser Asp
            100                 105                 110

```
Pro Leu Gly Phe Ile Glu Ser Ser Leu Phe Gln Pro Gly Glu Leu Ser
        115                 120                 125

His Leu Pro His Thr Asp Tyr Ile Leu Glu Leu Thr Gln Cys Tyr Gly
    130                 135                 140

Gln Pro Phe Val Thr Arg Ser Phe Pro Leu Ala Asp Asp Lys Val Lys
145                 150                 155                 160

Ala Leu Leu Leu Gly Pro Val Asp Ala Leu Tyr Thr Thr Ile His Val
                165                 170                 175

Leu Pro Gln Tyr Glu Trp Thr Leu Asp Val Thr Ile Gly Ala Glu Gln
            180                 185                 190

Glu Val Arg Glu Arg Ser Val Thr Glu Arg Lys Ala Glu Ala Leu Glu
        195                 200                 205

Glu Arg Lys Lys Ala Asn Pro His Ala Lys Arg Pro Gly Glu Asn Trp
    210                 215                 220

His Lys Arg Thr Ala Gly Tyr Glu Leu Thr Asp Thr Leu Thr Val Asp
225                 230                 235                 240

Gly Ser Phe Ala Tyr Thr Leu Gly Pro Tyr Ser His Thr Phe Thr Ser
                245                 250                 255

Glu Leu Glu Glu Glu Phe Lys Thr Lys Arg Arg Lys Leu Gly Leu Val
            260                 265                 270

Asn Lys Gly Leu Gln Ala Val Ala Val Glu Leu Ala Pro Leu Met Gly
    275                 280                 285

Ile Lys Leu Arg Leu Asp Leu Ile Gln Ala Phe Ala Thr Glu Phe Gly
290                 295                 300

Val Glu Lys Leu Ile Ala Leu Ile Arg Glu Gln Gly Leu Lys Gly Lys
305                 310                 315                 320

Ala Ala Val Asp Asp Gly Arg Asp Gly Ala Tyr Leu Gly Ala Gln Leu
                325                 330                 335

Asp Met Val Leu Glu Gly Ala Leu Asn Leu Ser Phe Lys Tyr Ala Ser
            340                 345                 350

Asn Glu Glu Arg Glu Met Gly Phe Gln Leu Gly Asp Met Val Lys Gly
        355                 360                 365

Thr Leu Ala Ile Arg Ala Glu Thr Asn Ile Gln Ala Gly Phe Lys Tyr
    370                 375                 380

Tyr Leu Val Glu Gly Tyr Phe Lys Ala Gly Ala Asp Ile Glu Ala Glu
385                 390                 395                 400

Gly Cys Phe Glu Leu Asp Lys Gln Asp Lys Gly Leu Cys Leu Val Phe
                405                 410                 415

Phe His Glu Gly Ile Val Ala Ser Tyr Tyr Val Glu Tyr Gly Val Gly
            420                 425                 430

Val Ala Pro Phe Asp Asn Asn Gly Lys Ser Ile Arg Ser Gly Ser Asn
        435                 440                 445

Val Asp Asn Lys Lys Gln Lys Lys Trp Glu Ile Tyr Pro Lys Leu Pro
    450                 455                 460

Lys Glu Lys Ser Thr Tyr Lys Leu Arg Leu Ser Gln
465                 470                 475

<210> SEQ ID NO 158
<211> LENGTH: 531
<212> TYPE: PRT
<213> ORGANISM: Photorhabdus heterorhabditis

<400> SEQUENCE: 158

Met Leu Ser Val Asn Met Arg Ser Ala Val Cys Asp Cys Lys Ile Pro
```

-continued

```
1               5                   10                  15
Asp Pro Cys Ile His Lys Leu Val Leu Lys Val Gly Lys Arg Val Phe
                20                  25                  30
Asn Tyr Asn Gln Ile Glu Pro Ile Gly Asp Ile Trp Val Ile Asp Glu
                35                  40                  45
Thr Gly Gly Ile Pro Val Thr Ile Ser Leu Val Gly Lys Arg Cys Ile
                50                  55                  60
Thr Glu Asn Ala Gln Cys Pro Arg Ala Ile Phe Tyr Ser Pro Asp Asn
65                  70                  75                  80
Ala Ala Phe Gln Phe Tyr Glu Leu Gly Lys Asn Pro Ile Ala Gly Pro
                85                  90                  95
Gly Thr Asp Tyr Lys Ile Ser Phe Ser Ser His Asn Leu Pro Val Asp
                100                 105                 110
Leu Val Glu Asn Asp Pro Leu Ser Phe Ile Ala Ser Ser Leu Phe Gln
                115                 120                 125
Arg Gly Asp Leu Asn His Leu Pro Arg Thr Asp Tyr Ile Leu Thr Leu
                130                 135                 140
Thr Gln Cys Tyr Gly Gln Pro Phe Ala Gln Arg Ser Phe Ser Leu Pro
145                 150                 155                 160
Asp Asp Lys Val Lys Ala Leu Leu Leu Gly Thr Val Asp Ala Leu Asp
                165                 170                 175
Thr Lys Ile His Val Leu Pro Gln Tyr Glu Trp Thr Ile Asp Ile Thr
                180                 185                 190
Leu Gly Ala Glu Gln Glu Ile Gln Glu Arg Ser Ala Glu Glu Arg Lys
                195                 200                 205
Ala Glu Ala Leu Glu Lys Arg Lys Lys Ala Asn Pro Asn Ala Lys Lys
                210                 215                 220
Pro Gly Gln Asn Trp His Lys His Thr Ala Gly Tyr Glu Leu Thr Asn
225                 230                 235                 240
Thr Leu Asn Ile Glu Gly Ser Phe Ala Tyr Thr Val Gly Pro Tyr Ser
                245                 250                 255
Arg Thr Leu Thr Arg Glu Leu Lys Lys Glu Phe Lys Glu Lys Arg His
                260                 265                 270
Lys Leu Gly Leu Leu Asn Lys Ser Ser Gln Ala Val Glu Thr Leu Gln
                275                 280                 285
Lys Leu Phe Ser Ser Glu Gly Ser Gln Glu Ile Lys Leu Leu Lys Thr
                290                 295                 300
Glu Ile Gln Thr Pro Glu Ile Lys Leu Gly Gly Gly Ser Lys Leu Val
305                 310                 315                 320
Asn Ala Thr His Gly Asn Gly Ala Tyr Phe Glu His Ala Val Glu Val
                325                 330                 335
Ala Leu Ser Pro Leu Ile Gly Val Lys Leu Gln Val Asp Leu Ile Gln
                340                 345                 350
Ala Phe Ala Thr Glu Phe Gly Ala Glu Lys Leu Ile Ala Leu Ile Arg
                355                 360                 365
Glu Gln Gly Leu Lys Gly Lys Glu Ala Val Glu Gly Arg Asn Gly
                370                 375                 380
Ala Tyr Leu Gly Ala Gln Leu Asp Met Ile Leu Glu Gly Ala Leu Asn
385                 390                 395                 400
Leu Ser Phe Lys Tyr Ala Ser Asn Glu Glu Arg Glu Met Glu Phe Gln
                405                 410                 415
Leu Gly Asp Met Val Lys Gly Thr Leu Ala Ile Arg Ala Glu Thr Asn
                420                 425                 430
```

```
Ile Gln Val Gly Phe Lys Tyr Tyr Leu Val Glu Gly Tyr Phe Lys Ala
            435                 440                 445

Asp Ala Asp Ile Glu Ala Gln Gly Cys Phe Glu Leu Asp Lys Gln Asp
    450                 455                 460

Lys Gly Leu Tyr Leu Val Phe Phe His Glu Gly Ile Thr Ala Ser Tyr
465                 470                 475                 480

Tyr Val Glu Phe Gly Met Gly Leu Val Pro Ser Glu Asn Asn Gly Lys
                485                 490                 495

Ser Ile Ile Lys Gly Ser Lys Val Asp Asn Lys Lys Gln Lys Lys Trp
            500                 505                 510

Glu Ile Tyr Pro Lys Leu Pro Lys Glu Lys Ser Thr Tyr Lys Leu Arg
            515                 520                 525

Leu Ser Glu
    530

<210> SEQ ID NO 159
<211> LENGTH: 530
<212> TYPE: PRT
<213> ORGANISM: Photorhabdus heterorhabditis

<400> SEQUENCE: 159

Met Leu Ser Val Asn Met Arg Ser Ala Val Cys Asp Cys Lys Ile Pro
1               5                   10                  15

Asp Pro Cys Ile His Lys Leu Val Leu Lys Val Gly Lys Arg Val Phe
            20                  25                  30

Asn Tyr Asn Gln Ile Glu Pro Ile Gly Asp Ile Trp Val Ile Asp Glu
        35                  40                  45

Thr Gly Gly Ile Pro Val Thr Ile Ser Leu Val Gly Lys Arg Cys Ile
    50                  55                  60

Thr Glu Asn Ala Gln Cys Pro Arg Ala Ile Phe Tyr Ser Pro Asp Asn
65                  70                  75                  80

Ala Ala Phe Gln Phe Tyr Glu Leu Gly Lys Asn Pro Ile Ala Gly Pro
                85                  90                  95

Gly Thr Asp Tyr Lys Ile Ser Phe Ser Ser His Asn Leu Pro Val Asp
            100                 105                 110

Leu Val Glu Asn Asp Pro Leu Ser Phe Ile Ala Ser Ser Leu Phe Gln
        115                 120                 125

Arg Gly Asp Leu Asn His Leu Pro Arg Thr Asp Tyr Ile Leu Thr Leu
    130                 135                 140

Thr Gln Cys Tyr Gly Gln Pro Phe Ala Gln Arg Ser Phe Ser Leu Pro
145                 150                 155                 160

Asp Asp Lys Val Lys Ala Leu Leu Gly Thr Val Asp Ala Leu Asp
                165                 170                 175

Thr Lys Ile His Val Leu Pro Gln Tyr Glu Trp Thr Ile Asp Ile Thr
            180                 185                 190

Leu Gly Ala Glu Gln Glu Ile Gln Glu Arg Ser Ala Glu Glu Arg Lys
        195                 200                 205

Ala Glu Ala Leu Glu Lys Arg Lys Lys Ala Asn Pro Asn Ala Lys Lys
    210                 215                 220

Pro Gly Gln Asn Trp His Lys His Thr Ala Gly Tyr Glu Leu Thr Asn
225                 230                 235                 240

Thr Leu Asn Ile Glu Gly Ser Phe Ala Tyr Thr Val Gly Pro Tyr Ser
                245                 250                 255

Arg Thr Leu Thr Arg Glu Leu Lys Lys Glu Phe Lys Glu Lys Arg His
```

```
                260                 265                 270
Lys Leu Gly Leu Leu Asn Lys Ser Ser Gln Ala Val Glu Thr Leu Gln
            275                 280                 285

Lys Leu Phe Ser Ser Glu Gly Ser Gln Glu Ile Lys Leu Leu Lys Thr
        290                 295                 300

Glu Ile Gln Thr Pro Glu Ile Lys Leu Gly Gly Ser Lys Leu Val
305                 310                 315                 320

Asn Ala Thr His Gly Asn Gly Ala Tyr Phe Glu His Ala Val Glu Val
                325                 330                 335

Ala Leu Ser Pro Leu Ile Gly Val Lys Leu Gln Val Asp Leu Ile Gln
            340                 345                 350

Ala Phe Ala Thr Glu Phe Gly Ala Glu Lys Leu Ile Ala Leu Ile Arg
        355                 360                 365

Glu Gln Gly Leu Lys Gly Lys Glu Ala Val Glu Gly Arg Asn Gly
            370                 375                 380

Ala Tyr Leu Gly Ala Gln Leu Asp Met Ile Leu Glu Gly Ala Leu Asn
385                 390                 395                 400

Leu Ser Phe Lys Tyr Ala Ser Asn Glu Glu Arg Glu Met Glu Phe Gln
                405                 410                 415

Leu Gly Asp Met Val Lys Gly Thr Leu Ala Ile Arg Ala Glu Thr Asn
            420                 425                 430

Ile Gln Val Gly Phe Lys Tyr Tyr Leu Val Glu Gly Tyr Phe Lys Ala
        435                 440                 445

Asp Ala Asp Ile Glu Ala Gln Gly Cys Phe Glu Leu Asp Lys Gln Asp
    450                 455                 460

Lys Gly Leu Tyr Leu Val Phe Phe His Glu Gly Ile Thr Ala Ser Tyr
465                 470                 475                 480

Tyr Val Glu Phe Gly Met Gly Ile Ala Pro Pro Lys Ser Asn Ser Asp
                485                 490                 495

Ser Ala Lys Gln Lys Asp Gly Lys Asp Ser Lys Thr Gln Lys Lys Trp
            500                 505                 510

Glu Ile Tyr Pro Lys Leu Pro Lys Glu Lys Ser Thr Tyr Lys Leu Arg
        515                 520                 525

Leu Ser
    530

<210> SEQ ID NO 160
<211> LENGTH: 528
<212> TYPE: PRT
<213> ORGANISM: Photorhabdus asymbiotica

<400> SEQUENCE: 160

Met Leu Ser Val Asn Met Arg Ser Ala Val Cys Asp Cys Lys Ile Pro
1               5                   10                  15

Asp Pro Cys Ile His Lys Leu Val Leu Lys Val Gly Lys Arg Val Phe
            20                  25                  30

Asn Tyr Asn Gln Ile Glu Pro Ile Gly Asp Ile Trp Val Val Asp Glu
        35                  40                  45

Thr Gly Gly Ile Pro Val Thr Ile Ser Leu Val Gly Lys Arg Cys Ile
    50                  55                  60

Thr Glu Asn Ala Gln Cys Pro Arg Ala Ile Phe Tyr Ser Pro Asp Asn
65                  70                  75                  80

Ala Ala Phe Gln Phe Tyr Glu Leu Gly Lys Asn Pro Met Ala Gly Pro
                85                  90                  95
```

```
Gly Thr Asp Tyr Lys Val Ser Phe Ala Arg Asp Asn Leu Leu Val Asp
            100                 105                 110

Leu Ile Glu Asn Asp Pro Leu Gly Phe Ile Ala Ser Ser Leu Phe Gln
        115                 120                 125

Arg Gly Glu Leu Asn His Leu Pro Arg Thr Asp Tyr Ile Leu Thr Leu
    130                 135                 140

Thr Gln Cys Tyr Gly Gln Pro Phe Ala Arg Arg Ser Phe Pro Leu Pro
145                 150                 155                 160

Asp Asp Lys Val Lys Ala Leu Leu Leu Gly Thr Val Asp Ala Leu Asp
                165                 170                 175

Thr Thr Ile His Val Leu Pro Gln Tyr Glu Trp Met Ile Asp Val Thr
            180                 185                 190

Ile Gly Ala Glu Gln Glu Ile Arg Glu Arg Ser Ala Glu Glu Arg Lys
        195                 200                 205

Ala Glu Ala Leu Glu Lys Arg Lys Lys Ala Asn Pro His Ala Lys Arg
    210                 215                 220

Pro Gly Gln Asn Trp His Lys His Thr Ala Gly Tyr Glu Leu Thr Asp
225                 230                 235                 240

Thr Leu Asn Leu Glu Gly Ser Phe Ala Tyr Thr Leu Gly Pro Tyr Ser
                245                 250                 255

Arg Thr Leu Thr Arg Glu Leu Glu Lys Glu Phe Lys Glu Lys Arg Asn
            260                 265                 270

Lys Leu Gly Val Leu Asn Lys Ser Gln Ala Ile Glu Thr Val Gln
        275                 280                 285

Lys Leu Phe Ser Ser Glu Gly Ser Gln Glu Ile Lys Leu Leu Lys Thr
    290                 295                 300

Glu Ile Gln Thr Pro Glu Ile Lys Leu Gly Gly Asp Ser Lys Leu Val
305                 310                 315                 320

Asn Ala Thr His Gly Asn Ala Ala Tyr Phe Glu His Ala Ile Glu Val
                325                 330                 335

Glu Leu Ala Pro Leu Ile Gly Ile Lys Leu Arg Leu Asp Leu Ile Glu
            340                 345                 350

Ala Phe Ala Thr Gln Phe Gly Val Glu Lys Leu Ile Lys Leu Ile Arg
        355                 360                 365

Glu Gln Gly Leu Lys Gly Lys Glu Val Val Glu Gly Arg Asn Gly
    370                 375                 380

Ala Tyr Leu Gly Ala Gln Leu Asp Met Val Leu Gly Ala Leu Asn
385                 390                 395                 400

Leu Ala Phe Lys Tyr Ala Ser Asn Glu Ala His Glu Met Glu Phe Glu
                405                 410                 415

Leu Gly Asp Leu Val Lys Gly Thr Leu Ala Ile Lys Ala Glu Thr Asn
            420                 425                 430

Ile Gln Ala Gly Phe Lys Tyr Tyr Leu Val Glu Gly Tyr Phe Lys Ala
        435                 440                 445

Asp Ala Asp Ile Glu Ala Gln Gly Cys Phe Glu Leu Asp Lys Gln Asp
    450                 455                 460

Lys Gly Leu Tyr Leu Val Phe Phe His Glu Gly Ile Thr Ala Ser Tyr
465                 470                 475                 480

Tyr Val Glu Phe Gly Val Gly Val Ala Pro Ser Glu Asn Lys Glu Asp
                485                 490                 495

Ser Phe Ser Gln Lys Ser Gly Asn Lys Lys Arg Glu Lys Trp Glu Val
            500                 505                 510

Tyr Pro Lys Leu Pro Lys Glu Lys Ser Thr Tyr Lys Leu Arg Leu Ser
```

<210> SEQ ID NO 161
<211> LENGTH: 531
<212> TYPE: PRT
<213> ORGANISM: Photorhabdus asymbiotica

<400> SEQUENCE: 161

```
Met Leu Ser Val Asn Met Arg Ser Ala Val Cys Asp Cys Lys Ile Pro
1               5                   10                  15

Asp Pro Cys Ile His Lys Leu Val Leu Lys Val Gly Lys Arg Val Phe
            20                  25                  30

Asn Tyr Asn Gln Ile Glu Pro Ile Gly Asp Ile Trp Val Val Asp Glu
        35                  40                  45

Thr Gly Gly Ile Pro Val Thr Ile Ser Leu Val Gly Lys Arg Cys Ile
50                  55                  60

Thr Glu Asn Ala Gln Cys Pro Arg Ala Ile Phe Tyr Ser Pro Asp Asn
65                  70                  75                  80

Ala Ala Phe Gln Phe Tyr Glu Leu Gly Lys Asn Pro Met Ala Gly Ser
                85                  90                  95

Gly Thr Asp Tyr Lys Val Ser Phe Ser Arg Asp Asn Leu Leu Val Asp
            100                 105                 110

Leu Ile Glu Asn Asp Pro Leu Gly Phe Ile Ala Ser Ser Leu Phe Gln
        115                 120                 125

Arg Gly Glu Leu Asn His Leu Pro Arg Thr Asp Tyr Ile Leu Thr Leu
130                 135                 140

Thr Gln Cys Tyr Gly Gln Pro Phe Ala Arg Arg Ser Phe Pro Leu Pro
145                 150                 155                 160

Asp Asp Lys Val Lys Ala Leu Leu Gly Thr Val Asp Ala Leu Asp
                165                 170                 175

Thr Thr Ile His Val Leu Pro Gln Tyr Glu Trp Met Ile Asp Val Thr
            180                 185                 190

Ile Gly Ala Glu Gln Glu Ile Arg Glu Arg Ser Ala Glu Glu Arg Lys
        195                 200                 205

Ala Glu Ala Leu Glu Lys Arg Lys Lys Ala Asn Pro His Ala Lys Arg
210                 215                 220

Pro Gly Gln Asn Trp His Lys His Thr Ala Gly Tyr Glu Leu Thr Asp
225                 230                 235                 240

Thr Leu Asn Leu Glu Gly Ser Phe Ala Tyr Thr Leu Gly Pro Tyr Ser
                245                 250                 255

Arg Thr Leu Thr Arg Glu Leu Glu Lys Glu Phe Lys Glu Lys Arg Asn
            260                 265                 270

Lys Leu Gly Val Leu Asn Lys Ser Ser Gln Ala Ile Glu Thr Val Gln
        275                 280                 285

Lys Leu Phe Ser Ser Glu Gly Ser Gln Glu Ile Lys Leu Leu Lys Thr
290                 295                 300

Glu Ile Gln Thr Pro Glu Ile Lys Leu Gly Gly Ser Lys Leu Val
305                 310                 315                 320

Asn Ala Thr His Gly Asn Ala Ala Tyr Phe Glu His Ala Ile Glu Val
                325                 330                 335

Glu Leu Ala Pro Leu Ile Gly Ile Lys Leu Arg Leu Asp Leu Ile Gly
            340                 345                 350

Ala Phe Ala Thr Gln Phe Gly Val Glu Lys Leu Ile Lys Leu Ile Arg
        355                 360                 365
```

```
Glu Gln Gly Leu Lys Gly Lys Glu Ala Val Glu Gly Arg Asn Gly
    370             375             380

Ala Tyr Leu Gly Ala Gln Leu Asp Met Val Leu Glu Gly Ala Leu Asn
385                 390                 395                 400

Leu Ala Phe Lys Tyr Ala Ser Asn Glu Ala His Glu Met Glu Phe Glu
            405                 410                 415

Leu Gly Asp Leu Val Lys Gly Thr Leu Ala Ile Lys Ala Glu Thr Asn
            420                 425                 430

Ile Gln Ala Gly Phe Arg Tyr Tyr Leu Val Glu Gly Tyr Phe Lys Ala
            435                 440                 445

Asp Ala Asp Ile Glu Ala Gln Gly Cys Phe Glu Leu Asp Lys Gln Asp
450                 455                 460

Lys Gly Leu Tyr Leu Val Phe Phe His Glu Gly Ile Thr Ala Ser Tyr
465                 470                 475                 480

Tyr Val Glu Phe Gly Val Gly Leu Val Pro Ser Glu Asn Asn Gly Lys
                485                 490                 495

Ser Ile Ile Lys Gly Ser Lys Val Asp Asn Lys Gln Lys Lys Trp
                500                 505                 510

Glu Ile Tyr Pro Arg Leu Pro Lys Glu Lys Ser Thr Tyr Lys Leu Arg
            515                 520                 525

Leu Ser Glu
    530

<210> SEQ ID NO 162
<211> LENGTH: 530
<212> TYPE: PRT
<213> ORGANISM: Photorhabdus asymbiotica

<400> SEQUENCE: 162

Met Leu Ser Val Asn Met Arg Ser Ala Val Cys Asp Cys Lys Ile Pro
1               5                   10                  15

Asp Pro Cys Ile His Lys Leu Val Leu Lys Val Gly Lys Arg Val Phe
                20                  25                  30

Asn Tyr Asn Gln Ile Glu Pro Ile Gly Asp Ile Trp Val Val Asp Glu
            35                  40                  45

Thr Gly Gly Ile Pro Val Thr Ile Ser Leu Val Gly Lys Arg Cys Ile
50                  55                  60

Thr Glu Asn Ala Gln Cys Pro Arg Ala Ile Phe Tyr Ser Pro Asp Asn
65                  70                  75                  80

Ala Ala Phe Gln Phe Tyr Glu Leu Gly Lys Asn Pro Met Ala Gly Ser
                85                  90                  95

Gly Thr Asp Tyr Lys Val Ser Phe Ser Arg Asp Asn Leu Leu Val Asp
            100                 105                 110

Leu Ile Glu Asn Asp Pro Leu Gly Phe Ile Ala Ser Ser Leu Phe Gln
            115                 120                 125

Arg Gly Glu Leu Asn His Leu Pro Arg Thr Asp Tyr Ile Leu Thr Leu
            130                 135                 140

Thr Gln Cys Tyr Gly Gln Pro Phe Ala Arg Arg Ser Phe Pro Leu Pro
145                 150                 155                 160

Asp Asp Lys Val Lys Ala Leu Leu Leu Gly Met Val Asp Ala Leu Asp
                165                 170                 175

Thr Thr Ile His Val Leu Pro Gln Tyr Glu Trp Met Ile Asp Val Thr
            180                 185                 190

Ile Gly Ala Glu Gln Glu Ile Arg Glu Arg Ser Ala Glu Glu Arg Lys
            195                 200                 205
```

Thr Glu Ala Leu Glu Lys Arg Lys Lys Ala Asn Pro His Ala Lys Arg
    210                 215                 220

Pro Gly Gln Asn Trp His Lys His Thr Ala Gly Tyr Glu Leu Thr Asn
225                 230                 235                 240

Thr Leu Asn Leu Glu Gly Ser Phe Ala Tyr Thr Leu Gly Pro Tyr Ser
                245                 250                 255

Arg Thr Leu Thr Arg Glu Leu Glu Lys Glu Phe Lys Glu Lys Arg Asn
            260                 265                 270

Lys Leu Gly Val Leu Asn Lys Ser Gln Ala Ile Glu Thr Val Gln
        275                 280                 285

Lys Leu Phe Ser Ser Glu Gly Ser Gln Glu Ile Lys Leu Leu Lys Thr
    290                 295                 300

Glu Ile Gln Thr Pro Glu Ile Lys Leu Gly Gly Gly Ser Lys Leu Val
305                 310                 315                 320

Asn Ala Thr His Gly Asn Ala Ala Tyr Phe Glu His Ala Ile Glu Val
                325                 330                 335

Glu Leu Ala Pro Leu Ile Gly Ile Lys Leu Arg Leu Asp Leu Ile Glu
            340                 345                 350

Ala Phe Ala Thr Gln Phe Gly Val Glu Lys Leu Ile Lys Leu Ile Arg
        355                 360                 365

Glu Gln Gly Leu Lys Gly Lys Glu Ala Val Glu Glu Gly Arg Asn Gly
    370                 375                 380

Ala Tyr Leu Gly Ala Gln Leu Asp Met Val Leu Glu Gly Ala Leu Asn
385                 390                 395                 400

Leu Ala Phe Lys Tyr Ala Ser Asn Glu Ala His Glu Met Glu Phe Glu
                405                 410                 415

Leu Gly Asp Leu Val Lys Gly Thr Leu Ala Ile Lys Ala Glu Thr Asn
            420                 425                 430

Ile Gln Ala Gly Phe Lys Tyr Tyr Leu Val Glu Gly Tyr Phe Lys Ala
        435                 440                 445

Asp Ala Asp Ile Glu Ala Gln Gly Cys Phe Glu Leu Asp Lys Gln Asp
    450                 455                 460

Lys Gly Leu Tyr Leu Val Phe Phe His Glu Gly Ile Thr Ala Ser Tyr
465                 470                 475                 480

Tyr Val Glu Phe Gly Ala Gly Val Ser Pro Ser Glu Asn Ser Asn Glu
                485                 490                 495

Ser Ser Lys Gln Asn Ser Lys Arg Asp Asp Lys Lys Gln Lys Lys Trp
            500                 505                 510

Glu Ile Tyr Pro Lys Leu Ser Lys Glu Lys Ser Thr Tyr Lys Leu Arg
        515                 520                 525

Leu Ser
    530

<210> SEQ ID NO 163
<211> LENGTH: 530
<212> TYPE: PRT
<213> ORGANISM: Photorhabdus luminescens

<400> SEQUENCE: 163

Met Leu Ser Val Asn Met Arg Ser Ala Val Cys Asp Cys Lys Thr Pro
1               5                   10                  15

Asp Leu Cys Ile His Lys Leu Val Leu Lys Val Gly Lys Arg Val Phe
            20                  25                  30

His Tyr Asn Gln Ile Glu Pro Ile Gly Asp Ile Trp Val Val Asp Glu

```
            35                  40                  45
Ala Glu Gly Ile Pro Val Ser Val Ser Leu Val Gly Lys Gln Cys Ile
 50                  55                  60

Thr Glu Asn Ala His Cys Pro Lys Ala Ile Phe Tyr Ser Pro Asp Asn
 65                  70                  75                  80

Pro Ala Phe Gln Phe Tyr Glu Leu Ser Lys Asn Pro Ile Lys Gly Pro
                 85                  90                  95

Gly Val Asp Tyr Glu Ile Ser Phe Ser Arg His Asn Leu Pro Val Asp
                100                 105                 110

Pro Ile Ala Ser Asp Pro Leu Gly Phe Ile Ala Ser Trp Leu Phe Gln
            115                 120                 125

Lys Gly Asp Leu Asn Cys Leu Pro His Thr Asp Tyr Ile Leu Thr Leu
        130                 135                 140

Thr Gln Cys Tyr Gly Gln Pro Phe Ala Gln Arg Ser Phe Leu Leu Pro
145                 150                 155                 160

Asp Asp Lys Val Lys Met Leu Met Leu Gly Arg Val Asp Ala Leu Ser
                165                 170                 175

Thr Lys Ile His Val Leu Pro Gln Tyr Glu Trp Thr Leu Asp Ile Thr
            180                 185                 190

Ile Gly Ala Glu Gln Glu Val Arg Glu Arg Ser Ala Glu Glu Arg Lys
        195                 200                 205

Ala Glu Ala Leu Glu Glu Arg Gln Lys Asn Asn Pro Asn Ala Lys Lys
210                 215                 220

Pro Gly Gln Asn Trp His Lys His Thr Ala Gly Tyr Glu Leu Thr Asn
225                 230                 235                 240

Thr Leu Thr Val Glu Gly Ser Phe Ala Tyr Thr Leu Gly Pro Tyr Ser
                245                 250                 255

His Thr Phe Thr Arg Glu Leu Glu Lys Glu Phe Lys Glu Lys Arg Lys
            260                 265                 270

Lys Leu Gly Leu Val Asn Lys Gly Leu Gln Ala Val Glu Thr Leu Gln
        275                 280                 285

Lys Leu Phe Ser Ser Glu Gly Ser Gln Glu Ile Lys Leu Leu Glu Val
    290                 295                 300

Glu Ile Gln Thr Pro Glu Ile Lys Leu Ser Gly Gly Ser Lys Leu Val
305                 310                 315                 320

Asn Ala Thr His Gly Asp Ala Ala Tyr Phe Glu His Ala Val Ser Val
                325                 330                 335

Ala Leu Glu Pro Leu Ile Gly Ile Lys Leu Arg Leu Asp Leu Ile Glu
            340                 345                 350

Ala Phe Ala Thr Glu Phe Gly Val Glu Lys Leu Ile Ala Leu Ile Arg
        355                 360                 365

Glu Gln Gly Leu Lys Gly Lys Ala Ala Val Glu Glu Gly Arg Asn Gly
    370                 375                 380

Ala Tyr Leu Gly Ala Gln Leu Asp Met Ile Leu Glu Gly Ala Leu Asn
385                 390                 395                 400

Leu Ser Phe Lys Tyr Ala Ser Asn Glu Glu His Lys Met Glu Phe Gln
                405                 410                 415

Leu Gly Asp Met Val Arg Gly Thr Leu Ala Ile Lys Ala Glu Thr Asn
            420                 425                 430

Ile Gln Ala Gly Phe Lys Tyr Tyr Leu Val Glu Gly Tyr Phe Asn Ala
        435                 440                 445

Glu Ala Asp Ile Glu Ala Glu Gly Cys Phe Glu Leu Asp Lys Gln Asp
    450                 455                 460
```

```
Lys Glu Leu Ser Leu Val Phe Phe His His Gly Ile Val Ala Ser Tyr
465                 470                 475                 480

Tyr Val Glu Tyr Gly Ala Gly Ile Ala Pro Pro Lys Ser Asn Arg Asp
                485                 490                 495

Ser Ala Lys Gln Lys Asp Gly Lys Asp Asn Lys Lys Gln Lys Lys Trp
                500                 505                 510

Glu Ile Tyr Pro Lys Leu Pro Lys Glu Lys Ser Thr Tyr Lys Leu Arg
                515                 520                 525

Leu Ser
    530

<210> SEQ ID NO 164
<211> LENGTH: 529
<212> TYPE: PRT
<213> ORGANISM: Photorhabdus luminescens

<400> SEQUENCE: 164

Met Leu Ser Val Asn Met Lys Ser Ala Val Cys Asp Cys Lys Thr Pro
1               5                   10                  15

Asp Pro Cys Ile His Lys Leu Val Leu Lys Val Gly Lys Arg Val Phe
                20                  25                  30

His Tyr Asn Gln Ile Glu Pro Ile Gly Asp Ile Trp Val Val Asp Glu
                35                  40                  45

Ala Glu Gly Ile Pro Val Ser Val Ser Leu Val Gly Lys Gln Cys Ile
            50                  55                  60

Thr Glu Asn Ala His Cys Pro Lys Ala Val Phe Tyr Ser Pro Asp Asn
65                  70                  75                  80

Pro Ala Phe Gln Phe Tyr Glu Leu Asp Lys Asn Pro Ile Lys Gly Pro
                85                  90                  95

Gly Val Asp Tyr Glu Ile Ser Phe Ser Arg His Ser Leu Ser Val Asp
                100                 105                 110

Pro Ile Ala Asn Asp Pro Leu Gly Phe Ile Ala Ser Trp Leu Phe Gln
                115                 120                 125

Lys Gly Asp Leu Asn Tyr Leu Pro His Thr Asp Tyr Ile Leu Thr Leu
            130                 135                 140

Thr Gln Cys Tyr Gly Gln Pro Phe Ala Gln Arg Ser Phe Leu Leu Pro
145                 150                 155                 160

Asp Asp Lys Met Lys Lys Val Leu Leu Gly Leu Val Asn Ala Leu Asp
                165                 170                 175

Thr Lys Ile His Val Leu Pro Gln Tyr Glu Trp Thr Leu Asp Val Thr
                180                 185                 190

Ile Gly Ala Glu Gln Glu Ala Arg Glu Arg Ser Ala Ala Glu Arg Lys
            195                 200                 205

Ala Glu Ala Leu Lys Glu Arg Lys Ile Asn Pro Asn Ala Lys Lys
        210                 215                 220

Pro Gly Gln Asn Trp His Lys His Thr Ala Gly Tyr Glu Leu Thr Asp
225                 230                 235                 240

Thr Leu Thr Val Glu Gly Ser Phe Ala Tyr Thr Leu Gly Pro Tyr Ser
                245                 250                 255

His Thr Val Thr Arg Glu Leu Glu Lys Phe Lys Glu Lys Arg Lys
                260                 265                 270

Lys Leu Gly Leu Val Asn Lys Gly Phe Gln Ala Val Glu Thr Leu Gln
            275                 280                 285

Lys Leu Phe Ser Ser Glu Gly Ser Gln Glu Ile Lys Leu Leu Glu Val
```

```
            290                 295                 300
Glu Ile Gln Thr Pro Glu Ile Lys Leu Ser Gly Gly Ser Lys Leu Val
305                 310                 315                 320

Asn Ala Thr His Gly Asn Glu Ala Tyr Phe Glu His Ala Val Ser Val
                325                 330                 335

Ala Leu Ala Pro Leu Ile Gly Met Lys Leu Arg Leu Asp Leu Ile Glu
                340                 345                 350

Ala Phe Ala Thr Glu Phe Gly Gly Glu Lys Leu Ile Ala Leu Ile Arg
                355                 360                 365

Glu Gln Gly Leu Lys Gly Gln Glu Ala Val Lys Glu Gly Arg Asn Gly
            370                 375                 380

Ala Tyr Leu Gly Ala Gln Leu Asp Met Ile Leu Glu Gly Ala Leu Asn
385                 390                 395                 400

Leu Ser Phe Lys Tyr Ala Ser Asn Glu Glu His Lys Met Glu Phe Gln
                405                 410                 415

Leu Gly Asp Met Val Arg Gly Thr Leu Ala Ile Lys Ala Glu Thr Asn
                420                 425                 430

Ile Gln Ala Gly Phe Lys Tyr Tyr Leu Val Glu Gly Tyr Phe Asn Ala
            435                 440                 445

Glu Ala Asp Ile Glu Ala Gly Cys Phe Glu Leu Asp Lys Gln Asp
        450                 455                 460

Lys Glu Leu Ser Leu Val Phe Phe His Glu Gly Ile Thr Ala Ser Tyr
465                 470                 475                 480

Tyr Val Asp Tyr Gly Val Gly Val Ala Pro Ser Glu Asn Lys Glu Asp
                485                 490                 495

Ser Phe Ser Lys Arg Ser Ser Asn Lys Lys Arg Lys Lys Trp Glu Ile
                500                 505                 510

Tyr Pro Lys Leu Ser Lys Glu Lys Ser Thr Tyr Lys Leu Arg Leu Ser
            515                 520                 525

Gln

<210> SEQ ID NO 165
<211> LENGTH: 529
<212> TYPE: PRT
<213> ORGANISM: Photorhabdus luminescens

<400> SEQUENCE: 165

Met Leu Ser Val Asn Met Lys Ser Ala Val Cys Asp Cys Lys Thr Pro
1               5                   10                  15

Asp Pro Cys Ile His Lys Leu Val Leu Lys Val Gly Lys Arg Val Phe
                20                  25                  30

His Tyr Asn Gln Ile Glu Pro Ile Gly Asp Ile Trp Val Val Asp Glu
            35                  40                  45

Ala Glu Gly Ile Pro Val Ser Val Ser Leu Val Gly Lys Gln Cys Ile
        50                  55                  60

Thr Glu Asn Ala His Cys Pro Lys Ala Val Phe Tyr Ser Pro Asp Asn
65                  70                  75                  80

Pro Ala Phe Gln Phe Tyr Glu Leu Asp Lys Asn Pro Ile Lys Gly Pro
                85                  90                  95

Gly Val Asp Tyr Glu Ile Ser Phe Ser Arg His Ser Leu Ser Val Asp
                100                 105                 110

Pro Ile Ala Asn Asp Pro Leu Gly Phe Ile Ala Ser Trp Leu Phe Gln
            115                 120                 125

Lys Gly Glu Leu Asn Tyr Leu Pro His Thr Asp Tyr Ile Leu Thr Leu
```

```
                130               135                140
Thr Gln Cys Tyr Gly Gln Pro Phe Ala Gln Arg Ser Phe Leu Leu Pro
145                 150                 155                 160

Asp Asp Lys Met Lys Val Leu Leu Gly Leu Val Asn Ala Leu Asp
                165                 170                 175

Thr Lys Ile His Val Leu Pro Gln Tyr Glu Trp Thr Leu Asp Val Thr
            180                 185                 190

Ile Gly Ala Glu Gln Glu Ala Arg Glu Arg Ser Ala Ala Glu Arg Lys
            195                 200                 205

Ala Glu Ala Leu Lys Glu Arg Lys Lys Ile Asn Pro Asn Ala Lys Lys
        210                 215                 220

Pro Gly Gln Asn Trp His Lys His Thr Ala Gly Tyr Glu Leu Thr Asp
225                 230                 235                 240

Thr Leu Thr Ala Glu Gly Ser Phe Ala Tyr Thr Leu Gly Pro Tyr Ser
                245                 250                 255

His Thr Val Thr Arg Glu Leu Glu Lys Glu Phe Lys Glu Lys Arg Lys
                260                 265                 270

Lys Leu Gly Leu Val Asn Lys Gly Phe Gln Ala Val Glu Thr Leu Gln
            275                 280                 285

Lys Leu Phe Ser Ser Glu Gly Ser Gln Glu Ile Lys Leu Leu Glu Val
        290                 295                 300

Glu Ile Gln Thr Pro Glu Ile Lys Leu Ser Gly Gly Ser Lys Leu Val
305                 310                 315                 320

Asn Ala Thr His Gly Asn Glu Ala Tyr Phe Glu His Ala Val Ser Val
                325                 330                 335

Ala Leu Ala Pro Leu Ile Gly Ile Lys Leu Arg Leu Asp Leu Ile Glu
                340                 345                 350

Ala Phe Ala Thr Glu Phe Gly Gly Glu Lys Leu Ile Ala Leu Ile Arg
            355                 360                 365

Glu Gln Gly Leu Lys Gly Gln Glu Ala Val Lys Glu Gly Arg Asn Gly
        370                 375                 380

Ala Tyr Leu Gly Ala Gln Leu Asp Met Ile Leu Glu Gly Ala Leu Asn
385                 390                 395                 400

Leu Ser Phe Lys Tyr Ala Ser Asn Glu Glu His Lys Met Glu Phe Gln
                405                 410                 415

Leu Gly Asp Met Val Arg Gly Thr Leu Ala Ile Lys Ala Glu Thr Asn
                420                 425                 430

Ile Gln Ala Gly Phe Lys Tyr Tyr Leu Val Glu Gly Tyr Phe Arg Ala
            435                 440                 445

Glu Ala Asp Ile Glu Ala Glu Gly Cys Phe Glu Leu Asp Lys Gln Asp
        450                 455                 460

Lys Glu Leu Ser Leu Val Phe Phe His Glu Gly Ile Thr Ala Ser Tyr
465                 470                 475                 480

Tyr Val Asp Tyr Gly Val Gly Val Ala Pro Ser Glu Asn Lys Glu Asp
                485                 490                 495

Ser Phe Ser Lys Arg Ser Ser Asn Lys Arg Lys Lys Trp Glu Ile
                500                 505                 510

Tyr Pro Lys Leu Ser Lys Glu Lys Ser Thr Tyr Lys Leu Arg Leu Ser
            515                 520                 525

Gln

<210> SEQ ID NO 166
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 166

Phe Trp Tyr His Lys Met Ile Leu Val Ala Gly Cys
1               5                   10

<210> SEQ ID NO 167
<211> LENGTH: 12
<212> TYPE: PRT
<213> ORGANISM: Artificial Sequence
<220> FEATURE:
<223> OTHER INFORMATION: Synthetic

<400> SEQUENCE: 167

Trp Tyr His Lys Arg Glu Asp Cys Ser Thr Asn Gln
1               5                   10

<210> SEQ ID NO 168
<211> LENGTH: 9
<212> TYPE: PRT
<213> ORGANISM: Artificial Sequence
<220> FEATURE:
<223> OTHER INFORMATION: Synthetic

<400> SEQUENCE: 168

Val Cys Ala Gly Ser Pro Thr Asn Asp
1               5

<210> SEQ ID NO 169
<211> LENGTH: 4
<212> TYPE: PRT
<213> ORGANISM: Artificial Sequence
<220> FEATURE:
<223> OTHER INFORMATION: Synthetic

<400> SEQUENCE: 169

Phe Trp Tyr His
1

<210> SEQ ID NO 170
<211> LENGTH: 5
<212> TYPE: PRT
<213> ORGANISM: Artificial Sequence
<220> FEATURE:
<223> OTHER INFORMATION: Synthetic

<400> SEQUENCE: 170

His Lys Arg Glu Asp
1               5

<210> SEQ ID NO 171
<211> LENGTH: 5
<212> TYPE: PRT
<213> ORGANISM: Artificial Sequence
<220> FEATURE:
<223> OTHER INFORMATION: Synthetic peptide

<400> SEQUENCE: 171

Arg Gly Asp Tyr Cys
1               5

<210> SEQ ID NO 172
<211> LENGTH: 5
<212> TYPE: PRT
```

-continued

```
<213> ORGANISM: Artificial Sequence
<220> FEATURE:
<223> OTHER INFORMATION: Synthetic peptide

<400> SEQUENCE: 172

Ala Ser Ser His Asn
1               5

<210> SEQ ID NO 173
<211> LENGTH: 6
<212> TYPE: PRT
<213> ORGANISM: Artificial Sequence
<220> FEATURE:
<223> OTHER INFORMATION: Synthetic peptide

<400> SEQUENCE: 173

Lys Cys Cys Tyr Ser Leu
1               5

<210> SEQ ID NO 174
<211> LENGTH: 7
<212> TYPE: PRT
<213> ORGANISM: Artificial Sequence
<220> FEATURE:
<223> OTHER INFORMATION: Synthetic peptide

<400> SEQUENCE: 174

Tyr Glu Val Gly His Arg Cys
1               5
```

TARGET RECOGNITION MOTIFS AND USES THEREOF

CROSS-REFERENCE TO RELATED APPLICATIONS

This application is a divisional application of U.S. application Ser. No. 16/374,670, filed Apr. 3, 2019, which claims the benefit of U.S. Provisional Application No. 62/652,278, filed Apr. 3, 2018. The entire contents of the above-identified applications are hereby fully incorporated herein by reference.

STATEMENT REGARDING FEDERALLY SPONSORED RESEARCH

This invention was made with government support under Grant Nos. HG009761, MH110049, and HL141201 awarded by the National Institutes of Health. The government has certain rights in the invention.

REFERENCE TO AN ELECTRONIC SEQUENCE LISTING

The contents of the electronic sequence listing ("BROD-2890US-DIV1_ST25.txt"; Size is 226,035 bytes and it was created on Dec. 15, 2022) is herein incorporated by reference in its entirety.

TECHNICAL FIELD

The invention provides novel programmable targeting sequences and applications thereof. The targeting sequences can be engineered for binding to proteins, polypeptides, and other macromolecules.

BACKGROUND

The harnessing of biological diversity is providing advances in human health, agriculture and industry. Available methods offer limited variability and do not offer the diversity of structure and function found in nature. The invention expands the repertoire of tools and techniques for targeting and modifying biological systems and components.

Citation or identification of any document in this application is not an admission that such document is available as prior art to the present invention.

SUMMARY

In certain embodiments, there is provided an engineered protein or polypeptide comprising one or more engineered *Photorhabdus* target recognition sequence (TRS) motifs. In one embodiment, the TRS motif is determined from *Photorhabdus* tandem repeat proteins.

The invention provides a TRS that comprises one or more amino acid sequences comprising: $X_1(E/K)(N/D)X_2(S/T)X_3$ (SEQ ID NO:1) flanking by a hydrophobic region and a charged region; wherein $X_1$ comprises 1-7 amino acid residues comprising at least one hydrophobic amino acid residue, at least one charged amino acid residue, and/or at least one polar amino acid residue, wherein $X_2$ comprises 0 to 12 polar, hydrophobic, and/or charged amino acid residues, and wherein $X_3$ comprises 1 to 7 amino acid residues comprising a polar amino acid residue, a hydrophobic amino acid residue and/or a charged amino acid residue, wherein the hydrophobic region comprises at least one hydrophobic amino acid residue, and wherein the charged region comprises at least one charged amino acid residue.

In some embodiments, the hydrophobic region further comprises a polar amino acid residue and/or a charged amino acid residue. In other embodiments, the charged region further comprises a polar amino acid residue and/or a hydrophobic amino acid residue.

In one embodiment, the TRS comprises one or more sequences comprising: $X_1(E/K)(N/D)X_2(S/T)X_3$ (SEQ ID NO:2) flanking by a hydrophobic region and a charged region; wherein $X_1$ comprises 1-7 amino acid residues comprising at least one polar amino acid residue and one hydrophobic amino acid residue, wherein $X_2$ comprises 0 to 12 polar, hydrophobic, and/or charged amino acid residues, and wherein $X_3$ comprises 1 to 7 amino acid residues comprising a polar amino acid residue, a hydrophobic amino acid residue and/or a charged amino acid residue, wherein the hydrophobic region comprises at least one hydrophobic amino acid residue, and wherein the charged region comprises at least one charged amino acid residue.

In another embodiment, the TRS comprises one or more sequences comprising $X_1(E/K)(N/D)X_2(S/T)X_3$ (SEQ ID NO:3) flanking by a hydrophobic region and a charged region, wherein $X_1$ comprises 1-4 amino acid residues comprising at least one hydrophobic residue and/or one polar residue, $X_2$ comprises 1 to 8 polar and/or charged amino acid residues, $X_3$ comprises 1 to 5 hydrophobic and/or charged amino acid residues, $X_4$ comprises 1 to 4 amino acids comprising at least one charged amino acid residue, the hydrophobic region comprises at least one hydrophobic residue, and the charged region comprises at least one charged amino acid residue. In one embodiment, the hydrophobic region comprises at least 2 hydrophobic residues or at least 3 hydrophobic residues. In yet another embodiment, the charged region comprises at least 2 charged amino acid residues, at least 3 charged amino acid residues, at least 4 charged amino acid residues, or at least 5 charged amino acid residues.

In yet another embodiment, the TRS comprises one or more sequences comprising $X_1(E/K)(N/D)X_2(S/T)X_3$ (SEQ ID NO:4) flanking by a hydrophobic region and a charged region, wherein $X_1$ comprises 1-7 amino acid residues comprising a charged residue, a polar residue, and/or a hydrophobic residue, $X_2$ comprises 0 to 12 polar, hydrophobic, and/or charged amino acid residues, $X_3$ comprises 1 to 7 amino acids comprising a charged residue and/or a polar residue, the hydrophobic region comprises at least one hydrophobic residue, and the charged region comprises at least one charged amino acid residue. In one embodiment, the hydrophobic region comprises at least 2 hydrophobic residues or at least 3 hydrophobic residues. In yet another embodiment, the charged region comprises at least 2 charged amino acid residues, at least 3 charged amino acid residues, at least 4 charged amino acid residues, or at least 5 charged amino acid residues.

In one embodiment, the TRS is about 15-75 amino acids in length. In another embodiment, the TRS is about 15 to 60 amino acids in length. In yet another embodiment, the TRS is about 15 to 50 amino acids in length. In other embodiments, the TRS is about 15 to 40 amino acids in length, about 18 to 40 amino acids in length, or about 19-39 amino acids in length. In other embodiments, the TRS is at least 15, at least 16, at least 17, at least 18, at least 19, or at least 20 amino acids in length.

In one embodiment, $X_1$ comprises 1-4 amino acid residues. In another embodiment, $X_2$ comprises 1-8 amino acid residues. In yet another embodiment, $X_3$ comprises 1-4 amino acid residues. In another embodiment, the hydrophobic region comprises at least 2 residues, at least 3 residues, at least 4 residues, at least 5 residues, at least 6 residues, at least 7 residues, at least 8 residues, at least 9 residues, at least 10 residues. In another embodiment, the hydrophobic region comprises 1-15 amino acid residues, or 1-12 amino acid residues, or 1-10 amino acid residues, or 1-5 amino acid residues. In another embodiment, the charged region comprises at least 2 amino acid residues, at least 3 amino acid residues, at least 4 amino acid residues, at least 5 amino acid residues, at least 6 amino acid residues, at least 7 amino acid residues, at least 8 amino acid residues, at least 9 amino acid residues, or at least 10 amino acid residues. In yet another embodiment, the charged region comprises 1-15 amino acid residues, or 1-12 amino acid residues, or 1-10 amino acid residues, or 1-8 amino acid residues, or 1-5 amino acid residues. In yet another embodiment, $X_1$ comprises 1-4 amino acid residues, $X_2$ comprises 1-8 amino acid residues, and $X_3$ comprises 1-4 amino acid residues, the hydrophobic region comprises 1-12 amino acid residues, and the charged region comprises 1-8 amino acid residues.

In any of the above embodiments, the hydrophobic residues comprise leucine (L), proline (P), methionine (M), alanine (A), isoleucine (I), glycine (G), valine (V), phenylalanine (F), and tryptophan (W), the polar residues comprise threonine (T), serine (S), tyrosine (Y), glutamine (Q), asparagine (N), and histidine (H), and the charged amino acid residues comprise lysine (K), arginine (R), glutamic acid (E), and aspartic acid (D).

In one embodiment, the TRS comprises one or more sequences comprising $X_1$(E/K)(N/D)$X_2$(S/T)$X_3$ (SEQ ID NO:5) flanking by a hydrophobic region and a charged region,
wherein $X_1$ comprises:
(a) a proline or a threonine or an isoleucine (P/T/I), or
(b) a proline, a serine, or a threonine (P/S/T);
wherein $X_2$ comprises
(a) a serine, a phenylalanine, or a valine (S/F/V),
(b) a asparagine or a glutamine (N/Q), or
(c) an arginine or a lysine (R/K);
wherein $X_3$ comprises
(a) a lysine, an arginine, or an asparagine (K/R/N), or
(b) an aspartic acid, a threonine, or a glycine (D/T/G);
wherein the hydrophobic region comprises
(a) a glycine (G), and/or
(b) a valine, a leucine, or an alanine (V/L/A); and/or
wherein the charged region comprises
(a) a lysine (K)
(b) a lysine or a glutamic acid (K/E), and/or
(c) a glutamine (Q).

In another embodiment, the TRS comprises one or more sequences comprising $X_1$(E/K)(N/D)$X_2$(S/T)$X_3$ (SEQ ID NO: 1) flanked by a hydrophobic region and a charged region, wherein $X_1$, $X_2$, and $X_3$, comprise the combinations as detailed in Table 1.

In some embodiments, at least one of the one or more TRS motifs comprises:
$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$, wherein $X_5$ is K or E, $X_6$ is N or D, $X_{15}$ is S or T, $X_{16}$ is K, N, or R, and each of $X_1$, $X_2$, $X_3$, $X_4$, $X_7$, $X_8$, $X_9$, $X_{10}$, $X_{11}$, $X_{12}$, $X_{13}$, $X_{14}$, $X_{17}$, and $X_{18}$ is any amino acid; or
$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$, wherein $X_1$ is K, T, V, or I, $X_2$ is A, K, S, or G, $X_3$ is P, I, or T, $X_4$ is T, P, or S, $X_5$ is K or E, $X_6$ is N or D, $X_7$ is N, E, I, or R, $X_8$ is D, E, G, or N, $X_9$ is D, S, A, E, or N, $X_{10}$ is S, F, or V, $X_{11}$ is F, S, I, T, or V, $X_{12}$ is K, N, E, or G, $X_{13}$ is Q, H, K, N, or P, $X_{14}$ is K, I, N, Q, or R, $X_{15}$ is S or T, $X_{16}$ is K, N, or R, $X_{17}$ is M, V, S, or T, $X_{18}$ is D, G, or T, and $X_{19}$ is T, N, D, or A.

In some embodiments, the protein or polypeptide comprises a functional domain. In some embodiments, the protein or polypeptide comprises an insecticidal toxin or component thereof.

In another aspect, the present disclosure provides for a polynucleotide encoding the engineered protein or polypeptide herein. In some embodiments, the sequence of the polynucleotide is optimized for expression in a host cell. In some embodiments, the host cell is a prokaryotic cell. In some embodiments, the host cell is a eukaryotic cell. In some embodiments, the eukaryotic cell is a human cell, a mammalian cell, a plant cell, or a yeast cell. In some embodiments, the polynucleotide comprises a regulatory element. In some embodiments, the regulatory element is inducible.

In another aspect, the present disclosure provides a vector comprising the polynucleotide herein. In some embodiments, the vector is a viral vector, a bacteriophage vector, or a plasmid vector.

In another aspect, the present disclosure provides a delivery system comprising the protein or polypeptide herein, the polynucleotide herein, and/or the vector herein.

In another aspect, the present disclosure provides a method of engineering a TRS of the proteins disclosed herein to bind to a target of interest, which comprises one or more of: duplicating the TRS, mutating the TRS, substituting the TRS, shuffling the TRS, linking a TRS from a different source; and detecting whether the TRS binds to the target. In some embodiments, the TRS is associated with a detectable moiety. In some embodiments, the TRS and the detectable moiety are covalently linked. In some embodiments, the target comprises a macromolecule. In some embodiments, the macromolecule comprises a protein or polypeptide. In some embodiments, the macromolecule comprises a nucleic acid.

In another aspect, the present disclosure provides a method of engineering a protease to bind to a target substrate of interest, which comprises: inserting or modifying a TRS herein in the protease; and detecting whether the engineered protease binds to the target substrate; or detecting whether the engineered protease cleaves the target substrate.

In another aspect, the present disclosure provides a method of cleaving a target substrate, which comprises contacting an engineered protease herein with the substrate of interest. In some embodiments, the engineered protease and the target substrate are contacted in vivo, ex vivo, or in vitro.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 3A-3C depict a *Photorhabdus* array encoding long and short proteins. A. Repeat structure of the locus. B. Repeated (long) proteins are characterized by a hypervariable region at the C-terminal. C. Highly variable region of the long hypervariable protein (HP) without insertions of deletions; relative frequencies of amino acids occurring at each position are depicted (SEQ ID NOS:6-13).

Figures 5A, 5B:
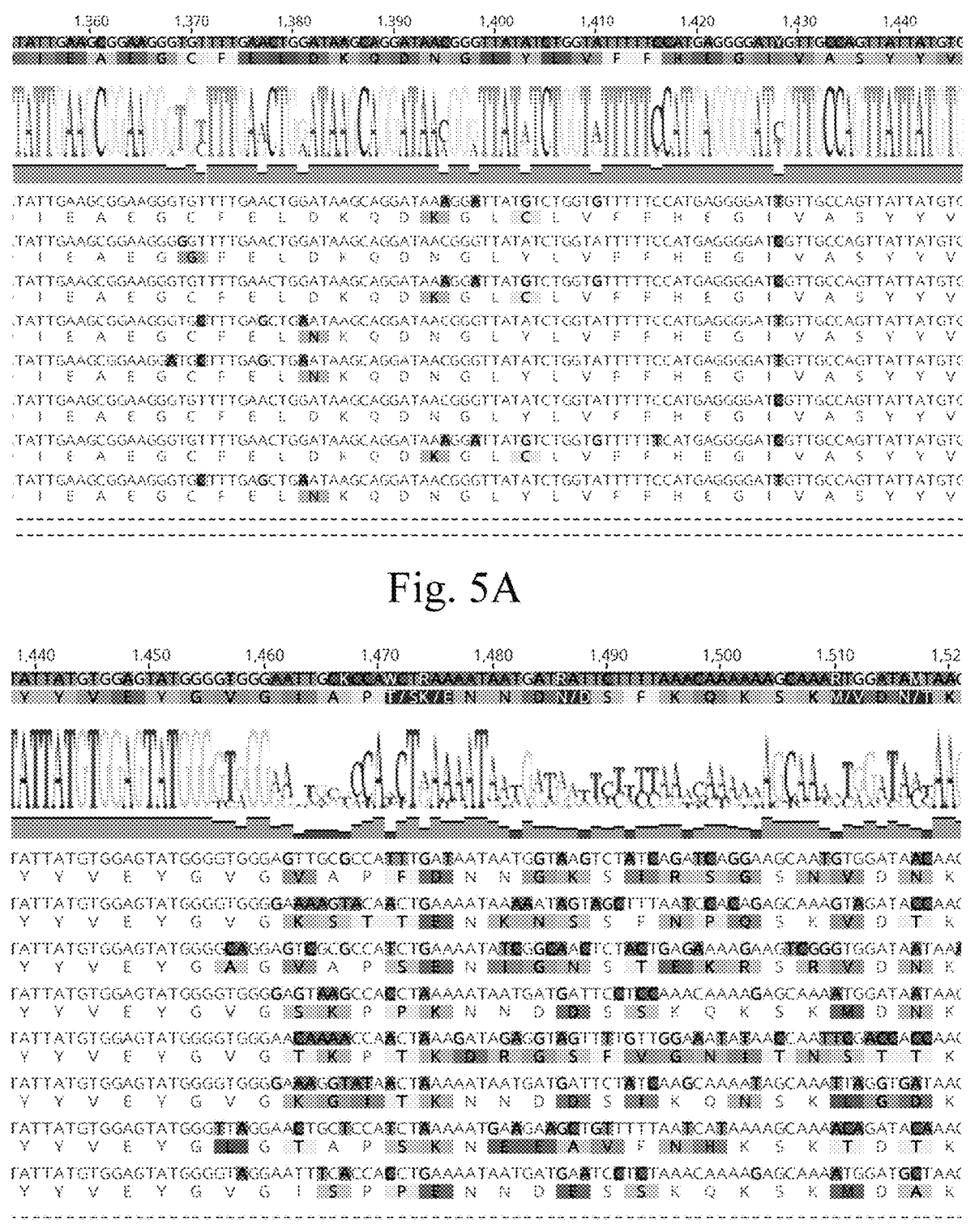

FIGS. 5A-5C depict a comparison of *Photorhabdus* hypervariable proteins (HP) focusing on the hypervariable region. (5A) SEQ ID NOS:14-31. (5B) SEQ ID NOS:32-49. (5C) SEQ ID NOS:50-67.

FIG. 6 presents an alignment of *Photorhabdus* hypervariable protein orthologs centered on the hypervariable region. Sequences (SEQ ID NOS:68-104) were aligned using Clustal Omega and default parameters.

Figure 1:
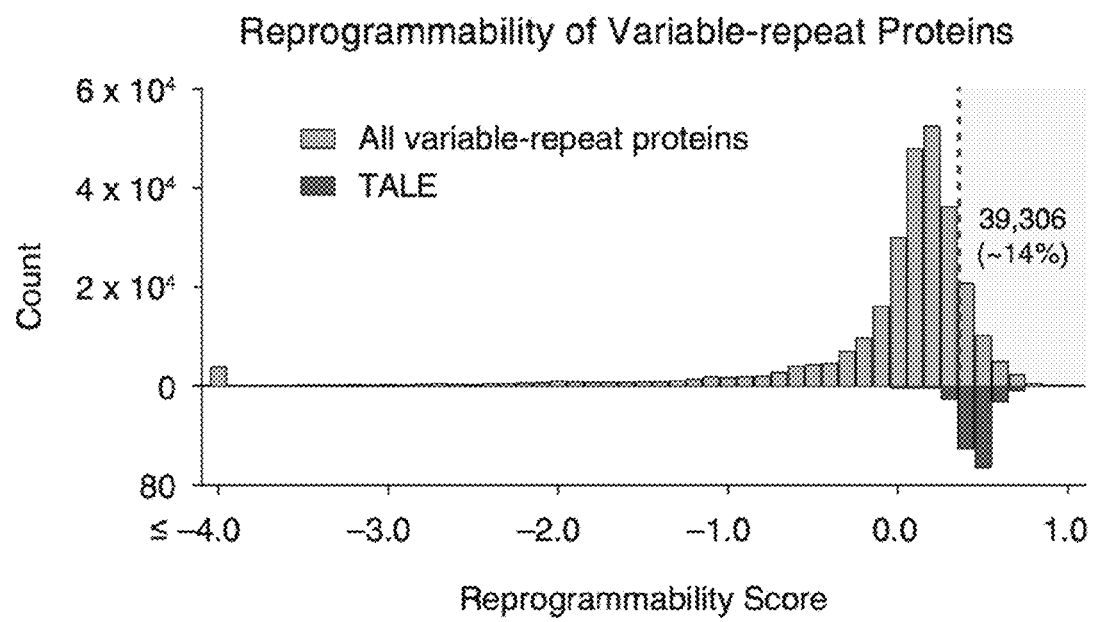
FIG. 1 is a chart showing reprogrammability as a function of repetition. 106,000,000 unique proteins of the UniProt database were analyzed, revealing 283,489 unique proteins with repetitive domains. Proteins were scored for reprogrammability based on i) repeats having common hypervariable regions, ii) evolutionary conservation of protein family, and iii) recombination of repeat domains.
Figure 2:
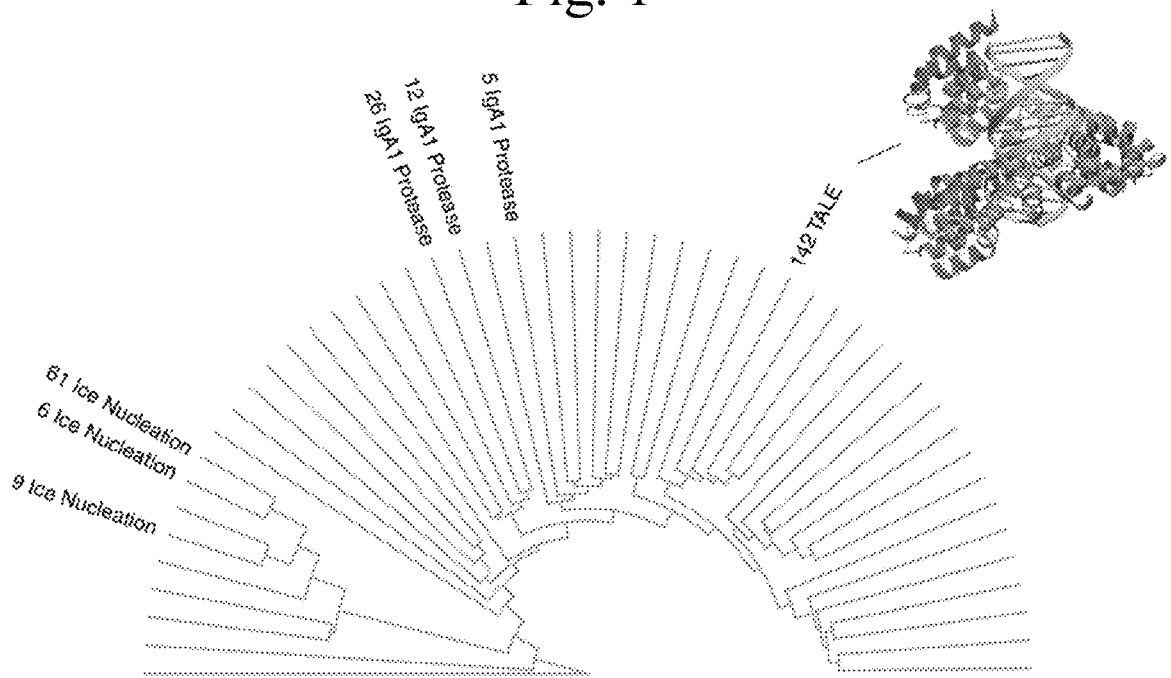
FIG. 2 exemplifies clustering of candidate proteins comprising repetitive domains.
Figure 4:
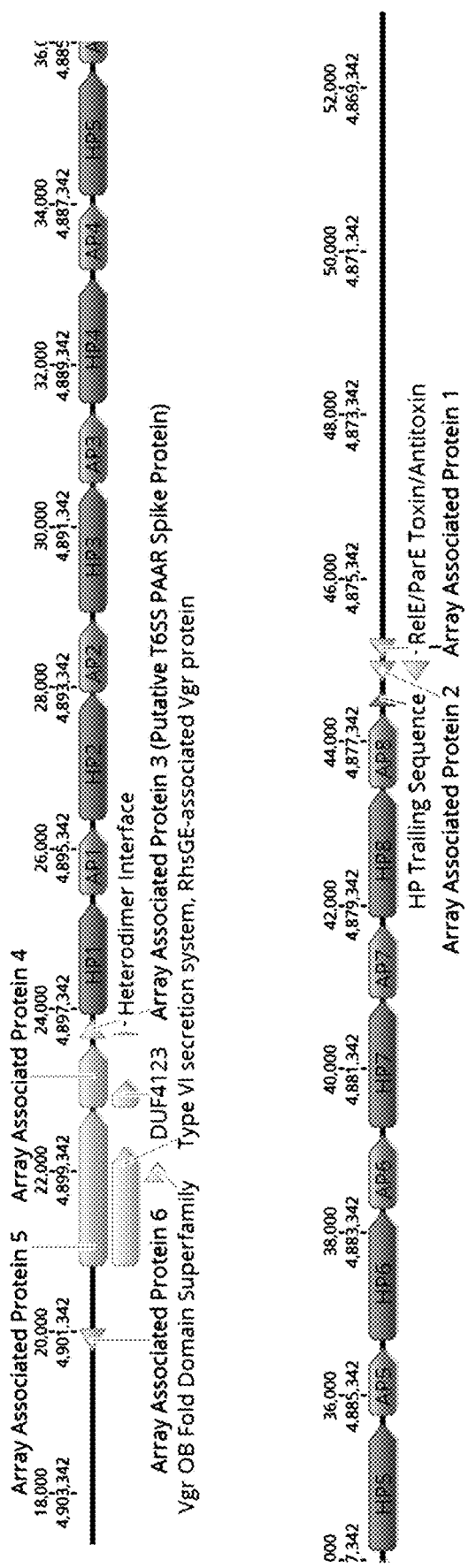
FIG. 4 depicts a *Photorhabdus* array where the different colors indicate different types of repeats.
Figure 5C:
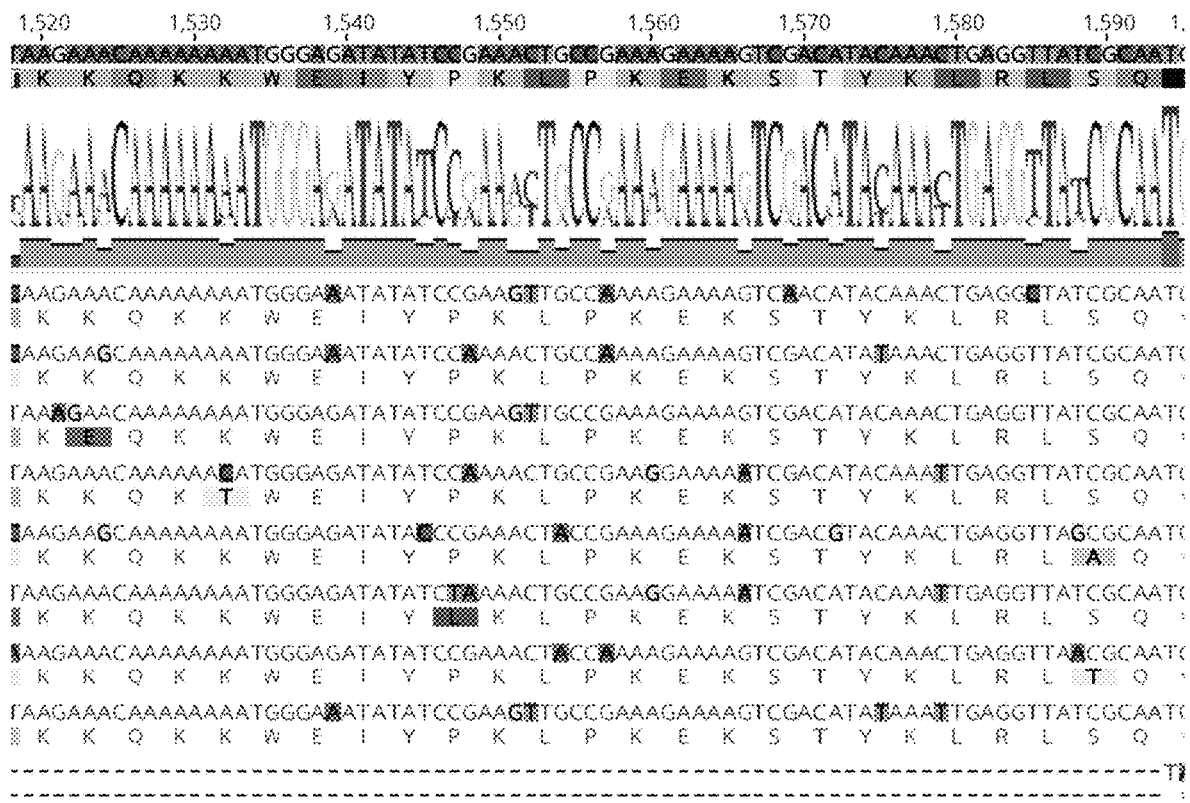

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

The terms "non-naturally occurring" or "engineered" are used interchangeably and indicate the involvement of the hand of man. The terms, when referring to proteins, nucleic acid molecules or polypeptides mean that the protein, nucleic acid molecule, or the polypeptide is at least substantially free from at least one other component with which they are naturally associated in nature and as found in nature. Furthermore, the terms "non-naturally occurring" and "engineered" may be used interchangeably and so can therefore be used alone or in combination and one or other may replace mention of both together. In particular, "engineered" is preferred in place of "non-naturally occurring" or "non-naturally occurring and/or engineered."

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

Homology modelling: Corresponding residues in the engineered protein and/or TRS can be identified by the methods of Zhang et al., 2012 (Nature; 490(7421): 556-60) and Chen et al., 2015 (PLoS Comput Biol; 11(5): e1004248) a computational protein-protein interaction (PPI) method to predict interactions mediated by domain-motif interfaces. PrePPI (Predicting PPI), a structure-based PPI prediction method, combines structural evidence with non-structural evidence using a Bayesian statistical framework. The method involves taking a pair of query proteins and using structural alignment to identify structural representatives that correspond to either their experimentally determined structures or homology models. Structural alignment is further used to identify both close and remote structural neighbors by considering global and local geometric relationships. Whenever two neighbors of the structural representatives form a complex reported in the Protein Data Bank, this defines a template for modelling the interaction between the two query proteins. Models of the complex are created by superimposing the representative structures on their corresponding structural neighbor in the template. This approach is further described in Dey et al., 2013 (Prot Sci; 22: 359-66).

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

All publications, published patent documents, and patent applications cited herein are hereby incorporated by reference to the same extent as though each individual publication, published patent document, or patent application was specifically and individually indicated as being incorporated by reference.

Overview

The invention involves discovery and application of new sources of biological diversity. In an aspect, the invention identifies genetic elements, including but not limited to protein domains and families and variable sequences among the domains, including but not limited to hypervariable regions. The elements can be engineered, including by duplication, mutation and shuffling to generate diversity in target recognition and catalysis.

*Photorhabdus* bacteria belong to the family of Enterobacteriaceae and express numerous toxins, including a variety of insecticidal toxins, as well as adhesins, proteases, and lipases. *Photorhabdus* bacteria are nematode-symbiotic, and pathogenic to a wide range of insects. The inventors have discovered a set of target recognition sequences among *Photorhabdus* bacterial proteins and orthologs. The set includes target recognition sequences associated with repetitive proteins encoded in tandem arrays and provides a basis for directing, altering, or otherwise engineering target binding of heterologous proteins as well as *Photorhabdus* proteins which can be linked to or comprise such target recognition sequences.

In an aspect of the invention, there is provided an engineered protein or polypeptide comprising one or more engineered *Photorhabdus* target recognition sequence (TRS) motifs. In one embodiment, the TRS motif is determined from *Photorhabdus* tandem repeat proteins. In an aspect the invention provides a cell or a population of cells as herein discussed comprising the engineered protein, wherein the cell is, optionally, a human cell or a mouse cell.

In an aspect the invention provides a nucleic acid molecule(s) encoding the engineered protein as herein discussed. In an aspect the invention provides a vector comprising: a nucleic acid molecule encoding the engineered protein or polypeptide as herein discussed. In an aspect a vector can further comprise regulatory element(s) operable in a eukaryotic cell operably linked to the nucleic acid molecule encoding the engineered protein or polypeptide and/or the optional nuclear localization sequence(s).

In one aspect, the invention provides a kit comprising one or more of the components described hereinabove. In some embodiments, the kit comprises a vector system as described above and instructions for using the kit.

Methods of engineering the proteins comprising TRS motifs are provided, as well as use of the engineered proteins for expression in cells is also provided.

In some embodiments, the method comprises allowing an engineered protein or polypeptide comprising a TRS to bind to the target. In some embodiments, the method comprises allowing an engineered protein or polypeptide comprising a TRS to cleave the target. In some embodiments, the method comprises allowing an engineered protein or polypeptide comprising a TRS to modify the target.

In another aspect, the invention provides a method of modifying expression of a substrate molecule in a eukaryotic cell. The substrate molecule may be a protein, polypeptide, nucleic acid, polysaccharide, lipid, or any other substrate molecule. In some embodiments, the method comprises allowing an engineered protein or polypeptide comprising a TRS to bind to the target such that said binding results in increased or decreased expression of said target. In some embodiments, the method comprises allowing an engineered protein or polypeptide comprising a TRS to cleave or modify the target such that said binding results in increased or decreased expression of said target.

Engineered Protein

In one aspect, the present disclosure provides for engineered proteins or polypeptides, or polynucleotides encoding an engineered protein or polypeptide comprising one or more engineered *Photorhabdus* tandem repeat protein target recognitions sequence (TRS) motifs. The engineered proteins can be used as targeting systems, which may further comprise components or moieties in addition to the engineered protein or polypeptide. In general, "targeting system" or "substrate targeting system" as used in the present application refers collectively to engineered proteins or polypeptides, nucleic acid molecules encoding engineered proteins or polypeptides thereof, functional domains or functional proteins associated with the engineered proteins or polypeptides with or without fusion, with or without a linker moiety, and any other component of the targeting system.

Target Recognition Sequence (TRS) Motif

In some embodiments, one or more elements of an engineered protein or targeting system is derived from a particular organism comprising an endogenous TRS or comprises one or more engineered TRS. In some embodiments, one or more elements of an engineered protein are derived from a prokaryotic organism. In some embodiments, one or more elements of an engineered protein is derived from a bacteria defense mechanism related protein. In some embodiments, one or more elements of a targeting system or engineered protein or polypeptide is derived from an organism comprising an endogenous IgA protease. In particular embodiments, the TRS is derived from an IgA protease of *Neisseria gonorrhoeae, Neisseria meningitidis, Haemophilus influenzae, Streptococcus pneumonia*, or any orthologs thereof. In some embodiments, the TRS may be derived from a Enterobacteriaceae family protein. In some embodiments, the TRS may be derived from a *Photorhabdus* bacteria protein. The bacteria protein may be toxins, including a variety of insecticidal toxins, as well as adhesins, proteases, and lipases, or any orthologs thereof.

In general, the engineered proteins and polypeptides as disclosed herein are characterized by elements that promote the formation of a target recognition sequence, structure, or formation.

In an aspect of the invention, there is provided an engineered protein or polypeptide comprising one or more engineered *Photorhabdus* target recognition sequence (TRS) motifs. In one embodiment, the TRS motif is determined from *Photorhabdus* tandem repeat proteins. In some examples, the engineered protein or polypeptide comprising one or more engineered *Photorhabdus* tandem repeat protein target recognition sequence (TRS) motifs.

The invention provides a TRS that comprises one or more amino acid sequences comprising:

$X_1$(E/K)(N/D)$X_2$(S/T)$X_3$ (SEQ ID NO:1) flanking by a hydrophobic region and a charged region; wherein $X_1$ comprises 1-7 amino acid residues comprising at least one hydrophobic amino acid residue, at least one charged amino acid residue, and/or at least one polar amino acid residue, wherein $X_2$ comprises 0 to 12 polar, hydrophobic, and/or charged amino acid residues, and wherein $X_3$ comprises 1 to 7 amino acid residues comprising a polar amino acid residue, a hydrophobic amino acid residue and/or a charged amino acid residue, wherein the hydrophobic region comprises at least one hydrophobic amino acid residue, and wherein the charged region comprises at least one charged amino acid residue.

In some embodiments, the hydrophobic region further comprises a polar amino acid residue and/or a charged amino acid residue. In other embodiments, the charged region further comprises a polar amino acid residue and/or a hydrophobic amino acid residue.

In one embodiment, the TRS comprises one or more sequences comprising:

$X_1$(E/K)(N/D)$X_2$(S/T)$X_3$ (SEQ ID NO:2) flanking by a hydrophobic region and a charged region;

wherein $X_1$ comprises 1-7 amino acid residues comprising at least one polar amino acid residue and one hydrophobic amino acid residue, wherein $X_2$ comprises 0 to 12 polar, hydrophobic, and/or charged amino acid residues, and wherein $X_3$ comprises 1 to 7 amino acid residues comprising a polar amino acid residue, a hydrophobic amino acid residue and/or a charged amino acid residue, wherein the hydrophobic region comprises at least one hydrophobic amino acid residue, and wherein the charged region comprises at least one charged amino acid residue.

In another embodiment, the TRS comprises one or more sequences comprising $X_1$(E/K)(N/D)$X_2$(S/T)$X_3$ (SEQ ID NO:3) flanking by a hydrophobic region and a charged region, wherein $X_1$ comprises 1-4 amino acid residues comprising at least one hydrophobic residue and/or one polar residue, $X_2$ comprises 1 to 8 polar and/or charged amino acid residues, $X_3$ comprises 1 to 5 hydrophobic and/or charged amino acid residues, $X_4$ comprises 1 to 4 amino acids comprising at least one charged amino acid residue, the hydrophobic region comprises at least one hydrophobic residue, and the charged region comprises at least one charged amino acid residue. In one embodiment, the hydrophobic region comprises at least 2 hydrophobic residues or at least 3 hydrophobic residues. In yet another embodiment, the charged region comprises at least 2 charged amino acid residues, at least 3 charged amino acid residues, at least 4 charged amino acid residues, or at least 5 charged amino acid residues.

In yet another embodiment, the TRS comprises one or more sequences comprising $X_1$(E/K)(N/D)$X_2$(S/T)$X_3$ (SEQ ID NO:4) flanking by a hydrophobic region and a charged region, wherein $X_1$ comprises 1-7 amino acid residues comprising a charged residue, a polar residue, and a hydrophobic residue, $X_2$ comprises 0 to 12 polar, hydrophobic, and/or charged amino acid residues, $X_3$ comprises 1 to 7 amino acids comprising a charged residue and/or a polar residue, the hydrophobic region comprises at least one hydrophobic residue, and the charged region comprises at least one charged amino acid residue. In one embodiment, the hydrophobic region comprises at least 2 hydrophobic residues or at least 3 hydrophobic residues. In yet another embodiment, the charged region comprises at least 2 charged amino acid residues, at least 3 charged amino acid residues, at least 4 charged amino acid residues, or at least 5 charged amino acid residues.

In one embodiment, the TRS is about 15-75 amino acids in length. In another embodiment, the TRS is about 15 to 60 amino acids in length. In yet another embodiment, the TRS is about 15 to 50 amino acids in length. In other embodiments, the TRS is about 15 to 40 amino acids in length, about 18 to 40 amino acids in length, or about 19-39 amino acids in length. In other embodiments, the TRS is at least 15, at least 16, at least 17, at least 18, at least 19, or at least 20 amino acids in length.

In one embodiment, $X_1$ comprises 1-4 amino acid residues. In another embodiment, $X_2$ comprises 1-8 amino acid residues. In yet another embodiment, $X_3$ comprises 1-4 amino acid residues. In another embodiment, the hydrophobic region comprises at least 2 residues, at least 3 residues, at least 4 residues, at least 5 residues, at least 6 residues, at least 7 residues, at least 8 residues, at least 9 residues, at least 10 residues. In another embodiment, the hydrophobic region comprises 1-15 amino acid residues, or 1-12 amino acid residues, or 1-10 amino acid residues, or 1-5 amino acid residues. In another embodiment, the charged region comprises at least 2 amino acid residues, at least 3 amino acid residues, at least 4 amino acid residues, at least 5 amino acid residues, at least 6 amino acid residues, at least 7 amino acid residues, at least 8 amino acid residues, at least 9 amino acid residues, or at least 10 amino acid residues. In yet another embodiment, the charged region comprises 1-15 amino acid residues, or 1-12 amino acid residues, or 1-10 amino acid residues, or 1-8 amino acid residues, or 1-5 amino acid residues. In yet another embodiment, $X_1$ comprises 1-4 amino acid residues, $X_2$ comprises 1-8 amino acid residues, and $X_3$ comprises 1-4 amino acid residues, the hydrophobic region comprises 1-12 amino acid residues, and the charged region comprises 1-8 amino acid residues.

In any of the above embodiments, the hydrophobic residues comprise leucine (L), proline (P), methionine (M), alanine (A), isoleucine (I), glycine (G), valine (V), phenylalanine (F), and tryptophan (W), the polar residues comprise threonine (T), serine (S), tyrosine (Y), glutamine (Q), asparagine (N), and histidine (H), and the charged amino acid residues comprise lysine (K), arginine (R), glutamic acid (E), and aspartic acid (D).

In one embodiment, the TRS comprises one or more sequences comprising $X_1$(E/K)(N/D)$X_2$(S/T)$X_3$ (SEQ ID NO:5) flanking by a hydrophobic region and a charged region, wherein $X_1$ comprises:
(a) a proline or a threonine or an isoleucine (P/T/I), or
(b) a proline, a serine, or a threonine (P/S/T);

wherein $X_2$ comprises
(a) a serine, a phenylalanine, or a valine (S/F/V),
(b) an asparagine or a glutamine (N/Q), or
(c) an arginine or a lysine (R/K);

wherein $X_3$ comprises
(a) a lysine, an arginine, or an asparagine (K/R/N), or
(b) an aspartic acid, a threonine, or a glycine (D/T/G);

wherein the hydrophobic region comprises
(a) a glycine (G), and/or
(b) a valine, a leucine, or an alanine (V/L/A); and/or wherein the charged region comprises
(a) a lysine (K)
(b) a lysine or a glutamic acid (K/E), and/or
(c) a glutamine (Q).

In certain examples, the $X_1$(E/K)(N/D)$X_2$(S/T)$X_3$ (SEQ ID NO:1) sequence is flanked on the 5' end by a hydrophobic region comprising $X_a$-$X_b$-$X_c$ and on the 3' end by a charged region comprising $X_x$-$X_y$-$X_z$ wherein: $X_a$ is G, $X_b$ is V, A, or L, $X_c$ is G, $X_x$ is K, $X_y$ is K or E, and $X_z$ is Q.

In another embodiment, the TRS comprises one or more sequences comprising $X_1$(E/K)(N/D)$X_2$(S/T)$X_3$ (SEQ ID NO:1) flanking by a hydrophobic region and a charged region, wherein $X_1$, $X_2$, and $X_3$, comprise the following combinations of Table 1:

TABLE 1

| $X_1$ | $X_2$ | $X_3$ | Hydrophobic region | Charged region |
| --- | --- | --- | --- | --- |
| (a) = P/T/I | (a) = S/F/V | (a) = K/R/N | (a) = G | (a) = K |
| (b) = P/S/T | (b) = N/Q | (b) = D/T/G | (b) = V/L/A | (b) = K/E |
|  | (c) = R/K |  |  | (c) = Q |
| (a) | (a) | (a) | (a) | (a) |
| (a) and (b) | (a) | (a) | (a) | (a) |
| (a) | (b) | (a) | (a) | (a) |
| (a) and (b) | (b) | (a) | (a) | (a) |
| (a) | (c) | (a) | (a) | (a) |
| (a) and (b) | (c) | (a) | (a) | (a) |
| (a) | (a) | (b) | (a) | (a) |
| (a) and (b) | (a) | (b) | (a) | (a) |
| (a) | (a) | (a) | (b) | (a) |
| (a) and (b) | (a) | (a) | (b) | (a) |
| (a) | (a) | (a) | (a) | (b) |
| (a) and (b) | (a) | (a) | (a) | (c) |
| (a) | (a) and (b) | (a) | (a) | (a) |
| (a) and (b) | (a) and (b) | (a) | (a) | (a) |
| (a) | (a) and (b) | (a) | (a) | (a) |
| (a) and (b) | (a) and (b) | (a) | (a) | (a) |
| (a) | (a) and (b) | (a) | (a) | (a) |
| (a) and (b) | (a) and (b) | (a) | (a) | (a) |
| (a) | (a) and (b) | (b) | (a) | (a) |
| (a) and (b) | (a) and (b) | (b) | (a) | (a) |
| (a) | (a) and (b) | (a) | (b) | (a) |
| (a) and (b) | (a) and (b) | (a) | (b) | (a) |
| (a) | (a) and (b) | (a) | (a) | (b) |
| (a) and (b) | (a) and (b) | (a) | (a) | (c) |
| (a) and (b) | (a) and (c) | (a) | (a) | (a) |
| (a) and (b) | (a) and (c) | (a) | (a) | (a) |
| (a) and (b) | (a) and (c) | (a) | (a) | (a) |
| (a) and (b) | (a) and (c) | (a) | (a) | (a) |
| (a) and (b) | (a) and (c) | (a) | (a) | (a) |
| (a) and (b) | (a) and (c) | (a) | (a) | (a) |
| (a) and (b) | (a) and (c) | (b) | (a) | (a) |
| (a) and (b) | (a) and (c) | (b) | (a) | (a) |
| (a) and (b) | (a) and (c) | (a) | (b) | (a) |
| (a) and (b) | (a) and (c) | (a) | (b) | (a) |
| (a) and (b) | (a) and (c) | (a) | (a) | (b) |
| (a) and (b) | (a) and (c) | (a) | (a) | (c) |
| (a) | (b) and (c) | (a) | (a) | (a) |
| (a) and (b) | (b) and (c) | (a) | (a) | (a) |
| (a) | (b) and (c) | (a) | (a) | (a) |
| (a) and (b) | (b) and (c) | (a) | (a) | (a) |
| (a) | (b) and (c) | (a) | (a) | (a) |
| (a) and (b) | (b) and (c) | (a) | (a) | (a) |
| (a) | (b) and (c) | (b) | (a) | (a) |
| (a) and (b) | (b) and (c) | (b) | (a) | (a) |
| (a) | (b) and (c) | (a) | (b) | (a) |
| (a) and (b) | (b) and (c) | (a) | (b) | (a) |
| (a) | (b) and (c) | (a) | (a) | (b) |
| (a) and (b) | (b) and (c) | (a) | (a) | (c) |
| (a) | (a) | (a) and (b) | (a) | (a) |
| (a) and (b) | (a) | (a) and (b) | (a) | (a) |
| (a) | (b) | (a) and (b) | (a) | (a) |
| (a) and (b) | (b) | (a) and (b) | (a) | (a) |
| (a) | (c) | (a) and (b) | (a) | (a) |
| (a) and (b) | (c) | (a) and (b) | (a) | (a) |
| (a) | (a) | (a) and (b) | (a) | (a) |
| (a) and (b) | (a) | (a) and (b) | (a) | (a) |
| (a) | (a) | (a) and (b) | (b) | (a) |
| (a) and (b) | (a) | (a) and (b) | (b) | (a) |
| (a) | (a) | (a) and (b) | (a) | (b) |
| (a) and (b) | (a) | (a) and (b) | (a) | (c) |
| (a) | (a) | (a) | (a) and (b) | (a) |
| (a) and (b) | (a) | (a) | (a) and (b) | (a) |
| (a) | (b) | (a) | (a) and (b) | (a) |
| (a) and (b) | (b) | (a) | (a) and (b) | (a) |
| (a) | (c) | (a) | (a) and (b) | (a) |
| (a) and (b) | (c) | (a) | (a) and (b) | (a) |
| (a) | (a) | (b) | (a) and (b) | (a) |

TABLE 1-continued

| $X_1$ | $X_2$ | $X_3$ | Hydrophobic region | Charged region |
|---|---|---|---|---|
| (a) and (b) | (a) | (b) | (a) and (b) | (a) |
| (a) | (a) | (a) | (a) and (b) | (a) |
| (a) and (b) | (a) | (a) | (a) and (b) | (a) |
| (a) | (a) | (a) | (a) and (b) | (b) |
| (a) and (b) | (a) | (a) | (a) and (b) | (c) |
| (a) | (a) | (a) | (a) | (a) and (b) |
| (a) and (b) | (a) | (a) | (a) | (a) and (b) |
| (a) | (b) | (a) | (a) | (a) and (b) |
| (a) and (b) | (b) | (a) | (a) | (a) and (b) |
| (a) | (c) | (a) | (a) | (a) and (b) |
| (a) and (b) | (c) | (a) | (a) | (a) and (b) |
| (a) | (a) | (b) | (a) | (a) and (b) |
| (a) and (b) | (a) | (b) | (a) | (a) and (b) |
| (a) | (a) | (a) | (b) | (a) and (b) |
| (a) and (b) | (a) | (a) | (b) | (a) and (b) |
| (a) | (a) | (a) | (a) | (a) and (b) |
| (a) and (b) | (a) | (a) | (a) | (a) and (b) |
| (a) | (a) | (a) | (a) | (a) and (c) |
| (a) and (b) | (a) | (a) | (a) | (a) and (c) |
| (a) | (b) | (a) | (a) | (a) and (c) |
| (a) and (b) | (b) | (a) | (a) | (a) and (c) |
| (a) | (c) | (a) | (a) | (a) and (c) |
| (a) and (b) | (c) | (a) | (a) | (a) and (c) |
| (a) | (a) | (b) | (a) | (a) and (c) |
| (a) and (b) | (a) | (b) | (a) | (a) and (c) |
| (a) | (a) | (a) | (b) | (a) and (c) |
| (a) and (b) | (a) | (a) | (b) | (a) and (c) |
| (a) | (a) | (a) | (a) | (a) and (c) |
| (a) and (b) | (a) | (a) | (a) | (a) and (c) |
| (a) | (a) | (a) | (a) | (b) and (c) |
| (a) and (b) | (a) | (a) | (a) | (b) and (c) |
| (a) | (b) | (a) | (a) | (b) and (c) |
| (a) and (b) | (b) | (a) | (a) | (b) and (c) |
| (a) | (c) | (a) | (a) | (b) and (c) |
| (a) and (b) | (c) | (a) | (a) | (b) and (c) |
| (a) | (a) | (b) | (a) | (b) and (c) |
| (a) and (b) | (a) | (b) | (a) | (b) and (c) |
| (a) | (a) | (a) | (b) | (b) and (c) |
| (a) and (b) | (a) | (a) | (b) | (b) and (c) |
| (a) | (a) | (a) | (a) | (b) and (c) |
| (a) and (b) | (a) | (a) | (a) | (b) and (c) |
| (a) | (a), (b), and (c) | (a) | (a) | (a) |
| (a) and (b) | (a), (b), and (c) | (a) | (a) | (a) |
| (a) | (a), (b), and (c) | (a) | (a) | (a) |
| (a) and (b) | (a), (b), and (c) | (a) | (a) | (a) |
| (a) | (a), (b), and (c) | (a) | (a) | (a) |
| (a) and (b) | (a), (b), and (c) | (a) | (a) | (a) |
| (a) | (a), (b), and (c) | (b) | (a) | (a) |
| (a) and (b) | (a), (b), and (c) | (b) | (a) | (a) |
| (a) | (a), (b), and (c) | (a) | (b) | (a) |
| (a) and (b) | (a), (b), and (c) | (a) | (b) | (a) |
| (a) | (a), (b), and (c) | (a) | (a) | (b) |
| (a) and (b) | (a), (b), and (c) | (a) | (a) | (c) |
| (a) | (a) | (a) | (a) | (a), (b), and (c) |
| (a) and (b) | (a) | (a) | (a) | (a), (b), and (c) |
| (a) | (b) | (a) | (a) | (a), (b), and (c) |
| (a) and (b) | (b) | (a) | (a) | (a), (b), and (c) |
| (a) | (c) | (a) | (a) | (a), (b), and (c) |
| (a) and (b) | (c) | (a) | (a) | (a), (b), and (c) |
| (a) | (a) | (b) | (a) | (a), (b), and (c) |
| (a) and (b) | (a) | (b) | (a) | (a), (b), and (c) |
| (a) | (a) | (a) | (b) | (a), (b), and (c) |
| (a) and (b) | (a) | (a) | (b) | (a), (b), and (c) |
| (a) | (a) | (a) | (a) | (a), (b), and (c) |
| (a) and (b) | (a) | (a) | (a) | (a), (b), and (c) |
| (a) | (a) and (b) | (a) and (b) | (a) | (a) |
| (a) and (b) | (a) and (b) | (a) and (b) | (a) | (a) |
| (a) | (a) and (b) | (a) and (b) | (a) | (a) |
| (a) and (b) | (a) and (b) | (a) and (b) | (a) | (a) |
| (a) | (a) and (b) | (a) and (b) | (a) | (a) |
| (a) and (b) | (a) and (b) | (a) and (b) | (a) | (a) |
| (a) | (a) and (b) | (a) and (b) | (a) | (a) |
| (a) and (b) | (a) and (b) | (a) and (b) | (a) | (a) |
| (a) | (a) and (b) | (a) and (b) | (b) | (a) |
| (a) and (b) | (a) and (b) | (a) and (b) | (b) | (a) |
| (a) | (a) and (b) | (a) and (b) | (a) | (b) |
| (a) and (b) | (a) and (b) | (a) and (b) | (a) | (c) |
| (a) | (a) and (c) | (a) and (b) | (a) | (a) |

TABLE 1-continued

| $X_1$ | $X_2$ | $X_3$ | Hydrophobic region | Charged region |
|---|---|---|---|---|
| (a) and (b) | (a) and (c) | (a) and (b) | (a) | (a) |
| (a) | (a) and (c) | (a) and (b) | (a) | (a) |
| (a) and (b) | (a) and (c) | (a) and (b) | (a) | (a) |
| (a) | (a) and (c) | (a) and (b) | (a) | (a) |
| (a) and (b) | (a) and (c) | (a) and (b) | (a) | (a) |
| (a) | (a) and (c) | (a) and (b) | (a) | (a) |
| (a) and (b) | (a) and (c) | (a) and (b) | (a) | (a) |
| (a) | (a) and (c) | (a) and (b) | (b) | (a) |
| (a) and (b) | (a) and (c) | (a) and (b) | (b) | (a) |
| (a) | (a) and (c) | (a) and (b) | (a) | (b) |
| (a) and (b) | (a) and (c) | (a) and (b) | (a) | (c) |
| (a) | (b) and (c) | (a) and (b) | (a) | (a) |
| (a) and (b) | (b) and (c) | (a) and (b) | (a) | (a) |
| (a) | (b) and (c) | (a) and (b) | (a) | (a) |
| (a) and (b) | (b) and (c) | (a) and (b) | (a) | (a) |
| (a) | (b) and (c) | (a) and (b) | (a) | (a) |
| (a) and (b) | (b) and (c) | (a) and (b) | (a) | (a) |
| (a) | (b) and (c) | (a) and (b) | (a) | (a) |
| (a) and (b) | (b) and (c) | (a) and (b) | (a) | (a) |
| (a) | (b) and (c) | (a) and (b) | (b) | (a) |
| (a) and (b) | (b) and (c) | (a) and (b) | (b) | (a) |
| (a) | (b) and (c) | (a) and (b) | (a) | (b) |
| (a) and (b) | (b) and (c) | (a) and (b) | (a) | (c) |
| (a) | (a) and (b) | (a) | (a) and (b) | (a) |
| (a) and (b) | (a) and (b) | (a) | (a) and (b) | (a) |
| (a) | (a) and (b) | (a) | (a) and (b) | (a) |
| (a) and (b) | (a) and (b) | (a) | (a) and (b) | (a) |
| (a) | (a) and (b) | (a) | (a) and (b) | (a) |
| (a) and (b) | (a) and (b) | (a) | (a) and (b) | (a) |
| (a) | (a) and (b) | (b) | (a) and (b) | (a) |
| (a) and (b) | (a) and (b) | (b) | (a) and (b) | (a) |
| (a) | (a) and (b) | (a) | (a) and (b) | (a) |
| (a) and (b) | (a) and (b) | (a) | (a) and (b) | (a) |
| (a) | (a) and (b) | (a) | (a) and (b) | (b) |
| (a) and (b) | (a) and (b) | (a) | (a) and (b) | (c) |
| (a) | (a) and (c) | (a) | (a) and (b) | (a) |
| (a) and (b) | (a) and (c) | (a) | (a) and (b) | (a) |
| (a) | (a) and (c) | (a) | (a) and (b) | (a) |
| (a) and (b) | (a) and (c) | (a) | (a) and (b) | (a) |
| (a) | (a) and (c) | (a) | (a) and (b) | (a) |
| (a) and (b) | (a) and (c) | (b) | (a) and (b) | (a) |
| (a) | (a) and (c) | (b) | (a) and (b) | (a) |
| (a) and (b) | (a) and (c) | (a) | (a) and (b) | (a) |
| (a) | (a) and (c) | (a) | (a) and (b) | (a) |
| (a) and (b) | (a) and (c) | (a) | (a) and (b) | (b) |
| (a) | (a) and (c) | (a) | (a) and (b) | (c) |
| (a) and (b) | (b) and (c) | (a) | (a) and (b) | (a) |
| (a) | (b) and (c) | (a) | (a) and (b) | (a) |
| (a) and (b) | (b) and (c) | (a) | (a) and (b) | (a) |
| (a) | (b) and (c) | (a) | (a) and (b) | (a) |
| (a) and (b) | (b) and (c) | (a) | (a) and (b) | (a) |
| (a) | (b) and (c) | (b) | (a) and (b) | (a) |
| (a) and (b) | (b) and (c) | (b) | (a) and (b) | (a) |
| (a) | (b) and (c) | (a) | (a) and (b) | (a) |
| (a) and (b) | (b) and (c) | (a) | (a) and (b) | (a) |
| (a) | (b) and (c) | (a) | (a) and (b) | (b) |
| (a) and (b) | (b) and (c) | (a) | (a) and (b) | (c) |
| (a) | (a) and (b) | (a) | (a) | (a) and (b) |
| (a) and (b) | (a) and (b) | (a) | (a) | (a) and (b) |
| (a) | (a) and (b) | (a) | (a) | (a) and (b) |
| (a) and (b) | (a) and (b) | (a) | (a) | (a) and (b) |
| (a) | (a) and (b) | (a) | (a) | (a) and (b) |
| (a) and (b) | (a) and (b) | (a) | (a) | (a) and (b) |
| (a) | (a) and (b) | (b) | (a) | (a) and (b) |
| (a) and (b) | (a) and (b) | (b) | (a) | (a) and (b) |
| (a) | (a) and (b) | (a) | (b) | (a) and (b) |
| (a) and (b) | (a) and (b) | (a) | (b) | (a) and (b) |
| (a) | (a) and (b) | (a) | (a) | (a) and (b) |
| (a) and (b) | (a) and (b) | (a) | (a) | (a) and (b) |
| (a) | (a) and (b) | (a) | (a) | (a) and (c) |
| (a) and (b) | (a) and (b) | (a) | (a) | (a) and (c) |
| (a) | (a) and (b) | (a) | (a) | (a) and (c) |
| (a) and (b) | (a) and (b) | (a) | (a) | (a) and (c) |
| (a) | (a) and (b) | (a) | (a) | (a) and (c) |
| (a) and (b) | (a) and (b) | (a) | (a) | (a) and (c) |
| (a) | (a) and (b) | (b) | (a) | (a) and (c) |

TABLE 1-continued

| $X_1$ | $X_2$ | $X_3$ | Hydrophobic region | Charged region |
|---|---|---|---|---|
| (a) and (b) | (a) and (b) | (b) | (a) | (a) and (c) |
| (a) | (a) and (b) | (a) | (b) | (a) and (c) |
| (a) and (b) | (a) and (b) | (a) | (b) | (a) and (c) |
| (a) | (a) and (b) | (a) | (a) | (a) and (c) |
| (a) and (b) | (a) and (b) | (a) | (a) | (a) and (c) |
| (a) | (a) and (b) | (a) | (a) | (b) and (c) |
| (a) and (b) | (a) and (b) | (a) | (a) | (b) and (c) |
| (a) | (a) and (b) | (a) | (a) | (b) and (c) |
| (a) and (b) | (a) and (b) | (a) | (a) | (b) and (c) |
| (a) | (a) and (b) | (a) | (a) | (b) and (c) |
| (a) and (b) | (a) and (b) | (a) | (a) | (b) and (c) |
| (a) | (a) and (b) | (b) | (a) | (b) and (c) |
| (a) and (b) | (a) and (b) | (b) | (a) | (b) and (c) |
| (a) | (a) and (b) | (a) | (b) | (b) and (c) |
| (a) and (b) | (a) and (b) | (a) | (b) | (b) and (c) |
| (a) | (a) and (b) | (a) | (a) | (b) and (c) |
| (a) and (b) | (a) and (b) | (a) | (a) | (b) and (c) |
| (a) | (a), (b), and (c) | (a) | (a) | (a) |
| (a) and (b) | (a), (b), and (c) | (a) | (a) | (a) |
| (a) | (a), (b), and (c) | (a) | (a) | (a) |
| (a) and (b) | (a), (b), and (c) | (a) | (a) | (a) |
| (a) | (a), (b), and (c) | (a) | (a) | (a) |
| (a) and (b) | (a), (b), and (c) | (a) | (a) | (a) |
| (a) | (a), (b), and (c) | (b) | (a) | (a) |
| (a) and (b) | (a), (b), and (c) | (b) | (a) | (a) |
| (a) | (a), (b), and (c) | (a) | (b) | (a) |
| (a) and (b) | (a), (b), and (c) | (a) | (b) | (a) |
| (a) | (a), (b), and (c) | (a) | (a) | (b) |
| (a) and (b) | (a), (b), and (c) | (a) | (a) | (c) |
| (a) | (a), (b), and (c) | (a) and (b) | (a) | (a) |
| (a) and (b) | (a), (b), and (c) | (a) and (b) | (a) | (a) |
| (a) | (a), (b), and (c) | (a) and (b) | (a) | (a) |
| (a) and (b) | (a), (b), and (c) | (a) and (b) | (a) | (a) |
| (a) | (a), (b), and (c) | (a) and (b) | (a) | (a) |
| (a) and (b) | (a), (b), and (c) | (a) and (b) | (a) | (a) |
| (a) | (a), (b), and (c) | (a) and (b) | (a) | (a) |
| (a) and (b) | (a), (b), and (c) | (a) and (b) | (a) | (a) |
| (a) | (a), (b), and (c) | (a) and (b) | (b) | (a) |
| (a) and (b) | (a), (b), and (c) | (a) and (b) | (b) | (a) |
| (a) | (a), (b), and (c) | (a) and (b) | (a) | (b) |
| (a) and (b) | (a), (b), and (c) | (a) and (b) | (a) | (c) |
| (a) | (a), (b), and (c) | (a) | (a) and (b) | (a) |
| (a) and (b) | (a), (b), and (c) | (a) | (a) and (b) | (a) |
| (a) | (a), (b), and (c) | (a) | (a) and (b) | (a) |
| (a) and (b) | (a), (b), and (c) | (a) | (a) and (b) | (a) |
| (a) | (a), (b), and (c) | (a) | (a) and (b) | (a) |
| (a) and (b) | (a), (b), and (c) | (a) | (a) and (b) | (a) |
| (a) | (a), (b), and (c) | (b) | (a) and (b) | (a) |
| (a) and (b) | (a), (b), and (c) | (b) | (a) and (b) | (a) |
| (a) | (a), (b), and (c) | (a) | (a) and (b) | (a) |
| (a) and (b) | (a), (b), and (c) | (a) | (a) and (b) | (a) |
| (a) | (a), (b), and (c) | (a) | (a) and (b) | (b) |
| (a) and (b) | (a), (b), and (c) | (a) | (a) and (b) | (c) |
| (a) | (a), (b), and (c) | (a) | (a) | (a) and (b) |
| (a) and (b) | (a), (b), and (c) | (a) | (a) | (a) and (b) |
| (a) | (a), (b), and (c) | (a) | (a) | (a) and (b) |
| (a) and (b) | (a), (b), and (c) | (a) | (a) | (a) and (b) |
| (a) | (a), (b), and (c) | (a) | (a) | (a) and (b) |
| (a) and (b) | (a), (b), and (c) | (a) | (a) | (a) and (b) |
| (a) | (a), (b), and (c) | (b) | (a) | (a) and (b) |
| (a) and (b) | (a), (b), and (c) | (b) | (a) | (a) and (b) |
| (a) | (a), (b), and (c) | (a) | (b) | (a) and (b) |
| (a) and (b) | (a), (b), and (c) | (a) | (b) | (a) and (b) |
| (a) | (a), (b), and (c) | (a) | (a) | (a) and (b) |
| (a) and (b) | (a), (b), and (c) | (a) | (a) | (a) and (b) |
| (a) | (a), (b), and (c) | (a) | (a) | (a) and (c) |
| (a) and (b) | (a), (b), and (c) | (a) | (a) | (a) and (c) |
| (a) | (a), (b), and (c) | (a) | (a) | (a) and (c) |
| (a) and (b) | (a), (b), and (c) | (a) | (a) | (a) and (c) |
| (a) | (a), (b), and (c) | (a) | (a) | (a) and (c) |
| (a) and (b) | (a), (b), and (c) | (a) | (a) | (a) and (c) |
| (a) | (a), (b), and (c) | (b) | (a) | (a) and (c) |
| (a) and (b) | (a), (b), and (c) | (b) | (a) | (a) and (c) |
| (a) | (a), (b), and (c) | (a) | (b) | (a) and (c) |
| (a) and (b) | (a), (b), and (c) | (a) | (b) | (a) and (c) |
| (a) | (a), (b), and (c) | (a) | (a) | (a) and (c) |
| (a) and (b) | (a), (b), and (c) | (a) | (a) | (a) and (c) |
| (a) | (a), (b), and (c) | (a) | (a) | (b) and (c) |

TABLE 1-continued

| $X_1$ | $X_2$ | $X_3$ | Hydrophobic region | Charged region |
|---|---|---|---|---|
| (a) and (b) | (a), (b), and (c) | (a) | (a) | (b) and (c) |
| (a) | (a), (b), and (c) | (a) | (a) | (b) and (c) |
| (a) and (b) | (a), (b), and (c) | (a) | (a) | (b) and (c) |
| (a) | (a), (b), and (c) | (a) | (a) | (b) and (c) |
| (a) and (b) | (a), (b), and (c) | (a) | (a) | (b) and (c) |
| (a) | (a), (b), and (c) | (b) | (a) | (b) and (c) |
| (a) and (b) | (a), (b), and (c) | (b) | (a) | (b) and (c) |
| (a) | (a), (b), and (c) | (a) | (b) | (b) and (c) |
| (a) and (b) | (a), (b), and (c) | (a) | (b) | (b) and (c) |
| (a) | (a), (b), and (c) | (a) | (a) | (b) and (c) |
| (a) and (b) | (a), (b), and (c) | (a) | (a) | (b) and (c) |
| (a) | (a), (b), and (c) | (a) | (a) | (a), (b), and (c) |
| (a) and (b) | (a), (b), and (c) | (a) | (a) | (a), (b), and (c) |
| (a) | (a), (b), and (c) | (a) | (a) | (a), (b), and (c) |
| (a) and (b) | (a), (b), and (c) | (a) | (a) | (a), (b), and (c) |
| (a) | (a), (b), and (c) | (a) | (a) | (a), (b), and (c) |
| (a) and (b) | (a), (b), and (c) | (a) | (a) | (a), (b), and (c) |
| (a) | (a), (b), and (c) | (b) | (a) | (a), (b), and (c) |
| (a) and (b) | (a), (b), and (c) | (b) | (a) | (a), (b), and (c) |
| (a) | (a), (b), and (c) | (a) | (b) | (a), (b), and (c) |
| (a) and (b) | (a), (b), and (c) | (a) | (b) | (a), (b), and (c) |
| (a) | (a), (b), and (c) | (a) | (a) | (a), (b), and (c) |
| (a) and (b) | (a), (b), and (c) | (a) | (a) | (a), (b), and (c) |
| (a) | (a), (b), and (c) | (a) and (b) | (a) and (b) | (a) |
| (a) and (b) | (a), (b), and (c) | (a) and (b) | (a) and (b) | (a) |
| (a) | (a), (b), and (c) | (a) and (b) | (a) and (b) | (a) |
| (a) and (b) | (a), (b), and (c) | (a) and (b) | (a) and (b) | (a) |
| (a) | (a), (b), and (c) | (a) and (b) | (a) and (b) | (a) |
| (a) and (b) | (a), (b), and (c) | (a) and (b) | (a) and (b) | (a) |
| (a) | (a), (b), and (c) | (a) and (b) | (a) and (b) | (a) |
| (a) and (b) | (a), (b), and (c) | (a) and (b) | (a) and (b) | (a) |
| (a) | (a), (b), and (c) | (a) and (b) | (a) and (b) | (a) |
| (a) and (b) | (a), (b), and (c) | (a) and (b) | (a) and (b) | (a) |
| (a) | (a), (b), and (c) | (a) and (b) | (a) and (b) | (b) |
| (a) and (b) | (a), (b), and (c) | (a) and (b) | (a) and (b) | (c) |
| (a) | (a), (b), and (c) | (a) and (b) | (a) | (a) and (b) |
| (a) and (b) | (a), (b), and (c) | (a) and (b) | (a) | (a) and (b) |
| (a) | (a), (b), and (c) | (a) and (b) | (a) | (a) and (b) |
| (a) and (b) | (a), (b), and (c) | (a) and (b) | (a) | (a) and (b) |
| (a) | (a), (b), and (c) | (a) and (b) | (a) | (a) and (b) |
| (a) and (b) | (a), (b), and (c) | (a) and (b) | (a) | (a) and (b) |
| (a) | (a), (b), and (c) | (a) and (b) | (a) | (a) and (b) |
| (a) and (b) | (a), (b), and (c) | (a) and (b) | (a) | (a) and (b) |
| (a) | (a), (b), and (c) | (a) and (b) | (b) | (a) and (b) |
| (a) and (b) | (a), (b), and (c) | (a) and (b) | (b) | (a) and (b) |
| (a) | (a), (b), and (c) | (a) and (b) | (a) | (a) and (b) |
| (a) and (b) | (a), (b), and (c) | (a) and (b) | (a) | (a) and (b) |
| (a) | (a), (b), and (c) | (a) and (b) | (a) | (a) and (c) |
| (a) and (b) | (a), (b), and (c) | (a) and (b) | (a) | (a) and (c) |
| (a) | (a), (b), and (c) | (a) and (b) | (a) | (a) and (c) |
| (a) and (b) | (a), (b), and (c) | (a) and (b) | (a) | (a) and (c) |
| (a) | (a), (b), and (c) | (a) and (b) | (a) | (a) and (c) |
| (a) and (b) | (a), (b), and (c) | (a) and (b) | (a) | (a) and (c) |
| (a) | (a), (b), and (c) | (a) and (b) | (b) | (a) and (c) |
| (a) and (b) | (a), (b), and (c) | (a) and (b) | (b) | (a) and (c) |
| (a) | (a), (b), and (c) | (a) and (b) | (a) | (a) and (c) |
| (a) and (b) | (a), (b), and (c) | (a) and (b) | (a) | (a) and (c) |
| (a) | (a), (b), and (c) | (a) and (b) | (a) | (b) and (c) |
| (a) and (b) | (a), (b), and (c) | (a) and (b) | (a) | (b) and (c) |
| (a) | (a), (b), and (c) | (a) and (b) | (a) | (b) and (c) |
| (a) and (b) | (a), (b), and (c) | (a) and (b) | (a) | (b) and (c) |
| (a) | (a), (b), and (c) | (a) and (b) | (a) | (b) and (c) |
| (a) and (b) | (a), (b), and (c) | (a) and (b) | (a) | (b) and (c) |
| (a) | (a), (b), and (c) | (a) and (b) | (a) | (b) and (c) |
| (a) and (b) | (a), (b), and (c) | (a) and (b) | (a) | (b) and (c) |
| (a) | (a), (b), and (c) | (a) and (b) | (b) | (b) and (c) |
| (a) and (b) | (a), (b), and (c) | (a) and (b) | (b) | (b) and (c) |
| (a) | (a), (b), and (c) | (a) and (b) | (a) | (b) and (c) |
| (a) and (b) | (a), (b), and (c) | (a) and (b) | (a) | (b) and (c) |
| (a) | (a), (b), and (c) | (a) and (b) | (a) | (a), (b), and (c) |
| (a) and (b) | (a), (b), and (c) | (a) and (b) | (a) | (a), (b), and (c) |
| (a) | (a), (b), and (c) | (a) and (b) | (a) | (a), (b), and (c) |
| (a) and (b) | (a), (b), and (c) | (a) and (b) | (a) | (a), (b), and (c) |
| (a) | (a), (b), and (c) | (a) and (b) | (a) | (a), (b), and (c) |
| (a) and (b) | (a), (b), and (c) | (a) and (b) | (a) | (a), (b), and (c) |
| (a) | (a), (b), and (c) | (a) and (b) | (a) | (a), (b), and (c) |

TABLE 1-continued

| X₁ | X₂ | X₃ | Hydrophobic region | Charged region |
|---|---|---|---|---|
| (a) and (b) | (a), (b), and (c) | (a) and (b) | (a) | (a), (b), and (c) |
| (a) | (a), (b), and (c) | (a) and (b) | (b) | (a), (b), and (c) |
| (a) and (b) | (a), (b), and (c) | (a) and (b) | (b) | (a), (b), and (c) |
| (a) | (a), (b), and (c) | (a) and (b) | (a) | (a), (b), and (c) |
| (a) and (b) | (a), (b), and (c) | (a) and (b) | (a) | (a), (b), and (c) |
| (a) | (a), (b), and (c) | (a) and (b) | (a) and (b) | (a) and (b) |
| (a) and (b) | (a), (b), and (c) | (a) and (b) | (a) and (b) | (a) and (b) |
| (a) | (a), (b), and (c) | (a) and (b) | (a) and (b) | (a) and (b) |
| (a) and (b) | (a), (b), and (c) | (a) and (b) | (a) and (b) | (a) and (b) |
| (a) | (a), (b), and (c) | (a) and (b) | (a) and (b) | (a) and (b) |
| (a) and (b) | (a), (b), and (c) | (a) and (b) | (a) and (b) | (a) and (b) |
| (a) | (a), (b), and (c) | (a) and (b) | (a) and (b) | (a) and (b) |
| (a) and (b) | (a), (b), and (c) | (a) and (b) | (a) and (b) | (a) and (b) |
| (a) | (a), (b), and (c) | (a) and (b) | (a) and (b) | (a) and (b) |
| (a) and (b) | (a), (b), and (c) | (a) and (b) | (a) and (b) | (a) and (b) |
| (a) | (a), (b), and (c) | (a) and (b) | (a) and (b) | (a) and (b) |
| (a) and (b) | (a), (b), and (c) | (a) and (b) | (a) and (b) | (a) and (b) |
| (a) | (a), (b), and (c) | (a) and (b) | (a) and (b) | (a) and (c) |
| (a) and (b) | (a), (b), and (c) | (a) and (b) | (a) and (b) | (a) and (c) |
| (a) | (a), (b), and (c) | (a) and (b) | (a) and (b) | (a) and (c) |
| (a) and (b) | (a), (b), and (c) | (a) and (b) | (a) and (b) | (a) and (c) |
| (a) | (a), (b), and (c) | (a) and (b) | (a) and (b) | (a) and (c) |
| (a) and (b) | (a), (b), and (c) | (a) and (b) | (a) and (b) | (a) and (c) |
| (a) | (a), (b), and (c) | (a) and (b) | (a) and (b) | (a) and (c) |
| (a) and (b) | (a), (b), and (c) | (a) and (b) | (a) and (b) | (a) and (c) |
| (a) | (a), (b), and (c) | (a) and (b) | (a) and (b) | (a) and (c) |
| (a) and (b) | (a), (b), and (c) | (a) and (b) | (a) and (b) | (a) and (c) |
| (a) | (a), (b), and (c) | (a) and (b) | (a) and (b) | (a) and (c) |
| (a) and (b) | (a), (b), and (c) | (a) and (b) | (a) and (b) | (a) and (c) |
| (a) | (a), (b), and (c) | (a) and (b) | (a) and (b) | (b) and (c) |
| (a) and (b) | (a), (b), and (c) | (a) and (b) | (a) and (b) | (b) and (c) |
| (a) | (a), (b), and (c) | (a) and (b) | (a) and (b) | (b) and (c) |
| (a) and (b) | (a), (b), and (c) | (a) and (b) | (a) and (b) | (b) and (c) |
| (a) | (a), (b), and (c) | (a) and (b) | (a) and (b) | (b) and (c) |
| (a) and (b) | (a), (b), and (c) | (a) and (b) | (a) and (b) | (b) and (c) |
| (a) | (a), (b), and (c) | (a) and (b) | (a) and (b) | (b) and (c) |
| (a) and (b) | (a), (b), and (c) | (a) and (b) | (a) and (b) | (b) and (c) |
| (a) | (a), (b), and (c) | (a) and (b) | (a) and (b) | (b) and (c) |
| (a) and (b) | (a), (b), and (c) | (a) and (b) | (a) and (b) | (b) and (c) |
| (a) | (a), (b), and (c) | (a) and (b) | (a) and (b) | (b) and (c) |
| (a) and (b) | (a), (b), and (c) | (a) and (b) | (a) and (b) | (b) and (c) |
| (a) | (a), (b), and (c) | (a) and (b) | (a) and (b) | (a), (b), and (c) |
| (a) and (b) | (a), (b), and (c) | (a) and (b) | (a) and (b) | (a), (b), and (c) |
| (a) | (a), (b), and (c) | (a) and (b) | (a) and (b) | (a), (b), and (c) |
| (a) and (b) | (a), (b), and (c) | (a) and (b) | (a) and (b) | (a), (b), and (c) |
| (a) | (a), (b), and (c) | (a) and (b) | (a) and (b) | (a), (b), and (c) |
| (a) and (b) | (a), (b), and (c) | (a) and (b) | (a) and (b) | (a), (b), and (c) |
| (a) | (a), (b), and (c) | (a) and (b) | (a) and (b) | (a), (b), and (c) |
| (a) and (b) | (a), (b), and (c) | (a) and (b) | (a) and (b) | (a), (b), and (c) |
| (a) | (a), (b), and (c) | (a) and (b) | (a) and (b) | (a), (b), and (c) |
| (a) and (b) | (a), (b), and (c) | (a) and (b) | (a) and (b) | (a), (b), and (c) |
| (a) | (a), (b), and (c) | (a) and (b) | (a) and (b) | (a), (b), and (c) |
| (a) and (b) | (a), (b), and (c) | (a) and (b) | (a) and (b) | (a), (b), and (c) |

In some examples, a TRS comprises:

$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$, wherein $X_5$ is K or E, $X_6$ is N or D, $X_{15}$ is S or T, $X_{16}$ is K, N, or R, and each of $X_1$, $X_2$, $X_3$, $X_4$, $X_7$, $X_8$, $X_9$, $X_{10}$, $X_{11}$, $X_{12}$, $X_{13}$, $X_{14}$, $X_{17}$, and $X_{18}$ is any amino acid; or $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$, wherein $X_1$ is K, T, V, or I, $X_2$ is A, K, 5, or G, $X_3$ is P, I, or T, $X_4$ is T, P, or 5, $X_5$ is K or E, $X_6$ is N or D, $X_7$ is N, E, I, or R, $X_8$ is D, E, G, or N, $X_9$ is D, S, A, E, or N, $X_{10}$ is S, F, or V, $X_{11}$ is F, S, I, T, or V, $X_{12}$ is K, N, E, or G, $X_{13}$ is Q, H, K, N, or P, $X_{14}$ is K, I, N, Q, or R, $X_{15}$ is S or T, $X_{16}$ is K, N, or R, $X_{17}$ is M, V, S, or T, $X_{18}$ is D, G, or T, and $X_{19}$ is T, N, D, or A.

Modifying TRS

In some embodiments, the engineered protein or polypeptide may be modified by altering the sequence of one or more TRS. For example, a TRS may be engineered by one or more of duplicating the TRS, mutating the TRS, substituting the TRS, shuffling the TRS, linking a TRS from a different source; and detecting whether the TRS binds to the target.

In some embodiments, the TRS is duplicated. In some embodiments, the TRS is mutated. In some embodiments, one or more amino acid residues in the TRS are substituted. In some embodiments, one or more amino acid residues in the TRS are substituted with one or more amino acid residues from a heterologous TRS derived from a different source. In some embodiments, one or more amino acid residues in the TRS are substituted with one or more amino acid residues from a TRS derived from the same species or related species. In some embodiments, the engineered protein or polypeptide comprises one or more TRS generated by shuffling of one or more TRS. In some embodiments, the engineered protein or polypeptide comprises one or more TRS generated by linking a TRS to one or more TRS from a different source. In some embodiments, one or more TRS is modified by introducing a mutation to a non-hypervariable region. In a preferred embodiment, one or more TRS is modified by introducing a mutation to a hypervariable region. In some embodiments, one or more TRS is modified by introducing a mutation to a non-hypervariable or conserved region, wherein the engineered protein or polypeptide comprises two or more TRS sequences.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4$^{th}$ Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

TABLE 2

| Set | | Sub-set | |
|---|---|---|---|
| Hydrophobic | F W Y H K M I L V A G C SEQ ID NO: 166 | Aromatic | F W Y H SEQ ID NO: 169 |
| | | Aliphatic | I L V |
| Polar | W Y H K R E D C S T N Q SEQ ID NO: 167 | Charged | H K R E D SEQ ID NO: 170 |
| | | Positively charged | H K R |

TABLE 2-continued

| Set | | Sub-set | |
|---|---|---|---|
| | | Negatively charged | E D |
| Small | V C A G S P T N D SEQ ID NO: 168 | Tiny | A G S |

Insecticidal Toxin

The engineered protein or polypeptide may comprise an insecticidal toxin or component thereof. Insecticidal toxins may be polypeptides that have insecticidal activity. Insecticidal toxins may be capable of fighting against insects, e.g., by killing or inactivating activities or functions such as appetite, growth, reproduction, etc. Examples of insecticidal toxins include insecticidal proteins derived from Bacillus cereus and Bacillus popilliae; insecticidal proteins such as δ-endotoxins derived from Bacillus thuringiensis (e.g. Cry1Ab, Cry1Ac, Cry1F, Cry1Fa2, Cry2Ab, Cry3A, Cry3Bb1 and Cry9C), VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl synthase; chitinase; and glucanase. Examples of insecticidal toxins also include hybrid toxins, partly deficient toxins and modified toxins of insecticidal proteins such as δ-endotoxin proteins (e.g., Cry1Ab, Cry1Ac, Cry1F, Cry1Fa2, Cry2Ab, Cry3A, Cry3Bb1 and Cry9C), VIP1, VIP2, VIP3, and VIP3A. The hybrid toxin may be made by combining different domains of the insecticidal proteins by a genetic engineering.

Functional Domains

In some embodiments, the engineered protein or polypeptide comprises one or more functional domains. In some embodiments, the functional domain is a heterologous functional domain. In some embodiments, the TRS is associated with one or more heterologous functional domains with or without fusion. In some embodiments, at least one or more heterologous functional domains may be at or near the amino-terminus of the engineered protein or polypeptide. In some embodiments, at least one or more heterologous functional domains may be at or near the amino-terminus of the engineered protein or polypeptide protein and/or wherein at least one or more heterologous functional domains is at or near the carboxy-terminus of the engineered protein. The one or more heterologous functional domains may be fused, or tethered to the engineered protein or polypeptide. The one or more heterologous functional domains may be linked to the engineered protein or polypeptide by a linker moiety. In some embodiments, the linker is a GlySer linker.

In some embodiments, the functional domain may be a transcription activation domain, a transcription repressor domain, a recombinase domain, a transposase domain, a histone remodeler, a demethylase, a methyltransferase, a cryptochrome, or a light inducible/controllable domain or a chemically inducible/controllable domain. In some embodiments, the one or more functional domains is an NLS (Nuclear Localization Sequence) or an NES (Nuclear Export Signal). In some embodiments, the one or more functional domains is a transcriptional activation domain comprises VP64, p65, MyoD1, HSF1, RTA, SET7/9 and a histone acetyltransferase. In some embodiments, the functional domain may be comprise protease activity, myristoyltransferase activity, acyltransferase activity, famesyltransferase activity, geranylgeranyltransferase activity, acetyltransferase activity, glycinamide ribonucleotide (GAR) transformylase activity, glutamylase activity, deglutamylase activity, carboxylase activity, glycosyltransferases activity, hydroxylases activity, nucleotidyl transferase activity, kinase activity, phosphotransferase activity, phosphatase activity, or other catalytic activities. Fusion protein may comprise any additional protein sequence, and optionally a linker sequence between any two domains. Examples of protein domains that may be fused to an engineered protein or polypeptide include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). An engineered protein may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinidase and histone tail protease. In some preferred embodiments, the functional domain is a transcriptional activation domain, such as, without limitation, VP64, p65, MyoD1, HSF1, RTA, SET7/9 or a histone acetyltransferase. In some embodiments, the functional domain is a deaminase, such as a cytidine deaminase. Cytidine deaminase may be directed to a target nucleic acid to where it directs conversion of cytidine to uridine, resulting in C to T substitutions (G to A on the complementary strand).

The term "associated with" is used here in relation to the association of the functional domain to engineered targeting protein or polypeptide. It is used in respect of how one molecule 'associates' with respect to another, for example between an engineered protein and a functional domain. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the engineered protein or polypeptide is associated with a functional domain by binding thereto. In other embodiments, the engineered protein or polypeptide is associated with a functional domain because the two are fused together, optionally via an intermediate linker.

Any of the herein described improved functionalities may be made to any engineered protein or polypeptide of the present invention. It will be appreciated that any of the functionalities described herein may be engineered into the engineered proteins or polypeptides from other orthologs, including chimeric functional protein domains comprising fragments from multiple orthologs.

Target Recognition Regions

The TRSs may be comprised in target recognition regions. In certain embodiments, engineering of target recognition regions comprising TRSs is guided by target characteristics. In some instances, targets will be large and distributed. In some instances, targets will be small and localized. In some instances, targets will be distinguishable to some degree by their environment, for example, a target located in a particular extracellular environment can influence engineering of a target recognition region compatible with the extracellular environment. In a non-limiting example, a macromolecule in a mucous environment can advantageously be targeted by a target recognition region compatible with that environment.

Accordingly, in embodiments of the invention, target recognition regions can comprise one or more TRS motifs, such as 2, 3, 4, 5, 6, 7, 8, 9, 10, 11, 12, 13, 14, 15, 16, 17, 18, 19, or 20 or more TRS motifs. In embodiments of the invention, TRS motifs can be short or long, for example, 2, 3, 4, 5, 6, 7, 8, 9, 10, 11, 12, 13, 14, 15, 16, 17, 18, 19, 20, or more amino acids. In certain embodiments, variation within a TRS motif encompasses only a subset of amino acid positions in the motif while other amino acids of the motif are comparatively constant. In certain embodiments, such motifs are advantageously employed in the engineering of large target recognition regions comprising multiple TRS motifs. In theory and without limitation, relatively invariant amino acids govern the overall structure of the recognition region whereas the variable amino acids determine target binding. In certain embodiments, variation within a TRS motif encompasses substantially all of the amino acids of the TRS motif. In certain embodiments, a TRS motif is defined to include relatively invariant amino acids that flank variable amino acids. For example, a TRS may include a series of adjacent hypervariable amino acids flanked by invariant amino acids. In theory and without being bound, invariant flanking amino acids govern the structure of the recognition region whereas the hypervariable amino acids determine target binding. In certain embodiments, such motifs may advantageously be employed in the engineering of small target recognition regions.

Nucleic Acids Encoding Engineered Proteins

In one aspect, the invention provides a non-naturally occurring or engineered composition, or one or more polynucleotides encoding components of said composition, or vector or delivery systems comprising one or more polynucleotides encoding components of said composition for use in modifying a target molecule or a target molecule in a target cell. In some embodiments, the composition comprises an engineered protein or polypeptide comprising one or more hypervariable amino acid residues. In preferred embodiments, a TRS may include a series of adjacent hypervariable amino acids flanked by invariant amino acids, and thus the nucleic acids encode for the hypervariable amino acid residues flanked by invariant amino acids. In some embodiments, the TRS is derived from a prokaryotic organism. In some embodiments, the TRS may be derived from a bacteria defense-mechanism related protein. In particular embodiments, the TRS is derived from an IgA protease of *Neisseria gonorrhoeae, Neisseria meningitidis, Haemophilus influenzae, Streptococcus pneumonia*, or any orthologs thereof. In some embodiments, the TRS may be derived from a Enterobacteriaceae family protein. In some embodiments, the TRS may be derived from a *Photorhabdus* bacteria protein. The bacteria protein may be toxins, including a variety of insecticidal toxins, as well as adhesins, proteases, and lipases, or any orthologs thereof.

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a targeting system is delivered to a cell.

In some embodiments, polynucleotides encoding the engineered proteins are provided and are codon optimized. In some embodiments, an enzyme coding sequence encoding the engineered protein is codon optimized for expression in particular cells. In some embodiments, the host cell is a prokaryotic cell. In some embodiments, the host cell is a eukaryotic cell. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis.

Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In some embodiments, nucleic acid molecule encoding the engineered protein is fused to one or more nuclear localization sequences (NLSs) or nuclear export signals (NESs), such as about or more than about 1, 2, 3, 4, 5, 6, 7, 8, 9, 10, or more NLSs or NESs. In some embodiments, the engineered protein comprises about or more than about 1, 2, 3, 4, 5, 6, 7, 8, 9, 10, or more NLSs or NESs at or near the amino-terminus, about or more than about 1, 2, 3, 4, 5, 6, 7, 8, 9, 10, or more NLSs or NESs at or near the carboxy-terminus, or a combination of these (e.g. zero or at least one or more NLS or NES at the amino-terminus and zero or at one or more NLS or NES at the carboxy terminus). When more than one NLS or NES is present, each may be selected independently of the others, such that a single NLS or NES may be present in more than one copy and/or in combination with one or more other NLSs or NESs present in one or more copies. In some embodiments, an NLS or NES is considered near the N- or C-terminus when the nearest amino acid of the NLS or NES is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 105); the NLS from nucleoplasmin (e.g. the nucleoplasmin bipartite NLS with the sequence KRPAATKKAGQAKKKK) (SEQ ID NO: 106); the c-myc NLS having the amino acid sequence PAAKRVKLD (SEQ ID NO: 107) or RQRRNELKRSP (SEQ ID NO: 108); the hRNPA1 M9 NLS having the sequence NQSSNFGPMKGGNFGGRSSGPYGGGGQYFAK-PRNQGGY (SEQ ID NO: 109); the sequence RMRIZFKNKGKDTAELRRRRVEVSVELRKAKKD-EQILKRRNV (SEQ ID NO: 110) of the IBB domain from importin-alpha; the sequences VSRKRPRP (SEQ ID NO: 111) and PPKKARED (SEQ ID NO: 112) of the myoma T protein; the sequence PQPKKKPL (SEQ ID NO: 113) of human p53; the sequence SALIKKKKKMAP (SEQ ID NO: 114) of mouse c-abl IV; the sequences DRLRR (SEQ ID NO: 115) and PKQKKRK (SEQ ID NO: 116) of the influenza virus NS1; the sequence RKLKKKIKKL (SEQ ID NO: 117) of the Hepatitis virus delta antigen; the sequence REKKKFLKRR (SEQ ID NO: 118) of the mouse Mx1 protein; the sequence KRKGDEVDGVDEVAKKKSKK (SEQ ID NO: 119) of the human poly(ADP-ribose) polymerase; and the sequence RKCLQAGMNLEARKTKK (SEQ ID NO: 120) of the steroid hormone receptors (human) glucocorticoid. Non-limiting examples of NESs include an NES sequence LYPERLRRILT (SEQ ID NO:121) (ctgtaccctgagcggctgcggcggatcctgacc (SEQ ID NO:122)). In general, the one or more NLSs or NESs are of sufficient strength to drive accumulation of the engineered protein in a detectable amount in respectively the nucleus or the cytoplasm of a eukaryotic cell. In general, strength of nuclear localization/export activity may derive from the number of NLSs/NESs in the engineered protein, the particular NLS(s) or NES(s) used, or a combination of these factors.

Inducible Systems

In one embodiment, fusion complexes comprising the engineered protein capable of binding and/or cleaving or modifying a target are designed to be inducible, for instance light inducible or chemically inducible. Such inducibility allows for activation of the engineered protein and/or the effector component at a desired moment in time. Accordingly, in some embodiments, an engineered protein or polypeptide may form a component of an inducible targeting system. The inducible nature of the system would allow for spatiotemporal control of gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome).

Light inducibility is for instance achieved by designing a fusion complex wherein CRY2 PHR/CIBN pairing is used for fusion. This system is particularly useful for light induction of protein interactions in living cells (Konermann S, et al. Nature. 2013; 500:472-476). Chemical inducibility is for instance provided for by designing a fusion complex wherein FKBP/FRB (FK506 binding protein/FKBP rapamycin binding) pairing is used for fusion. Using this system rapamycin is required for binding of proteins (Zetsche et al. Nat Biotechnol. 2015; 33(2):139-42 describes the use of this system for Cas9).

Further, when introduced in the cell as DNA, the engineered protein of the invention can be modulated by inducible promoters, such as tetracycline or doxycycline controlled transcriptional activation (Tet-On and Tet-Off expression system), hormone inducible gene expression system such as for instance an ecdysone inducible gene expression system and an arabinose-inducible gene expression system. When delivered as RNA, expression of the engineered protein can be modulated via a riboswitch, which can sense a small molecule like tetracycline (as described in Goldfless et al. Nucleic Acids Res. 2012; 40(9):e64). A riboswitch (also known as an aptozyme) is a regulatory segment of a messenger RNA molecule that binds a small molecule. This typically results in a change in production of the proteins encoded by the mRNA. This may be through cleavage of, or binding to, the riboswitch. In particular, reduction of riboswitch activity is envisaged. This may be useful in assaying riboswitch function in vivo or in vitro, but also as a means of controlling therapies based on riboswitch activity, in vivo or in vitro.

Aspects of the invention also encompass methods and uses of the compositions and systems described herein in genome or proteome engineering, e.g. for altering or manipulating the (protein) expression of or one or more gene products, in prokaryotic or eukaryotic cells, in vitro, in vivo or ex vivo. In an aspect, the invention provides methods and compositions for modulating, e.g., reducing, expression of a target protein in cells. In the subject methods, the invention provides a system with the engineered protein that interferes with expression, stability, and modification of a target protein.

In certain embodiments, an effective amount of the engineered protein is used to cleave a target protein or polypeptide, or interfere with target expression. In an advantageous embodiment, the engineered protein binds to the target specifically.

In some aspects, the invention provides methods comprising delivering one or more polynucleotides, such as or one or more vectors as described elsewhere herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a targeting system is delivered to a cell.

Destabilization Domains

In certain embodiments, the engineered protein according to the invention as described herein is associated with or fused to a destabilization domain (DD). In some embodiments, the DD is ER50. A corresponding stabilizing ligand for this DD is, in some embodiments, 4HT. As such, in some embodiments, one of the at least one DDs is ER50 and a stabilizing ligand therefor is 4HT or CMP8. In some embodiments, the DD is DHFR50. A corresponding stabilizing ligand for this DD is, in some embodiments, TMP. As such, in some embodiments, one of the at least one DDs is DHFR50 and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT.

In some embodiments, one or two DDs may be fused to the N-terminal end of the engineered protein with one or two DDs fused to the C-terminal of the engineered protein of the present invention. In some embodiments, the at least two DDs are associated with the engineered protein and the DDs are the same DD, i.e. the DDs are homologous. Thus, both (or two or more) of the DDs could be ER50 DDs. Alternatively, both (or two or more) of the DDs could be DHFR50 DDs. In some embodiments, at least two DDs are associated with the engineered protein and the DDs are different DDs, i.e. the DDs are heterologous. Thus, one of the DDS could be ER50 while one or more of the DDs or any other DDs could be DHFR50. Having two or more DDs which are heterologous may be advantageous as it would provide a greater level of degradation control. A tandem fusion of more than one DD at the N or C-term may enhance degradation. It is envisaged that high levels of degradation would occur in the absence of either stabilizing ligand, intermediate levels of degradation would occur in the absence of one stabilizing ligand and the presence of the other (or another) stabilizing ligand, while low levels of degradation would occur in the presence of both (or two of more) of the stabilizing ligands. Control may also be imparted by having an N-terminal ER50 DD and a C-terminal DHFR50 DD.

In some embodiments, the fusion of the engineered protein with the DD comprises a linker between the DD and engineered protein. In some embodiments, the linker is a GlySer linker. In some embodiments, the fusion of the engineered protein with the DD further comprises at least one Nuclear Export Signal (NES). In some embodiments, the fusion of the engineered protein with the DD comprises two or more NESs. In some embodiments, the fusion of the engineered protein with the DD comprises at least one Nuclear Localization Signal (NLS). This may be in addition to an NES. HA or Flag tags are also within the ambit of the invention as linkers. Applicants use NLS and/or NES as linker and also use Glycine Serine linkers as short as GS up to (GGGGS)3 (SEQ ID NO:123).

Destabilizing domains have general utility to confer instability to a wide range of proteins; see, e.g., Miyazaki, J Am Chem Soc. Mar. 7, 2012; 134(9): 3942-3945, incorporated herein by reference. CMP8 or 4-hydroxytamoxifen can be destabilizing domains. More generally, a temperature-sensitive mutant of mammalian DHFR (DHFRts), a destabilizing residue by the N-end rule, was found to be stable at a permissive temperature but unstable at 37° C. The addition of methotrexate, a high-affinity ligand for mammalian DHFR, to cells expressing DHFRts inhibited degradation of the protein partially. This was an important demonstration that a small molecule ligand can stabilize a protein otherwise targeted for degradation in cells. A rapamycin derivative was used to stabilize an unstable mutant of the FRB domain of mTOR (FRB*) and restore the function of the fused kinase, GSK-3β.6,7 This system demonstrated that ligand-dependent stability represented an attractive strategy to regulate the function of a specific protein in a complex biological environment. A system to control protein activity can involve the DD becoming functional when the ubiquitin complementation occurs by rapamycin induced dimerization of FK506-binding protein and FKBP12. Mutants of human FKBP12 or ecDHFR protein can be engineered to be metabolically unstable in the absence of their high-affinity ligands, Shield-1 or trimethoprim (TMP), respectively. These mutants are some of the possible destabilizing domains (DDs) useful in the practice of the invention and instability of a DD as a fusion with the engineered protein confers to protein degradation of the entire fusion protein by the proteasome. Shield-1 and TMP bind to and stabilize the DD in a dose-dependent manner. The estrogen receptor ligand binding domain (ERLBD, residues 305-549 of ERS1) can also be engineered as a destabilizing domain. Since the estrogen receptor signaling pathway is involved in a variety of diseases such as breast cancer, the pathway has been widely studied and numerous agonist and antagonists of estrogen receptor have been developed. Thus, compatible pairs of ERLBD and drugs are known. There are ligands that bind to mutant but not wild-type forms of the ERLBD. By using one of these mutant domains encoding three mutations (L384M, M421G, G521R)12, it is possible to regulate the stability of an ERLBD-derived DD using a ligand that does not perturb endogenous estrogen-sensitive networks. An additional mutation (Y537S) can be introduced to further destabilize the ERLBD and to configure it as a potential DD candidate. This tetra-mutant is an advantageous DD development. The mutant ERLBD can be fused to the engineered protein of this invention and its stability can be regulated or perturbed using a ligand. Another DD can be a 12-kDa (107-amino-acid) tag based on a mutated FKBP protein, stabilized by Shield1 ligand; see, e.g., Nature Methods 5, (2008). For instance, a DD can be a modified FK506 binding protein 12 (FKBP12) that binds to and is reversibly stabilized by a synthetic, biologically inert small molecule, Shield-1; see, e.g., Banaszynski L A, Chen L C, Maynard-Smith L A, Ooi A G, Wandless T J. A rapid, reversible, and tunable method to regulate protein function in living cells using synthetic small molecules. Cell. 2006; 126:995-1004; Banaszynski L A, Sellmyer M A, Contag C H, Wandless T J, Thorne S H. Chemical control of protein stability and function in living mice. Nat Med. 2008; 14:1123-1127; Maynard-Smith L A, Chen L C, Banaszynski L A, Ooi A G, Wandless T J. A directed approach for engineering conditional protein stability using biologically silent small molecules. The Journal of biological chemistry. 2007; 282: 24866-24872; and Rodriguez, Chem Biol. Mar. 23, 2012; 19(3): 391-398—all of which are incorporated herein by reference and may be employed in the practice of the invention in selected a DD to associate with a engineered protein in the practice of this invention.

Administration and Delivery

Through this disclosure and the knowledge in the art, the engineered protein, or components thereof or nucleic acid molecules encoding the engineered protein thereof or nucleic acid molecules encoding or providing components thereof may be delivered by a delivery system herein described both generally and in detail.

In an aspect the invention provides a method for modifying gene expression comprising the administration to a host or expression in a host in vivo of one or more of the compositions comprising the engineered protein as herein discussed.

In an aspect the invention provides a herein-discussed method comprising the delivery of the composition or nucleic acid molecule(s) coding therefor, wherein said nucleic acid molecule(s) are operatively linked to regulatory sequence(s) and expressed in vivo. In an aspect the invention provides a herein-discussed method wherein the expression in vivo is via a lentivirus, an adenovirus, or an AAV.

Vectors

In certain aspects the invention involves vectors, e.g. for delivering or introducing in a cell nucleic acid molecule encoding the engineered protein. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein. With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of the engineered protein or polypeptide (e.g., nucleic acid transcripts, proteins, or enzymes) in prokaryotic or eukaryotic cells. For example, nucleic acid molecules encoding the engineered protein or polypeptides, including DNA and RNA molecules, can be introduced and/or expressed in bacterial cells such as Escherichia coli, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g., amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in Escherichia coli with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion E. coli expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast Saccharomyces cerevisiae include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid molecule encoding the engineered protein or polypeptide of the present invention preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873, 316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety.

Administration to a host or a host cell may be performed via viral vectors known to the skilled person or described herein for delivery to a host (e.g. lentiviral vector, adenoviral vector, AAV vector). Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (*Mol. Cell. Biol.*, Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., the engineered proteins, enzymes, modified or mutant forms thereof, fusion proteins thereof, etc.).

Advantageous vectors include lentiviruses and adeno-associated viruses, and types of such vectors can also be selected for targeting particular types of cells.

Use of different selection markers may be advantageous for eliciting an improved effect.

The engineered protein or nucleic acid molecules encoding the engineered protein can be delivered using any suitable vector, e.g., plasmid or viral vectors, such as adeno associated virus (AAV), lentivirus, adenovirus or other viral vector types, or combinations thereof. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc. In some cases, the vectors may be bacteriophage vectors. Examples of bacteriophage vectors include λgt10, λgt11, λgt18-23, λZAP/R, the EMBL series of bacteriophage vectors, M13mp vectors (Pharmacia Biotech), pCANTAB 5e, pCOMB3 and M13KE.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

Example Delivery Approaches and Methods

In an embodiment herein the delivery is via an adenovirus, which may be at a single booster dose containing at least $1\times10^5$ particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^7$ particles, more preferably at least about $1\times10^8$ particles (e.g., about $1\times10^8$-$1\times10^{11}$ particles or about $1\times10^8$-$1\times10^{12}$ particles), and most preferably at least about $1\times10^0$ particles (e.g., about $1\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{10}$ functional AAV/ml solution. The dosage may be adjusted to balance the therapeutic benefit against any side effects. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg per 70 kg individual. Plasmids of the invention will generally comprise (i) a promoter; (ii) a sequence encoding an engineered protein comprising a hypervariable domain, operably linked to said promoter; (iii) a selectable marker; (iv) an origin of replication; and (v) a transcription terminator downstream of and operably linked to (ii). In some embodiments, the engineered protein comprises a TRS. In some embodiments, the engineered protein comprises a TRS of IgA protease. In particular embodiments, the engineered protein comprises a TRS of modified IgA protease. In some embodiments, the engineered protein comprises a hypervariable domain of micro-organism derived toxins. In some embodiments, the engineered protein comprises a hypervariable domain derived from *Photorhabdus* insect-related" (Pir) toxins.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

In some embodiments the nucleic acid molecules encoding the engineered protein of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

mRNA delivery methods are especially promising for liver delivery currently. Much clinical work on RNA delivery has focused on RNAi or antisense, but these systems can be adapted for delivery of RNA for implementing the present invention. References below to RNAi etc. should be read accordingly.

Means of delivery of nucleic acid molecules also preferred include delivery of nucleic acid molecules via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-

3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the RNA-targeting system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purified and characterized from transfected cell supernatant, then RNA is loaded into the exosomes. Delivery or administration according to the invention can be performed with exosomes, in particular but not limited to the brain. Vitamin E ($\alpha$-tocopherol) may be conjugated with the engineered protein or polypeptide comprising target recognition regions and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain.

In terms of local delivery to the brain, this can be achieved in various ways. For instance, material can be delivered intrastriatally e.g., by injection. Injection can be performed stereotactically via a craniotomy.

Adeno Associated Virus (AAV)

Engineered protein or polypeptide comprising one or more target recognition region can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome/transcriptome modification, the expression of engineered protein or polypeptide can be driven by a cell-type specific promoter. For example, liver-specific expression might use the Albumin promoter and neuron-specific expression (e.g., for targeting CNS disorders) might use the Synapsin I promoter.

In terms of in vivo delivery, AAV is advantageous over other viral vectors for a couple of reasons:

Low toxicity (this may be due to the purification method not requiring ultra centrifugation of cell particles that can activate the immune response) and Low probability of causing insertional mutagenesis because it doesn't integrate into the host genome.

AAV has a packaging limit of 4.5 or 4.75 Kb. This means that engineered protein comprising hypervariable regions of this invention as well as any fused or linked functional domain, a promoter and transcription terminator have to all fit into the same viral vector. Therefore, embodiments of the invention include utilizing homologs of the engineered protein or functional domain that are shorter.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

TABLE 3

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

In one embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the targeting system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the sequence specific targeting system of the present invention. A minimum of 2.5×106 CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (CellGenix) at a density of 2×106 cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

Particle Delivery Systems and/or Formulations

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of targeting system of this invention, e.g. the engineered protein or polypeptide, nucleic acid molecules encoding the engineered protein or polypeptide, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi: 10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Particles

Engineered protein or polypeptide comprising a hypervariable domain, nucleic acid molecules encoding the engineered protein or polypeptide, or other components of the protein or polypeptide targeting system may be delivered using particles or lipid envelopes; for instance, as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84).

In one embodiment, particles based on self-assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles that can deliver RNA to a cancer cell to stop tumor growth developed by Dan Anderson's lab at MIT may be used/and or adapted to the engineered protein and the protein or polypeptide targeting system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32): 12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the targeting system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the targeting system of the present invention.

In another embodiment, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the targeting system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated. LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding the engineered protein of the present invention to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011).

Preparation of LNPs and encapsulation of components of the protein targeting system may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(ω-methoxy-poly(ethylene glycol)2000) carbamoyl]-1,2-dimyristyloxypropyl-3-amine (PEG-C-DOMG) may be provided by Tekmira Pharmaceuticals (Vancouver, Canada) or synthesized. Cholesterol may be purchased from Sigma (St Louis, MO). Components of the protein targeting system may be encapsulated in LNPs containing DLinDAP, DLinDMA, DLinK-DMA, and DLinKC2-DMA (cationic lipid:DSPC:CHOL:PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nucleopore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Particle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted particles and quantified at 260 nm. RNA to lipid ratio was determined by measurement of cholesterol content in vesicles using the Cholesterol E enzymatic assay from Wako Chemicals USA (Richmond, VA). In conjunction with the herein discussion of LNPs and PEG lipids, PEGylated liposomes or LNPs are likewise suitable for delivery of a nucleic targeting system or components thereof.

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate:DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at a RNA to total lipid ratio of approximately 1:10 (wt:wt), followed by incubation for 30 minutes at 37° C. to form loaded LNPs. The mixture may be subsequently dialyzed overnight in PBS and filtered with a 0.45-μm syringe filter.

Spherical Nucleic Acid (SNA™) constructs and other particles (particularly gold particles) are also contemplated as a means to delivery nucleic acid molecules encoding the engineered protein to intended targets. Significant data show that AuraSense Therapeutics' Spherical Nucleic Acid (SNA™) constructs, based upon nucleic acid-functionalized gold particles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling particles with nucleic acid molecules may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes.

In terms of this invention, it is preferred to have one or more components of yjr protein or polypeptide targeting system delivered using particles or lipid envelopes. Other delivery systems or vectors may be used in conjunction with the particle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, particles of the invention have a greatest dimension of 100 nm or less. In other preferred embodiments, nanoparticles of the invention have a greatest dimension ranging between 35 nm and 60 nm.

Particles encompassed in the present invention may be provided in different forms, e.g., as solid particles (e.g., metal such as silver, gold, iron, titanium), non-metal, lipid-based solids, polymers), suspensions of particles, or combinations thereof. Metal, dielectric, and semiconductor particles may be prepared, as well as hybrid structures (e.g., core-shell particles). Particles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft particles have been manufactured, and are within the scope of the present invention. A prototype particle of semi-solid nature is the liposome. Various types of liposome particles are currently used clinically as delivery systems for anticancer drugs and vaccines. Particles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material.

U.S. Pat. No. 5,855,913, incorporated herein by reference, provides a particulate composition having aerodynamically light particles having a tap density of less than 0.4 g/cm3 with a mean diameter of between 5 μm and 30 μm, incorporating a surfactant on the surface thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable particles having a biodegradable solid core containing a biologically active material and poly(alkylene glycol) moieties on the surface.

WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can be envisioned that such methods and materials of herein-cited documents, e.g., conjugated lipomers can be used in the context of the targeting system to achieve in vitro, ex vivo and in vivo genomic perturbations to modify gene expression, including modulation of protein expression.

In one embodiment, the particle may be epoxide-modified lipid-polymer, advantageously 7C1 (see, e.g., James E. Dahlman and Carmen Barnes et al. Nature Nanotechnology (2014) published online 11 May 2014, doi:10.1038/nnano.2014.84). C71 was synthesized by reacting C15 epoxide-terminated lipids with PEI600 at a 14:1 molar ratio, and was formulated with C14PEG2000 to produce particles (diameter between 35 and 60 nm) that were stable in PBS solution for at least 40 days.

An epoxide-modified lipid-polymer may be utilized to deliver the engineered protein or the protein targeting system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

Exosomes

Exosomes are endogenous nano-vesicles that transport nucleic acids, proteins and other macromolecules and can deliver macromolecules to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide.

El-Andaloussi et al. (Nature Protocols 7, 2112-2126 (2012)) discloses how exosomes derived from cultured cells can be harnessed for delivery of nucleic acids in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of this invention.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16,500 g for 30 min followed by filtration through a 0.22 mm filter. Exosomes are pelleted by ultracentrifugation at 120,000 g for 70 min. The exosomes may be co-cultured with monocytes and lymphocytes isolated from the peripheral blood of healthy donors. Therefore, it may be contemplated that exosomes containing the targeting system of the present invention may be introduced to monocytes and lymphocytes of and autologously reintroduced into a human. Accordingly, delivery or administration according to the invention may be performed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoyl-sn-glycero-3-phosphatidylcholine (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis.

In another embodiment, the targeting system or components thereof may be administered in liposomes, such as a stable nucleic-acid-lipid particle (SNALP) (see, e.g., Morrissey et al., Nature Biotechnology, Vol. 23, No. 8, August 2005) whereby nucleic acid molecules encoding the engineered protein or polypeptide may be encapsulated. Daily intravenous injections of about 1, 3 or 5 mg/kg/day of a specific targeting system targeted in a SNALP are contemplated. The daily treatment may be over about three days and then weekly for about five weeks. In another embodiment, a specific targeting system encapsulated SNALP may be administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(ω-methoxypoly (ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780).

In yet another embodiment, a SNALP may comprise synthetic cholesterol (Sigma-Aldrich, St Louis, MO, USA), dipalmitoylphosphatidylcholine (Avanti Polar Lipids, Alabaster, AL, USA), 3-N-[(ω-methoxy poly(ethylene glycol) 2000)carbamoyl]-1,2-dimyristyloxypropylamine, and cationic 1,2-dilinoleyloxy-3-N,N-dimethylaminopropane (see, e.g., Geisbert et al., Lancet 2010; 375: 1896-905). A dosage of about 2 mg/kg total of targeting system per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N,N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subject at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC)—both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at≥0.4 mg/kg; all responded to slowing of the infusion rate and all continued on study. Minimal and transient elevations of serum cytokines IL-6, IP-10 and IL-lra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Biotechnology, Volume 28 Number 2 Feb. 2010, pp. 172-177).

The lipid, lipid particle, or lipid bilayer or lipid entity of the invention can be prepared by methods well known in the art. See Wang et al., ACS Synthetic Biology, 1, 403-07 (2012); Wang et al., PNAS, 113(11) 2868-2873 (2016); Manoharan, et al., WO 2008/042973; Zugates et al., U.S. Pat. No. 8,071,082; Xu et al., WO 2014/186366 A1 (US20160082126). Xu et provides a way to make a nanocomplex for the delivery of saporin wherein the nanocomplex comprising saporin and a lipid-like compound, and wherein the nanocomplex has a particle size of 50 nm to 1000 nm; the saporin binds to the lipid-like compound via non-covalent interaction or covalent bonding; and the lipid-like compound has a hydrophilic moiety, a hydrophobic moiety, and a linker joining the hydrophilic moiety and the hydrophobic moiety, the hydrophilic moiety being optionally charged and the hydrophobic moiety having 8 to 24 carbon atoms. Xu et al., WO 2014/186348 (US20160129120) provides examples of nanocomplexes of modified peptides or proteins comprising a cationic delivery agent and an anionic pharmaceutical agent, wherein the nanocomplex has a particle size of 50 to 1000 nm, the cationic delivery agent binds to the anionic pharmaceutical agent, and the anionic pharmaceutical agent is a modified peptide or protein formed of a peptide and a protein and an added chemical moiety that contains an anionic group. The added chemical moiety is linked to the peptide or protein via an amide group, an ester group, an ether group, a thioether group, a disulfide group, a hydrazone group, a sulfenate ester group, an amidine group, a urea group, a carbamate group, an imidoester group, or a carbonate group. More particularly these documents provide examples of lipid or lipid-like compounds that can be used to make the particle delivery system of the present invention, including compounds of the formula $B_1$-$K_1$-A-$K_2$—$B_2$, in which A, the hydrophilic moiety, is

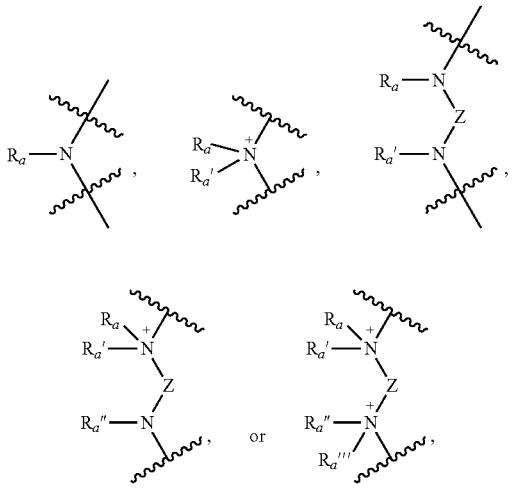

each of $R_a$, $R_a'$, $R_a''$, and $R_a'''$, independently, being a $C_1$-$C_{20}$ monovalent aliphatic radical, a $C_1$-$C_{20}$ monovalent heteroaliphatic radical, a monovalent aryl radical, or a monovalent heteroaryl radical; and Z being a $C_1$-$C_{20}$ bivalent aliphatic radical, a $C_1$-$C_{20}$ bivalent heteroaliphatic radical, a bivalent aryl radical, or a bivalent heteroaryl radical; each of $B_1$, the hydrophobic moiety, and $B_2$, also the hydrophobic moiety, independently, is a $C_{12-20}$ aliphatic radical or a $C_{12-20}$ heteroaliphatic radical; and each of $K_1$, the linker, and $K_2$, also the linker, independently, is O, S, Si, $C_1$-$C_6$ alkylene

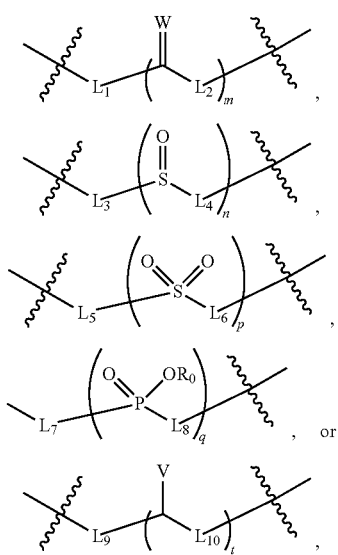

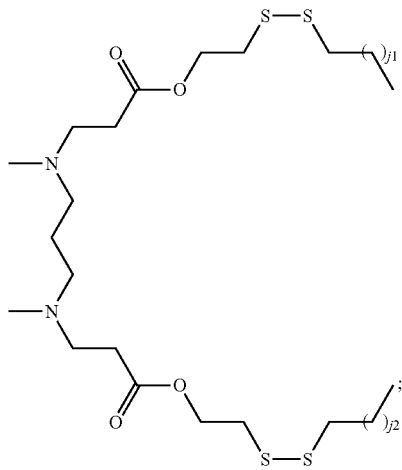

1-O16B, j1, j2 = 10; and
1-O18B, j1, j2 = 12 in which each of m, n, p, q, and t, independently, is 1-6; W is O, S, or $NR_C$; each of $L_1$, $L_3$, $L_5$, $L_7$, and $L_9$, independently, is a bond, O, S, or $NR_d$; each of L2, $L_4$, $L_6$, $L_8$, and $L_{10}$, independently, is a bond, O, S, or $NR_e$; and V is $OR_f$, $SR_g$, or $NR_hR_i$, each of $R_b$, $R_c$, $R_d$, $R_e$, $R_f$, $R_g$, $R_h$, and $R_i$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical and specific compounds:

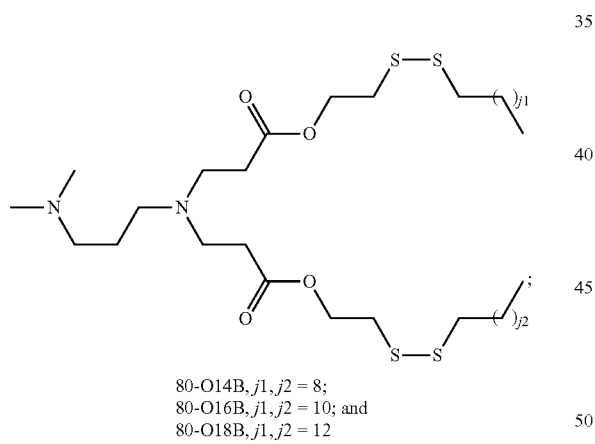

80-O14B, j1, j2 = 8;
80-O16B, j1, j2 = 10; and
80-O18B, j1, j2 = 12

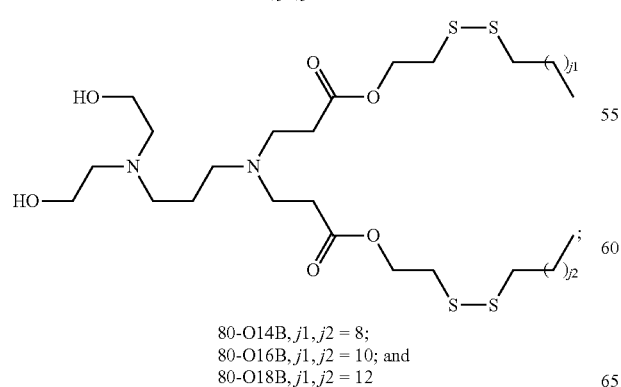

80-O14B, j1, j2 = 8;
80-O16B, j1, j2 = 10; and
80-O18B, j1, j2 = 12

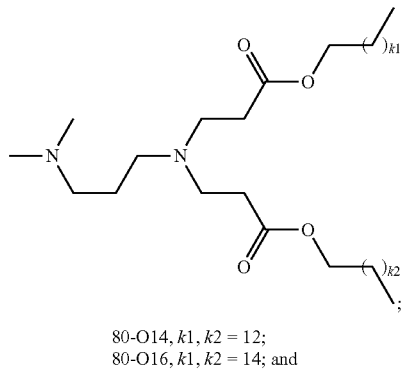

80-O14, k1, k2 = 12;
80-O16, k1, k2 = 14; and
80-O18, k1, k2 = 16

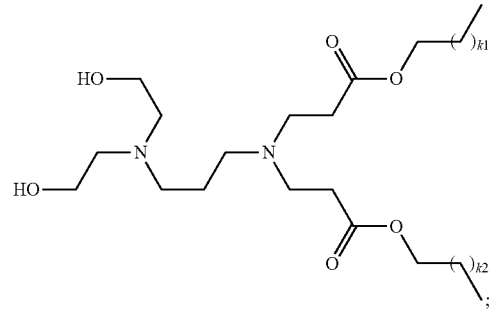

87-O14, k1, k2 = 12;
87-O16, k1, k2 = 14; and
87-O18, k1, k2 = 16

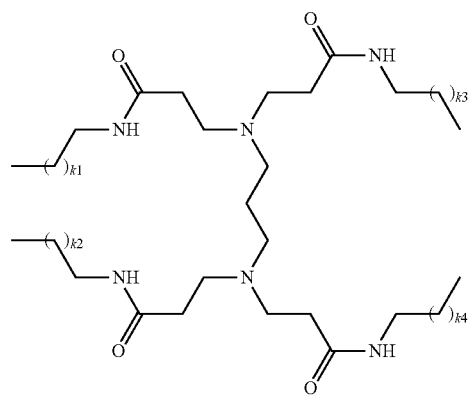

1-N16, k1, k2, k3, k4 = 14
1-N18, k1 = 12, k2 = 13, k3 = 15, and k4 = 16;

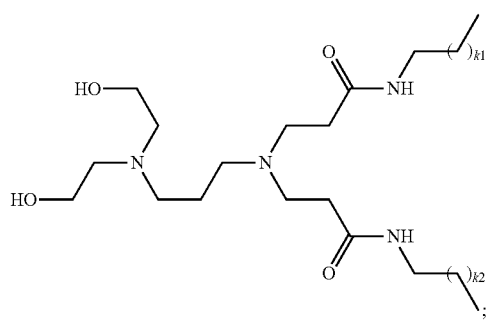

87-N17, k1 = 13 and k2 = 15;
87-N16, k1, k2 = 14; and
87-N18, k1, k2 = 16.

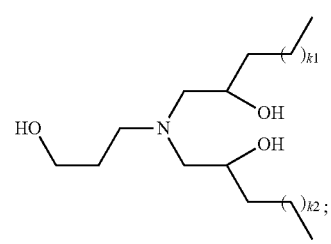

EC16-1, k1, k2 = 14;

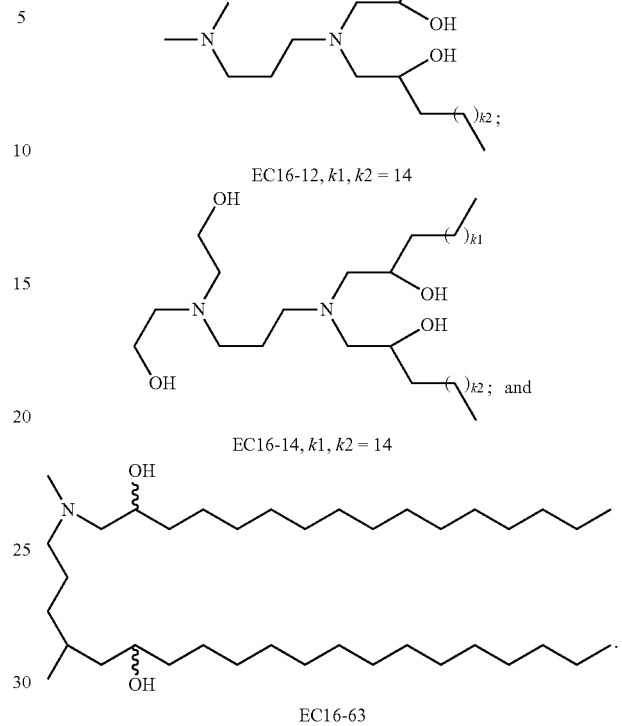

EC16-3, k1, k2 = 14

EC16-12, k1, k2 = 14

EC16-14, k1, k2 = 14; and

EC16-63

Additional examples of cationic lipid that can be used to make the particle delivery system of the invention can be found in US20150140070, wherein the cationic lipid has the formula

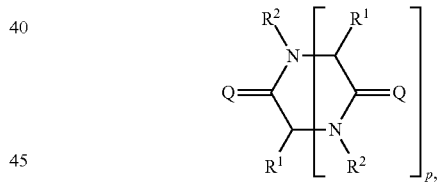

wherein p is an integer between 1 and 9, inclusive; each instance of Q is independently O, S, or $NR^Q$; $R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii) or (iii); each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, —$OR^{A1}$,—$N(R^{A1})_2$, —$SR^{A1}$, or a group of formula:

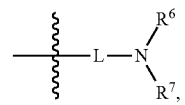

L is an optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, or combination thereof, and each of $R^6$ and $R^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii); each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{41}$ groups, together with the nitrogen atom to which they are attached, are joined to form an optionally substituted heterocyclic or optionally substituted heteroaryl ring; each instance of $R^2$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii); Formulae (i), (ii), and (iii) are:

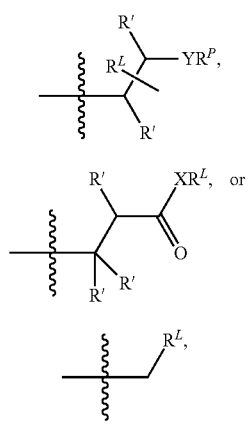

each instance of R' is independently hydrogen or optionally substituted alkyl; X is O, S, or $NR^X$; $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; Y is O, S, or $NR^Y$; $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; $R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; $R^L$ is optionally substituted $C_{1-50}$ alkyl, optionally substituted $C_{2-50}$ alkenyl, optionally substituted $C_{2-50}$ alkynyl, optionally substituted heteroC$_{1-50}$ alkyl, optionally substituted heteroC$_{2-50}$ alkenyl, optionally substituted heteroC$_{2-50}$ alkynyl, or a polymer; provided that at least one instance of $R^Q$, $R^2$, $R^6$, or $R^7$ is a group of the formula (i), (ii), or (iii); in Liu et al., (US 20160200779, US 20150118216, US 20150071903, and US 20150071903), which provide examples of cationic lipids to include polyethylenimine, polyamidoamine (PAMAM) starburst dendrimers, Lipofectin (a combination of DOTMA and DOPE), Lipofectase, LIPOFECTAMINE® (e.g., LIPOFECTAMINE® 2000, LIPOFECTAMINE® 3000, LIPOFECTAMINE® RNAiMAX, LIPOFECTAMINE® LTX), SAINT-RED (Synvolux Therapeutics, Groningen Netherlands), DOPE, Cytofectin (Gilead Sciences, Foster City, Calif.), and Eufectins (JBL, San Luis Obispo, Calif.). Exemplary cationic liposomes can be made from N-[1-(2,3-dioleoyloxy)-propyl]-N,N,N-trimethylammonium chloride (DOTMA), N-[1-(2,3-dioleoyloxy)-propyl]-N,N,N-trimethylammonium methylsulfate (DOTAP), 3.beta.-[N—(N',N'-dimethylaminoethane)carbamoyl]cholesterol (DC-Chol), 2,3,-dioleyloxy-N-[2(sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB); in WO2013/093648 which provides cationic lipids of formula n

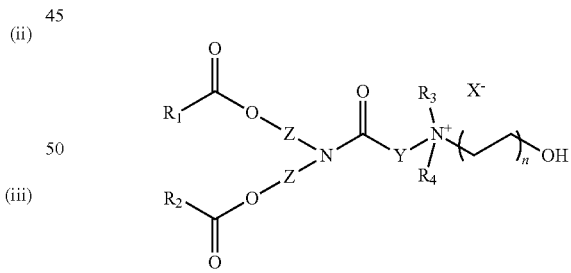

which Z=an alkyl linker, $C_2$-$C_4$ alkyl, Y=an alkyl linker, $C_1$-$C_6$ alkyl, $R_1$ and $R_2$ are each independently $C_{10}$-$C_{30}$alkyl, $C_{10}$-$C_{30}$alkenyl, or $C_{10}$-$C_{30}$alkynyl, $C_{10}$-$C_{30}$alkyl, $C_{10}$-$C_{20}$alkyl, $C_{12}$-$C_{18}$alkyl, $C_{13}$-$C_{17}$alkyl, $C_{13}$alkyl, $C_{10}$-$C_{30}$alkenyl, $C_{10}$-$C_{20}$alkenyl, $C_{12}$-$C_{18}$alkenyl, $C_{13}$-$C_{17}$alkenyl, $C_{17}$alkenyl; R3 and R4 are each independently hydrogen, $C_1$-$C_6$ alkyl, or —$CH_2CH_2OH$, $C_1$-$C_6$ alkyl, $C_1$-$C_3$alkyl; n is 1-6; and X is a counterion, including any nitrogen counterion, as that term is readily understood in the art, and specific cationic lipids including, and

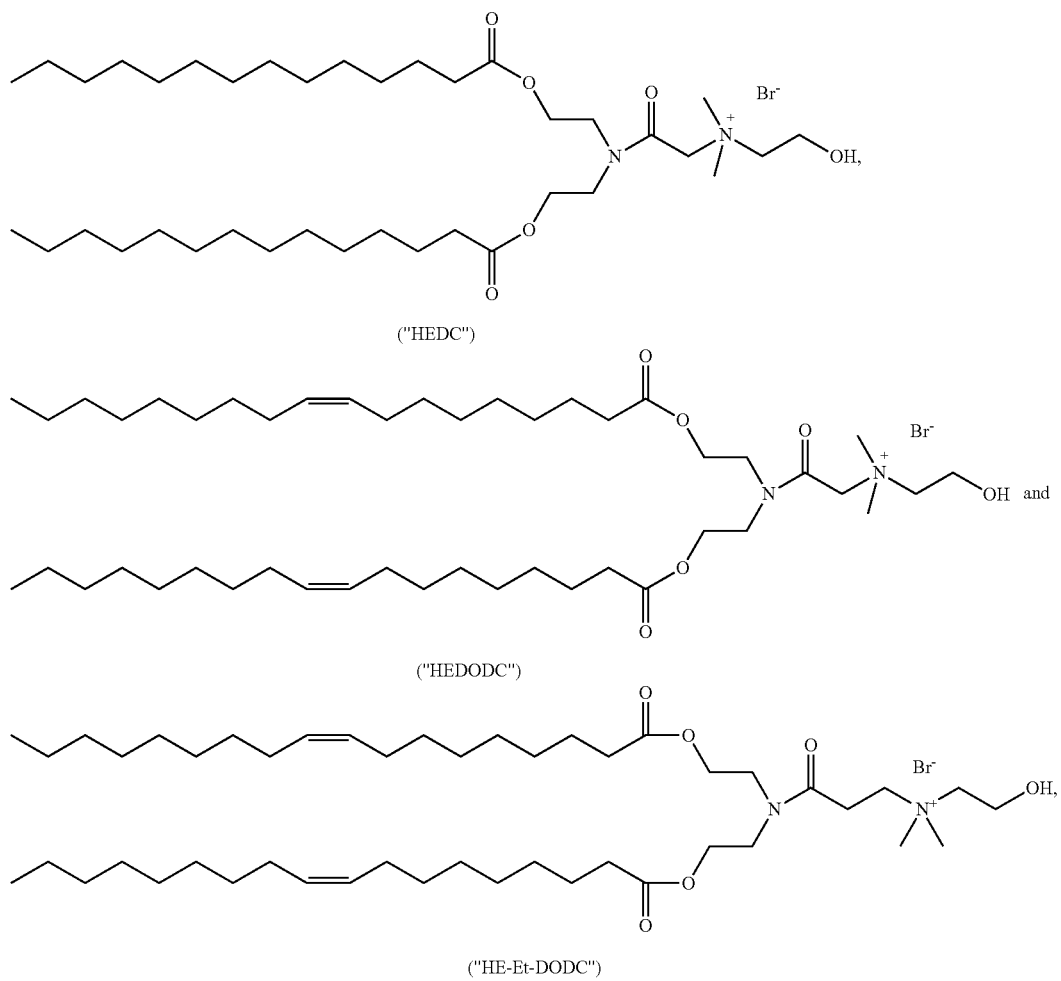

("HEDC")

("HEDODC")

("HE-Et-DODC")

WO2013/093648 also provides examples of other cationic charged lipids at physiological pH including N,N-dioleyl-N,N-dimethylammonium chloride (DODAC), N,N-distearyl-N,N-dimethylammonium bromide (DDAB); N-(1,2-dimyristyloxyprop-3-yl)-N,N-dimethyl-N-hydroxyethylammonium bromide (DMRIE) and dioctadecylamidoglycyl carboxyspermidine (DOGS); in US 20160257951, which provides cationic lipids with a general formula

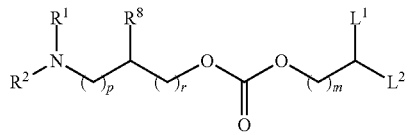

or a pharmacologically acceptable salt thereof, wherein $R^1$ and $R^2$ are each independently a hydrogen atom, a $C_1$-$C_6$ alkyl group optionally substituted with one or more substituents selected from substituent group α, a $C_2$-$C_6$ alkenyl group optionally substituted with one or more substituents selected from substituent group α, a $C_2$-$C_6$ alkynyl group optionally substituted with one or more substituents selected from substituent group α, or a $C_3$-$C_7$ cycloalkyl group optionally substituted with one or more substituents selected from substituent group a, or $R^1$ and $R^2$ form a 3- to 10-membered heterocyclic ring together with the nitrogen atom bonded thereto, wherein the heterocyclic ring is optionally substituted with one or more substituents selected from substituent group α and optionally contains one or more atoms selected from a nitrogen atom, an oxygen atom, and a sulfur atom, in addition to the nitrogen atom bonded to $R^1$ and $R^2$, as atoms constituting the heterocyclic ring; $R^1$ is a hydrogen atom or a $C_1$-$C_6$ alkyl group optionally substituted with one or more substituents selected from substituent group α; or $R^1$ and $R^8$ together are the group —$(CH_2)_q$—; substituent group α consists of a halogen atom, an oxo group, a hydroxy group, a sulfanyl group, an amino group, a cyano group, a $C_1$-$C_6$alkyl group, a $C_1$-$C_6$ halogenated alkyl group, a $C_1$-$C_6$ alkoxy group, a $C_1$-$C_6$ alkylsulfanyl group, a $C_1$-$C_6$ alkylamino group, and a $C_1$-$C_7$ alkanoyl group; $L^1$ is a $C_{10}$-$C_{24}$ alkyl group optionally substituted with one or more substituents selected from substituent group β1, a $C_{10}$-$C_{24}$ alkenyl group optionally substituted with one or more substituents selected from substituent group β1, a $C_3$-$C_{24}$ alkynyl group optionally substituted with one or more substituents selected from substituent group β1, or a ($C_1$-$C_{10}$ alkyl)-$(Q)_k$-($C_1$-$C_{10}$ alkyl) group optionally substituted with one or more substituents selected from substituent group β1; $L^2$ is, independently of $L^1$, a $C_{10}$-$C_{24}$ alkyl group optionally substituted with one or more substituents selected from substituent group β1, a $C_{10}$-$C_{24}$ alkenyl group optionally substituted with one or more substituents selected from substituent group β1, a $C_3$-$C_{24}$ alkynyl group optionally substituted with one or more substituents selected from substituent group β1, a ($C_1$-$C_{10}$ alkyl)-$(Q)_k$-($C_1$-$C_{10}$ alkyl) group optionally substituted with having one or more substituents selected from substituent group β1, a ($C_{10}$-$C_{24}$ alkoxy)methyl group optionally substituted with one or more substituents selected from substituent group β1, a ($C_{10}$-$C_{24}$ alkenyl)oxymethyl group optionally substituted with one or more substituents selected from substituent group β1, a ($C_3$-$C_{24}$ alkynyl)oxymethyl group optionally substituted with one or more substituents selected from substituent group β1, or a ($C_1$-$C_{10}$ alkyl)-$(Q)_k$-($C_1$-$C_{10}$ alkoxy)methyl group optionally substituted with one or more substituents selected from substituent group β1; substituent group β1 consists of a halogen atom, an oxo group, a cyano group, a $C_1$-$C_6$ alkyl group, a $C_1$-$C_6$ halogenated alkyl group, a $C_1$-$C_6$ alkoxy group, a $C_1$-$C_6$ alkylsulfanyl group, a $C_1$-$C_7$ alkanoyl group, a $C_1$-$C_7$ alkanoyloxy group, a $C_3$-$C_7$ alkoxyalkoxy group, a ($C_1$-$C_6$ alkoxy)carbonyl group, a ($C_1$-$C_6$ alkoxy)carboxyl group, a ($C_1$-$C_6$ alkoxy)carbamoyl group, and a ($C_1$-$C_6$ alkylamino)carboxyl group; Q is a group of formula:

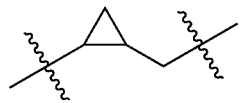 [SMILES: *CC1CC1*]

when $L^1$ and $L^2$ are each substituted with one or more substituents selected from substituent group β1 and substituent group β1 is a $C_1$-$C_6$ alkyl group, a $C_1$-$C_6$ alkoxy group, a $C_1$-$C_6$ alkylsulfanyl group, a $C_1$-$C_7$ alkanoyl group, or a $C_1$-$C_7$ alkanoyloxy group, the substituent or substituents selected from substituent group β1 in $L^1$ and the substituent or substituents selected from substituent group β1 in $L^2$ optionally bind to each other to form a cyclic structure; k is 1, 2, 3, 4, 5, 6, or 7; m is 0 or 1; p is 0, 1, or 2; q is 1, 2, 3, or 4; and r is 0, 1, 2, or 3, provided that p+r is 2 or larger, or q+r is 2 or larger, and specific cationic lipids including

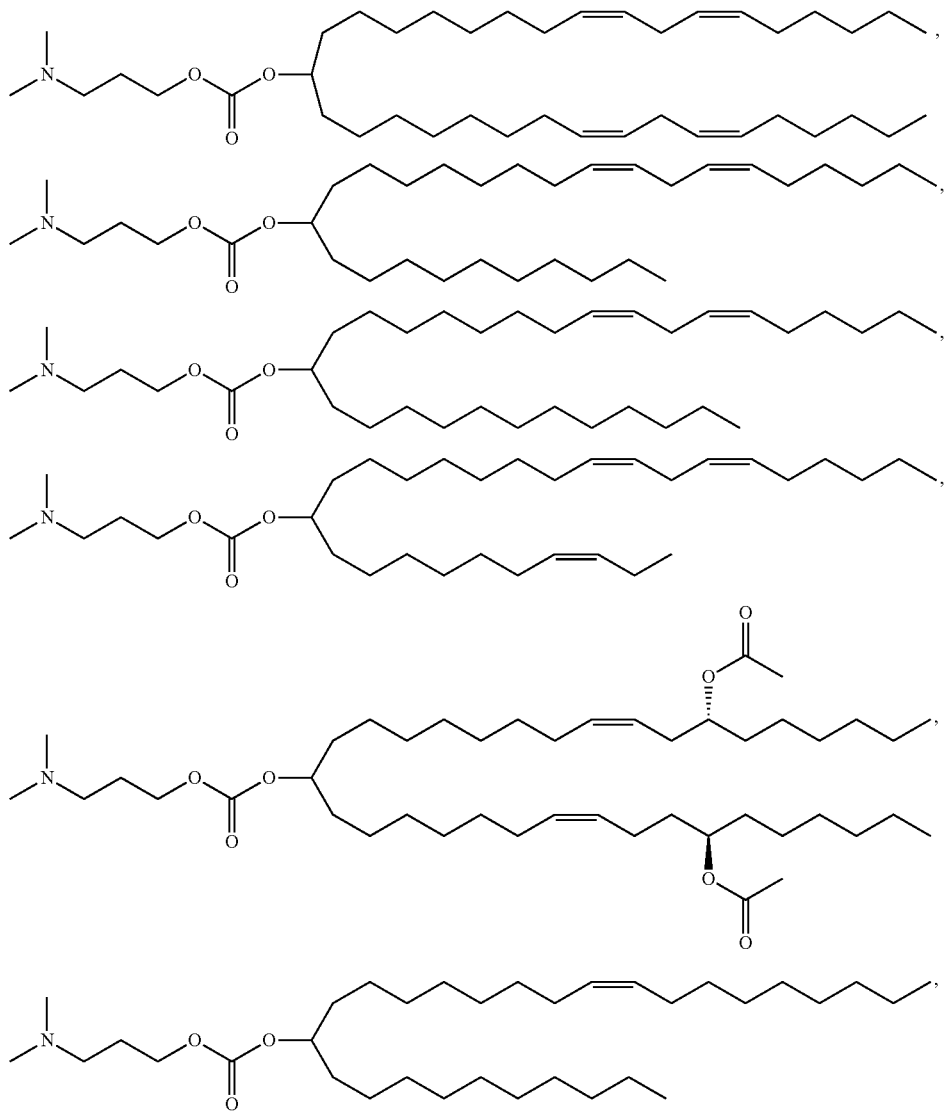

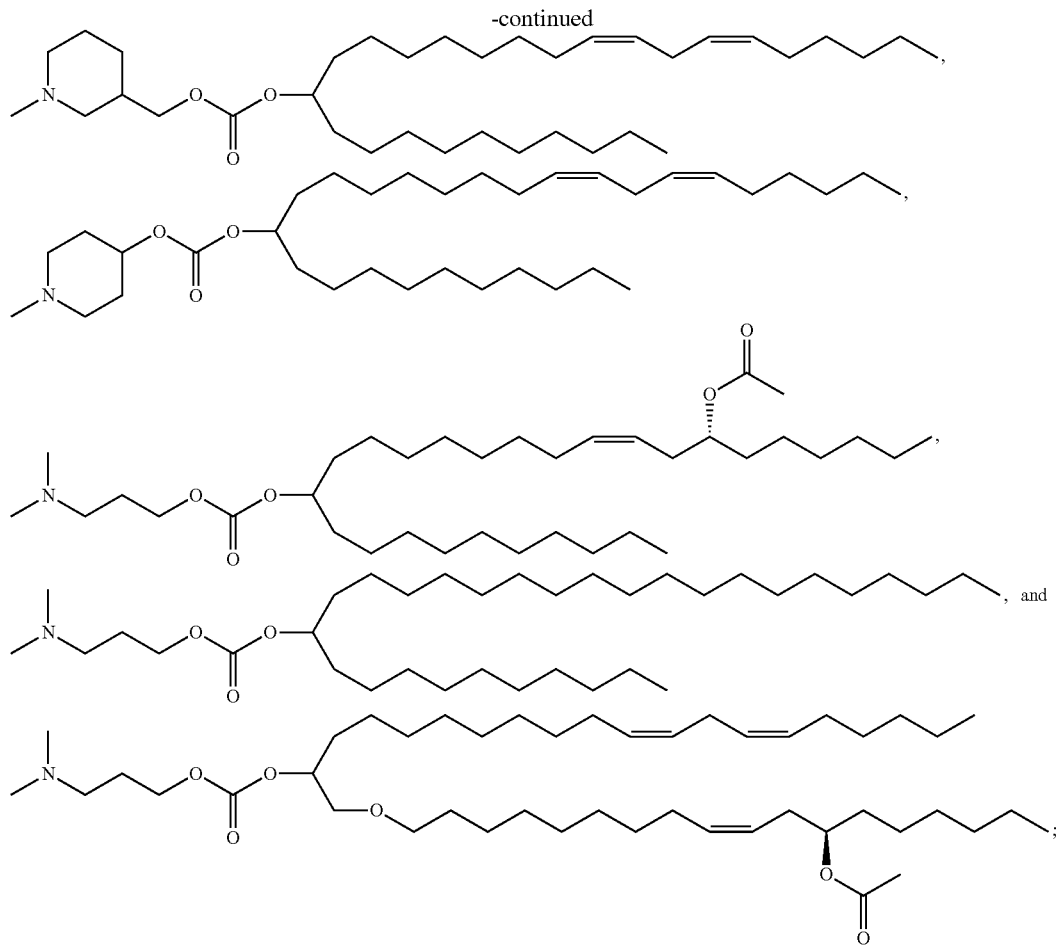

and in US 20160244761, which provides cationic lipids that include 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA), 1,2-di-.gamma.-linolenyloxy-N,N-dimethylaminopropane (.gamma.-DLenDMA), 1,2-dilinoleyloxy-keto-N,N-dimethyl-3-aminopropane (DLin-K-DMA), 1,2-dilinoleyl-4-(2-dimethylaminoethyl)-[1,3]-dioxolane (DLin-K—C2-DMA) (also known as DLin-C2K-DMA, XTC2, and C2K), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 1,2-dilinolenyloxy-4-(2-dimethylaminoethyl)-[1,3]-dioxolane (DLen-C2K-DMA), 1,2-di-.gamma.-linolenyloxy-4-(2-dimethylaminoethyl)-[1,3]-dioxolane (.gamma.-DLen-C2K-DMA), dilinoleylmethyl-3-dimethylaminopropionate (DLin-M-C2-DMA) (also known as MC2), (6Z,9Z,28Z,31Z)-heptatriaconta-6,9,28,31-tetraen-19-yl 4-(dimethylamino) butanoate (DLin-M-C3-DMA) (also known as MC3) and 3-(dilinoleylmethoxy)-N,N-dimethylpropan-1-amine (DLin-MP-DMA) (also known as 1-B1 1).

In one embodiment, the lipid compound is preferably a bio-reducible material, e.g., a bio-reducible polymer and a bio-reducible lipid-like compound.

In embodiment, the lipid compound comprises a hydrophilic head, and a hydrophobic tail, and optionally a linker.

In one embodiment, the hydrophilic head contains one or more hydrophilic functional groups, e.g., hydroxyl, carboxyl, amino, sulfhydryl, phosphate, amide, ester, ether, carbamate, carbonate, carbamide and phosphodiester. These groups can form hydrogen bonds and are optionally positively or negatively charged, in particular at physiological conditions such as physiological pH.

In one embodiment, the hydrophobic tail is a saturated or unsaturated, linear or branched, acyclic or cyclic, aromatic or nonaromatic hydrocarbon moiety, wherein the saturated or unsaturated, linear or branched, acyclic or cyclic, aromatic or nonaromatic hydrocarbon moiety optionally contains a disulfide bond and/or 8-24 carbon atoms. One or more of the carbon atoms can be replaced with a heteroatom, such as N, O, P, B, S, Si, Sb, Al, Sn, As, Se, and Ge. The lipid or lipid-like compounds containing disulfide bond can be bioreducible.

In one embodiment, the linker of the lipid or lipid-like compound links the hydrophilic head and the hydrophobic tail. The linker can be any chemical group that is hydrophilic or hydrophobic, polar or non-polar, e.g., O, S, Si, amino, alkylene, ester, amide, carbamate, carbamide, carbonate phosphate, phosphite, sulfate, sulfite, and thiosulfate.

The lipid or lipid-like compounds described above include the compounds themselves, as well as their salts and solvates, if applicable. A salt, for example, can be formed between an anion and a positively charged group (e.g., amino) on a lipid-like compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a lipid-like compound. Suitable cations include sodium ion, potassium ion, magnesium ion, calcium ion, and an ammonium cation such as tetramethylammonium ion. The lipid-like compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

Other Lipids

Other cationic lipids, such as amino lipid 2,2-dilinoleyl-4-dimethylaminoethyl-[1,3]-dioxolane (DLin-KC2-DMA) may be utilized to encapsulate the targeting system of the present invention or components thereof and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011)) describes the use of lipid envelopes to deliver nucleic acids. Use of lipid envelopes is also preferred in the present invention.

In another embodiment, lipids may be formulated with the targeting system of the present invention or component(s) thereof or nucleic acid molecule(s) coding therefor to form lipid nanoparticles (LNPs). Lipids include, but are not limited to, DLin-KC2-DMA4, C12-200 and colipids distearoylphosphatidylcholine, cholesterol, and PEG-DMG.

The targeting system of the present invention or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesized from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or N—P($O_2$)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of targeting system(s) of the present invention or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of targeting system or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112). David Liu's lab has further found+36 GFP to be an effective plasmid delivery reagent in a range of cells.

The nonviral delivery of RNA and plasmid DNA into mammalian cells are valuable both for research and therapeutic applications (Akinc et al., 2010, Nat. Biotech. 26, 561-569).

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the targeting system of the present invention. These systems of Dr. Lui and documents herein in conjunction with herein teachings can be employed in the delivery of the targeting system(s) or component(s) thereof or nucleic acid molecule(s) coding therefor.

Cell Penetrating Peptides (CPPs)

In yet another embodiment, cell penetrating peptides (CPPs) are contemplated for the delivery of the targeting system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles including nanoparticles, liposomes, chromophores, small molecules and radioactive materials. In aspects of the invention, the cargo may also comprise any component of targeting system of the present invention. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intraarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl).

U.S. Pat. No. 8,372,951 provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8,614,194 and 8,044,019. CPPs can be used to deliver the targeting system or components thereof.

Implantable Devices

In another embodiment, implantable devices are also contemplated for delivery of the targeting system of the present invention or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used/and or adapted to the targeting system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

US Patent Publication 20110195123 provides a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 m$^3$ to 1000 mm$^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide or protein or polypeptide based therapeutic agent from degradation, whether chemical in nature or due to attack from enzymes and other factors in the body of the subject.

The drug delivery system of US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and/or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group comprising, consisting essentially of, or consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear—auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the targeting system of the present invention.

As another example of a specific application, neuro and muscular degenerative diseases develop due to abnormal gene expression. Local delivery of the targeting system may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the targeting system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the targeting system of the present invention.

As another example of a specific application, silencing of innate and/or adaptive immune mediators at local sites enables the prevention of organ transplant rejection. Local delivery of the targeting system and/or immunomodulating reagents with the Loder implanted into the transplanted organ and/or the implanted site renders local immune suppression by repelling immune cells such as CD8 activated against the transplanted organ. All of this may be used/and or adapted to the targeting system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Implantable device technology herein discussed can be employed with herein teachings and hence by this disclosure and the knowledge in the art, the targeting system or components thereof or nucleic acid molecules thereof or encoding or providing components may be delivered via an implantable device.

Nanoclews

The targeting system may be delivered using nanoclews, for example as described in Sun W et al, Cocoon-like self-degradable DNA nanoclew for anticancer drug delivery., J Am Chem Soc. 2014 Oct. 22; 136(42):14722-5. doi: 10.1021/ja5088024. Epub 2014 Oct. 13. LNP In some embodiments, delivery is by encapsulation of the engineered protein or polypeptide or nucleic acid molecules encoding thereof form in a lipid particle such as an LNP. In some embodiments, therefore, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the targeting system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding the engineered targeting protein to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011).

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling nanoparticles with nucleic acid molecules may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of the engineered targeting protein is envisioned for delivery in the self-assembling nanoparticles of Schiffelers et al.

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material.

U.S. Pat. No. 5,855,913, incorporated herein by reference, provides a particulate composition having aerodynamically light particles having a tap density of less than 0.4 g/cm3 with a mean diameter of between 5 μm and 30 μm, incorporating a surfactant on the surface thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable particles having a biodegradable solid core containing a biologically active material and poly(alkylene glycol) moieties on the surface.

WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can envisioned that such conjugated lipomers can be used in the context of the targeting system to achieve in vitro, ex vivo and in vivo genomic perturbations to modify gene expression, including modulation of protein expression.

In one embodiment, the nanoparticle may be epoxide-modified lipid-polymer, advantageously 7C1 (see, e.g., James E. Dahlman and Carmen Barnes et al. Nature Nanotechnology (2014) published online 11 May 2014, doi: 10.1038/nnano.2014.84). 7C1 was synthesized by reacting C15 epoxide-terminated lipids with PEI600 at a 14:1 molar ratio, and was formulated with C14PEG2000 to produce nanoparticles (diameter between 35 and 60 nm) that were stable in PBS solution for at least 40 days.

An epoxide-modified lipid-polymer may be utilized to deliver the targeting system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

In some embodiments, the LNP for delivering nucleic acid molecules or protein components of the targeting system is prepared by methods known in the art, such as those described in, for example, WO 2005/105152 (PCT/EP2005/004920), WO 2006/069782 (PCT/EP2005/014074), WO 2007/121947 (PCT/EP2007/003496), and WO 2015/082080 (PCT/EP2014/003274), which are herein incorporated by reference. LNPs aimed specifically at the enhanced and improved delivery of siRNA into mammalian cells are described in, for example, Aleku et al., Cancer Res., 68(23): 9788-98 (Dec. 1, 2008), Strumberg et al., Int. J. Clin. Pharmacol. Ther., 50(1): 76-8 (January 2012), Schultheis et al., J. Clin. Oncol., 32(36): 4141-48 (Dec. 20, 2014), and Fehring et al., Mol. Ther., 22(4): 811-20 (Apr. 22, 2014), which are herein incorporated by reference and may be applied to the present technology.

In some embodiments, the LNP includes any LNP disclosed in WO 2005/105152 (PCT/EP2005/004920), WO 2006/069782 (PCT/EP2005/014074), WO 2007/121947 (PCT/EP2007/003496), and WO 2015/082080 (PCT/EP2014/003274).

In some embodiments, the LNP includes at least one lipid having Formula I:

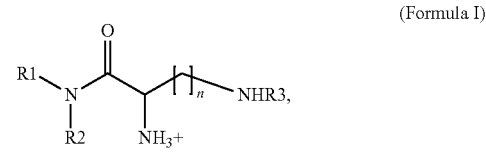

(Formula I)

wherein R1 and R2 are each and independently selected from the group comprising alkyl, n is any integer between 1 and 4, and R3 is an acyl selected from the group comprising lysyl, ornithyl, 2,4-diaminobutyryl, histidyl and an acyl moiety according to Formula II:

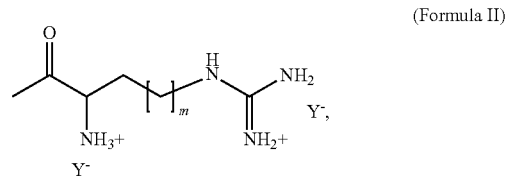

(Formula II)

wherein m is any integer from 1 to 3 and $Y^-$ is a pharmaceutically acceptable anion. In some embodiments, a lipid according to Formula I includes at least two asymmetric C atoms. In some embodiments, enantiomers of Formula I include, but are not limited to, R—R; S—S; R—S and S—R enantiomer.

In some embodiments, R1 is lauryl and R2 is myristyl. In another embodiment, R1 is palmityl and R2 is oleyl. In some embodiments, m is 1 or 2. In some embodiments, Y— is selected from halogenids, acetate or trifluoroacetate.

In some embodiments, the LNP comprises one or more lipids select from:

β-arginyl-2,3-diamino propionic acid-N-palmityl-N-oleyl-amide trihydrochloride (Formula III):

(Formula III)

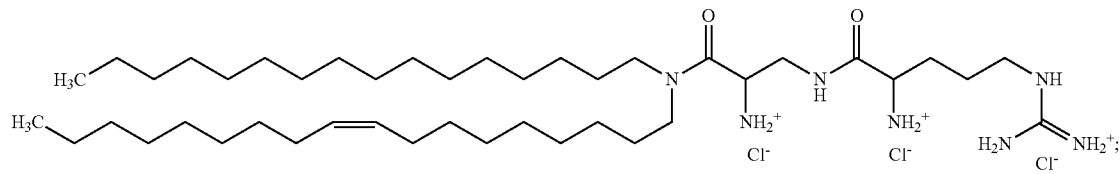

β-arginyl-2,3-diamino propionic acid-N-lauryl-N-myristyl-amide trihydrochloride (Formula IV);

(Formula IV)

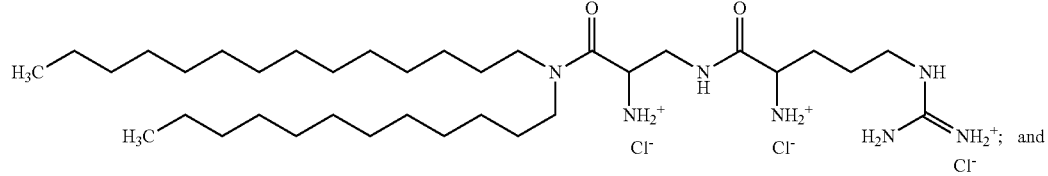

ε-arginyl-lysine-N-lauryl-N-myristyl-amide trihydrochloride (Formula V);

(Formula V)

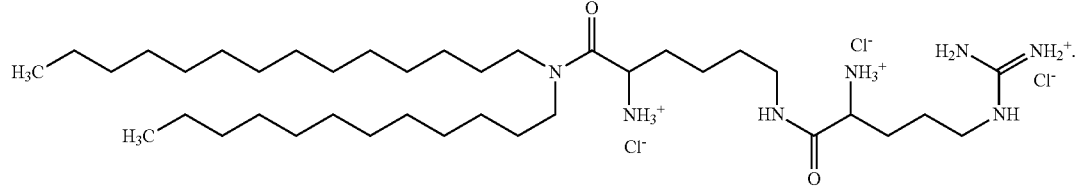

In some embodiments, the LNP also includes a constituent. By way of example, but not by way of limitation, in some embodiments, the constituent is selected from peptides, proteins, oligonucleotides, polynucleotides, nucleic acids, or a combination thereof. In some embodiments, the constituent is an antibody, e.g., a monoclonal antibody. In some embodiments, the constituent is a nucleic acid selected from, e.g., ribozymes, aptamers, spiegelmers, DNA, RNA, PNA, LNA, or a combination thereof.

In some embodiments, the constituent of the LNP comprises the engineered protein or polypeptide of the targeting system. In some embodiments, the constituent of the LNP comprises a DNA or an mRNA encoding the engineered protein or polypeptide of the targeting system.

In some embodiments, the LNP also includes at least one helper lipid. In some embodiments, the helper lipid is selected from phospholipids and steroids. In some embodiments, the phospholipids are di- and/or monoester of the phosphoric acid. In some embodiments, the phospholipids are phosphoglycerides and/or sphingolipids. In some embodiments, the steroids are naturally occurring and/or synthetic compounds based on the partially hydrogenated cyclopenta[a]phenanthrene. In some embodiments, the steroids contain 21 to 30 C atoms. In some embodiments, the steroid is cholesterol. In some embodiments, the helper lipid is selected from 1,2-diphytanoyl-sn-glycero-3-phosphoethanolamine (DPhyPE), ceramide, and 1,2-dioleoyl-sn-glycero-3-phosphoethanolamine (DOPE).

In some embodiments, the at least one helper lipid comprises a moiety selected from the group comprising a PEG moiety, a HEG moiety, a polyhydroxyethyl starch (poly-HES) moiety and a polypropylene moiety. In some embodiments, the moiety has a molecule weight between about 500 to 10,000 Da or between about 2,000 to 5,000 Da. In some embodiments, the PEG moiety is selected from 1,2-distearoyl-sn-glycero-3 phosphoethanolamine, 1,2-dialkyl-sn-glycero-3-phosphoethanolamine, and Ceramide-PEG. In some embodiments, the PEG moiety has a molecular weight between about 500 to 10,000 Da or between about 2,000 to 5,000 Da. In some embodiments, the PEG moiety has a molecular weight of 2,000 Da.

In some embodiments, the helper lipid is between about 20 mol % to 80 mol % of the total lipid content of the composition. In some embodiments, the helper lipid component is between about 35 mol % to 65 mol % of the total lipid content of the LNP. In some embodiments, the LNP includes lipids at 50 mol % and the helper lipid at 50 mol % of the total lipid content of the LNP.

In some embodiments, the LNP includes any of β-3-arginyl-2,3-diaminopropionic acid-N-palmityl-N-oleyl-amide trihydrochloride, β-arginyl-2,3-diaminopropionic acid-N-lauryl-N-myristyl-amide trihydrochloride or ε-arginyl-lysine-N-lauryl-N-myristyl-amide trihydrochloride in combination with DPhyPE, wherein the content of DPhyPE is about 80 mol %, 65 mol %, 50 mol % and 35 mol % of the overall lipid content of the LNP. In some embodiments, the LNP includes β-arginyl-2,3-diamino propionic acid-N-palmityl-N-oleyl-amide trihydrochloride (lipid) and 1,2-diphytanoyl-sn-glycero-3-phosphoethanolamine (helper lipid). In some embodiments, the LNP includes β-arginyl-2,3-diamino propionic acid-N-palmityl-N-oleyl-amide trihydrochloride (lipid), 1,2-diphytanoyl-sn-glycero-3-phosphoethanolamine (first helper lipid), and 1,2-distearoyl-sn-glycero-3-phosphoethanolamine-PEG2000 (second helper lipid).

In some embodiments, the second helper lipid is between about 0.05 mol % to 4.9 mol % or between about 1 mol % to 3 mol % of the total lipid content. In some embodiments, the LNP includes lipids at between about 45 mol % to 50 mol % of the total lipid content, a first helper lipid between about 45 mol % to 50 mol % of the total lipid content, under the proviso that there is a PEGylated second helper lipid between about 0.1 mol % to 5 mol %, between about 1 mol % to 4 mol %, or at about 2 mol % of the total lipid content, wherein the sum of the content of the lipids, the first helper lipid, and of the second helper lipid is 100 mol % of the total lipid content and wherein the sum of the first helper lipid and the second helper lipid is 50 mol % of the total lipid content. In some embodiments, the LNP comprises: (a) 50 mol % of β-arginyl-2,3-diamino propionic acid-N-palmityl-N-oleyl-amide trihydrochloride, 48 mol % of 1,2-diphytanoyl-sn-glycero-3-phosphoethanolamine; and 2 mol % of 1,2-distearoyl-sn-glycero-3-phosphoethanolamine-PEG2000; or (b) 50 mol % of β-arginyl-2,3-diamino propionic acid-N-palmityl-N-oleyl-amide trihydrochloride, 49 mol % 1,2-diphytanoyl-sn-glycero-3-phosphoethanolamine; and 1 mol % of N(Carbonyl-methoxypolyethylenglycol-2000)-1,2-distearoyl-sn-glycero3-phosphoethanolamine, or a sodium salt thereof.

In some embodiments, the LNP contains a nucleic acid, wherein the charge ratio of nucleic acid backbone phosphates to cationic lipid nitrogen atoms is about 1: 1.5-7 or about 1:4.

In some embodiments, the LNP also includes a shielding compound, which is removable from the lipid composition under in vivo conditions. In some embodiments, the shielding compound is a biologically inert compound. In some embodiments, the shielding compound does not carry any charge on its surface or on the molecule as such. In some embodiments, the shielding compounds are polyethylene glycols (PEGs), hydroxyethylglucose (HEG) based polymers, polyhydroxyethyl starch (polyHES) and polypropylene. In some embodiments, the PEG, HEG, polyHES, and a polypropylene weight between about 500 to 10,000 Da or between about 2000 to 5000 Da. In some embodiments, the shielding compound is PEG2000 or PEG5000.

In some embodiments, the LNP includes at least one lipid, a first helper lipid, and a shielding compound that is removable from the lipid composition under in vivo conditions. In some embodiments, the LNP also includes a second helper lipid. In some embodiments, the first helper lipid is ceramide. In some embodiments, the second helper lipid is ceramide. In some embodiments, the ceramide comprises at least one short carbon chain substituent of from 6 to 10 carbon atoms. In some embodiments, the ceramide comprises 8 carbon atoms. In some embodiments, the shielding compound is attached to a ceramide. In some embodiments, the shielding compound is attached to a ceramide. In some embodiments, the shielding compound is covalently attached to the ceramide. In some embodiments, the shielding compound is attached to a nucleic acid in the LNP. In some embodiments, the shielding compound is covalently attached to the nucleic acid. In some embodiments, the shielding compound is attached to the nucleic acid by a linker. In some embodiments, the linker is cleaved under physiological conditions. In some embodiments, the linker is selected from ssRNA, ssDNA, dsRNA, dsDNA, peptide, S—S-linkers and pH sensitive linkers. In some embodiments, the linker moiety is attached to the 3' end of the sense strand of the nucleic acid. In some embodiments, the shielding compound comprises a pH-sensitive linker or a pH-sensitive moiety. In some embodiments, the pH-sensitive linker or pH-sensitive moiety is an anionic linker or an anionic moiety. In some embodiments, the anionic linker or anionic moiety is less anionic or neutral in an acidic environment. In some embodiments, the pH-sensitive linker or the pH-sensitive moiety is selected from the oligo (glutamic acid), oligophenolate(s) and diethylenetriaminepentaacetic acid.

In any of the LNP embodiments in the previous paragraph, the LNP can have an osmolality between about 50 to 600 mosmole/kg, between about 250 to 350 mosmole/kg, or between about 280 to 320 mosmole/kg, and/or wherein the LNP formed by the lipid and/or one or two helper lipids and the shielding compound have a particle size between about 20 to 200 nm, between about 30 to 100 nm, or between about 40 to 80 nm.

In some embodiments, the shielding compound provides for a longer circulation time in vivo and allows for a better biodistribution of the nucleic acid containing LNP. In some embodiments, the shielding compound prevents immediate interaction of the LNP with serum compounds or compounds of other bodily fluids or cytoplasm membranes, e.g., cytoplasm membranes of the endothelial lining of the vasculature, into which the LNP is administered. Additionally or alternatively, in some embodiments, the shielding compounds also prevent elements of the immune system from immediately interacting with the LNP. Additionally or alternatively, in some embodiments, the shielding compound acts as an anti-opsonizing compound. Without wishing to be bound by any mechanism or theory, in some embodiments, the shielding compound forms a cover or coat that reduces the surface area of the LNP available for interaction with its environment. Additionally or alternatively, in some embodiments, the shielding compound shields the overall charge of the LNP.

In another embodiment, the LNP includes at least one cationic lipid having Formula VI:

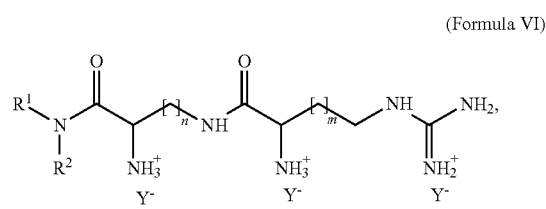

(Formula VI)

wherein n is 1, 2, 3, or 4, wherein in is 1, 2, or 3, wherein Y— is anion, wherein each of $R^1$ and $R^2$ is individually and independently selected from the group consisting of linear C12-C18 alkyl and linear C12-C18 alkenyl, a sterol compound, wherein the sterol compound is selected from the group consisting of cholesterol and stigmasterol, and a PEGylated lipid, wherein the PEGylated lipid comprises a PEG moiety, wherein the PEGylated lipid is selected from the group consisting of:

a PEGylated phosphoethanolamine of Formula VII:

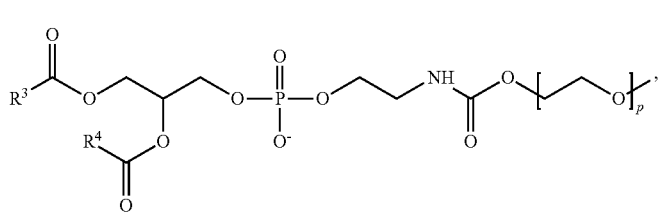
(Formula VII)

wherein $R^3$ and $R^4$ are individually and independently linear C13-C17 alkyl, and p is any integer between 15 to 130;

a PEGylated ceramide of Formula VIII:

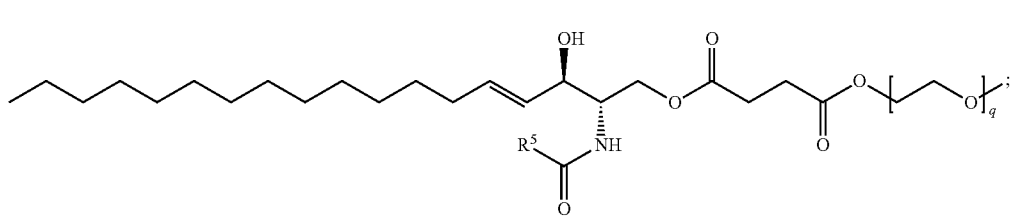
(Formula VIII)

wherein $R^5$ is linear C7-C15 alkyl, and q is any number between 15 to 130; and a PEGylated diacylglycerol of Formula IX:

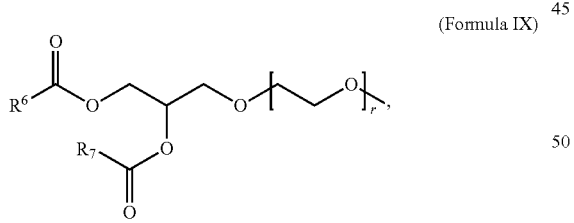
(Formula IX)

wherein each of $R^6$ and $R^7$ is individually and independently linear C11-C17 alkyl, and r is any integer from 15 to 130.

In some embodiments, $R^1$ and $R^2$ are different from each other. In some embodiments, $R^1$ is palmityl and $R^2$ is oleyl. In some embodiments, $R^1$ is lauryl and $R^2$ is myristyl. In some embodiments, $R^1$ and $R^2$ are the same. In some embodiments, each of $R^1$ and $R^2$ is individually and independently selected from the group consisting of C12 alkyl, C14 alkyl, C16 alkyl, C18 alkyl, C12 alkenyl, C14 alkenyl, C16 alkenyl and C18 alkenyl. In some embodiments, each of C12 alkenyl, C14 alkenyl, C16 alkenyl and C18 alkenyl comprises one or two double bonds. In some embodiments, C18 alkenyl is C18 alkenyl with one double bond between C9 and C10. In some embodiments, C18 alkenyl is cis-9-octadecyl.

In some embodiments, the cationic lipid is a compound of Formula X:

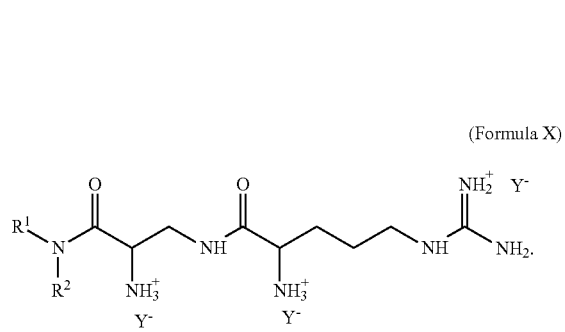
(Formula X)

In some embodiments, $Y^-$ is selected from halogenids, acetate and trifluoroacetate. In some embodiments, the cationic lipid is β-arginyl-2,3-diamino propionic acid-N-palmityl-N-oleyl-amide trihydrochloride of Formula III:

(Formula III)

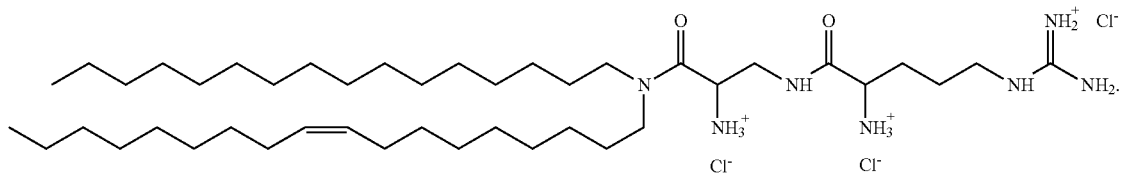

In some embodiments, the cationic lipid is β-arginyl-2,3-diamino propionic acid-N-lauryl-N-myristyl-amide trihydrochloride of Formula IV:

(Formula IV)

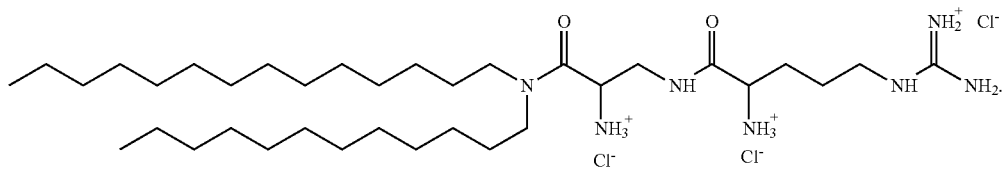

some embodiments, the cationic lipid is ε-arginyl-lysine-N-lauryl-N-myristyl-amide trihydrochloride of Formula V:

(Formula V)

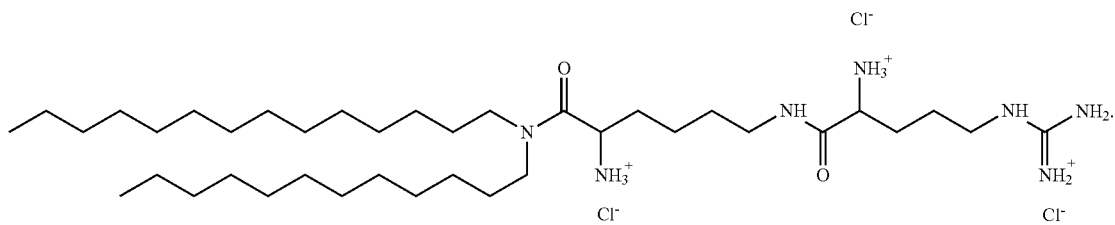

In some embodiments, the sterol compound is cholesterol. In some embodiments, the sterol compound is stigmasterin. In some embodiments, the PEG moiety of the PEGylated lipid has a molecular weight from about 800 to 5,000 Da. In some embodiments, the molecular weight of the PEG moiety of the PEGylated lipid is about 800 Da. In some embodiments, the molecular weight of the PEG moiety of the PEGylated lipid is about 2,000 Da. In some embodiments, the molecular weight of the PEG moiety of the PEGylated lipid is about 5,000 Da. In some embodiments, the PEGylated lipid is a PEGylated phosphoethanolamine of Formula VII, wherein each of $R^3$ and $R^4$ is individually and independently linear C13-C17 alkyl, and p is any integer from 18, 19 or 20, or from 44, 45 or 46 or from 113, 114 or 115. In some embodiments, $R^3$ and $R^4$ are the same. In some embodiments, $R^3$ and $R^4$ are different. In some embodiments, each of $R^3$ and $R^4$ is individually and independently selected from the group consisting of C13 alkyl, C15 alkyl and C17 alkyl. In some embodiments, the PEGylated phosphoethanolamine of Formula VII is 1,2-distearoyl-sn-glycero-3-phosphoethanolamine-N-[methoxy(polyethylene glycol)-2000](ammonium salt):

(Formula XI)

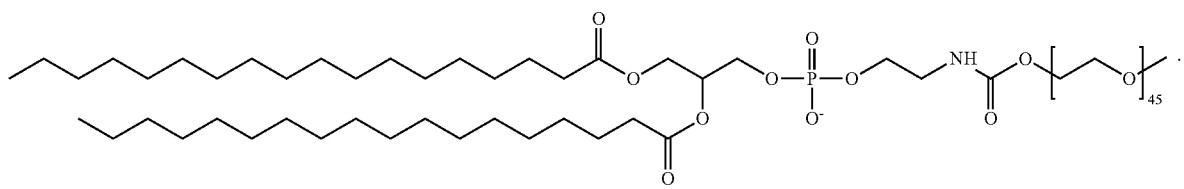

In some embodiments, the PEGylated phosphoethanolamine of Formula VII is 1,2-distearoyl-sn-glycero-3-phosphoethanolamine-N-[methoxy(polyethylene glycol)-5000](ammonium salt):

(Formula XII)

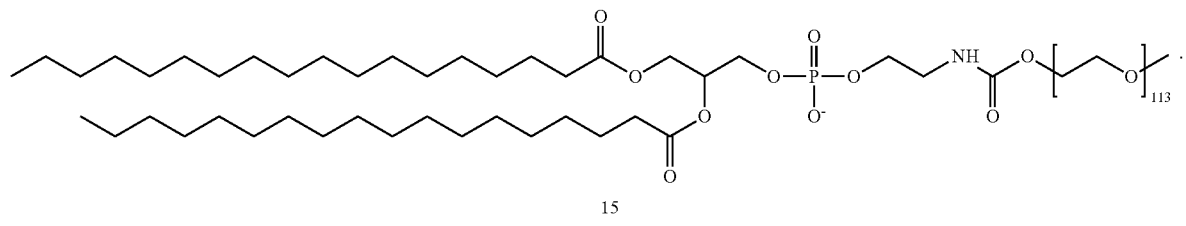

In some embodiments, the PEGylated lipid is a PEGylated ceramide of Formula VIII, wherein $R^5$ is linear C7-C15 alkyl, and q is any integer from 18, 19 or 20, or from 44, 45 or 46 or from 113, 114 or 115. In some embodiments, $R^5$ is linear C7 alkyl. In some embodiments, $R^5$ is linear C15 alkyl. In some embodiments, the PEGylated ceramide of Formula VIII is N-octanoyl-sphingosine-1-{succinyl[methoxy(polyethylene glycol)2000]}:

(Formula XIII)

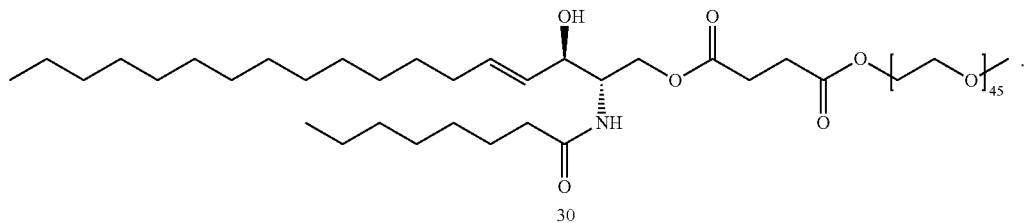

In some embodiments, the PEGylated ceramide of Formula VIII is N-palmitoyl-sphingosine-1-{succinyl[methoxy(polyethylene glycol)2000]}

(Formula XIV)

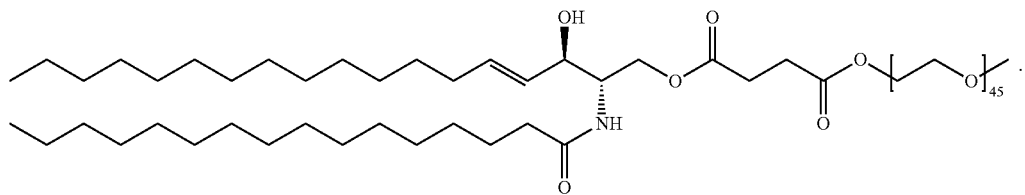

In some embodiments, the PEGylated lipid is a PEGylated diacylglycerol of Formula IX, wherein each of $R^6$ and $R^7$ is individually and independently linear C11-C17 alkyl, and r is any integer from 18, 19 or 20, or from 44, 45 or 46 or from 113, 114 or 115. In some embodiments, $R^6$ and $R^7$ are the same. In some embodiments, $R^6$ and $R^7$ are different. In some embodiments, each of $R^6$ and $R^7$ is individually and independently selected from the group consisting of linear C17 alkyl, linear C15 alkyl and linear C13 alkyl. In some embodiments, the PEGylated diacylglycerol of Formula IX 1,2-Distearoyl-sn-glycerol [methoxy(polyethylene glycol) 2000]:

(Formula XV)

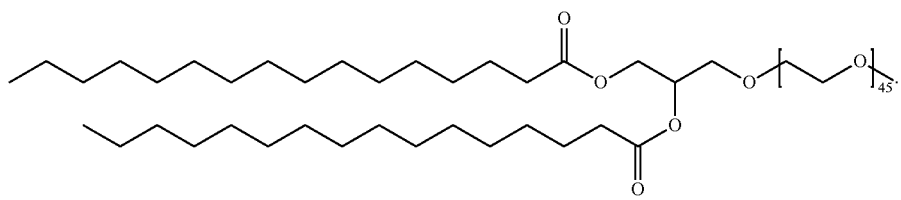

In some embodiments, the PEGylated diacylglycerol of Formula IX is 1,2-Dipalmitoyl-sn-glycerol [methoxy(polyethylene glycol)2000]:

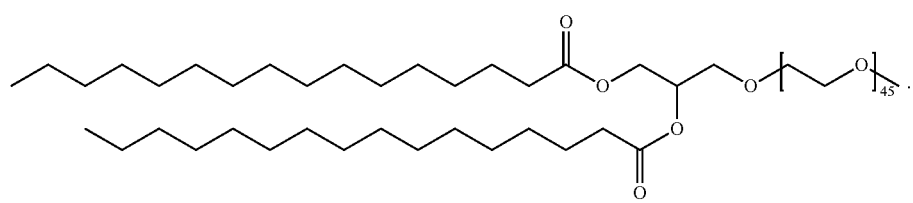

(Formula XVI)

In some embodiments, the PEGylated diacylglycerol of Formula IX is:

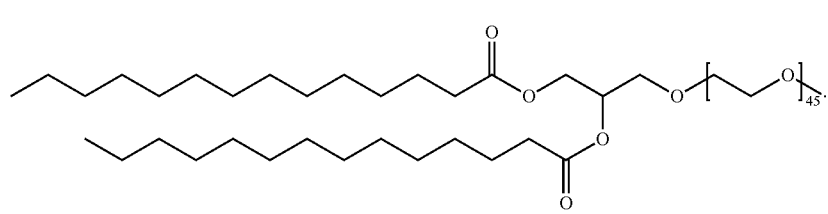

(Formula XVII)

In some embodiments, the LNP includes at least one cationic lipid selected from of Formulas III, IV, and V, at least one sterol compound selected from a cholesterol and stigmasterin, and wherein the PEGylated lipid is at least one selected from Formulas XI and XII. In some embodiments, the LNP includes at least one cationic lipid selected from Formulas III, IV, and V, at least one sterol compound selected from a cholesterol and stigmasterin, and wherein the PEGylated lipid is at least one selected from Formulas XIII and XIV. In some embodiments, the LNP includes at least one cationic lipid selected from Formulas III, IV, and V, at least one sterol compound selected from a cholesterol and stigmasterin, and wherein the PEGylated lipid is at least one selected from Formulas XV and XVI. In some embodiments, the LNP includes a cationic lipid of Formula III, a cholesterol as the sterol compound, and wherein the PEGylated lipid is Formula XI.

In any of the LNP embodiments in the previous paragraph, wherein the content of the cationic lipid composition is between about 65 mole % to 75 mole %, the content of the sterol compound is between about 24 mole % to 34 mole % and the content of the PEGylated lipid is between about 0.5 mole % to 1.5 mole %, wherein the sum of the content of the cationic lipid, of the sterol compound and of the PEGylated lipid for the lipid composition is 100 mole %. In some embodiments, the cationic lipid is about 70 mole %, the content of the sterol compound is about 29 mole % and the content of the PEGylated lipid is about 1 mole %. In some embodiments, the LNP is 70 mole % of Formula III, 29 mole % of cholesterol, and 1 mole % of Formula XI.

Aerosol Delivery

Subjects treated for a lung disease may for example receive pharmaceutically effective amount of aerosolized AAV vector system per lung endobronchially delivered while spontaneously breathing. As such, aerosolized delivery is preferred for AAV delivery in general. An adenovirus or an AAV particle may be used for delivery. Suitable gene constructs, each operably linked to one or more regulatory sequences, may be cloned into the delivery vector.

Hybrid Viral Capsid Delivery Systems

In one aspect, the invention provides a particle delivery system comprising a hybrid virus capsid protein or hybrid viral outer protein, wherein the hybrid virus capsid or outer protein comprises a virus capsid or outer protein attached to at least a portion of a non-capsid protein or peptide. The genetic material of a virus is stored within a viral structure called the capsid. The capsid of certain viruses are enclosed in a membrane called the viral envelope. The viral envelope is made up of a lipid bilayer embedded with viral proteins including viral glycoproteins. As used herein, an "envelope protein" or "outer protein" means a protein exposed at the surface of a viral particle that is not a capsid protein. For example, envelope or outer proteins typically comprise proteins embedded in the envelope of the virus. Non-limiting examples of outer or envelope proteins include, without limit, gp41 and gp120 of HIV, hemagglutinin, neuraminidase and M2 proteins of influenza virus.

In one example embodiment of the delivery system, the non-capsid protein or peptide has a molecular weight of up to a megadalton, or has a molecular weight in the range of 110 to 160 kDa, 160 to 200 kDa, 200 to 250 kDa, 250 to 300 kDa, 300 to 400 kDa, or 400 to 500 kDa, the non-capsid protein or peptide comprises an engineered protein or polypeptide of the targeting system.

The present application provides a vector for delivering an effector protein and at least one targeting system comprising an engineered protein or polypeptide or nucleic acid molecule encoding thereof to a cell comprising a minimal promoter operably linked to a polynucleotide sequence encoding the effector protein and a second minimal promoter operably linked to a polynucleotide sequence encoding at least one guide RNA, wherein the length of the vector sequence comprising the minimal promoters and polynucleotide sequences is less than 4.4 Kb. In an embodiment, the virus is an adeno-associated virus (AAV) or an adenovirus.

In an embodiment of the delivery system, the virus is lentivirus or murine leukemia virus (MuMLV).

In an embodiment of the delivery system, the virus is an Adenoviridae or a Parvoviridae or a retrovirus or a Rhabdoviridae or an enveloped virus having a glycoprotein protein (G protein).

In an embodiment of the delivery system, the virus is VSV or rabies virus.

In an embodiment of the delivery system, the capsid or outer protein comprises a capsid protein having VP1, VP2 or VP3.

In an embodiment of the delivery system, the capsid protein is VP3, and the non-capsid protein is inserted into or attached to VP3 loop 3 or loop 6.

In an embodiment of the delivery system, the virus is delivered to the interior of a cell.

In an embodiment of the delivery system, the capsid or outer protein and the non-capsid protein can dissociate after delivery into a cell.

In an embodiment of the delivery system, the capsid or outer protein is attached to the protein by a linker.

In an embodiment of the delivery system, the linker comprises amino acids.

In an embodiment of the delivery system, the linker is a chemical linker.

In an embodiment of the delivery system, the linker is cleavable.

In an embodiment of the delivery system, the linker is biodegradable.

In an embodiment of the delivery system, the linker comprises (GGGGS)1-3 (SEQ ID NOS:124, 125, and 123, respectively), ENLYFQG (SEQ ID NO:126), or a disulfide.

In an embodiment, the delivery system comprises a protease or nucleic acid molecule(s) encoding a protease that is expressed, said protease being capable of cleaving the linker, whereby there can be cleavage of the linker. In an embodiment of the invention, a protease is delivered with a particle component of the system, for example packaged, mixed with, or enclosed by lipid and/or capsid. Entry of the particle into a cell is thereby accompanied or followed by cleavage and dissociation of payload from particle. In certain embodiments, an expressible nucleic acid encoding a protease is delivered, whereby at entry or following entry of the particle into a cell, there is protease expression, linker cleavage, and dissociation of payload from capsid. In certain embodiments, dissociation of payload occurs with viral replication. In certain embodiments, dissociation of payload occurs in the absence of productive virus replication.

In an embodiment of the delivery system, each terminus of a engineered targeting protein is attached to the capsid or outer protein by a linker.

In an embodiment of the delivery system, the non-capsid protein is attached to the exterior portion of the capsid or outer protein.

In an embodiment of the delivery system, the non-capsid protein is attached to the interior portion of the capsid or outer protein.

In an embodiment of the delivery system, the capsid or outer protein and the non-capsid protein are a fusion protein.

In an embodiment of the delivery system, the non-capsid protein is encapsulated by the capsid or outer protein.

In an embodiment of the delivery system, the non-capsid protein is attached to a component of the capsid protein or a component of the outer protein prior to formation of the capsid or the outer protein.

In an embodiment of the delivery system, the protein is attached to the capsid or outer protein after formation of the capsid or outer protein.

Targeting Moiety

In an embodiment, the delivery system comprises a targeting moiety, such as active targeting of a lipid entity of the invention, e.g., lipid particle or nanoparticle or liposome or lipid bilayer of the invention comprising a targeting moiety for active targeting.

With regard to targeting moieties, mention is made of Deshpande et al, "Current trends in the use of liposomes for tumor targeting," Nanomedicine (Lond). 8(9), doi:10.2217/nnm.13.118 (2013), and the documents it cites, all of which are incorporated herein by reference. Mention is also made of WO/2016/027264, and the documents it cites, all of which are incorporated herein by reference. And mention is made of Lorenzer et al, "Going beyond the liver: Progress and challenges of targeted delivery of siRNA therapeutics," Journal of Controlled Release, 203: 1-15 (2015), and the documents it cites, all of which are incorporated herein by reference.

An actively targeting lipid particle or nanoparticle or liposome or lipid bilayer delivery system (generally as to embodiments of the invention, "lipid entity of the invention" delivery systems) are prepared by conjugating targeting moieties, including small molecule ligands, peptides and monoclonal antibodies, on the lipid or liposomal surface; for example, certain receptors, such as folate and transferrin (Tf) receptors (TfR), are overexpressed on many cancer cells and have been used to make liposomes tumor cell specific. Liposomes that accumulate in the tumor microenvironment can be subsequently endocytosed into the cells by interacting with specific cell surface receptors. To efficiently target liposomes to cells, such as cancer cells, it is useful that the targeting moiety have an affinity for a cell surface receptor and to link the targeting moiety in sufficient quantities to have optimum affinity for the cell surface receptors; and determining these aspects are within the ambit of the skilled artisan. In the field of active targeting, there are a number of cell-, e.g., tumor-, specific targeting ligands.

Also as to active targeting, with regard to targeting cell surface receptors such as cancer cell surface receptors, targeting ligands on liposomes can provide attachment of liposomes to cells, e.g., vascular cells, via a noninternalizing epitope; and this can increase the extracellular concentration of that which is being delivered, thereby increasing the amount delivered to the target cells. A strategy to target cell surface receptors, such as cell surface receptors on cancer cells, such as overexpressed cell surface receptors on cancer cells, is to use receptor-specific ligands or antibodies. Many cancer cell types display upregulation of tumor-specific receptors. For example, TfRs and folate receptors (FRs) are greatly overexpressed by many tumor cell types in response to their increased metabolic demand. Folic acid can be used as a targeting ligand for specialized delivery owing to its ease of conjugation to nanocarriers, its high affinity for FRs and the relatively low frequency of FRs, in normal tissues as compared with their overexpression in activated macrophages and cancer cells, e.g., certain ovarian, breast, lung, colon, kidney and brain tumors. Overexpression of FR on macrophages is an indication of inflammatory diseases, such as psoriasis, Crohn's disease, rheumatoid arthritis and atherosclerosis; accordingly, folate-mediated targeting of the invention can also be used for studying, addressing or treating inflammatory disorders, as well as cancers. Folate-linked lipid particles or nanoparticles or liposomes or lipid bilayers of the invention ("lipid entity of the invention") deliver their cargo intracellularly through receptor-mediated endocytosis. Intracellular trafficking can be directed to acidic compartments that facilitate cargo release, and, most importantly, release of the cargo can be altered or delayed until it reaches the cytoplasm or vicinity of target organelles. Delivery of cargo using a lipid entity of the invention having a targeting moiety, such as a folate-linked lipid entity of the invention, can be superior to nontargeted lipid entity of the invention. The attachment of folate directly to the lipid head groups may not be favorable for intracellular delivery of folate-conjugated lipid entity of the invention, since they may not bind as efficiently to cells as folate attached to the lipid entity of the invention surface by a spacer, which may can enter cancer cells more efficiently. A lipid entity of the invention coupled to folate can be used for the delivery of complexes of lipid, e.g., liposome, e.g., anionic liposome and virus or capsid or envelope or virus outer protein, such as those herein discussed such as adenovirus or AAV. Tf is a monomeric serum glycoprotein of approximately 80 KDa involved in the transport of iron throughout the body. Tf binds to the TfR and translocates into cells via receptor-mediated endocytosis. The expression of TfR can be higher in certain cells, such as tumor cells (as compared with normal cells and is associated with the increased iron demand in rapidly proliferating cancer cells. Accordingly, the invention comprehends a TfR-targeted lipid entity of the invention, e.g., as to liver cells, liver cancer, breast cells such as breast cancer cells, colon such as colon cancer cells, ovarian cells such as ovarian cancer cells, head, neck and lung cells, such as head, neck and non-small-cell lung cancer cells, cells of the mouth such as oral tumor cells.

Also as to active targeting, a lipid entity of the invention can be multifunctional, i.e., employ more than one targeting moiety such as CPP, along with Tf; a bifunctional system; e.g., a combination of Tf and poly-L-arginine which can provide transport across the endothelium of the blood-brain barrier. EGFR is a tyrosine kinase receptor belonging to the ErbB family of receptors that mediates cell growth, differentiation and repair in cells, especially non-cancerous cells, but EGF is overexpressed in certain cells such as many solid tumors, including colorectal, non-small-cell lung cancer, squamous cell carcinoma of the ovary, kidney, head, pancreas, neck and prostate, and especially breast cancer. The invention comprehends EGFR-targeted monoclonal antibody(ies) linked to a lipid entity of the invention. HER-2 is often overexpressed in patients with breast cancer, and is also associated with lung, bladder, prostate, brain and stomach cancers. HER-2, encoded by the ERBB2 gene. The invention comprehends a HER-2-targeting lipid entity of the invention, e.g., an anti-HER-2-antibody (or binding fragment thereof)-lipid entity of the invention, a HER-2-targeting-PEGylated lipid entity of the invention (e.g., having an anti-HER-2-antibody or binding fragment thereof), a HER-2-targeting-maleimide-PEG polymer-lipid entity of the invention (e.g., having an anti-HER-2-antibody or binding fragment thereof). Upon cellular association, the receptor-antibody complex can be internalized by formation of an endosome for delivery to the cytoplasm. With respect to receptor-mediated targeting, the skilled artisan takes into consideration ligand/target affinity and the quantity of receptors on the cell surface, and that PEGylation can act as a barrier against interaction with receptors. The use of antibody-lipid entity of the invention targeting can be advantageous. Multivalent presentation of targeting moieties can also increase the uptake and signaling properties of antibody fragments. In practice of the invention, the skilled person takes into account ligand density (e.g., high ligand densities on a lipid entity of the invention may be advantageous for increased binding to target cells). Preventing early by macrophages can be addressed with a sterically stabilized lipid entity of the invention and linking ligands to the terminus of molecules such as PEG, which is anchored in the lipid entity of the invention (e.g., lipid particle or nanoparticle or liposome or lipid bilayer). The microenvironment of a cell mass such as a tumor microenvironment can be targeted; for instance, it may be advantageous to target cell mass vasculature, such as the tumor vasculature microenvironment. Thus, the invention comprehends targeting VEGF. VEGF and its receptors are well-known proangiogenic molecules and are well-characterized targets for antiangiogenic therapy. Many small-molecule inhibitors of receptor tyrosine kinases, such as VEGFRs or basic FGFRs, have been developed as anticancer agents and the invention comprehends coupling any one or more of these peptides to a lipid entity of the invention, e.g., phage IVO peptide(s) (e.g., via or with a PEG terminus), tumor-homing peptide APRPG (SEQ ID NO: 175) such as APRPG-PEG-modified. VCAM, the vascular endothelium plays a key role in the pathogenesis of inflammation, thrombosis and atherosclerosis. CAMs are involved in inflammatory disorders, including cancer, and are a logical target, E- and P-selectins, VCAM-1 and ICAMs. Can be used to target a lipid entity of the invention., e.g., with PEGylation. Matrix metalloproteases (MMPs) belong to the family of zinc-dependent endopeptidases. They are involved in tissue remodeling, tumor invasiveness, resistance to apoptosis and metastasis. There are four MMP inhibitors called TIMP1-4, which determine the balance between tumor growth inhibition and metastasis; a protein involved in the angiogenesis of tumor vessels is MT1-MMP, expressed on newly formed vessels and tumor tissues. The proteolytic activity of MT1-MMP cleaves proteins, such as fibronectin, elastin, collagen and laminin, at the plasma membrane and activates soluble MMPs, such as MMP-2, which degrades the matrix. An antibody or fragment thereof such as a Fab' fragment can be used in the practice of the invention such as for an antihuman MT1-MMP monoclonal antibody linked to a lipid entity of the invention, e.g., via a spacer such as a PEG spacer. αβ-integrins or integrins are a group of transmembrane glycoprotein receptors that mediate attachment between a cell and its surrounding tissues or extracellular matrix. Integrins contain two distinct chains (heterodimers) called α- and β-subunits. The tumor tissue-specific expression of integrin receptors can be utilized for targeted delivery in the invention, e.g., whereby the targeting moiety can be an RGD peptide such as a cyclic RGD. Aptamers are ssDNA or RNA oligonucleotides that impart high affinity and specific recognition of the target molecules by electrostatic interactions, hydrogen bonding and hydrophobic interactions as opposed to the Watson-Crick base pairing, which is typical for the bonding interactions of oligonucleotides. Aptamers as a targeting moiety can have advantages over antibodies: aptamers can demonstrate higher target antigen recognition as compared with antibodies; aptamers can be more stable and smaller in size as compared with antibodies; aptamers can be easily synthesized and chemically modified for molecular conjugation; and aptamers can be changed in sequence for improved selectivity and can be developed to recognize poorly immunogenic targets. Such moieties as a sgc8 aptamer can be used as a targeting moiety (e.g., via covalent linking to the lipid entity of the invention, e.g., via a spacer, such as a PEG spacer). The targeting moiety can be stimuli-sensitive, e.g., sensitive to an externally applied stimuli, such as magnetic fields, ultrasound or light; and pH-triggering can also be used, e.g., a labile linkage can be used between a hydrophilic moiety such as PEG and a hydrophobic moiety such as a lipid entity of the invention, which is cleaved only upon exposure to the relatively acidic conditions characteristic of a particular environment or microenvironment such as an endocytic vacuole or the acidotic tumor mass. pH-sensitive copolymers can also be incorporated in embodiments of the invention can provide shielding; diortho esters, vinyl esters, cysteine-cleavable lipopolymers, double esters and hydrazones are a few examples of pH-sensitive bonds that are quite stable at pH 7.5, but are hydrolyzed relatively rapidly at pH 6 and below, e.g., a terminally alkylated copolymer of N-isopropylacrylamide and methacrylic acid that copolymer facilitates destabilization of a lipid entity of the invention and release in compartments with decreased pH value; or, the invention comprehends ionic polymers for generation of a pH-responsive lipid entity of the invention (e.g., poly (methacrylic acid), poly(diethylaminoethyl methacrylate), poly(acrylamide) and poly(acrylic acid)). Temperature-triggered delivery is also within the ambit of the invention. Many pathological areas, such as inflamed tissues and tumors, show a distinctive hyperthermia compared with normal tissues. Utilizing this hyperthermia is an attractive strategy in cancer therapy since hyperthermia is associated with increased tumor permeability and enhanced uptake. This technique involves local heating of the site to increase microvascular pore size and blood flow, which, in turn, can result in an increased extravasation of embodiments of the invention. Temperature-sensitive lipid entity of the invention can be prepared from thermosensitive lipids or polymers with a low critical solution temperature. Above the low critical solution temperature (e.g., at site such as tumor site or inflamed tissue site), the polymer precipitates, disrupting the liposomes to release. Lipids with a specific gel-to-liquid phase transition temperature are used to prepare these lipid entities of the invention; and a lipid for a thermosensitive embodiment can be dipalmitoylphosphatidylcholine. Thermosensitive polymers can also facilitate destabilization followed by release, and a useful thermosensitive polymer is poly (N-isopropylacrylamide). Another temperature triggered system can employ lysolipid temperature-sensitive liposomes. The invention also comprehends redox-triggered delivery. The difference in redox potential between normal and inflamed or tumor tissues, and between the intra- and extra-cellular environments has been exploited for delivery, e.g., GSH is a reducing agent abundant in cells, especially in the cytosol, mitochondria and nucleus. The GSH concentrations in blood and extracellular matrix are just one out of 100 to one out of 1000 of the intracellular concentration, respectively. This high redox potential difference caused by GSH, cysteine and other reducing agents can break the reducible bonds, destabilize a lipid entity of the invention and result in release of payload. The disulfide bond can be used as the cleavable/reversible linker in a lipid entity of the invention, because it causes sensitivity to redox owing to the disulfide to thiol reduction reaction; a lipid entity of the invention can be made reduction sensitive by using two (e.g., two forms of a disulfide-conjugated multifunctional lipid as cleavage of the disulfide bond (e.g., via tris(2-carboxyethyl)phosphine, dithiothreitol, L-cysteine or GSH), can cause removal of the hydrophilic head group of the conjugate and alter the membrane organization leading to release of payload. Calcein release from reduction-sensitive lipid entity of the invention containing a disulfide conjugate can be more useful than a reduction-insensitive embodiment. Enzymes can also be used as a trigger to release payload. Enzymes, including MMPs (e.g. MMP2), phospholipase A2, alkaline phosphatase, transglutaminase or phosphatidylinositol-specific phospholipase C, have been found to be overexpressed in certain tissues, e.g., tumor tissues. In the presence of these enzymes, specially engineered enzyme-sensitive lipid entity of the invention can be disrupted and release the payload. An MMP2-cleavable octapeptide (Gly-Pro-Leu-Gly-Ile-Ala-Gly-Gln (SEQ ID NO:127)) can be incorporated into a linker, and can have antibody targeting, e.g., antibody 2C5. The invention also comprehends light- or energy-triggered delivery, e.g., the lipid entity of the invention can be light-sensitive, such that light or energy can facilitate structural and conformational changes, which lead to direct interaction of the lipid entity of the invention with the target cells via membrane fusion, photo-isomerism, photofragmentation or photopolymerization; such a moiety therefor can be benzoporphyrin photosensitizer. Ultrasound can be a form of energy to trigger delivery; a lipid entity of the invention with a small quantity of particular gas, including air or perfluorinated hydrocarbon can be triggered to release with ultrasound, e.g., low-frequency ultrasound (LFUS). Magnetic delivery: A lipid entity of the invention can be magnetized by incorporation of magnetites, such as Fe3O4 or γ-Fe2O3, e.g., those that are less than 10 nm in size. Targeted delivery can be then by exposure to a magnetic field.

Also as to active targeting, the invention also comprehends intracellular delivery. Since liposomes follow the endocytic pathway, they are entrapped in the endosomes (pH 6.5-6) and subsequently fuse with lysosomes (pH<5), where they undergo degradation that results in a lower therapeutic potential. The low endosomal pH can be taken advantage of to escape degradation. Fusogenic lipids or peptides, which destabilize the endosomal membrane after the conformational transition/activation at a lowered pH. Amines are protonated at an acidic pH and cause endosomal swelling and rupture by a buffer effect Unsaturated dioleoylphosphatidylethanolamine (DOPE) readily adopts an inverted hexagonal shape at a low pH, which causes fusion of liposomes to the endosomal membrane. This process destabilizes a lipid entity containing DOPE and releases the cargo into the cytoplasm; fusogenic lipid GALA (SEQ ID NO: 176), cholesteryl-GALA and PEG-GALA may show a highly efficient endosomal release; a pore-forming protein listeriolysin O may provide an endosomal escape mechanism; and, histidine-rich peptides have the ability to fuse with the endosomal membrane, resulting in pore formation, and can buffer the proton pump causing membrane lysis.

Also as to active targeting, cell-penetrating peptides (CPPs) facilitate uptake of macromolecules through cellular membranes and, thus, enhance the delivery of CPP-modified molecules inside the cell. CPPs can be split into two classes: amphipathic helical peptides, such as transportan and MAP, where lysine residues are major contributors to the positive charge; and Arg-rich peptides, such as TATp, Antennapedia or penetratin. TATp is a transcription-activating factor with 86 amino acids that contains a highly basic (two Lys and six Arg among nine residues) protein transduction domain, which brings about nuclear localization and RNA binding. Other CPPs that have been used for the modification of liposomes include the following: the minimal protein transduction domain of Antennapedia, a *Drosophila* homeoprotein, called penetratin, which is a 16-mer peptide (residues 43-58) present in the third helix of the homeodomain; a 27-amino acid-long chimeric CPP, containing the peptide sequence from the amino terminus of the neuropeptide galanin bound via the Lys residue, mastoparan, a wasp venom peptide; VP22, a major structural component of HSV-1 facilitating intracellular transport and transportan (18-mer) amphipathic model peptide that translocates plasma membranes of mast cells and endothelial cells by both energy-dependent and -independent mechanisms. The invention comprehends a lipid entity of the invention modified with CPP(s), for intracellular delivery that may proceed via energy dependent macropinocytosis followed by endosomal escape. The invention further comprehends organelle-specific targeting. A lipid entity of the invention surface-functionalized with the triphenylphosphonium (TPP) moiety or a lipid entity of the invention with a lipophilic cation, rhodamine 123 can be effective in delivery of cargo to mitochondria. DOPE/sphingomyelin/stearyl-octa-arginine can delivers cargos to the mitochondrial interior via membrane fusion. A lipid entity of the invention surface modified with a lysosomotropic ligand, octadecyl rhodamine B can deliver cargo to lysosomes. Ceramides are useful in inducing lysosomal membrane permeabilization; the invention comprehends intracellular delivery of a lipid entity of the invention having a ceramide. The invention further comprehends a lipid entity of the invention targeting the nucleus, e.g., via a DNA-intercalating moiety. The invention also comprehends multifunctional liposomes for targeting, i.e., attaching more than one functional group to the surface of the lipid entity of the invention, for instance to enhances accumulation in a desired site and/or promotes organelle-specific delivery and/or target a particular type of cell and/or respond to the local stimuli such as temperature (e.g., elevated), pH (e.g., decreased), respond to externally applied stimuli such as a magnetic field, light, energy, heat or ultrasound and/or promote intracellular delivery of the cargo. All of these are considered actively targeting moieties.

An embodiment of the invention includes the delivery system comprising an actively targeting lipid particle or nanoparticle or liposome or lipid bilayer delivery system; or comprising a lipid particle or nanoparticle or liposome or lipid bilayer comprising a targeting moiety whereby there is active targeting or wherein the targeting moiety is an actively targeting moiety. A targeting moiety can be one or more targeting moieties, and a targeting moiety can be for any desired type of targeting such as, e.g., to target a cell such as any herein-mentioned; or to target an organelle such as any herein-mentioned; or for targeting a response such as to a physical condition such as heat, energy, ultrasound, light, pH, chemical such as enzymatic, or magnetic stimuli; or to target to achieve a particular outcome such as delivery of payload to a particular location, such as by cell penetration.

Methods of Use
Modifying Cells

The methods according to the invention as described herein comprehend inducing one or more modifications in a host cell as herein discussed comprising delivering to cell a vector as herein discussed. In some embodiments, the host cell is a eukaryotic cell. In some embodiments, the host cell is a prokaryotic cell. The cell may be a mammalian cell. The mammalian cell many be a non-human primate, bovine, porcine, rodent or mouse cell. The cell may be a non-mammalian eukaryotic cell such as poultry, fish or shrimp. The cell may also be a plant cell. The plant cell may be of a crop plant such as cassava, corn, sorghum, wheat, or rice. The plant cell may also be of an algae, tree or vegetable. The modification introduced to the cell by the present invention may be such that the cell and progeny of the cell are altered for improved production of biologic products such as an antibody, starch, alcohol or other desired cellular output. The modification introduced to the cell by the present invention may be such that the cell and progeny of the cell include an alteration that changes the biologic product produced.

For minimization of toxicity, it will be important to control the concentration of the engineered protein delivered to the host cell. Optimal concentrations of the engineered protein can be determined by testing different concentrations in a cellular or non-human eukaryote animal model.

Engineering Proteins

In another aspect, the present disclosure provides for methods for engineering proteins, e.g., engineering proteins to bind to a target of interest. The methods may comprise inserting or modifying a TRS of any one of claims disclosed herein in the protein; and detecting whether the engineered protein binds to the target; or detecting whether the engineered protein exhibits enzymatic activity against the target. In some embodiments, the method may be used for modifying a target. The method may comprise contacting an engineered protein with the target. The engineered protein and the target may be contacted in vivo, ex vivo, or in vitro.

In another aspect, the present disclosure provides a method of engineering a protease to bind to a target substrate of interest, which comprises: inserting or modifying a TRS herein in the protease; and detecting whether the engineered protease binds to the target substrate; or detecting whether the engineered protease cleaves the target substrate.

In another aspect, the present disclosure provides a method of cleaving a target substrate, which comprises contacting an engineered protease herein with the substrate of interest. In some embodiments, the engineered protease and the target substrate are contacted in vivo, ex vivo, or in vitro.

Methods of Engineering a TRS Motif

The invention provides engineered target recognition regions comprising TRS motifs disclosed herein. According to the invention, engineering of target recognition regions involves one or more of varying the number of TRSs (e.g., increasing or decreasing the number of TRSs), varying the sequence of TRSs (e.g., introducing mutations, insertions and/or deletions), varying the order of TRSs (i.e. shuffling), varying the spacing between TRSs (e.g., inserting or deleting amino acids between TRSs), and incorporating TRSs from other sources. Whereas the instant application discloses TRSs and TRS motifs associated with IgA proteases, other sources of TRSs and TRS motifs include, without limitation, TALES, variable lymphocyte receptors, pumilio repeats, and TRSs and TRS motifs disclosed by U.S. Provisional Application No. 62/652,267.

In one aspect, the invention provides a non-naturally occurring or engineered composition, or one or more polynucleotides encoding components of said composition, or vector or delivery systems comprising one or more polynucleotides encoding components of said composition for use in recognizing or targeting a target molecule or a target molecule in a target cell. In some embodiments, the composition comprises an engineered protein or polypeptide comprising one or more target recognition regions comprising one or more engineered target recognition sequences (TRSs). In preferred embodiments, a TRS may include a series of adjacent hypervariable amino acids flanked by invariant amino acids. In some embodiments, the TRS is derived from a prokaryotic organism. In some embodiments, the TRS may be derived from a bacteria defense-mechanism related protein. In particular embodiments, the TRS is derived from an IgA protease of *Neisseria gonorrhoeae, Neisseria meningitidis, Haemophilus influenzae, Streptococcus pneumonia*, or any orthologs thereof. In some embodiments, the TRS may be derived from a Enterobacteriaceae family protein. In some embodiments, the TRS may be derived from a *Photorhabdus* bacteria protein. The bacteria protein may be toxins, including a variety of insecticidal toxins, as well as adhesins, proteases, and lipases, or any orthologs thereof.

In one aspect, the invention provides a non-naturally occurring or engineered composition, or one or more polynucleotides encoding components of said composition, or vector or delivery systems comprising one or more polynucleotides encoding components of said composition for use in modifying a target molecule or a target molecule in a target cell. In some embodiments, the composition comprises an engineered protein or polypeptide comprising one or more hypervariable amino acid residues. In some embodiments, the composition comprises an engineered protein or polypeptide comprising one or more engineered target recognition sequence (TRS). In some embodiments, the TRS is derived from a prokaryotic organism. In some embodiments, the TRS may be derived from a bacteria defense-mechanism related protein. In particular embodiments, the TRS is derived from an IgA protease of *Neisseria gonorrhoeae, Neisseria meningitidis, Haemophilus influenzae, Streptococcus pneumonia*, or any orthologs thereof. In some embodiments, the TRS may be derived from a Enterobacteriaceae family protein. In some embodiments, the TRS may be derived from a *Photorhabdus* bacteria protein. The bacteria protein may be toxins, including a variety of insecticidal toxins, as well as adhesins, proteases, and lipases, or any orthologs thereof.

In some embodiments, the engineered protein comprises one or more TRS derived from a particular organism comprising an endogenous Ig protease. In some embodiments, the engineered protein comprises one or more TRS derived from a particular organism comprising an endogenous IgA protease. In some embodiments, the TRS may be derived from a bacteria defense-mechanism related protein. In particular embodiments, the TRS is derived from an IgA protease of *Neisseria gonorrhoeae, Neisseria meningitidis, Haemophilus influenzae, Streptococcus pneumonia*, or any orthologs thereof. In some embodiments, the TRS may be derived from a Enterobacteriaceae family protein. In some embodiments, the TRS may be derived from a *Photorhabdus* bacteria protein. The bacteria protein may be toxins, including a variety of insecticidal toxins, as well as adhesins, proteases, and lipases, or any orthologs thereof.

According to the invention, libraries of target recognition regions are prepared, each region comprising one or more TRS, wherein the TRSs have undergone one or more of varying the number of TRSs, varying the sequence of TRSs, varying the order of TRSs, varying the spacing between TRSs, and incorporating TRSs from other sources. The libraries are then screened to identify candidates having desired binding characteristics for a target of interest, including but not limited to target affinity and/or target specificity.

In one aspect, the invention provides an engineered protein or polypeptide capable of recognizing a target comprising one or more TRS. In some embodiments, the TRS is derived from a prokaryotic organism. In some embodiments, the TRS is derived from a bacteria defense-mechanism related protein. In one aspect, the invention provides a non-naturally occurring or engineered composition, or one or more polynucleotides encoding components of said composition, or vector or delivery systems comprising one or more polynucleotides encoding components of said composition for use in recognizing or targeting a target molecule or a target molecule in a target cell. In some embodiments, the composition comprises an engineered protein or polypeptide comprising one or more target recognition regions comprising one or more engineered target recognition sequences (TRSs). In preferred embodiments, a TRS may include a series of adjacent hypervariable amino acids flanked by invariant amino acids. In some embodiments, the TRS is derived from a prokaryotic organism. In some embodiments, the TRS may be derived from a bacteria defense-mechanism related protein. In particular embodiments, the TRS is derived from an IgA protease of *Neisseria gonorrhoeae, Neisseria meningitidis, Haemophilus influenzae, Streptococcus pneumonia*, or any orthologs thereof. In some embodiments, the TRS may be derived from a Enterobacteriaceae family protein. In some embodiments, the TRS may be derived from a *Photorhabdus* bacteria protein. The bacteria protein may be toxins, including a variety of insecticidal toxins, as well as adhesins, proteases, and lipases, or any orthologs thereof.

In one aspect, the invention provides a non-naturally occurring or engineered composition, or one or more polynucleotides encoding components of said composition, or vector or delivery systems comprising one or more polynucleotides encoding components of said composition for use in modifying a target molecule or a target molecule in a target cell. In some embodiments, the composition comprises an engineered protein or polypeptide comprising one or more hypervariable amino acid residues. In some embodiments, the composition comprises an engineered protein or polypeptide comprising one or more engineered target recognition sequence (TRS). In some embodiments, the TRS is derived from a prokaryotic organism. In some embodiments, the TRS may be derived from a bacteria defense-mechanism related protein. In particular embodiments, the TRS is derived from an IgA protease of *Neisseria gonorrhoeae, Neisseria meningitidis, Haemophilus influenzae, Streptococcus pneumonia*, or any orthologs thereof. In some embodiments, the TRS may be derived from a Enterobacteriaceae family protein. In some embodiments, the TRS may be derived from a *Photorhabdus* bacteria protein. The bacteria protein may be toxins, including a variety of insecticidal toxins, as well as adhesins, proteases, and lipases, or any orthologs thereof.

In some embodiments, the engineered protein comprises one or more TRS derived from a particular organism comprising an endogenous Ig protease. In some embodiments, the engineered protein comprises one or more TRS motifs derived from a particular organism comprising an endogenous IgA protease. In some embodiments, the TRS may be derived from a bacteria defense-mechanism related protein. In particular embodiments, the TRS is derived from an IgA protease of *Neisseria gonorrhoeae, Neisseria meningitidis, Haemophilus influenzae, Streptococcus pneumonia*, or any orthologs thereof. In some embodiments, the TRS may be derived from a Enterobacteriaceae family protein. In some embodiments, the TRS may be derived from a *Photorhabdus* bacteria protein. The bacteria protein may be toxins, including a variety of insecticidal toxins, as well as adhesins, proteases, and lipases, or any orthologs thereof.

In certain embodiments, the engineered protein domain binds to specific sequences of a target. In some embodiments, the target is a protein. In some embodiments, the target is a polypeptide. In some embodiments, binding between the engineered protein and the target is directed by the TRS.

Targets

In some embodiments, a target may comprise a protein or polypeptide, a protein or polypeptide structure, a protein or polypeptide sequence, and any protein or polypeptide homologs or modifications, including protein phosphorylation, glycosylation, nitrosylation, methylation, acetylation, lipidation, myristoylation, palmitoylation, prenylation and any other modification thereof.

In some embodiments, a target may comprise nucleic acid molecules, sugar molecules, or other macromolecules. In some embodiments, a target is located in the nucleus or cytoplasm of a cell. In some embodiments, the target may be within an organelle of a eukaryotic cell, for example, mitochondrion or chloroplast. In some embodiments, the target may be located on the surface of a cell. In some embodiments, the target may be located across a cell membrane structure. In some embodiments, the target may be located in intercellular space of a tissue or an organism. In some embodiments, the target may be located in a specific cell type, tissue, organ, or structure of an organism, such as muscle, neuron, bone, skin, blood, liver, pancreas, lymphocytes.

In one aspect, the invention provides for methods of recognizing a target substrate. In some embodiments, the target substrate is a macromolecule. In some embodiments, the target substrate is a protein, polypeptide, nucleic acid molecule, or a sugar molecule. In some embodiments, the target substrate is in a host cell, which may be in vivo, ex vivo or in vitro. The host cell may be a prokaryotic cell, a eukaryotic cell, a plant cell, a fungal cell, an animal cell, an insect cell, a non-human mammalian cell, or a human cell.

In another aspect, the invention provides for methods of modifying a target substrate. In some embodiments, the target substrate is a macromolecule. In some examples, the macromolecule may be a protein, polypeptide, or a nucleic acid. In some embodiments, the target substrate is a protein, polypeptide, nucleic acid molecule, or a sugar molecule. In some embodiments, the target substrate is in a host cell, which may be in vivo, ex vivo or in vitro. The host cell may be a prokaryotic cell, a eukaryotic cell, a plant cell, a fungal cell, an animal cell, a non-human mammalian cell, or a human cell.

Cells

In one aspect, the invention provides a method of modifying a target cell in vivo, ex vivo or in vitro. The target cell may be a prokaryotic cell, a eukaryotic cell, a plant cell, a fungal cell, an animal cell, a non-human mammalian cell, or a human cell. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate.

In some embodiments, modification may be conducted in a manner alters the cell such that once modified the progeny or cell line of the modified cell retains the altered phenotype. The modified cells and progeny may be part of a multicellular organism such as a plant or animal with ex vivo or in vivo application of system to desired cell types. The invention may be a therapeutic method of treatment. The therapeutic method of treatment may comprise gene or genome editing, gene therapy, or protein based therapy. In some embodiments, the method comprises sampling a cell or population of cells from a human or non-human animal, and modifying the cell or cells. Culturing may occur at any stage ex vivo. The cell or cells may be re-introduced into the non-human animal or plant. In some embodiments, the re-introduced cells are stem cells. These sampling, culturing and re-introduction options apply across the aspects of the present invention.

In some embodiments, the method comprises allowing an engineered protein or polypeptide comprising a TRS to bind to the target. In some embodiments, the method comprises allowing an engineered protein or polypeptide comprising a TRS to cleave the target. In some embodiments, the method comprises allowing an engineered protein or polypeptide comprising a TRS to modify the target.

In one aspect, the invention provides a method of modifying expression of a substrate molecule in a eukaryotic cell. The substrate molecule may be a protein, polypeptide, nucleic acid, polysaccharide, lipid, or any other substrate molecule. In some embodiments, the method comprises allowing an engineered protein or polypeptide comprising a TRS to bind to the target such that said binding results in increased or decreased expression of said target. In some embodiments, the method comprises allowing an engineered protein or polypeptide comprising a TRS to cleave or modify the target such that said binding results in increased or decreased expression of said target.

In certain embodiments, modulations of binding efficiency can be exploited by modifying the engineered protein. In some embodiments, modulations of binding efficiency can be exploited by modifying the TRS. In some embodiments, modification of binding efficiency can be achieved by introducing mutations to the hypervariable regions of the engineered protein. In some embodiments, modification of binding efficiency can be achieved by introducing mismatches, e.g. one or more mismatches, between TRS and the target.

In certain embodiments, the engineered protein cleaves a target. In some embodiments, the target is a protein. In some embodiments, the target is a polypeptide. In some embodiments, binding between the engineered protein and the target is directed by the TRS. In certain embodiments, modulations of cleavage efficiency can be exploited by modifying the engineered protein. In some embodiments, modulations of cleavage efficiency can be exploited by modifying the TRS.

In one aspect, the invention provides for methods of engineering a TRS of an engineered protein or polypeptide. In some embodiments, the method comprises i) modifying or altering a TRS, duplicating a TRS, substituting one or more amino acid residues in a TRS with one or more amino acid residues from a different source, substituting one or more amino acid residues in a TRS with one or more amino acid residues derived from the same species or related species, mutating a TRS, linking a TRS to one or more TRS from a different source, or shuffling amino acid residues from one or more TRS, and ii) detecting whether the TRS binds to the target. In some embodiments, the TRS is modified by introducing a mutation to a hypervariable region. In some embodiments, the TRS is modified by introducing a mutation to a non-hypervariable region.

In certain embodiments, a detectable marker may be fused to the engineered protein, such that location within a cell may be visualized, such as in combination with a means for detecting the location of the nucleus (e.g. a stain specific for the nucleus such as DAPI) or cytoplasm. In certain embodiments, other localization tags may be fused to the engineered protein, such as without limitation for localizing the engineered protein to particular sites in a cell, such as organelles, such mitochondria, plastids, chloroplast, vesicles, golgi, (nuclear or cellular) membranes, ribosomes, nucleolus, ER, cytoskeleton, vacuoles, centrosome, nucleosome, granules, centrioles, etc.

Targeting Moiety

It should be understood that as to each possible targeting or active targeting moiety herein-discussed, there is an aspect of the invention wherein the delivery system comprises such a targeting or active targeting moiety. Likewise, the following table provides exemplary targeting moieties that can be used in the practice of the invention an as to each an aspect of the invention provides a delivery system that comprises such a targeting moiety.

TABLE 4

| Targeting Moiety | Target Molecule | Target Cell or Tissue |
| --- | --- | --- |
| Folate | folate receptor | cancer cells |
| Transferrin | transferrin receptor | cancer cells |
| Antibody CC52 | rat CC531 | rat colon adenocarcinoma CC531 |
| anti-HER2 antibody | HER2 | HER2-overexpressing tumors |
| anti-GD2 | GD2 | neuroblastoma, melanoma |
| anti-EGFR | EGFR | tumor cells overexpressing EGFR |
| pH-dependent fusogenic peptide diINF-7 | | ovarian carcinoma |
| anti-VEGFR | VEGF Receptor | tumor vasculature |
| anti-CD19 | CD19 (B cell marker) | leukemia, lymphoma |
| cell-penetrating peptide | | blood-brain barrier |
| cyclic arginine-glycine-aspartic acid-tyrosine-cysteine peptide (c(RGDyC)-LP) | $\alpha v \beta 3$ | glioblastoma cells, human umbilical vein endothelial cells, tumor angiogenesis |
| ASSHN peptide | | endothelial progenitor cells; anti-cancer |
| PR_b peptide | $\alpha_5\beta_1$ integrin | cancer cells |
| AG86 peptide | $\alpha_6\beta_4$ integrin | cancer cells |
| KCCYSL (P6.1 peptide) | HER-2 receptor | cancer cells |
| affinity peptide LN (YEVGHRC) | Aminopeptidase N (APN/CD13) | APN-positive tumor |
| synthetic somatostatin analogue | Somatostatin receptor 2 (SSTR2) | breast cancer |
| anti-CD20 monoclonal antibody | B-lymphocytes | B cell lymphoma |

Thus, in an embodiment of the delivery system, the targeting moiety comprises a receptor ligand, such as, for example, hyaluronic acid for CD44 receptor, galactose for hepatocytes, or antibody or fragment thereof such as a binding antibody fragment against a desired surface receptor, and as to each of a targeting moiety comprising a receptor ligand, or an antibody or fragment thereof such as a binding fragment thereof, such as against a desired surface receptor, there is an aspect of the invention wherein the delivery system comprises a targeting moiety comprising a receptor ligand, or an antibody or fragment thereof such as a binding fragment thereof, such as against a desired surface receptor, or hyaluronic acid for CD44 receptor, galactose for hepatocytes (see, e.g., Surace et al, "Lipoplexes targeting the CD44 hyaluronic acid receptor for efficient transfection of breast cancer cells," J. Mol Pharm 6(4):1062-73; doi: 10.1021/mp800215d (2009); Sonoke et al, "Galactose-modified cationic liposomes as a liver-targeting delivery system for small interfering RNA," Biol Pharm Bull. 34(8): 1338-42 (2011); Torchilin, "Antibody-modified liposomes for cancer chemotherapy," Expert Opin. Drug Deliv. 5 (9), 1003-1025 (2008); Manjappa et al, "Antibody derivatization and conjugation strategies: application in preparation of stealth immunoliposome to target chemotherapeutics to tumor," J. Control. Release 150 (1), 2-22 (2011); Sofou S "Antibody-targeted liposomes in cancer therapy and imaging," Expert Opin. Drug Deliv. 5 (2): 189-204 (2008); Gao J et al, "Antibody-targeted immunoliposomes for cancer treatment," Mini. Rev. Med. Chem. 13(14): 2026-2035 (2013); Molavi et al, "Anti-CD30 antibody conjugated liposomal doxorubicin with significantly improved therapeutic efficacy against anaplastic large cell lymphoma," Biomaterials 34(34):8718-25 (2013), each of which and the documents cited therein are hereby incorporated herein by reference).

Moreover, in view of the teachings herein the skilled artisan can readily select and apply a desired targeting moiety in the practice of the invention as to a lipid entity of the invention. The invention comprehends an embodiment wherein the delivery system comprises a lipid entity having a targeting moiety.

Functional Alteration and Screening

In one aspect, the present invention provides a composition comprising a library of engineered protein or polypeptide each comprising one or more TRS. The TRS may be derived from same or different organisms. The TRS may be generated by duplication, introductions of mutations, substitution of one or more amino acid residues, or shuffling of one or more TRS. In some embodiments, the TRS sequences of a library recognize different targets. In some embodiments, the TRS sequences of a library recognize same or similar targets. In some embodiments, the TRS sequences of a library recognize targets that share more than 10%, 20%, 30%, 40%, 50%, 60%, 70%, 80%, 90%, or 95% amino acid or nucleotide sequence identity with each other. In some embodiments, the TRS sequences of a library recognize targets that share structural similarities. In some embodiments, the TRS sequences of a library recognize targets that are involved in one or more cellular or biological functions, such as a metabolic pathway or a catalytic cascade. In some embodiments, the TRS is duplicated. In some embodiments, the TRS is mutated. In some embodiments, one or more amino acid residues in the TRS are substituted. In some embodiments, one or more amino acid residues in the TRS are substituted with one or more amino acid residues from a heterologous TRS derived from a different source. In some embodiments, one or more amino acid residues in the TRS are substituted with one or more amino acid residues from a TRS derived from the same species or related species. In some embodiments, the engineered protein or polypeptide comprises one or more TRS generated by shuffling of one or more TRS. In some embodiments, the engineered protein or polypeptide comprises one or more TRS generated by linking a TRS to one or more TRS from a different source. In some embodiments, one or more TRS is modified by introducing a mutation to a non-hypervariable region. In a preferred embodiment, one or more TRS is modified by introducing a mutation to a hypervariable region. In some embodiments, one or more TRS is modified by introducing a mutation to a non-hypervariable or conserved region, wherein the engineered protein or polypeptide comprises two or more TRS sequences.

In one aspect, the present invention provides for a method of functional evaluation and screening of genes and gene products. The use of the targeting system of the present invention to precisely deliver functional domains to specific targets, to modify the expression level of genes and gene products can be applied to a single cell or population of cells or with a library applied to the entire proteome in a pool of cells ex vivo or in vivo comprising the administration or expression of a library comprising a plurality of TRS and wherein the screening further comprises use of engineered targeting protein or polypeptide, wherein the engineered protein or polypeptide is associated with a functional domain. In an aspect the invention provides a method for screening a genome, transcriptome, or proteome comprising the administration to a host or expression in a host in vivo of a library comprising a plurality of TRS and wherein the screening further comprises use of engineered targeting protein or polypeptide, wherein the engineered protein or polypeptide is associated with a functional domain. In some embodiments, the functional domain may be a transcription activation domain, a transcription repressor domain, a recombinase domain, a transposase domain, a histone remodeler, a demethylase, a methyltransferase, a cryptochrome, or a light inducible/controllable domain or a chemically inducible/controllable domain. In some embodiments, the one or more functional domains is an NLS (Nuclear Localization Sequence) or an NES (Nuclear Export Signal). In some embodiments, the one or more functional domains is a transcriptional activation domain comprises VP64, p65, MyoD1, HSF1, RTA, SET7/9 and a histone acetyltransferase. In some embodiments, the functional domain may be comprise protease activity, myristoyltransferase activity, acyltransferase activity, farnesyltransferase activity, geranylgeranyltransferase activity, acetyltransferase activity, glycinamide ribonucleotide (GAR) transformylase activity, glutamylase activity, deglutamylase activity, carboxylase activity, glycosyltransferases activity, hydroxylases activity, nucleotidyl transferase activity, kinase activity, phosphotransferase activity, phosphatase activity, or other catalytic activities. Fusion protein may comprise any additional protein sequence, and optionally a linker sequence between any two domains. Examples of protein domains that may be fused to an engineered protein or polypeptide include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). An engineered protein may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinidase and histone tail protease. In some preferred embodiments, the functional domain is a transcriptional activation domain, such as, without limitation, VP64, p65, MyoD1, HSF1, RTA, SET7/9 or a histone acetyltransferase. In some embodiments, the functional domain is a deaminase, such as a cytidine deaminase.

In an aspect the invention provides a method as herein discussed, wherein the screening comprises affecting and detecting gene activation, gene inhibition, or cleavage in the locus.

In an aspect, the invention provides efficient on-target activity and minimizes off target activity. In an aspect, the invention provides efficient on-target modification, including cleavage, by the engineered targeting protein or polypeptide optionally associated with a functional domain and minimizes off-target modification or cleavage by the functional domain. Accordingly, in an aspect, the invention provides target-specific regulation of protein or gene expression.

In an aspect the invention provides a method as herein discussed, wherein the host is a eukaryotic cell. In an aspect the invention provides a method as herein discussed, wherein the host is a mammalian cell. In an aspect the invention provides a method as herein discussed, wherein the host is a non-human eukaryote. In an aspect the invention provides a method as herein discussed, wherein the non-human eukaryote is a non-human mammal. In an aspect the invention provides a method as herein discussed, wherein the non-human mammal is a mouse. An aspect the invention provides a method as herein discussed comprising the delivery of the targeting system or component(s) thereof or nucleic acid molecule(s) coding therefor, wherein said nucleic acid molecule(s) are operatively linked to regulatory sequence(s) and expressed in vivo. In an aspect the invention provides a method as herein discussed wherein the expressing in vivo is via a lentivirus, an adenovirus, or an AAV. In an aspect the invention provides a method as herein discussed wherein the delivery is via a particle, a nanoparticle, a lipid or a cell penetrating peptide (CPP).

The targeting system and the engineered protein or polypeptide described herein can be used to perform screening for substrates such as proteins in conjunction with a cellular phenotype—for instance, for determining critical minimal features and discrete vulnerabilities of functional elements required for gene expression, drug resistance, and reversal of disease. In some embodiments, the targeting system and the engineered protein or polypeptide may be used to screen for specific domains involved in functions such as drug resistance or reversal of disease by targeting sequences or structures in given protein domains. In some embodiments, a library of engineered proteins or polypeptides, or a library of nucleic acids molecules encoding a plurality of engineered proteins, or a library of vectors comprising nucleic acid molecules encoding a plurality of engineered proteins or polypeptides may be introduced into a population of cells. The library may be introduced, such that each cell receives a single engineered protein or a single vector comprising an engineered protein or coding nucleic acid molecule thereof. In the case where the library is introduced by transduction of a viral vector, as described herein, a low multiplicity of infection (MOI) is used. The engineered protein or polypeptide may include any orthologs or modifications, or may be associated with a heterologous functional domain. Any phenotype determined to be associated with modification or cleavage of the target may be confirmed by detecting cellular level(s) of the target. The library of targeting system(s) can be used in eukaryotic cells, including but not limited to mammalian and plant cells. The population of cells may be prokaryotic cells. The population of eukaryotic cells may be a population of embryonic stem (ES) cells, neuronal cells, epithelial cells, immune cells, endocrine cells, muscle cells, erythrocytes, lymphocytes, plant cells, or yeast cells.

In one aspect, the present invention provides for a method of screening for functional elements associated with a change in a phenotype. The library may be introduced into a population of cells that are adapted to contain a protein comprising a functional domain. The cells may be sorted into at least two groups based on the phenotype. The phenotype may be expression of a gene, cell growth, or cell viability. The change in phenotype may be a change in expression of a gene of interest. The target substrate of interest may be detected or modified. The cells may be sorted into a high expression group and a low expression group. The population of cells may include a reporter construct that is used to determine the phenotype. The reporter construct may include a detectable marker. Cells may be sorted by use of the detectable marker.

In another aspect, the present invention provides for a method of screening for loci associated with resistance to a chemical compound. The chemical compound may be a drug or pesticide. The library may be introduced into a population of cells, wherein each cell of the population contains no more than one engineered protein or polypeptide or no more than one TRS. The population of cells are treated with the chemical compound; and the representation of the engineered protein or polypeptide is determined after treatment with the chemical compound at a later time point as compared to an early time point, whereby target substrates associated with resistance to the chemical compound may be determined by enrichment of the engineered protein or polypeptide.

Aspects of the invention relate to screening and identification of novel effector proteins associated with the function(s) of the engineered protein. In some embodiments, the effector protein is a substrate of the engineered protein. In some embodiments, the effector protein is associated with in a regulatory pathway in which the engineered protein is involved. In particular embodiments, the regulatory pathway is a kinase cascade. In some embodiments, the engineered protein is a protease. In particular embodiments, the engineered protein is an IgA1 protease. In a further embodiment, the effector protein is functional in prokaryotic or eukaryotic cells for in vitro, in vivo or ex vivo applications. An aspect of the invention encompasses computational methods and algorithms to predict novel effector proteins associated with the engineered protein.

The protein or polypeptide acids-targeting systems, the vector systems, the vectors and the compositions described herein may be used in various protein or peptide-targeting applications, altering or modifying a genetic element such as a protein or polypeptide, trafficking and visualization of target protein, detecting and tracing of target protein or polypeptide, isolation of target protein, etc.

Therapeutic Applications

As will be apparent, it is envisaged that the present system can be used to target any polynucleotide sequence of interest. The invention provides a non-naturally occurring or engineered composition, or one or more polynucleotides encoding components of said composition, or vector or delivery systems comprising one or more polynucleotides encoding components of said composition for use in a modifying a target cell in vivo, ex vivo or in vitro and, may be conducted in a manner alters the cell such that once modified the progeny or cell line of the modified cell retains the altered phenotype. The modified cells and progeny may be part of a multi-cellular organism such as a plant or animal with ex vivo or in vivo application of targeting system to desired cell types. The invention may be a therapeutic method of treatment. The therapeutic method of treatment may comprise gene or genome editing, or gene therapy.

Patient-Specific Screening Methods

The targeting system of the present invention that targets protein, polypeptide, nucleic acid, polysaccharides, or other macromolecules can be used to detect and screen patients or patient samples for the presence of such macromolecules. For example, a targeting system that targets trinucleotide repeats (associated with a class of disorders such as Huntington's disease) can be used to screen patients or patent samples for the presence of such repeats. The repeats can be the target targeting system, and if there is binding thereto by the targeting system, that binding can be detected, to thereby indicate that such a repeat is present. The patient can then be administered suitable compound(s) to address the condition; or, can be administered a targeting system to bind to and modification or reduction of the macromolecule that causes the condition and alleviate the condition.

Anti-Inflammatory and Auto-Immune Disease Treatment

In certain embodiments, the targeting system or the engineered protein or polypeptide is used in an anti-inflammatory treatment. In certain embodiments, the engineered protein or polypeptide is used in treatment for acute or sub-acute inflammation. In some embodiments, the engineered protein or polypeptide is used in treatment for glomerulonephritis. In particular embodiments, the engineered protein or polypeptide is used in treatment for IgA nephropathy (IgAN) or Berger's disease. In some embodiments, the engineered protein or polypeptide is used in treatment for glomerular inflammation, mesangial hypercellularity, and expansion of mesangial matrix. In some embodiments, the engineered protein or polypeptide is used in treatment for progressive chronic kidney disease related to IgAN.

In certain embodiments, the engineered protein or polypeptide is used in treatment of sinusitis, asthma, bronchitis, or autoimmune disorders chronic obstructive pulmonary disease. In some embodiments, the engineered protein or polypeptide is used in treatment of chronic rhinosinusitis caused by allergies, bacterial and fungal infection, or anatomical abnormalities. In particular embodiments, the engineered protein or polypeptide is used to treat chronic rhinosinusitis with or without nasal polyps. In particular embodiments, the engineered protein or polypeptide is administered during sinus surgery.

In certain embodiments, the engineered protein of the targeting system provides methods of treatment for celiac disease. Celiac disease (CD) is an autoimmune condition affecting the small intestine, triggered by the ingestion of gluten, the protein fraction of wheat, barley, and rye. Strong linkage has been shown between CD and HLA-DQ2 and HLA-DQ8 haplotypes. More than 95% of those with CD express HLA-DQ2 while the remainder expresses HLA-DQ8. However, about 30-40% of the general population expresses HLA-DQ2, so while these HLA genes are necessary, they are not sufficient for developing CD and clearly non HLA genes are also involved. To date, at least 39 non-HLA genes have been identified through genome-wide association studies as strongly associated with CD, as reviewed in Kumar and Wijmenga, From genome-wide association studies to disease mechanisms: celiac disease as a model for autoimmune diseases. Semin Immunopathol. 2012 July; 34(4):567-80. The hallmark of CD is an immune-mediated enteropathy that involves both the innate and adaptive immune system. Initially gut paracellular permeability is increased in CD in part due to peptide-induced CXCR3 activated upregulation of zonulin, an intestinal peptide involved in epithelial tight junction control. Paracellular passage of gliadin peptides follows. α-gliadin has been shown to induce apoptosis of enterocytes, upregulate MHC class I molecules, activate MAP kinase pathway, and upregulate expression of CD83, a maturation marker of dendritic cells. This peptide, and others, enhances IL15 production leading to an expansion of intraepithelial lymphocytes (IELs) and triggering the innate immune system. IL15 plays a key role in enhanced cytolytic activity of IELs via induction of NK receptors on the IEL and also contributes to promoting the CD4+ T cell adaptive response leading to production of the pro-inflammatory cytokine interferon-γ (IFN-γ) [7]. Tissue transglutaminase (TTG), now known to be the autoantigen in CD, plays a key role in this process. By means of deamidation, TTG converts glutamine to glutamic acid at key sites within the gliadin peptide. This increases the negative charge on the peptide molecule and enhances binding of the peptide within the peptide binding groove of the HLA-DQ2 molecule on the surface of the antigen-presenting cells. See Denham and Hill, Celiac Disease and Autoimmunity: Review and Controversies. Curr. Allergy. Asthma Rep. 2013 13(4): 347-353. Among other approaches, use of oral proteases to help degrade toxic gliadin peptides before reaching the mucosa has been proposed as an advanced therapy. Accordingly, the targeting system of the present invention may be used to provide treatment or ameliorate symptoms of celiac disease. In some embodiments, the targeting system comprises an engineered protein or polypeptide, preferably associated with a functional domain, that blocks deamination of gluten peptides by tTG and/or interrupts HLA-DQ2/8 and gluten peptide binding. In some embodiments, the targeting system comprises an engineered protein or polypeptide, preferably associated with a functional domain, that targets and modifies anti-gluten antibodies and thereby silences gluten-reactive T cells. In some embodiments, the engineered protein comprises a TRS derived from an IgA protease. In some embodiments, the engineered protein comprises an IgA protease. In some embodiments, the engineered protein comprises an dipeptidyl peptidase, an aminopeptidase, or a prolylendopeptidase.

In certain embodiments, the engineered protein or polypeptide is used in treatment of Ischemic strokes. Ishemic strokes occur as a result of an obstruction within a blood vessel supplying blood to the brain. Proteases, including serine protease tissue plasminogen activator (tPA) have been studied and applied in treatment of Ischemic strokes as demonstrated in Lapchak and Boitano, Effect of the Pleiotropic Drug CNB-001 on Tissue Plasminogen Activator (tPA) Protease Activity in vitro: Support for Combination Therapy to Treat Acute Ischemic Stroke. J. Neurol. Neurophysiol., 5(4): 214 (2014); Wang et al., Activated Protein C Analog Protects from Ischemic Stroke and Extends the Therapeutic Window of Tissue-type Plasminogen Activator in Aged Female Mice and Hypertensive Rats. Stroke 44(12): 3529-36 (2013). In particular embodiments, the engineered protein or peptide is used in treatment of acute ischemic strokes, brain trauma, spinal cord injury, amyotrophic lateral sclerosis and multiple sclerosis.

In certain embodiments, the engineered protein or polypeptide is used in treatment for wound healing and debridement. In certain embodiments, the engineered protein or polypeptide is involved in development and removal of perivascular fibrin cuffs and removal of dead tissues following inflammation. In certain embodiments, the engineered protein or polypeptide is used for removal of necrotic tissue from chronic wounds and burns. In certain embodiments, the engineered protein or polypeptide is used for treatment and removal of necrotic tissue in chronic limb wounds in patients with diabetes. In certain embodiments, the engineered protein or polypeptide is administered in the form of an ointment. In particular embodiments, the engineered protein or polypeptide is administered with continuous streaming and washing as described in Yaakobi et al., Wound Debridement by Continuous Streaming of Proteolytic Enzyme Solutions: Effects on Experimental Chronic Wound Model in Porcin. Wounds. 19(7): 192-200 (2007).

In certain embodiments, the engineered protein or polypeptide is used in treatment for bacterial infection. In certain embodiments, the engineered protein or polypeptide is used to prevent formation of biofilm and adherent of biofilm to subject tissues. In certain embodiments, the engineered protein or polypeptide is used to disrupt biofilm. In certain embodiments, the engineered protein or polypeptide is used in treatment for bacterial infection in conjunction with an anti-microbial agent. In certain embodiments, the engineered protein or polypeptide is used in treatment for bacterial infection in conjunction with antibiotics. In particular embodiments, the engineered protein or polypeptide is used in treatment for bacterial infection around implanted orthopaedic devices. In certain embodiments, the engineered protein or polypeptide is used in treatment for sepsis.

In certain embodiments, the engineered protein or polypeptide is used in treatment for pancreatic insufficiency. In certain embodiments, the engineered protein or polypeptide is used in pancreatic enzyme replacement therapies. In some embodiments, the engineered protein or polypeptide is used in treatment for nutrient malabsorption related to pancreatic insufficiency. In some embodiments, the engineered protein or polypeptide is used to treat or ameliorate symptoms caused by cystic fibrosis or cancer.

In certain embodiments, the engineered protein or polypeptide is used for treatment of muscular contraction disorders. In some embodiments, the engineered protein or polypeptide is used for the treatment of dystonia, strabismus or blepharospasm. In particular embodiments, the engineered protein or polypeptide is used for treatment of glabellar lines, muscle spasticity, overactive bladder, alopecia areata, or prostatic hyperplasia.

In certain embodiments, the engineered protein or polypeptide is used to treat or ameliorate cancer symptoms. In certain embodiments, the engineered protein or polypeptide is used in disruption of fibrin associated to cancer cells. In some embodiments, the engineered protein or polypeptide is administered along with chemotherapy treatment. In some embodiments, the engineered protein or polypeptide is used to limit waste build up during chemotherapy treatment. In certain embodiments, the engineered protein or polypeptide is used to prevent scarring and diminishing fibrosis. In some embodiments, the engineered protein or polypeptide is used along with radiation therapy treatment.

Proteopathy Treatment

In an aspect, the present invention provides treatments for disease and symptoms caused by protein conformational disorders, or proteopathies. Proteopathy refers to a class of diseases related to structural abnormality of certain proteins and disruption of the function of cells, tissues and organs. In certain embodiment, the targeting system recognizes abnormally conformed proteins or protein aggregates. In certain embodiment, the targeting system, optionally comprising one or more engineered protein or polypeptide associated with a functional domain, cleaves or modifies abnormally conformed proteins or protein aggregates. In certain embodiment, the targeting system, optionally comprising one or more engineered protein or polypeptide associated with a functional domain, cleaves or modifies proteins or protein aggregates in excessive amounts that are associated with the disease or symptoms. In preferred embodiments, the functional domain is a chaperone. An example and method of chaperone based therapy for protein mis-folding related disease is discussed in Cahudhuri and Paul, Protein-misfolding diseases and Chaperone-based Therapeutic Approaches. FEBS J. 273(7): 1331-49 (2006) and is incorporated herein by reference.

The targeting system of the present invention may be used for treatment or symptom amelioration of diseases include but not limited to:

TABLE 5

| Proteopathy | Major aggregating protein |
|---|---|
| Alzheimer's Disease | Amyloid β peptide (Aβ); Tau protein |
| Cerebral β-amyloid angiopathy | Amyloid β peptide |
| Retinal ganglion cell degeneration in glaucoma | Amyloid β peptide |
| Prion disease | Prion protein |
| Parkionson's disease, synucleinopathies | α-Synuclein |
| Tauopathies | Microtubule-associated protein tau |
| Frontotemporal lobar degeneration | TDP-43 |
| FTLD-FUS | Fused in sarcoma (FUS) protein |
| Amyotrophic lateral sclerosis (ALS) | Superoxide dismutase, TDP-43 |
| Hungtington's disease, trinucleotide repeat disorders | Proteins with tandem glutamine expansions |
| Familial British Dementia | ABri |
| Familial Danish Dementia | ADan |
| Hereditary Cerebral Hemorrhage with Amyloidosis | Cystatin C |
| CADASIL | Notch 3 |
| Alexander Disease | GFAP |
| Seipinopathies | Seipin |
| Familial amyloidotic neuropathy | Transthyretin |
| Serpinopathies | Serpins |
| Light chain amyloidosis | Monoclonal immunoglobulin light chains |
| Heavy chain amyloidosis | Monoclonal immunoglobulin heavy chains |
| Amyloidosis | Amyloid A protein |
| Type II diabetes | Islet amyloid polypeptide |
| Aortic medial amyloidosis | Medin (lactadherin) |
| ApoAI amyloidosis | Apolipoprotein AI |
| ApoAII amyloidosis | Apolipoprotein AII |
| ApoAIV amyloidosis | Apolipoprotein AIV |
| Familial amyloidosis of the Finnish type (FAF) | Gelsolin |
| Lysozyme amyloidosis | Lysozyme |
| Fibrinogen amyloidosis | Fibrinogen |
| Dialysis amyloidosis | Beta-2 microglobulin |
| Inclusion body myositis/myopathy | Amyloid β peptide |
| Cataracts | Crystallins |
| Retinitis pigmentosa with rhodopsin mutations | rhodopsin |
| Medullary thyroid carcinoma | Calcitonin |
| Cardiac atrial amyloidosis | Atrial natriuretic factor |
| Pituitary prolactinoma | Prolactin |
| Hereditary lattice corneal dystrophy | Keratoepithelin |
| Cutaneous lichen amyloidosis | Keratins |
| Mallory bodies | Keratin intermediate filament |
| Corneal lactoferrin amyloidosis | Lactoferrin |
| Pulmonary alveolar proteinosis | Surfactant protein C (SP-C) |
| Odontogenic (Pindborg) tumor amyloid | Odontogenic ameloblast-associated protein |
| Seminal vesicle amyloid | Semenogelin |
| Apolipoprotein C2 amyloidosis | Apolipoprotein C2 (ApoC2) |
| Apolipoprotein C3 amyloidosis | Apolipoprotein C3 (ApoC3) |
| Lect2 amyloidosis | Leukocyte chemotactic factor-2 (Lect2) |

TABLE 5-continued

| Proteopathy | Major aggregating protein |
|---|---|
| Insulin amyloidosis | Insulin |
| Galectin-7 amyloidosis (primary localized cutaneous amyloidosis) | Galectin-7 (Gal7) |
| Corneodesmosin amyloidosis | Corneodesmosin |
| Enfuvirtide amyloidosis | Enfuvirtide |
| Cystic Fibrosis | Cystic fibrosis transmembrane conductance regulator (CFTR) protein |
| Sickle cell disease | Hemoglobin |

The present invention may also be applied to treat bacterial, fungal and parasitic pathogens. Most research efforts have focused on developing new antibiotics, which once developed, would nevertheless be subject to the same problems of drug resistance. The invention provides novel alternatives which overcome those difficulties. Furthermore, unlike existing antibiotics, treatments provided by the present can be made pathogen specific, inducing bacterial cell death of a target pathogen while avoiding beneficial bacteria.

In an aspect, the present invention provides treatments for disease and symptoms caused by gene mutations causing amino acid changes in proteins. In certain embodiment, the targeting system recognizes mutated amino acid sequences in target substrates. In certain embodiment, the targeting system, optionally comprising one or more engineered protein or polypeptide associated with a functional domain, cleaves or modifies proteins comprising mutations associated with or protein aggregates. In certain embodiment, the targeting system, optionally comprising one or more engineered protein or polypeptide associated with a functional domain, cleaves or modifies proteins or protein aggregates in excessive amounts that are associated with the disease or symptoms.

In an aspect, the present invention provides treatment for disease and symptoms related to malfunction or loss of function mutations of regulatory proteins. In some embodiments, the engineered protein or polypeptide targets substrates involved in protein phosphorylation. In some embodiments, the engineered protein or polypeptide is associated with functional domain, optionally with protein kinase or protein phosphatase activity. In some embodiments, the target substrate is involved in stabilizing microtubules in cells, including neurons. In particular embodiments, the target substrate is a Tau protein. In some embodiments, the targeting system of the present invention is used for treatment of Alzheimer's disease, Parkinson's disease, and other degenerative disorders.

Accordingly, in some embodiments, the treatment, prophylaxis or diagnosis of Retinitis Pigmentosa is provided. A number of different genes are known to be associated with or result in Retinitis Pigmentosa, such as RP1, RP2 and so forth. These genes are targeted in some embodiments and either knocked out or repaired through provision of suitable a template. In some embodiments, delivery is to the eye by injection.

One or more Retinitis Pigmentosa genes can, in some embodiments, be selected from: RP1 (Retinitis pigmentosa-1), RP2 (Retinitis pigmentosa-2), RPGR (Retinitis pigmentosa-3), PRPH2 (Retinitis pigmentosa-7), RP9 (Retinitis pigmentosa-9), IMPDH1 (Retinitis pigmentosa-10), PRPF31 (Retinitis pigmentosa-11), CRB1 (Retinitis pigmentosa-12, autosomal recessive), PRPF8 (Retinitis pigmentosa-13), TULP1 (Retinitis pigmentosa-14), CA4 (Retinitis pigmentosa-17), HPRPF3 (Retinitis pigmentosa-18), ABCA4 (Retinitis pigmentosa-19), EYS (Retinitis pigmentosa-25), CERKL (Retinitis pigmentosa-26), FSCN2 (Retinitis pigmentosa-30), TOPORS (Retinitis pigmentosa-31), SNRNP200 (Retinitis pigmentosa 33), SEMA4A (Retinitis pigmentosa-35), PRCD (Retinitis pigmentosa-36), NR2E3 (Retinitis pigmentosa-37), MERTK (Retinitis pigmentosa-38), USH2A (Retinitis pigmentosa-39), PROM1 (Retinitis pigmentosa-41), KLHL7 (Retinitis pigmentosa-42), CNGB1 (Retinitis pigmentosa-45), BEST1 (Retinitis pigmentosa-50), TTC8 (Retinitis pigmentosa 51), C2orf71 (Retinitis pigmentosa 54), ARL6 (Retinitis pigmentosa 55), ZNF513 (Retinitis pigmentosa 58), DHDDS (Retinitis pigmentosa 59), BEST1 (Retinitis pigmentosa, concentric), PRPH2 (Retinitis pigmentosa, digenic), LRAT (Retinitis pigmentosa, juvenile), SPATA7 (Retinitis pigmentosa, juvenile, autosomal recessive), CRX (Retinitis pigmentosa, late-onset dominant), and/or RPGR (Retinitis pigmentosa, X-linked, and sinorespiratory infections, with or without deafness).

In some embodiments, the Retinitis Pigmentosa gene is MERTK (Retinitis pigmentosa-38) or USH2A (Retinitis pigmentosa-39).

Mention is also made of WO 2015/138510 and through the teachings herein the invention (using a CRISPR-Cas9 system) comprehends providing a treatment or delaying the onset or progression of Leber's Congenital Amaurosis 10 (LCA 10). LCA 10 is caused by a mutation in the CEP290 gene, e.g., a c.2991+1655, adenine to guanine mutation in the CEP290 gene which gives rise to a cryptic splice site in intron 26. This is a mutation at nucleotide 1655 of intron 26 of CEP290, e.g., an A to G mutation. CEP290 is also known as: CT87; MKS4; POC3; rd16; BBS14; JBTS5; LCAJO; NPHP6; SLSN6; and 3H11Ag (see, e.g., WO 2015/138510). In an aspect of gene therapy, the invention involves introducing one or more breaks near the site of the LCA target position (e.g., c.2991+1655; A to G) in at least one allele of the CEP290 gene. Altering the LCA10 target position refers to (1) break-induced introduction of an indel (also referred to herein as NHEJ-mediated introduction of an indel) in close proximity to or including a LCA10 target position (e.g., c.2991+1655A to G), or (2) break-induced deletion (also referred to herein as NHEJ-mediated deletion) of genomic sequence including the mutation at a LCA10 target position (e.g., c.2991+1655A to G). Both approaches give rise to the loss or destruction of the cryptic splice site resulting from the mutation at the LCA 10 target position.

Treating Diseases of the Circulatory System

The present invention also contemplates delivering the targeting system described herein, to the blood or hematopoietic stem cells. The plasma exosomes of Wahlgren et al. (Nucleic Acids Research, 2012, Vol. 40, No. 17 e130) were previously described and may be utilized to deliver a protein-RNA (CRISPR) system to the blood. The targeting system of the present invention is also contemplated to treat hemoglobinopathies, such as thalassemia and sickle cell disease. See, e.g., International Patent Publication No. WO 2013/126794 for potential targets, including genes and gene products that may be targeted by the targeting system of the present invention.

With the knowledge in the art and the teachings in this disclosure, the skilled person can correct HSCs as to a genetic hematologic disorder, e.g., β-Thalassemia, Hemophilia, or a genetic lysosomal storage disease.

The term "Hematopoietic Stem Cell" or "HSC" is meant to include broadly those cells considered to be an HSC, e.g., blood cells that give rise to all the other blood cells and are derived from mesoderm; located in the red bone marrow, which is contained in the core of most bones. HSCs of the invention include cells having a phenotype of hematopoietic stem cells, identified by small size, lack of lineage (lin) markers, and markers that belong to the cluster of differentiation series, like: CD34, CD38, CD90, CD133, CD105, CD45, and also c-kit,—the receptor for stem cell factor. Hematopoietic stem cells are negative for the markers that are used for detection of lineage commitment, and are, thus, called Lin−; and, during their purification by FACS, a number of up to 14 different mature blood-lineage markers, e.g., CD13 & CD33 for myeloid, CD71 for erythroid, CD19 for B cells, CD61 for megakaryocytic, etc. for humans; and, B220 (murine CD45) for B cells, Mac-1 (CD11b/CD18) for monocytes, Gr-1 for Granulocytes, Ter119 for erythroid cells, Il7Ra, CD3, CD4, CD5, CD8 for T cells, etc. Mouse HSC markers: CD34lo/−, SCA-1+, Thy1.1+/lo, CD38+, C-kit+, lin−, and Human HSC markers: CD34+, CD59+, Thy1/CD90+, CD38lo/−, C-kit/CD117+, and lin−. HSCs are identified by markers. Hence in embodiments discussed herein, the HSCs can be CD34+ cells. HSCs can also be hematopoietic stem cells that are CD34−/CD38−. Stem cells that may lack c-kit on the cell surface that are considered in the art as HSCs are within the ambit of the invention, as well as CD133+ cells likewise considered HSCs in the art.

In an aspect, the targeting system of the present invention is used for treatment of disease related to mutations causing alteration in post-translational target sites. Mutations in post-translational modification target sites have been shown as involved in many diseases, as discussed in Li et al., Loss of Post-translational modification Sites in Disease. Pac. Symp. Biocomput. 337-347 (2010). One example is a loss of N-linked glycosylation in the prion protein (PRNP), where amino acid substitution T183A was shown to be involved in autosomal dominant spongiform encephalopathy. This particular variant causes numerous clinical symptoms such as early-onset dementia, cerebral atrophy, and hypometabolism. Another example is a loss of acetylation sites in androgen receptor (AR). Loss of AR acetylation has been implicated in Kennedy's disease, an inherited neurodegenerative disorder. Amino acid substitution K630A or both K632A and K633A have been shown to cause a significant slowdown of ligand-dependent nuclear translocation. The non-acetylated mutants misfold and form aggregates with several other proteins, including ubiquitin ligase E3, thus affecting proteasomal degradation. And yet another example involves serine phosphorylation in the period circadian protein homolog 2 protein (PER2). Mutation of S662 is associated with the familial advanced sleep phase syndrome, an autosomal dominant disorder with early sleep onset (around 7:30 μm) and early awakening (around 4:30 am), but normal sleep duration Biochemical studies have shown that phosphorylation of S662 affects phosphorylation (by casein kinase CKIε) of several other residues in PER2, resulting in an overall hypophosphorylation of PER2. Interestingly, creation of a negative charge by S662D or an excess of CKIε restores the phosphorylation patterns of PER2. The current working hypothesis regarding PER2 is that phosphorylation of S662 likely creates a recognition site for CKIε and triggers a cascade of downstream effects. However, functional roles of phosphorylated PER2 are still largely unknown.

The targeting system of the present invention may also be used in the treatment of various tauopathies, including primary and secondary tauopathies, such as primary age-related tauopathy (PART)/Neurofibrillary tangle-predominant senile dementia, with NFTs similar to AD, but without plaques, dementia pugilistica (chronic traumatic encephalopathy), progressive supranuclear palsy, corticobasal degeneration, frontotemporal dementia and parkinsonism linked to chromosome 17, lytico-Bodig disease (Parkinson-dementia complex of Guam), ganglioglioma and gangliocytoma, meningioangiomatosis, postencephalitic parkinsonism, subacute sclerosing panencephalitis, as well as lead encephalopathy, tuberous sclerosis, Hallervorden-Spatz disease, and lipofuscinosis, alzheimers disease. The enzymes of the present invention may also target mutations disrupting the cis-acting splicing code cause splicing defects and disease (summarized in Cell. 2009 Feb. 20; 136(4): 777-793). The motor neuron degenerative disease SMA results from deletion of the SMN1 gene. The remaining SMN2 gene has a C→T substitution in exon 7 that inactivates an exonic splicing enhancer (ESE), and creates an exonic splicing silencer (ESS), leading to exon 7 skipping and a truncated protein (SMNΔ7). A T→A substitution in exon 31 of the dystrophin gene simultaneously creates a premature termination codon (STOP) and an ESS, leading to exon 31 skipping. This mutation causes a mild form of DMD because the mRNA lacking exon 31 produces a partially functional protein. Mutations within and downstream of exon 10 of the MAPT gene encoding the tau protein affect splicing regulatory elements and disrupt the normal 1:1 ratio of mRNAs including or excluding exon 10. This results in a perturbed balance between tau proteins containing either four or three microtubule-binding domains (4R-tau and 3R-tau, respectively), causing the neuropathological disorder FTDP-17. The example shown is the N279K mutation which enhances an ESE function promoting exon 10 inclusion and shifting the balance toward increased 4R-tau. Polymorphic (UG)m (U)n tracts within the 3' splice site of the CFTR gene exon 9 influence the extent of exon 9 inclusion and the level of full-length functional protein, modifying the severity of cystic fibrosis (CF) caused by a mutation elsewhere in the CFTR gene.

In some embodiments, the engineered protein or polypeptide targets proteins comprising mutations at one or more post-translational modification recognition sites. The post-translation modification may be with particular chemical groups (e.g. phosphoryl), lipids (e.g. palmitic acid), carbohydrates (e.g. glucose) or other proteins or polypeptides (e.g. ubiquitin). In preferred embodiments, the engineered protein or polypeptide is associated with at least one functional domain. In some embodiments, the functional domain may be a transcription activation domain, a transcription repressor domain, a recombinase domain, a transposase domain, a histone remodeler, a demethylase, a methyltransferase, a cryptochrome, or a light inducible/controllable domain or a chemically inducible/controllable domain. In some embodiments, the one or more functional domains is an NLS (Nuclear Localization Sequence) or an NES (Nuclear Export Signal). In some embodiments, the one or more functional domains is a transcriptional activation domain comprises VP64, p65, MyoD1, HSF1, RTA, SET7/9 and a histone acetyltransferase. In some embodiments, the functional domain may be comprise protease activity, myristoyltransferase activity, acyltransferase activity, farnesyltransferase activity, geranylgeranyltransferase activity, acetyltransferase activity, glycinamide ribonucleotide (GAR) transformylase activity, glutamylase activity, deglutamylase activity, carboxylase activity, glycosyltransferases activity, hydroxylases activity, nucleotidyl transferase activity, kinase activity, phosphotransferase activity, phosphatase activity, or other catalytic activities. Fusion protein may comprise any additional protein sequence, and optionally a linker sequence between any two domains. Examples of protein domains that may be fused to an engineered protein or polypeptide include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). An engineered protein may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinidase and histone tail protease. In some preferred embodiments, the functional domain is a transcriptional activation domain, such as, without limitation, VP64, p65, MyoD1, HSF1, RTA, SET7/9 or a histone acetyltransferase. In some embodiments, the functional domain is a deaminase, such as a cytidine deaminase. Cytidine deaminase may be directed to a target nucleic acid to where it directs conversion of cytidine to uridine, resulting in C to T substitutions (G to A on the complementary strand).

Mutations in genes and pathways that can result in production of improper proteins or proteins in improper amounts which affect function may be targeted by the methods and composition provided in the present invention. Examples of disease-associated genes and polynucleotides are listed in Tables 6 and 7. Examples of signaling biochemical pathway-associated genes and polynucleotides are listed in Table 8.

TABLE 6

| DISEASE/DISORDERS | GENE(S) |
| --- | --- |
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion - related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |

TABLE 6-continued

| DISEASE/DISORDERS | GENE(S) |
|---|---|
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE 7

| | |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, |

TABLE 7-continued

| | |
|---|---|
| | EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx) FXN/X25 (Friedrich's Ataxia), ATX3 (Machado- Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBAl, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE 8

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; |

TABLE 8-continued

| CELLULAR FUNCTION | GENES |
|---|---|
| | MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; |

TABLE 8-continued

| CELLULAR FUNCTION | GENES |
|---|---|
| | NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; |

TABLE 8-continued

| CELLULAR FUNCTION | GENES |
|---|---|
| | MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; |

TABLE 8-continued

| CELLULAR FUNCTION | GENES |
|---|---|
| PDGF Signaling | PIM1; PIK3C2A; DYRK1A; MAP2K2; PIP5K1A; PIK3R1; MAP2K1; PAK3; ATM; TTK; CSNK1A1; BRAF; SGK EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; |

TABLE 8-continued

| CELLULAR FUNCTION | GENES |
|---|---|
| VDR/RXR Activation | IKBKG; RELB; MAP3K7; JAK1; CHUK; STAT3; NFKB1; JUN; IL1R1; IL6 PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |

TABLE 8-continued

| CELLULAR FUNCTION | GENES |
|---|---|
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |

TABLE 8-continued

| CELLULAR FUNCTION | GENES |
|---|---|
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln |

The targeting system of the present invention can further be used for antiviral activity, against virion proteins or virus DNA or RNA wherein the engineered protein or polypeptide of the present invention is preferably associated with at least one functional domain that has nuclease activity. The engineered protein can be targeted to the virion proteins or polypeptides. In some embodiments, the hypervariable region of the TRS motives may be shuffled, edited, and/or multiplexed to target, bind to, and/or cleave variable polypeptides of virion proteins. In some embodiments, the engineered protein or polypeptide may be associated with or without fusion by to an active nuclease that cleaves DNA or RNA.

Therapeutic dosages of the enzyme system of the present invention are contemplated to be about 0.1 to about 2 mg/kg the dosages may be administered sequentially with a monitored response, and repeated dosages if necessary, up to about 7 to 10 doses per patient. Advantageously, samples are collected from each patient during the treatment regimen to ascertain the effectiveness of treatment. For example, tissue samples comprising target molecules may be isolated and quantified to determine if expression is reduced or ameliorated. Such a diagnostic is within the purview of one of skill in the art.

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011—Medical). Specific aspects of tandem repeat sequences have been found to be responsible for more than twenty human diseases (New insights into repeat instability: role of RNA·DNA hybrids. McIvor EI, Polak U, Napierala M. RNA Biol. 2010 September-October; 7(5):551-8). The present effector protein systems may be harnessed to correct these defects of genomic instability.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

The present invention also contemplates correction of hematopoietic disorders. For example, Severe Combined Immune Deficiency (SCID) results from a defect in lymphocytes T maturation, always associated with a functional defect in lymphocytes B (Cavazzana-Calvo et al., Annu. Rev. Med., 2005, 56, 585-602; Fischer et al., Immunol. Rev., 2005, 203, 98-109). In the case of Adenosine Deaminase (ADA) deficiency, one of the SCID forms, patients can be treated by injection of recombinant Adenosine Deaminase enzyme. Since the ADA gene has been shown to be mutated in SCID patients (Giblett et al., Lancet, 1972, 2, 1067-1069), several other genes involved in SCID have been identified (Cavazzana-Calvo et al., Annu. Rev. Med., 2005, 56, 585-602; Fischer et al., Immunol. Rev., 2005, 203, 98-109). There are four major causes for SCID: (i) the most frequent form of SCID, SCID-X1 (X-linked SCID or X-SCID), is caused by mutation in the IL2RG gene, resulting in the absence of mature T lymphocytes and NK cells. IL2RG encodes the gamma C protein (Noguchi, et al., Cell, 1993, 73, 147-157), a common component of at least five interleukin receptor complexes. These receptors activate several targets through the JAK3 kinase (Macchi et al., Nature, 1995, 377, 65-68), which inactivation results in the same syndrome as gamma C inactivation; (ii) mutation in the ADA gene results in a defect in purine metabolism that is lethal for lymphocyte precursors, which in turn results in the quasi absence of B, T and NK cells; (iii) V(D)J recombination is an essential step in the maturation of immunoglobulins and T lymphocytes receptors (TCRs). Mutations in Recombination Activating Gene 1 and 2 (RAG1 and RAG2) and Artemis, three genes involved in this process, result in the absence of mature T and B lymphocytes; and (iv) Mutations in other genes such as CD45, involved in T cell specific signaling have also been reported, although they represent a minority of cases (Cavazzana-Calvo et al., Annu. Rev. Med., 2005, 56, 585-602; Fischer et al., Immunol. Rev., 2005, 203, 98-109). In aspect of the invention, relating to the targeting system and targeting and/or modification of the target molecules involved with disease, the invention contemplates that it may be used to correct ocular defects that arise from several genetic mutations further described in Genetic Diseases of the Eye, Second Edition, edited by Elias I. Traboulsi, Oxford University Press, 2012. Non-limiting examples of ocular defects to be corrected include macular degeneration (MD), retinitis pigmentosa (RP). Non-limiting examples of genes and proteins associated with ocular defects include but are not limited to the following proteins: (ABCA4) ATP-binding cassette, sub-family A (ABC1), member 4 ACHM1 achromatopsia (rod monochromacy) 1 ApoE Apolipoprotein E (ApoE) C1QTNF5 (CTRP5) C1q and tumor necrosis factor related protein 5 (C1QTNF5) C2 Complement component 2 (C2) C3 Complement components (C3) CCL2 Chemokine (C—C motif) Ligand 2 (CCL2) CCR2 Chemokine (C—C motif) receptor 2 (CCR2) CD36 Cluster of Differentiation 36 CFB Complement factor B CFH Complement factor CFH H CFHR1 complement factor H-related 1 CFHR3 complement factor H-related 3

CNGB3 cyclic nucleotide gated channel beta 3 CP ceruloplasmin (CP) CRP C reactive protein (CRP) CST3 cystatin C or cystatin 3 (CST3) CTSD Cathepsin D (CTSD) CX3CR1 chemokine (C-X3-C motif) receptor 1 ELOVL4 Elongation of very long chain fatty acids 4 ERCC6 excision repair cross-complementing rodent repair deficiency, complementation group 6 FBLN5 Fibulin-5 FBLN5 Fibulin 5 FBLN6 Fibulin 6 FSCN2 fascin (FSCN2) HMCN1 Hemicentrin 1 HMCN1 hemicentin 1 HTRA1 HtrA serine peptidase 1 (HTRA1) HTRA1 HtrA serine peptidase 1 IL-6 Interleukin 6 IL-8 Interleukin 8 LOC387715 Hypothetical protein PLEKHA1 Pleckstrin homology domain-containing family A member 1 (PLEKHA1) PROM1 Prominin 1(PROM1 or CD133) PRPH2 Peripherin-2 RPGR retinitis pigmentosa GTPase regulator SERPING1 serpin peptidase inhibitor, clade G, member 1 (C1-inhibitor) TCOF1 Treacle TIMP3 Metalloproteinase inhibitor 3 (TIMP3) TLR3 Toll-like receptor 3.

The present invention, with regard the targeting system also contemplates delivering to the heart. For the heart, a myocardium tropic adeno-associated virus (AAVM) is preferred, in particular AAVM41 which showed preferential gene transfer in the heart (see, e.g., Lin-Yanga et al., PNAS, Mar. 10, 2009, vol. 106, no. 10). For example, US Patent Publication No. 20110023139, describes use of zinc finger nucleases to genetically modify cells, animals and proteins associated with cardiovascular disease. Cardiovascular diseases generally include high blood pressure, heart attacks, heart failure, and stroke and TIA. By way of example, the chromosomal sequence may comprise, but is not limited to, IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), CTSK (cathepsin K), PTGIR (prostaglandin 12 (prostacyclin) receptor (IP)), KCNJ11 (potassium inwardly-rectifying channel, subfamily J, member 11), INS (insulin), CRP (C-reactive protein, pentraxin-related), PDGFRB (platelet-derived growth factor receptor, beta polypeptide), CCNA2 (cyclin A2), PDGFB (platelet-derived growth factor beta polypeptide (simian sarcoma viral (v-sis) oncogene homolog)), KCNJ5 (potassium inwardly-rectifying channel, subfamily J, member 5), KCNN3 (potassium intermediate/small conductance calcium-activated channel, subfamily N, member 3), CAPN10 (calpain 10), PTGES (prostaglandin E synthase), ADRA2B (adrenergic, alpha-2B-, receptor), ABCG5 (ATP-binding cassette, sub-family G (WHITE), member 5), PRDX2 (peroxiredoxin 2), CAPN5 (calpain 5), PARP14 (poly (ADP-ribose) polymerase family, member 14), MEX3C (mex-3 homolog C (C. elegans)), ACE angiotensin I converting enzyme (peptidyl-dipeptidase A) 1), TNF (tumor necrosis factor (TNF superfamily, member 2)), IL6 (interleukin 6 (interferon, beta 2)), STN (statin), SERPINE1 (serpin peptidase inhibitor, clade E (nexin, plasminogen activator inhibitor type 1), member 1), ALB (albumin), ADIPOQ (adiponectin, C1Q and collagen domain containing), APOB (apolipoprotein B (including Ag(x) antigen)), APOE (apolipoprotein E), LEP (leptin), MTHFR (5,10-methylenetetrahydrofolate reductase (NADPH)), APOA1 (apolipoprotein A-I), EDN1 (endothelin 1), NPPB (natriuretic peptide precursor B), NOS3 (nitric oxide synthase 3 (endothelial cell)), PPARG (peroxisome proliferator-activated receptor gamma), PLAT (plasminogen activator, tissue), PTGS2 (prostaglandin-endoperoxide synthase 2 (prostaglandin G/H synthase and cyclooxygenase)), CETP (cholesteryl ester transfer protein, plasma), AGTR1 (angiotensin II receptor, type 1), HMGCR (3-hydroxy-3-methylglutaryl-Coenzyme A reductase), IGF1 (insulin-like growth factor 1 (somatomedin C)), SELE (selectin E), REN (renin), PPARA (peroxisome proliferator-activated receptor alpha), PON1 (paraoxonase 1), KNG1 (kininogen 1), CCL2 (chemokine (C—C motif) ligand 2), LPL (lipoprotein lipase), VWF (von Willebrand factor), F2 (coagulation factor II (thrombin)), ICAM1 (intercellular adhesion molecule 1), TGFB1 (transforming growth factor, beta 1), NPPA (natriuretic peptide precursor A), IL10 (interleukin 10), EPO (erythropoietin), SOD1 (superoxide dismutase 1, soluble), VCAM1 (vascular cell adhesion molecule 1), IFNG (interferon, gamma), LPA (lipoprotein, Lp(a)), MPO (myeloperoxidase), ESR1 (estrogen receptor 1), MAPK1 (mitogen-activated protein kinase 1), HP (haptoglobin), F3 (coagulation factor III (thromboplastin, tissue factor)), CST3 (cystatin C), COG2 (component of oligomeric golgi complex 2), MMP9 (matrix metallopeptidase 9 (gelatinase B, 92 kDa gelatinase, 92 kDa type IV collagenase)), SERPINC1 (serpin peptidase inhibitor, clade C (antithrombin), member 1), F8 (coagulation factor VIII, procoagulant component), HMOX1 (heme oxygenase (decycling) 1), APOC3 (apolipoprotein C-III), IL8 (interleukin 8), PROK1 (prokineticin 1), CBS (cystathionine-beta-synthase), NOS2 (nitric oxide synthase 2, inducible), TLR4 (toll-like receptor 4), SELP (selectin P (granule membrane protein 140 kDa, antigen CD62)), ABCA1 (ATP-binding cassette, sub-family A (ABC1), member 1), AGT (angiotensinogen (serpin peptidase inhibitor, clade A, member 8)), LDLR (low density lipoprotein receptor), GPT (glutamic-pyruvate transaminase (alanine aminotransferase)), VEGFA (vascular endothelial growth factor A), NR3C2 (nuclear receptor subfamily 3, group C, member 2), IL18 (interleukin 18 (interferon-gamma-inducing factor)), NOS1 (nitric oxide synthase 1 (neuronal)), NR3C1 (nuclear receptor subfamily 3, group C, member 1 (glucocorticoid receptor)), FGB (fibrinogen beta chain), HGF (hepatocyte growth factor (hemopoietin A; scatter factor)), IL1A (interleukin 1, alpha), RETN (resistin), AKT1 (v-akt murine thymoma viral oncogene homolog 1), LIPC (lipase, hepatic), HSPD1 (heat shock 60 kDa protein 1 (chaperonin)), MAPK14 (mitogen-activated protein kinase 14), SPP1 (secreted phosphoprotein 1), ITGB3 (integrin, beta 3 (platelet glycoprotein 111a, antigen CD61)), CAT (catalase), UTS2 (urotensin 2), THBD (thrombomodulin), F10 (coagulation factor X), CP (ceruloplasmin (ferroxidase)), TNFRSF11B (tumor necrosis factor receptor superfamily, member 11b), EDNRA (endothelin receptor type A), EGFR (epidermal growth factor receptor (erythroblastic leukemia viral (v-erb-b) oncogene homolog, avian)), MMP2 (matrix metallopeptidase 2 (gelatinase A, 72 kDa gelatinase, 72 kDa type IV collagenase)), PLG (plasminogen), NPY (neuropeptide Y), RHOD (ras homolog gene family, member D), MAPK8 (mitogen-activated protein kinase 8), MYC (v-myc myelocytomatosis viral oncogene homolog (avian)), FN1 (fibronectin 1), CMA1 (chymase 1, mast cell), PLAU (plasminogen activator, urokinase), GNB3 (guanine nucleotide binding protein (G protein), beta polypeptide 3), ADRB2 (adrenergic, beta-2-, receptor, surface), APOA5 (apolipoprotein A-V), SOD2 (superoxide dismutase 2, mitochondrial), F5 (coagulation factor V (proaccelerin, labile factor)), VDR (vitamin D (1,25-dihydroxyvitamin D3) receptor), ALOX5 (arachidonate 5-lipoxygenase), HLA-DRB1 (major histocompatibility complex, class II, DR beta 1), PARP1 (poly (ADP-ribose) polymerase 1), CD40LG (CD40 ligand), PON2 (paraoxonase 2), AGER (advanced glycosylation end product-specific receptor), IRS1 (insulin receptor substrate 1), PTGS1 (prostaglandin-endoperoxide synthase 1 (prostaglandin G/H synthase and cyclooxygenase)), ECE1 (endothelin converting enzyme 1), F7 (coagulation factor VII (serum prothrombin conversion accelerator)), URN (interleukin 1 receptor antagonist), EPHX2 (epoxide hydrolase 2, cytoplasmic), IGFBP1 (insulin-like growth factor binding protein 1), MAPK10 (mitogen-activated protein kinase 10), FAS (Fas (TNF receptor superfamily, member 6)), ABCB1 (ATP-binding cassette, sub-family B (MDR/TAP), member 1), JUN (jun oncogene), IGFBP3 (insulin-like growth factor binding protein 3), CD14 (CD14 molecule), PDE5A (phosphodiesterase 5A, cGMP-specific), AGTR2 (angiotensin II receptor, type 2), CD40 (CD40 molecule, TNF receptor superfamily member 5), LCAT (lecithin-cholesterol acyltransferase), CCR5 (chemokine (C—C motif) receptor 5), MMP1 (matrix metallopeptidase 1 (interstitial collagenase)), TIMP1 (TIMP metallopeptidase inhibitor 1), ADM (adrenomedullin), DYT10 (dystonia 10), STAT3 (signal transducer and activator of transcription 3 (acute-phase response factor)), MMP3 (matrix metallopeptidase 3 (stromelysin 1, progelatinase)), ELN (elastin), USF1 (upstream transcription factor 1), CFH (complement factor H), HSPA4 (heat shock 70 kDa protein 4), MMP12 (matrix metallopeptidase 12 (macrophage elastase)), MME (membrane metallo-endopeptidase), F2R (coagulation factor II (thrombin) receptor), SELL (selectin L), CTSB (cathepsin B), ANXA5 (annexin A5), ADRB1 (adrenergic, beta-1-, receptor), CYBA (cytochrome b-245, alpha polypeptide), FGA (fibrinogen alpha chain), GGT1 (gamma-glutamyltransferase 1), LIPG (lipase, endothelial), HIF1A (hypoxia inducible factor 1, alpha subunit (basic helix-loop-helix transcription factor)), CXCR4 (chemokine (C—X—C motif) receptor 4), PROC (protein C (inactivator of coagulation factors Va and VIIIa)), SCARB1 (scavenger receptor class B, member 1), CD79A (CD79a molecule, immunoglobulin-associated alpha), PLTP (phospholipid transfer protein), ADD1 (adducin 1 (alpha)), FGG (fibrinogen gamma chain), SAA1 (serum amyloid A1), KCNH2 (potassium voltage-gated channel, subfamily H (eag-related), member 2), DPP4 (dipeptidyl-peptidase 4), G6PD (glucose-6-phosphate dehydrogenase), NPR1 (natriuretic peptide receptor A/guanylate cyclase A (atrial natriuretic peptide receptor A)), VTN (vitronectin), KIAA0101 (KIAA0101), FOS (FBJ murine osteosarcoma viral oncogene homolog), TLR2 (toll-like receptor 2), PPIG (peptidylprolyl isomerase G (cyclophilin G)), IL1R1 (interleukin 1 receptor, type I), AR (androgen receptor), CYP1A1 (cytochrome P450, family 1, subfamily A, polypeptide 1), SERPINA1 (serpin peptidase inhibitor, clade A (alpha-1 antiproteinase, antitrypsin), member 1), MTR (5-methyltetrahydrofolate-homocysteine methyltransferase), RBP4 (retinol binding protein 4, plasma), APOA4 (apolipoprotein A-IV), CDKN2A (cyclin-dependent kinase inhibitor 2A (melanoma, p16, inhibits CDK4)), FGF2 (fibroblast growth factor 2 (basic)), EDNRB (endothelin receptor type B), ITGA2 (integrin, alpha 2 (CD49B, alpha 2 subunit of VLA-2 receptor)), CABIN1 (calcineurin binding protein 1), SHBG (sex hormone-binding globulin), HMGB1 (high-mobility group box 1), HSP90B2P (heat shock protein 90 kDa beta (Grp94), member 2 (pseudogene)), CYP3A4 (cytochrome P450, family 3, subfamily A, polypeptide 4), GJA1 (gap junction protein, alpha 1, 43 kDa), CAV1 (caveolin 1, caveolae protein, 22 kDa), ESR2 (estrogen receptor 2 (ER beta)), LTA (lymphotoxin alpha (TNF superfamily, member 1)), GDF15 (growth differentiation factor 15), BDNF (brain-derived neurotrophic factor), CYP2D6 (cytochrome P450, family 2, subfamily D, polypeptide 6), NGF (nerve growth factor (beta polypeptide)), SP1 (Sp1 transcription factor), TGIF1 (TGFB-induced factor homeobox 1), SRC (v-src sarcoma (Schmidt-Ruppin A-2) viral oncogene homolog (avian)), EGF (epidermal growth factor (beta-urogastrone)), PIK3CG (phosphoinositide-3-kinase, catalytic, gamma polypeptide), HLA-A (major histocompatibility complex, class I, A), KCNQ1 (potassium voltage-gated channel, KQT-like subfamily, member 1), CNR1 (cannabinoid receptor 1 (brain)), FBN1 (fibrillin 1), CHKA (choline kinase alpha), BEST1 (bestrophin 1), APP (amyloid beta (A4) precursor protein), CTNNB1 (catenin (cadherin-associated protein), beta 1, 88 kDa), IL2 (interleukin 2), CD36 (CD36 molecule (thrombospondin receptor)), PRKAB1 (protein kinase, AMP-activated, beta 1 non-catalytic subunit), TPO (thyroid peroxidase), ALDH7A1 (aldehyde dehydrogenase 7 family, member A1), CX3CR1 (chemokine (C-X3-C motif) receptor 1), TH (tyrosine hydroxylase), F9 (coagulation factor IX), GH1 (growth hormone 1), TF (transferrin), HFE (hemochromatosis), IL17A (interleukin 17A), PTEN (phosphatase and tensin homolog), GSTM1 (glutathione S-transferase mu 1), DMD (dystrophin), GATA4 (GATA binding protein 4), F13A1 (coagulation factor XIII, A1 polypeptide), TTR (transthyretin), FABP4 (fatty acid binding protein 4, adipocyte), PON3 (paraoxonase 3), APOC1 (apolipoprotein C-I), INSR (insulin receptor), TNFRSF1B (tumor necrosis factor receptor superfamily, member 1B), HTR2A (5-hydroxytryptamine (serotonin) receptor 2A), CSF3 (colony stimulating factor 3 (granulocyte)), CYP2C9 (cytochrome P450, family 2, subfamily C, polypeptide 9), TXN (thioredoxin), CYP11B2 (cytochrome P450, family 11, subfamily B, polypeptide 2), PTH (parathyroid hormone), CSF2 (colony stimulating factor 2 (granulocyte-macrophage)), KDR (kinase insert domain receptor (a type III receptor tyrosine kinase)), PLA2G2A (phospholipase A2, group IIA (platelets, synovial fluid)), B2M (beta-2-microglobulin), THBS1 (thrombospondin 1), GCG (glucagon), RHOA (ras homolog gene family, member A), ALDH2 (aldehyde dehydrogenase 2 family (mitochondrial)), TCF7L2 (transcription factor 7-like 2 (T-cell specific, HMG-box)), BDKRB2 (bradykinin receptor B2), NFE2L2 (nuclear factor (erythroid-derived 2)-like 2), NOTCH1 (Notch homolog 1, translocation-associated (*Drosophila*)), UGT1A1 (UDP glucuronosyltransferase 1 family, polypeptide A1), IFNA1 (interferon, alpha 1), PPARD (peroxisome proliferator-activated receptor delta), SIRT1 (sirtuin (silent mating type information regulation 2 homolog) 1 (*S. cerevisiae*)), GNRH1 (gonadotropin-releasing hormone 1 (luteinizing-releasing hormone)), PAPPA (pregnancy-associated plasma protein A, pappalysin 1), ARR3 (arrestin 3, retinal (X-arrestin)), NPPC (natriuretic peptide precursor C), AHSP (alpha hemoglobin stabilizing protein), PTK2 (PTK2 protein tyrosine kinase 2), IL13 (interleukin 13), MTOR (mechanistic target of rapamycin (serine/threonine kinase)), ITGB2 (integrin, beta 2 (complement component 3 receptor 3 and 4 subunit)), GSTT1 (glutathione S-transferase theta 1), IL6ST (interleukin 6 signal transducer (gp130, oncostatin M receptor)), CPB2 (carboxypeptidase B2 (plasma)), CYP1A2 (cytochrome P450, family 1, subfamily A, polypeptide 2), HNF4A (hepatocyte nuclear factor 4, alpha), SLC6A4 (solute carrier family 6 (neurotransmitter transporter, serotonin), member 4), PLA2G6 (phospholipase A2, group VI (cytosolic, calcium-independent)), TNFSF11 (tumor necrosis factor (ligand) superfamily, member 11), SLC8A1 (solute carrier family 8 (sodium/calcium exchanger), member 1), F2RL1 (coagulation factor II (thrombin) receptor-like 1), AKR1A1 (aldo-keto reductase family 1, member A1 (aldehyde reductase)), ALDH9A1 (aldehyde dehydrogenase 9 family, member A1), BGLAP (bone gamma-carboxyglutamate (gla)

protein), MTTP (microsomal triglyceride transfer protein), MTRR (5-methyltetrahydrofolate-homocysteine methyltransferase reductase), SULT1A3 (sulfotransferase family, cytosolic, 1A, phenol-preferring, member 3), RAGE (renal tumor antigen), C4B (complement component 4B (Chido blood group), P2RY12 (purinergic receptor P2Y, G-protein coupled, 12), RNLS (renalase, FAD-dependent amine oxidase), CREB1 (cAMP responsive element binding protein 1), POMC (proopiomelanocortin), RAC1 (ras-related C3 botulinum toxin substrate 1 (rho family, small GTP binding protein Rac1)), LMNA (lamin NC), CD59 (CD59 molecule, complement regulatory protein), SCN5A (sodium channel, voltage-gated, type V, alpha subunit), CYP1B1 (cytochrome P450, family 1, subfamily B, polypeptide 1), MIF (macrophage migration inhibitory factor (glycosylation-inhibiting factor)), MMP13 (matrix metallopeptidase 13 (collagenase 3)), TTMP2 (TTMP metallopeptidase inhibitor 2), CYP19A1 (cytochrome P450, family 19, subfamily A, polypeptide 1), CYP21A2 (cytochrome P450, family 21, subfamily A, polypeptide 2), PTPN22 (protein tyrosine phosphatase, non-receptor type 22 (lymphoid)), MYH14 (myosin, heavy chain 14, non-muscle), MBL2 (mannose-binding lectin (protein C) 2, soluble (opsonic defect)), SELPLG (selectin P ligand), AOC3 (amine oxidase, copper containing 3 (vascular adhesion protein 1)), CTSL1 (cathepsin L1), PCNA (proliferating cell nuclear antigen), IGF2 (insulin-like growth factor 2 (somatomedin A)), ITGB1 (integrin, beta 1 (fibronectin receptor, beta polypeptide, antigen CD29 includes MDF2, MSK12)), CAST (calpastatin), CXCL 12 (chemokine (C—X—C motif) ligand 12 (stromal cell-derived factor 1)), IGHE (immunoglobulin heavy constant epsilon), KCNE1 (potassium voltage-gated channel, Isk-related family, member 1), TFRC (transferrin receptor (p90, CD71)), COL1A1 (collagen, type I, alpha 1), COL1A2 (collagen, type I, alpha 2), IL2RB (interleukin 2 receptor, beta), PLA2G10 (phospholipase A2, group X), ANGPT2 (angiopoietin 2), PROCR (protein C receptor, endothelial (EPCR)), NOX4 (NADPH oxidase 4), HAMP (hepcidin antimicrobial peptide), PTPN11 (protein tyrosine phosphatase, non-receptor type 11), SLC2A1 (solute carrier family 2 (facilitated glucose transporter), member 1), IL2RA (interleukin 2 receptor, alpha), CCL5 (chemokine (C—C motif) ligand 5), IRF1 (interferon regulatory factor 1), CFLAR (CASP8 and FADD-like apoptosis regulator), CALCA (calcitonin-related polypeptide alpha), EIF4E (eukaryotic translation initiation factor 4E), GSTP1 (glutathione S-transferase pi 1), JAK2 (Janus kinase 2), CYP3A5 (cytochrome P450, family 3, subfamily A, polypeptide 5), HSPG2 (heparan sulfate proteoglycan 2), CCL3 (chemokine (C—C motif) ligand 3), MYD88 (myeloid differentiation primary response gene (88)), VIP (vasoactive intestinal peptide), SOAT1 (sterol O-acyltransferase 1), ADRBK1 (adrenergic, beta, receptor kinase 1), NR4A2 (nuclear receptor subfamily 4, group A, member 2), MMP8 (matrix metallopeptidase 8 (neutrophil collagenase)), NPR2 (natriuretic peptide receptor B/guanylate cyclase B (atrial natriuretic peptide receptor B)), GCH1 (GTP cyclohydrolase 1), EPRS (glutamyl-prolyl-tRNA synthetase), PPARGC1A (peroxisome proliferator-activated receptor gamma, coactivator 1 alpha), F12 (coagulation factor XII (Hageman factor)), PECAM1 (platelet/endothelial cell adhesion molecule), CCL4 (chemokine (C—C motif) ligand 4), SERPINA3 (serpin peptidase inhibitor, clade A (alpha-1 antiproteinase, antitrypsin), member 3), CASR (calcium-sensing receptor), GJA5 (gap junction protein, alpha 5, 40 kDa), FABP2 (fatty acid binding protein 2, intestinal), TTF2 (transcription termination factor, RNA polymerase II), PROS1 (protein S (alpha)), CTF1 (cardiotrophin 1), SGCB (sarcoglycan, beta (43 kDa dystrophin-associated glycoprotein)), YME1L1 (YME1-like 1 (S. cerevisiae)), CAMP (cathelicidin antimicrobial peptide), ZC3H12A (zinc finger CCCH-type containing 12A), AKR1B1 (aldo-keto reductase family 1, member B1 (aldose reductase)), DES (desmin), MMP7 (matrix metallopeptidase 7 (matrilysin, uterine)), AHR (aryl hydrocarbon receptor), CSF1 (colony stimulating factor 1 (macrophage)), HDAC9 (histone deacetylase 9), CTGF (connective tissue growth factor), KCNMA1 (potassium large conductance calcium-activated channel, subfamily M, alpha member 1), UGT1A (UDP glucuronosyltransferase 1 family, polypeptide A complex locus), PRKCA (protein kinase C, alpha), COMT (catechol-.beta.-methyltransferase), S100B (S100 calcium binding protein B), EGR1 (early growth response 1), PRL (prolactin), IL15 (interleukin 15), DRD4 (dopamine receptor D4), CAMK2G (calcium/calmodulin-dependent protein kinase II gamma), SLC22A2 (solute carrier family 22 (organic cation transporter), member 2), CCL11 (chemokine (C—C motif) ligand 11), PGF (B321 placental growth factor), THPO (thrombopoietin), GP6 (glycoprotein VI (platelet)), TACR1 (tachykinin receptor 1), NTS (neurotensin), HNF1A (HNF1 homeobox A), SST (somatostatin), KCND1 (potassium voltage-gated channel, Shal-related subfamily, member 1), LOC646627 (phospholipase inhibitor), TBXAS1 (thromboxane A synthase 1 (platelet)), CYP2J2 (cytochrome P450, family 2, subfamily J, polypeptide 2), TBXA2R (thromboxane A2 receptor), ADH1C (alcohol dehydrogenase 1C (class I), gamma polypeptide), ALOX12 (arachidonate 12-lipoxygenase), AHSG (alpha-2-HS-glycoprotein), BHMT (betaine-homocysteine methyltransferase), GJA4 (gap junction protein, alpha 4, 37 kDa), SLC25A4 (solute carrier family 25 (mitochondrial carrier; adenine nucleotide translocator), member 4), ACLY (ATP citrate lyase), ALOX5AP (arachidonate 5-lipoxygenase-activating protein), NUMA1 (nuclear mitotic apparatus protein 1), CYP27B1 (cytochrome P450, family 27, subfamily B, polypeptide 1), CYSLTR2 (cysteinyl leukotriene receptor 2), SOD3 (superoxide dismutase 3, extracellular), LTC4S (leukotriene C4 synthase), UCN (urocortin), GHRL (ghrelin/obestatin prepropeptide), APOC2 (apolipoprotein C-II), CLEC4A (C-type lectin domain family 4, member A), KBTBD10 (kelch repeat and BTB (POZ) domain containing 10), TNC (tenascin C), TYMS (thymidylate synthetase), SHC1 (SHC (Src homology 2 domain containing) transforming protein 1), LRP1 (low density lipoprotein receptor-related protein 1), SOCS3 (suppressor of cytokine signaling 3), ADH1B (alcohol dehydrogenase 1B (class I), beta polypeptide), KLK3 (kallikrein-related peptidase 3), HSD11B1 (hydroxysteroid (11-beta) dehydrogenase 1), VKORC1 (vitamin K epoxide reductase complex, subunit 1), SERPINB2 (serpin peptidase inhibitor, clade B (ovalbumin), member 2), TNS1 (tensin 1), RNF19A (ring finger protein 19A), EPOR (erythropoietin receptor), ITGAM (integrin, alpha M (complement component 3 receptor 3 subunit)), PITX2 (paired-like homeodomain 2), MAPK7 (mitogen-activated protein kinase 7), FCGR3A (Fc fragment of IgG, low affinity 111a, receptor (CD16a)), LEPR (leptin receptor), ENG (endoglin), GPX1 (glutathione peroxidase 1), GOT2 (glutamic-oxaloacetic transaminase 2, mitochondrial (aspartate aminotransferase 2)), HRH1 (histamine receptor H1), NR1I2 (nuclear receptor subfamily 1, group I, member 2), CRH (corticotropin releasing hormone), HTR1A (5-hydroxytryptamine (serotonin) receptor 1A), VDAC1 (voltage-dependent anion channel 1), HPSE (heparanase), SFTPD (surfactant protein D), TAP2 (transporter 2, ATP-binding cassette, sub-family B (MDR/TAP)), RNF123 (ring finger protein 123), PTK2B (PTK2B protein tyrosine kinase 2 beta), NTRK2 (neurotrophic tyrosine kinase, receptor, type 2), IL6R (interleukin 6 receptor), ACHE (acetylcholinesterase (Yt blood group)), GLP1R (glucagon-like peptide 1 receptor), GHR (growth hormone receptor), GSR (glutathione reductase), NQO1 (NAD(P)H dehydrogenase, quinone 1), NR5A1 (nuclear receptor subfamily 5, group A, member 1), GJB2 (gap junction protein, beta 2, 26 kDa), SLC9A1 (solute carrier family 9 (sodium/hydrogen exchanger), member 1), MAOA (monoamine oxidase A), PCSK9 (proprotein convertase subtilisin/kexin type 9), FCGR2A (Fc fragment of IgG, low affinity IIa, receptor (CD32)), SERPINF1 (serpin peptidase inhibitor, clade F (alpha-2 antiplasmin, pigment epithelium derived factor), member 1), EDN3 (endothelin 3), DHFR (dihydrofolate reductase), GAS6 (growth arrest-specific 6), SMPD1 (sphingomyelin phosphodiesterase 1, acid lysosomal), UCP2 (uncoupling protein 2 (mitochondrial, proton carrier)), TFAP2A (transcription factor AP-2 alpha (activating enhancer binding protein 2 alpha)), C4BPA (complement component 4 binding protein, alpha), SERPINF2 (serpin peptidase inhibitor, clade F (alpha-2 antiplasmin, pigment epithelium derived factor), member 2), TYMP (thymidine phosphorylase), ALPP (alkaline phosphatase, placental (Regan isozyme)), CXCR2 (chemokine (C—X—C motif) receptor 2), SLC39A3 (solute carrier family 39 (zinc transporter), member 3), ABCG2 (ATP-binding cassette, sub-family G (WHITE), member 2), ADA (adenosine deaminase), JAK3 (Janus kinase 3), HSPA1A (heat shock 70 kDa protein 1A), FASN (fatty acid synthase), FGF1 (fibroblast growth factor 1 (acidic)), F11 (coagulation factor XI), ATP7A (ATPase, Cu++ transporting, alpha polypeptide), CR1 (complement component (3b/4b) receptor 1 (Knops blood group)), GFAP (glial fibrillary acidic protein), ROCK1 (Rho-associated, coiled-coil containing protein kinase 1), MECP2 (methyl CpG binding protein 2 (Rett syndrome)), MYLK (myosin light chain kinase), BCHE (butyrylcholinesterase), LIPE (lipase, hormone-sensitive), PRDX5 (peroxiredoxin 5), ADORA1 (adenosine A1 receptor), WRN (Werner syndrome, RecQ helicase-like), CXCR3 (chemokine (C—X—C motif) receptor 3), CD81 (CD81 molecule), SMAD7 (SMAD family member 7), LAMC2 (laminin, gamma 2), MAP3K5 (mitogen-activated protein kinase kinase kinase 5), CHGA (chromogranin A (parathyroid secretory protein 1)), IAPP (islet amyloid polypeptide), RHO (rhodopsin), ENPP1 (ectonucleotide pyrophosphatase/phosphodiesterase 1), PTHLH (parathyroid hormone-like hormone), NRG1 (neuregulin 1), VEGFC (vascular endothelial growth factor C), ENPEP (glutamyl aminopeptidase (aminopeptidase A)), CEBPB (CCAAT/enhancer binding protein (C/EBP), beta), NAGLU (N-acetylglucosaminidase, alpha-), F2RL3 (coagulation factor II (thrombin) receptor-like 3), CX3CL1 (chemokine (C—X3-C motif) ligand 1), BDKRB1 (bradykinin receptor B1), ADAMTS13 (ADAM metallopeptidase with thrombospondin type 1 motif, 13), ELANE (elastase, neutrophil expressed), ENPP2 (ectonucleotide pyrophosphatase/phosphodiesterase 2), CISH (cytokine inducible SH2-containing protein), GAST (gastrin), MYOC (myocilin, trabecular meshwork inducible glucocorticoid response), ATP1A2 (ATPase, Na+/K+ transporting, alpha 2 polypeptide), NF1 (neurofibromin 1), GJB1 (gap junction protein, beta 1, 32 kDa), MEF2A (myocyte enhancer factor 2A), VCL (vinculin), BMPR2 (bone morphogenetic protein receptor, type II (serine/threonine kinase)), TUBB (tubulin, beta), CDC42 (cell division cycle 42 (GTP binding protein, 25 kDa)), KRT18 (keratin 18), HSF1 (heat shock transcription factor 1), MYB (v-myb myeloblastosis viral oncogene homolog (avian)), PRKAA2 (protein kinase, AMP-activated, alpha 2 catalytic subunit), ROCK2 (Rho-associated, coiled-coil containing protein kinase 2), TFPI (tissue factor pathway inhibitor (lipoprotein-associated coagulation inhibitor)), PRKG1 (protein kinase, cGMP-dependent, type I), BMP2 (bone morphogenetic protein 2), CTNND1 (catenin (cadherin-associated protein), delta 1), CTH (cystathionase (cystathionine gamma-lyase)), CTSS (cathepsin S), VAV2 (vav 2 guanine nucleotide exchange factor), NPY2R (neuropeptide Y receptor Y2), IGFBP2 (insulin-like growth factor binding protein 2, 36 kDa), CD28 (CD28 molecule), GSTA1 (glutathione S-transferase alpha 1), PPIA (peptidylprolyl isomerase A (cyclophilin A)), APOH (apolipoprotein H (beta-2-glycoprotein I)), S100A8 (S100 calcium binding protein A8), IL11 (interleukin 11), ALOX15 (arachidonate 15-lipoxygenase), FBLN1 (fibulin 1), NR1H3 (nuclear receptor subfamily 1, group H, member 3), SCD (stearoyl-CoA desaturase (delta-9-desaturase)), GIP (gastric inhibitory polypeptide), CHGB (chromogranin B (secretogranin 1)), PRKCB (protein kinase C, beta), SRD5A1 (steroid-5-alpha-reductase, alpha polypeptide 1 (3-oxo-5 alpha-steroid delta 4-dehydrogenase alpha 1)), HSD11B2 (hydroxysteroid (11-beta) dehydrogenase 2), CALCRL (calcitonin receptor-like), GALNT2 (UDP-N-acetyl-alpha-D-galactosamine: polypeptide N-acetylgalactosaminyltransferase 2 (GalNAc-T2)), ANGPTL4 (angiopoietin-like 4), KCNN4 (potassium intermediate/small conductance calcium-activated channel, subfamily N, member 4), PIK3C2A (phosphoinositide-3-kinase, class 2, alpha polypeptide), HBEGF (heparin-binding EGF-like growth factor), CYP7A1 (cytochrome P450, family 7, subfamily A, polypeptide 1), HLA-DRB5 (major histocompatibility complex, class II, DR beta 5), BNIP3 (BCL2/adenovirus E1B 19 kDa interacting protein 3), GCKR (glucokinase (hexokinase 4) regulator), S100A12 (S100 calcium binding protein A12), PADI4 (peptidyl arginine deiminase, type IV), HSPA14 (heat shock 70 kDa protein 14), CXCR1 (chemokine (C—X—C motif) receptor 1), H19 (H19, imprinted maternally expressed transcript (non-protein coding)), KRTAP19-3 (keratin associated protein 19-3), IDDM2 (insulin-dependent diabetes mellitus 2), RAC2 (ras-related C3 botulinum toxin substrate 2 (rho family, small GTP binding protein Rac2)), RYR1 (ryanodine receptor 1 (skeletal)), CLOCK (clock homolog (mouse)), NGFR (nerve growth factor receptor (TNFR superfamily, member 16)), DBH (dopamine beta-hydroxylase (dopamine beta-monooxygenase)), CHRNA4 (cholinergic receptor, nicotinic, alpha 4), CACNA1C (calcium channel, voltage-dependent, L type, alpha 1C subunit), PRKAG2 (protein kinase, AMP-activated, gamma 2 non-catalytic subunit), CHAT (choline acetyltransferase), PTGDS (prostaglandin D2 synthase 21 kDa (brain)), NR1H2 (nuclear receptor subfamily 1, group H, member 2), TEK (TEK tyrosine kinase, endothelial), VEGFB (vascular endothelial growth factor B), MEF2C (myocyte enhancer factor 2C), MAPKAPK2 (mitogen-activated protein kinase-activated protein kinase 2), TNFRSF11A (tumor necrosis factor receptor superfamily, member 11a, NFKB activator), HSPA9 (heat shock 70 kDa protein 9 (mortalin)), CYSLTR1 (cysteinyl leukotriene receptor 1), MAT1A (methionine adenosyltransferase I, alpha), OPRL1 (opiate receptor-like 1), IMPA1 (inositol(myo)-1(or 4)-monophosphatase 1), CLCN2 (chloride channel 2), DLD (dihydrolipoamide dehydrogenase), PSMA6 (proteasome (prosome, macropain) subunit, alpha type, 6), PSMB8 (proteasome (prosome, macropain) subunit, beta type, 8 (large multifunctional peptidase 7)), CHI3L1 (chitinase 3-like 1 (cartilage glycoprotein-39)), ALDH1B1 (aldehyde dehydrogenase 1 family, member B1), PARP2 (poly (ADP-ribose) polymerase 2), STAR (steroidogenic acute regulatory protein), LBP (lipopolysaccharide binding protein), ABCC6 (ATP-binding cassette, sub-family C(CFTR/MRP), member 6), RGS2 (regulator of G-protein signaling 2, 24 kDa), EFNB2 (ephrin-B2), GJB6 (gap junction protein, beta 6, 30 kDa), APOA2 (apolipoprotein A-II), AMPD1 (adenosine monophosphate deaminase 1), DYSF (dysferlin, limb girdle muscular dystrophy 2B (autosomal recessive)), FDFT1 (farnesyl-diphosphate farnesyltransferase 1), EDN2 (endothelin 2), CCR6 (chemokine (C—C motif) receptor 6), GJB3 (gap junction protein, beta 3, 31 kDa), IL1RL1 (interleukin 1 receptor-like 1), ENTPD1 (ectonucleoside triphosphate diphosphohydrolase 1), BBS4 (Bardet-Biedl syndrome 4), CELSR2 (cadherin, EGF LAG seven-pass G-type receptor 2 (flamingo homolog, *Drosophila*)), F11R (F11 receptor), RAPGEF3 (Rap guanine nucleotide exchange factor (GEF) 3), HYAL1 (hyaluronoglucosaminidase 1), ZNF259 (zinc finger protein 259), ATOX1 (ATX1 antioxidant protein 1 homolog (yeast)), ATF6 (activating transcription factor 6), KHK (ketohexokinase (fructokinase)), SAT1 (spermidine/spermine N1-acetyltransferase 1), GGH (gamma-glutamyl hydrolase (conjugase, folylpolygammaglutamyl hydrolase)), TIMP4 (TIMP metallopeptidase inhibitor 4), SLC4A4 (solute carrier family 4, sodium bicarbonate cotransporter, member 4), PDE2A (phosphodiesterase 2A, cGMP-stimulated), PDE3B (phosphodiesterase 3B, cGMP-inhibited), FADS1 (fatty acid desaturase 1), FADS2 (fatty acid desaturase 2), TMSB4X (thymosin beta 4, X-linked), TXNIP (thioredoxin interacting protein), LIMS1 (LIM and senescent cell antigen-like domains 1), RHOB (ras homolog gene family, member B), LY96 (lymphocyte antigen 96), FOXO1 (forkhead box O1), PNPLA2 (patatin-like phospholipase domain containing 2), TRH (thyrotropin-releasing hormone), GJC1 (gap junction protein, gamma 1, 45 kDa), SLC17A5 (solute carrier family 17 (anion/sugar transporter), member 5), FTO (fat mass and obesity associated), GJD2 (gap junction protein, delta 2, 36 kDa), PSRC1 (proline/serine-rich coiled-coil 1), CASP12 (caspase 12 (gene/pseudogene)), GPBAR1 (G protein-coupled bile acid receptor 1), PXK (PX domain containing serine/threonine kinase), IL33 (interleukin 33), TRIB1 (tribbles homolog 1 (*Drosophila*)), PBX4 (pre-B-cell leukemia homeobox 4), NUPR1 (nuclear protein, transcriptional regulator, 1), 15-September (15 kDa selenoprotein), CILP2 (cartilage intermediate layer protein 2), TERC (telomerase RNA component), GGT2 (gamma-glutamyltransferase 2), MT-CO1 (mitochondrially encoded cytochrome c oxidase I), and UOX (urate oxidase, pseudogene). In an additional embodiment, the chromosomal sequence may further be selected from Pon1 (paraoxonase 1), LDLR (LDL receptor), ApoE (Apolipoprotein E), Apo B-100 (Apolipoprotein B-100), ApoA (Apolipoprotein(a)), ApoA1 (Apolipoprotein A1), CBS (Cystathionine B-synthase), Glycoprotein IIb/IIb, MTHRF (5,10-methylenetetrahydrofolate reductase (NADPH), and combinations thereof. In one iteration, the chromosomal sequences and proteins encoded by chromosomal sequences involved in cardiovascular disease may be chosen from Cacna1C, Sod1, Pten, Ppar(alpha), Apo E, Leptin, and combinations thereof.

Method of Using the Targeting Systems to Modify a Cell or Organism

The invention in some embodiments comprehends a method of modifying a cell or organism. The cell may be a prokaryotic cell or a eukaryotic cell. The cell may be a mammalian cell. The mammalian cell many be a non-human primate, bovine, porcine, rodent or mouse cell. The cell may be a non-mammalian eukaryotic cell such as poultry, fish or shrimp. The cell may also be a plant cell. The plant cell may be of a crop plant such as cassava, corn, sorghum, wheat, or rice. The plant cell may also be of an algae, tree or vegetable. The modification introduced to the cell by the present invention may be such that the cell and progeny of the cell are altered for improved production of biologic products such as an antibody, starch, alcohol or other desired cellular output. The modification introduced to the cell by the present invention may be such that the cell and progeny of the cell include an alteration that changes the biologic product produced.

The system may comprise one or more different vectors. In an aspect of the invention, the effector protein is codon optimized for expression the desired cell type, preferentially a eukaryotic cell, preferably a mammalian cell or a human cell.

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO—IR, CHO-K1, CHO-K2, CHO-T, CHO Dhfr-/-, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepalclc7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of targeting system or nucleic acid molecules encoding thereof as described herein (such as by transient transfection of one or more vectors, or transfection with RNA), and modified through the activity of a targeting complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. In certain embodiments, the organism or subject is a plant. In certain embodiments, the organism or subject or plant is algae. Methods for producing transgenic plants and animals are known in the art, and generally begin with a method of cell transfection, such as described herein.

In one aspect, the invention provides for methods of modifying a target polynucleotide in a eukaryotic cell. In some embodiments, the method comprises allowing a target recognition region of an engineered protein or polypeptide to bind to the target polynucleotide to effect cleavage of said target polynucleotide thereby modifying the target polynucleotide, wherein the nucleic acid-targeting complex comprises a nucleic acid-targeting effector protein complexed with a guide RNA hybridized to a target sequence within said target polynucleotide.

In one aspect, the invention provides a method of modifying expression of a polynucleotide, protein, or polypeptide in a eukaryotic cell. In some embodiments, the method comprises allowing a targeting system comprising a target recognition region of an engineered protein or polypeptide to bind to the target such that said binding results in increased or decreased expression of said target; wherein the targeting system optionally comprises a functional domain associated with said engineered protein or polypeptide.

Safety

The extended presence of an engineered protein or polypeptide after having performed its function at the target site is a potential safety concern, both for off-target effects and direct toxicity of the effector protein. Where the effector protein is to be expressed from a plasmid, strategies to actively reduce the half-life of the protein may be of interest.

In certain embodiments, the engineered protein according to the invention as described herein is associated with or fused to a destabilization domain (DD). In some embodiments, the DD is ER50. A corresponding stabilizing ligand for this DD is, in some embodiments, 4HT. As such, in some embodiments, one of the at least one DDs is ER50 and a stabilizing ligand therefor is 4HT or CMP8. In some embodiments, the DD is DHFR50. A corresponding stabilizing ligand for this DD is, in some embodiments, TMP. As such, in some embodiments, one of the at least one DDs is DHFR50 and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT.

In some embodiments, one or two DDs may be fused to the N-terminal end of the engineered protein with one or two DDs fused to the C-terminal of the engineered protein of the present invention. In some embodiments, the at least two DDs are associated with the engineered protein and the DDs are the same DD, i.e. the DDs are homologous. Thus, both (or two or more) of the DDs could be ER50 DDs. Alternatively, both (or two or more) of the DDs could be DHFR50 DDs. In some embodiments, at least two DDs are associated with the engineered protein and the DDs are different DDs, i.e. the DDs are heterologous. Thus, one of the DDS could be ER50 while one or more of the DDs or any other DDs could be DHFR50. Having two or more DDs which are heterologous may be advantageous as it would provide a greater level of degradation control. A tandem fusion of more than one DD at the N or C-term may enhance degradation. It is envisaged that high levels of degradation would occur in the absence of either stabilizing ligand, intermediate levels of degradation would occur in the absence of one stabilizing ligand and the presence of the other (or another) stabilizing ligand, while low levels of degradation would occur in the presence of both (or two of more) of the stabilizing ligands. Control may also be imparted by having an N-terminal ER50 DD and a C-terminal DHFR50 DD.

In some embodiments, the fusion of the engineered protein with the DD comprises a linker between the DD and engineered protein. In some embodiments, the linker is a GlySer linker. In some embodiments, the fusion of the engineered protein with the DD further comprises at least one Nuclear Export Signal (NES). In some embodiments, the fusion of the engineered protein with the DD comprises two or more NESs. In some embodiments, the fusion of the engineered protein with the DD comprises at least one Nuclear Localization Signal (NLS). This may be in addition to an NES. HA or Flag tags are also within the ambit of the invention as linkers. Applicants use NLS and/or NES as linker and also use Glycine Serine linkers as short as GS up to (GGGGS)3 (SEQ ID NO:123).

Destabilizing domains have general utility to confer instability to a wide range of proteins; see, e.g., Miyazaki, J Am Chem Soc. Mar. 7, 2012; 134(9): 3942-3945, incorporated herein by reference. CMP8 or 4-hydroxytamoxifen can be destabilizing domains. More generally, a temperature-sensitive mutant of mammalian DHFR (DHFRts), a destabilizing residue by the N-end rule, was found to be stable at a permissive temperature but unstable at 37° C. The addition of methotrexate, a high-affinity ligand for mammalian DHFR, to cells expressing DHFRts inhibited degradation of the protein partially. This was an important demonstration that a small molecule ligand can stabilize a protein otherwise targeted for degradation in cells. A rapamycin derivative was used to stabilize an unstable mutant of the FRB domain of mTOR (FRB*) and restore the function of the fused kinase, GSK-3β.6,7 This system demonstrated that ligand-dependent stability represented an attractive strategy to regulate the function of a specific protein in a complex biological environment. A system to control protein activity can involve the DD becoming functional when the ubiquitin complementation occurs by rapamycin induced dimerization of FK506-binding protein and FKBP12. Mutants of human FKBP12 or ecDHFR protein can be engineered to be metabolically unstable in the absence of their high-affinity ligands, Shield-1 or trimethoprim (TMP), respectively. These mutants are some of the possible destabilizing domains (DDs) useful in the practice of the invention and instability of a DD as a fusion with the engineered protein confers to protein degradation of the entire fusion protein by the proteasome. Shield-1 and TMP bind to and stabilize the DD in a dose-dependent manner. The estrogen receptor ligand binding domain (ERLBD, residues 305-549 of ERS1) can also be engineered as a destabilizing domain. Since the estrogen receptor signaling pathway is involved in a variety of diseases such as breast cancer, the pathway has been widely studied and numerous agonist and antagonists of estrogen receptor have been developed. Thus, compatible pairs of ERLBD and drugs are known. There are ligands that bind to mutant but not wild-type forms of the ERLBD. By using one of these mutant domains encoding three mutations (L384M, M421G, G521R)12, it is possible to regulate the stability of an ERLBD-derived DD using a ligand that does not perturb endogenous estrogen-sensitive networks. An additional mutation (Y537S) can be introduced to further destabilize the ERLBD and to configure it as a potential DD candidate. This tetra-mutant is an advantageous DD development. The mutant ERLBD can be fused to the engineered protein of this invention and its stability can be regulated or perturbed using a ligand. Another DD can be a 12-kDa (107-amino-acid) tag based on a mutated FKBP protein, stabilized by Shield1 ligand; see, e.g., Nature Methods 5, (2008). For instance, a DD can be a modified FK506 binding protein 12 (FKBP12) that binds to and is reversibly stabilized by a synthetic, biologically inert small molecule, Shield-1; see, e.g., Banaszynski L A, Chen L C, Maynard-Smith L A, Ooi A G, Wandless T J. A rapid, reversible, and tunable method to regulate protein function in living cells using synthetic small molecules. Cell. 2006; 126:995-1004; Banaszynski L A, Sellmyer M A, Contag C H, Wandless T J, Thorne S H. Chemical control of protein stability and function in living mice. Nat Med. 2008; 14:1123-1127; Maynard-Smith L A, Chen L C, Banaszynski L A, Ooi A G, Wandless T J. A directed approach for engineering conditional protein stability using biologically silent small molecules. The Journal of biological chemistry. 2007; 282: 24866-24872; and Rodriguez, Chem Biol. Mar. 23, 2012; 19(3): 391-398—all of which are incorporated herein by reference and may be employed in the practice of the invention in selected a DD to associate with a engineered protein in the practice of this invention.

When administering an agent to a mammal, there is always the risk of an immune response to the agent and/or its delivery vehicle. Circumventing the immune response is a major challenge for most delivery vehicles. Viral vectors, which express immunogenic epitopes within the organism typically induce an immune response. Nanoparticle and lipid-based vectors to some extent address this problem. The engineered targeting proteins or polypeptides, which may comprise motifs including TRS motifs of bacterial origin, also inherently carry the risk of eliciting an immune response. This may be addressed by optimizing or humanizing the engineered targeting protein or polypeptide.

Methods of Using the Targeting System in Plants and Yeast

In general, the term "plant" relates to any various photosynthetic, eukaryotic, unicellular or multicellular organism of the kingdom Plantae characteristically growing by cell division, containing chloroplasts, and having cell walls comprised of cellulose. The term plant encompasses monocotyledonous and dicotyledonous plants. Specifically, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, blueberry, broccoli, Brussel's sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, *eucalyptus*, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, *papaya*, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, yams, yew, and zucchini. The term plant also encompasses Algae, which are mainly photoautotrophs unified primarily by their lack of roots, leaves and other organs that characterize higher plants.

The methods for genome editing using the targeting system as described herein can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the methods and targeting systems can be used over a broad range of plants, such as for example with dicotyledonous plants belonging to the orders Magnoliales, Illiciales, Laurales, Piperales, Aristolochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales; the methods and targeting systems can be used with monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Liliales, and Orchidales, or with plants belonging to Gymnospermae, e.g those belonging to the orders Pinales, Ginkgoales, Cycadales, Araucariales, Cupressales and Gnetales.

The targeting systems and methods of use described herein can be used over a broad range of plant species, included in the non-limitative list of dicot, monocot or gymnosperm genera hereunder: *Atropa, Alseodaphne, Anacardium, Arachis, Beilschmiedia, Brassica, Carthamus, Cocculus, Croton, Cucumis, Citrus, Citrullus, Capsicum, Catharanthus, Cocos, Coffea, Cucurbita, Daucus, Duguetia, Eschscholzia, Ficus, Fragaria, Glaucium, Glycine, Gossypium, Helianthus, Hevea, Hyoscyamus, Lactuca, Landolphia, Linum, Litsea, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca, Vilis,* and *Vigna*; and the genera *Allium, Andropogon, Eragrostis, Asparagus, Avena, Cynodon, Elaeis, Festuca, Festulolium, Heterocallis, Hordeum, Lemna, Lolium, Musa, Oryza, Panicum, Pennisetum, Phleum, Poa, Secale, Sorghum, Triticum, Zea, Abies, Cunninghamia, Ephedra, Picea, Pinus,* and *Pseudotsuga*.

The targeting systems and methods of use can also be used over a broad range of "algae" or "algae cells"; including for example algae selected from several eukaryotic phyla, including the Rhodophyta (red algae), Chlorophyta (green algae), Phaeophyta (brown algae), Bacillariophyta (diatoms), Eustigmatophyta and dinoflagellates as well as the prokaryotic phylum Cyanobacteria (blue-green algae). The term "algae" includes for example algae selected from: *Amphora, Anabaena, Ankistrodesmus, Botryococcus, Chaetoceros, Chlamydomonas, Chlorella, Chlorococcum, Cyclotella, Cylindrotheca, Dunaliella, Emiliana, Euglena, Haematococcus, Isochrysis, Monochrysis, Monoraphidium, Nannochloris, Nannochloropsis, Navicula, Nephrochloris, Nephroselmis, Nitzschia, Nodularia, Nostoc, Oochromonas, Oocystis, Oscillatoria, Pavlova, Phaeodactylum, Platymonas, Pleurochrysis, Porphyra, Pseudoanabaena, Pyramimonas, Stichococcus, Synechococcus, Synechocystis, Tetraselmis, Thalassiosira,* and *Trichodesmium*.

A part of a plant, i.e., a "plant tissue" may be treated according to the methods of the present invention to produce an improved plant. Plant tissue also encompasses plant cells. The term "plant cell" as used herein refers to individual units of a living plant, either in an intact whole plant or in an isolated form grown in in vitro tissue cultures, on media or agar, in suspension in a growth media or buffer or as a part of higher organized unites, such as, for example, plant tissue, a plant organ, or a whole plant.

A "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

The term "transformation" broadly refers to the process by which a plant host is genetically modified by the introduction of DNA by means of Agrobacteria or one of a variety of chemical or physical methods. As used herein, the term "plant host" refers to plants, including any cells, tissues, organs, or progeny of the plants. Many suitable plant tissues or plant cells can be transformed and include, but are not limited to, protoplasts, somatic embryos, pollen, leaves, seedlings, stems, calli, stolons, microtubers, and shoots. A plant tissue also refers to any clone of such a plant, seed, progeny, propagule whether generated sexually or asexually, and descendents of any of these, such as cuttings or seed.

The term "transformed" as used herein, refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is transmitted to the subsequent progeny. In these embodiments, the "transformed" or "transgenic" cell or plant may also include progeny of the cell or plant and progeny produced from a breeding program employing such a transformed plant as a parent in a cross and exhibiting an altered phenotype resulting from the presence of the introduced DNA molecule. Preferably, the transgenic plant is fertile and capable of transmitting the introduced DNA to progeny through sexual reproduction.

The term "progeny", such as the progeny of a transgenic plant, is one that is born of, begotten by, or derived from a plant or the transgenic plant. The introduced DNA molecule may also be transiently introduced into the recipient cell such that the introduced DNA molecule is not inherited by subsequent progeny and thus not considered "transgenic". Accordingly, as used herein, a "non-transgenic" plant or plant cell is a plant which does not contain a foreign DNA stably integrated into its genome.

The term "plant promoter" as used herein is a promoter capable of initiating transcription in plant cells, whether or not its origin is a plant cell. Exemplary suitable plant promoters include, but are not limited to, those that are obtained from plants, plant viruses, and bacteria such as *Agrobacterium* or *Rhizobium* which comprise genes expressed in plant cells.

As used herein, a "fungal cell" refers to any type of eukaryotic cell within the kingdom of fungi. Phyla within the kingdom of fungi include Ascomycota, Basidiomycota, Blastocladiomycota, Chytridiomycota, Glomeromycota, Microsporidia, and Neocallimastigomycota. Fungal cells may include yeasts, molds, and filamentous fungi. In some embodiments, the fungal cell is a yeast cell.

As used herein, the term "yeast cell" refers to any fungal cell within the phyla Ascomycota and Basidiomycota. Yeast cells may include budding yeast cells, fission yeast cells, and mold cells. Without being limited to these organisms, many types of yeast used in laboratory and industrial settings are part of the phylum Ascomycota. In some embodiments, the yeast cell is an *S. cerevisiae, Kluyveromyces marxianus,* or *Issatchenkia orientalis* cell. Other yeast cells may include without limitation *Candida* spp. (e.g., *Candida albicans*), *Yarrowia* spp. (e.g., *Yarrowia lipolytica*), *Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and *Issatchenkia* spp. (e.g., *Issatchenkia orientalis*, a.k.a. *Pichia kudriavzevii* and *Candida acidother-*

*mophilum*). In some embodiments, the fungal cell is a filamentous fungal cell. As used herein, the term "filamentous fungal cell" refers to any type of fungal cell that grows in filaments, i.e., hyphae or mycelia. Examples of filamentous fungal cells may include without limitation *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella isabellina*).

In some embodiments, the fungal cell is an industrial strain. As used herein, "industrial strain" refers to any strain of fungal cell used in or isolated from an industrial process, e.g., production of a product on a commercial or industrial scale. Industrial strain may refer to a fungal species that is typically used in an industrial process, or it may refer to an isolate of a fungal species that may be also used for non-industrial purposes (e.g., laboratory research). Examples of industrial processes may include fermentation (e.g., in production of food or beverage products), distillation, biofuel production, production of a compound, and production of a polypeptide. Examples of industrial strains may include, without limitation, JAY270 and ATCC4124.

In some embodiments, the fungal cell is a polyploid cell. As used herein, a "polyploid" cell may refer to any cell whose genome is present in more than one copy. A polyploid cell may refer to a type of cell that is naturally found in a polyploid state, or it may refer to a cell that has been induced to exist in a polyploid state (e.g., through specific regulation, alteration, inactivation, activation, or modification of meiosis, cytokinesis, or DNA replication). A polyploid cell may refer to a cell whose entire genome is polyploid, or it may refer to a cell that is polyploid in a particular genomic locus of interest. Without wishing to be bound to theory, it is thought that the abundance of guide RNA may more often be a rate-limiting component in genome engineering of polyploid cells than in haploid cells, and thus the methods using the targeting system described herein may take advantage of using a certain fungal cell type.

In some embodiments, the fungal cell is a diploid cell. As used herein, a "diploid" cell may refer to any cell whose genome is present in two copies. A diploid cell may refer to a type of cell that is naturally found in a diploid state, or it may refer to a cell that has been induced to exist in a diploid state (e.g., through specific regulation, alteration, inactivation, activation, or modification of meiosis, cytokinesis, or DNA replication). For example, the *S. cerevisiae* strain S228C may be maintained in a haploid or diploid state. A diploid cell may refer to a cell whose entire genome is diploid, or it may refer to a cell that is diploid in a particular genomic locus of interest. In some embodiments, the fungal cell is a haploid cell. As used herein, a "haploid" cell may refer to any cell whose genome is present in one copy. A haploid cell may refer to a type of cell that is naturally found in a haploid state, or it may refer to a cell that has been induced to exist in a haploid state (e.g., through specific regulation, alteration, inactivation, activation, or modification of meiosis, cytokinesis, or DNA replication). For example, the *S. cerevisiae* strain S228C may be maintained in a haploid or diploid state. A haploid cell may refer to a cell whose entire genome is haploid, or it may refer to a cell that is haploid in a particular genomic locus of interest.

As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in Yeast Protocols, 2nd edition, Xiao, W., ed. (Humana Press, New York, 2007) and Buckholz, R. G. and Gleeson, M. A. (1991) Biotechnology (NY) 9(11): 1067-72. Yeast vectors may contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2μ plasmids, yeast integrative plasmids, yeast replicative plasmids, shuttle vectors, and episomal plasmids.

In one aspect, the present invention provides a method of gene targeting and/or editing in host cells. The engineered protein or polypeptide of the targeting system may be associated with one or more functional domains with regulatory activities, such as nucleotide recognition and/or manipulation activities. Accordingly, the targeting system can be used for rapid investigation and/or selection and/or interrogations and/or comparison and/or manipulations and/or transformation of plant genes or genomes, e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. The targeting system can be used with regard to plants in Site-Directed Integration (SDI) or Gene Editing (GE) or any Near Reverse Breeding (NRB) or Reverse Breeding (RB) techniques. Aspects of utilizing the herein described targeting systems and engineered proteins or polypeptides may be analogous to the use of the CRISPR-Cas (e.g. CRISPR-Cas9) system in plants, and mention is made of the University of Arizona website "CRISPR-PLANT" (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR-Cas system," Plant Methods 2013, 9:39 (doi:10.1186/1746-4811-9-39); Brooks, "Efficient gene editing in tomato in the first generation using the CRISPR-Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi:10.1038/cr.2013.114; published online 20 Aug. 2013; Xie, "RNA-guided genome editing in plants using a CRISPR-Cas system," Mol Plant. 2013 November; 6(6):1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4; Caliando et al, "Targeted DNA degradation using a CRISPR device stably carried in the host genome, NATURE COMMUNICATIONS 6:6989, DOI: 10.1038/ncomms7989; U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent; and the enzymes herein having reduced off-target effects and systems employing such enzymes can be used in plant applications, including those mentioned herein.

The targeting system of the invention may be used in the detection of plant viruses. Gambino et al. (Phytopathology. 2006 November; 96(11):1223-9. doi: 10.1094/PHYTO-96-1223) relied on amplification and multiplex PCR for simultaneous detection of nine grapevine viruses. The targeting systems and proteins of the instant invention may similarly be used to detect multiple targets in a host related to plant virus infection and virus-host interaction mechanism.

Murray et al. (Proc Biol Sci. 2013 Jun. 26; 280(1765): 20130965. doi: 10.1098/rspb.2013.0965; published 2013 Aug. 22) analyzed 12 plant RNA viruses to investigate evolutionary rates and found evidence of episodic selection possibly due to shifts between different host genotypes or species. The targeting systems and proteins of the instant invention may be used to target or immunize against such viruses in a host. For example, the systems of the invention can be used to target and cleave virion proteins, or block viral RNA expression hence replication. Moreover, the systems of the invention can be multiplexed with multiple TRS so as to hit multiple targets or multiple isolate of the same virus.

The targeting system of the invention may be used in detecting and providing resistance against plant pathogens. For example, Proteobacteria in *Xanthomonas* genus infect plants by secretion of transcription effector like proteins through type III secretion pathway to impact expression of plant genes (Wichmann et al., The noncanonical type III secretion system of *Xanthomonas translucens* pv. *graminis* is essential for forage grass infection. Mol Plant Pathol. 2013 August; 14(6):576-88). The targeting system and proteins of the present invention may be used to target and/or cleave or inactivate bacteria proteins delivered to plant host cells by such pathogen, either transiently or transgenic by introduction of the targeting system or nucleic acid molecules encoding thereof to the plant genome.

Organisms such as yeast and microalgae are widely used for synthetic biology. Stovicek et al. (Metab. Eng. Comm., 2015; 2:13 describes genome editing of industrial yeast, for example, *Saccharomyces cerevisiae*, to efficiently produce robust strains for industrial production.

Kurthe t al, J Virol. 2012 June; 86(11):6002-9. doi: 10.1128/JVI.00436-12. Epub 2012 Mar. 21) developed an RNA virus-based vector for the introduction of desired traits into grapevine without heritable modifications to the genome. The vector provided the ability to regulate expression of endogenous genes by virus-induced gene silencing. The targeting systems and proteins of the instant invention can similarly be used to silence genes and proteins without heritable modification to the genome.

In some embodiments, the plant may be a legume plant. Peanut allergies and allergies to legumes generally are a real and serious health concern. The targeting system of the present invention can be used to identify, bind to, inactivate or modify allergenic proteins of such legumes. Without limitation as to such genes and proteins, Nicolaou et al. identifies allergenic proteins in peanuts, soybeans, lentils, peas, lupin, green beans, and mung beans. See, Nicolaou et al., Current Opinion in Allergy and Clinical Immunology 2011; 11(3):222).

In plants, pathogens are often host-specific. For example, *Fusarium oxysporum* f. sp. *lycopersici* causes tomato wilt but attacks only tomato, and *F. oxysporum* f. *dianthii* Puccinia graminis f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, the hypervariability of the targeting system of the present invention may be used to develop and confer broad resistance to plants. The natural sources of resistance genes include native or foreign Varieties, Heirloom Varieties, Wild Plant Relatives, and Induced Mutations, e.g., treating plant material with mutagenic agents. Using the present invention, plant breeders are provided with a new tool to transiently or stably (where the targeting system or nucleic acid molecules encoding thereof is introduced to plant genome) confer pathogen resistance. Accordingly, one skilled in the art can analyze the genome and proteome of sources of resistance genes, and in Varieties having desired characteristics or traits employ the present invention to target, modify, activate or inactivate target molecules, with more precision than previous mutagenic agents and hence accelerate and improve plant breeding programs.

Aside from the plants otherwise discussed herein and above, engineered plants modified by the effector protein and suitable guide, and progeny thereof, as provided. These may include disease or drought resistant crops, such as wheat, barley, rice, soybean or corn; plants modified to remove or reduce the ability to self-pollinate (but which can instead, optionally, hybridize instead); and allergenic foods such as peanuts and nuts where the immunogenic proteins have been disabled, destroyed or disrupted by targeting via a effector protein and suitable guide.

Stable Integration of the Targeting System Components in the Genome of Plants and Plant Cells In particular embodiments, it is envisaged that the polynucleotides encoding the components of the targeting system are introduced for stable integration into the genome of a plant cell. In these embodiments, the design of the transformation vector or the expression system can be adjusted depending on for when, where and under what conditions the engineered protein or polypeptide is expressed.

In particular embodiments, it is envisaged to introduce the components of the targeting system stably into the genomic DNA of a plant cell. Additionally or alternatively, it is envisaged to introduce the components of the targeting system for stable integration into the DNA of a plant organelle such as, but not limited to a plastid, mitochondrion or a chloroplast.

The expression system for stable integration into the genome of a plant cell may contain one or more of the following elements: a promoter element that can be used to express the components of the targeting system in a plant cell; a 5' untranslated region to enhance expression; an intron element to further enhance expression in certain cells, such as monocot cells; a multiple-cloning site to provide convenient restriction sites for inserting the nucleic acid sequences and other desired elements; and a 3' untranslated region to provide for efficient termination of the expressed transcript.

The elements of the expression system may be on one or more expression constructs which are either circular such as a plasmid or transformation vector, or non-circular such as linear double stranded DNA.

DNA construct(s) containing and/or encoding the components of the targeting system, and, where applicable, template sequence may be introduced into the genome of a plant, plant part, or plant cell by a variety of conventional techniques. The process generally comprises the steps of selecting a suitable host cell or host tissue, introducing the construct(s) into the host cell or host tissue, and regenerating plant cells or plants therefrom.

In particular embodiments, the DNA construct may be introduced into the plant cell using techniques such as but not limited to electroporation, microinjection, aerosol beam injection of plant cell protoplasts, or the DNA constructs can be introduced directly to plant tissue using biolistic methods, such as DNA particle bombardment (see also Fu et al., Transgenic Res. 2000 February; 9(1):11-9). The basis of particle bombardment is the acceleration of particles coated with gene/s of interest toward cells, resulting in the penetration of the protoplasm by the particles and typically stable integration into the genome. (see e.g. Klein et al, Nature (1987), Klein et ah, Bio/Technology (1992), Casas et ah, Proc. Natl. Acad. Sci. USA (1993).

In particular embodiments, the DNA constructs containing components of the targeting system may be introduced into the plant by *Agrobacterium*-mediated transformation. The DNA constructs may be combined with suitable T-DNA flanking regions and introduced into a conventional *Agrobacterium tumefaciens* host vector. The foreign DNA can be incorporated into the genome of plants by infecting the plants or by incubating plant protoplasts with *Agrobacterium* bacteria, containing one or more Ti (tumor-inducing) plasmids. (see e.g. Fraley et al., (1985), Rogers et al., (1987) and U.S. Pat. No. 5,563,055).

Plant Promoters

In order to ensure appropriate expression in a plant cell, the components of the targeting system described herein are typically placed under control of a plant promoter, i.e. a promoter operable in plant cells. The use of different types of promoters is envisaged.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. "Regulated promoter" refers to promoters that direct gene expression not constitutively, but in a temporally- and/or spatially-regulated manner, and includes tissue-specific, tissue-preferred and inducible promoters. Different promoters may direct the expression of a gene in different tissues or cell types, or at different stages of development, or in response to different environmental conditions. In particular embodiments, one or more of the targeting system components are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed.

Examples of promoters that are inducible and that allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc), or light inducible systems (Phytochrome, LOV domains, or cryptochrome), such as a Light Inducible Transcriptional Effector (LITE) that direct changes in transcriptional activity in a sequence-specific manner. The components of a light inducible system may include an engineered protein or polypeptide of the targeting system, an enzyme or functional domain associated thereby, a light-responsive cytochrome heterodimer (e.g. from *Arabidopsis thaliana*), and a transcriptional activation/repression domain.

In particular embodiments, transient or inducible expression can be achieved by using, for example, chemical-regulated promotors, i.e. whereby the application of an exogenous chemical induces gene expression. Modulating of gene expression can also be obtained by a chemical-repressible promoter, where application of the chemical represses gene expression. Chemical-inducible promoters include, but are not limited to, the maize ln2-2 promoter, activated by benzene sulfonamide herbicide safeners (De Veylder et al., (1997) Plant Cell Physiol 38:568-77), the maize GST promoter (GST-ll-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

Translocation to and/or Expression in Specific Plant Organelles

The expression system may comprise elements for translocation to and/or expression in a specific plant organelle.

Chloroplast Targeting

In particular embodiments, it is envisaged that the targeting system is used to specifically modify chloroplast genes or to ensure expression in the chloroplast. For this purpose, use is made of chloroplast transformation methods or compartmentalization of the targeting system components to the chloroplast. For instance, the introduction of genetic modifications in the plastid genome can reduce biosafety issues such as gene flow through pollen.

Methods of chloroplast transformation are known in the art and include Particle bombardment, PEG treatment, and microinjection. Additionally, methods involving the translocation of transformation cassettes from the nuclear genome to the plastid can be used as described in WO2010061186.

Alternatively, it is envisaged to localize one or more of the targeting system components to the plant chloroplast. This is achieved by incorporating in the expression construct a sequence encoding a chloroplast transit peptide (CTP) or plastid transit peptide, operably linked to the 5' region of the sequence encoding the engineered targeting protein. The CTP is removed in a processing step during translocation into the chloroplast. Chloroplast targeting of expressed proteins is well known to the skilled artisan (see for instance Protein Transport into Chloroplasts, 2010, Annual Review of Plant Biology, Vol. 61: 157-180).

Introduction of Polynucleotides Encoding the Engineered Protein in Algal Cells

Transgenic algae (or other plants such as rape) may be particularly useful in the production of vegetable oils or biofuels such as alcohols (especially methanol and ethanol) or other products. These may be engineered to express or overexpress high levels of oil or alcohols for use in the oil or biofuel industries.

Introduction of Polynucleotides Encoding Targeting System Components in Yeast Cells In particular embodiments, the invention relates to the use of the targeting system for genome editing of yeast cells. Methods for transforming yeast cells which can be used to introduce polynucleotides encoding the targeting system components are well known to the artisan and are reviewed by Kawai et al., 2010, Bioeng Bugs. 2010 November-December; 1(6): 395-403). Non-limiting examples include transformation of yeast cells by lithium acetate treatment (which may further include carrier DNA and PEG treatment), bombardment or by electroporation.

Transient Expression of the Targeting System Components in Plants and Plant Cell In particular embodiments, it is envisaged that nucleic acid molecules encoding the engineered targeting protein are transiently expressed in the plant cell. As the expression of the engineered protein is transient, plants regenerated from such plant cells typically contain no foreign DNA.

In particular embodiments, the targeting system components can be introduced in the plant cells using a plant viral vector (Scholthof et al. 1996, Annu Rev Phytopathol. 1996; 34:299-323). In further particular embodiments, said viral vector is a vector from a DNA virus. For example, geminivirus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., *Faba* bean necrotic yellow virus). In other particular embodiments, said viral vector is a vector from an RNA virus. For example, tobravirus (e.g., tobacco rattle virus, tobacco mosaic virus), potexvirus (e.g., potato virus X), or hordeivirus (e.g., barley stripe mosaic virus). The replicating genomes of plant viruses are non-integrative vectors.

In particular embodiments, the vector used for transient expression of the engineered protein is for instance a pEAQ vector, which is tailored for *Agrobacterium*-mediated transient expression (Sainsbury F. et al., Plant Biotechnol J. 2009 September; 7(7):682-93) in the protoplast. In particular embodiments, double-stranded DNA fragments encoding the engineered protein can be transiently introduced into the plant cell. In such embodiments, the introduced double-stranded DNA fragments are provided in sufficient quantity to modify the cell but do not persist after a contemplated period of time has passed or after one or more cell divisions. Methods for direct DNA transfer in plants are known by the skilled artisan (see for instance Davey et al. Plant Mol Biol. 1989 September; 13(3):273-85.)

In other embodiments, an RNA polynucleotide encoding the engineered targeting protein is introduced into the plant cell, which is then translated and processed by the host cell generating the protein in sufficient quantity to modify the cell (in the presence of at least one guide RNA) but which does not persist after a contemplated period of time has passed or after one or more cell divisions. Methods for introducing mRNA to plant protoplasts for transient expression are known by the skilled artisan (see for instance in Gallie, Plant Cell Reports (1993), 13; 119-122).

Combinations of the different methods described above are also envisaged.

Delivery of Targeting System Components to the Plant Cell

In particular embodiments, it is of interest to deliver one or more components of the targeting system directly to the plant cell. This is of interest, inter alia, for the generation of non-transgenic plants (see below). In particular embodiments, one or more of the targeting system components is prepared outside the plant or plant cell and delivered to the cell. For instance, in particular embodiments, the engineered targeting protein is prepared in vitro prior to introduction to the plant cell. The engineered targeting protein can be prepared by various methods known by one of skill in the art and include recombinant production. After expression, the engineered targeting protein is isolated, refolded if needed, purified and optionally treated to remove any purification tags, such as a His-tag. Once crude, partially purified, or more completely purified targeting protein is obtained, the protein may be introduced to the plant cell.

The individual components or pre-assembled ribonucleoprotein can be introduced into the plant cell via electroporation, by bombardment with coated particles, by chemical transfection or by some other means of transport across a cell membrane.

In particular embodiments, the targeting system components are introduced into the plant cells using nanoparticles. The components, either as protein or nucleic acid or in a combination thereof, can be uploaded onto or packaged in nanoparticles and applied to the plants (such as for instance described in WO 2008042156 and US 20130185823). In particular, embodiments of the invention comprise nanoparticles uploaded with or packed with DNA molecule(s) encoding the C2cl protein, DNA molecules encoding the guide RNA and/or isolated guide RNA as described in WO2015089419.

Further means of introducing one or more components of the targeting system to the plant cell is by using cell penetrating peptides (CPP). Accordingly, in particular, embodiments the invention comprises compositions comprising a cell penetrating peptide linked to the engineered targeting protein. In particular embodiments of the present invention, the engineered protein is coupled to one or more CPPs to effectively transport them inside plant protoplasts; see also Ramakrishna (20140 Genome Res. 2014 June; 24(6):1020-7 for Cas9 in human cells). In other embodiments, the engineered protein is encoded by one or more circular or non-circular DNA molecule(s) which are coupled to one or more CPPs for plant protoplast delivery. The plant protoplasts are then regenerated to plant cells and further to plants. CPPs are generally described as short peptides of fewer than 35 amino acids either derived from proteins or from chimeric sequences which are capable of transporting biomolecules across cell membrane in a receptor independent manner. CPP can be cationic peptides, peptides having hydrophobic sequences, amphipathic peptides, peptides having proline-rich and anti-microbial sequence, and chimeric or bipartite peptides (Pooga and Langel 2005). CPPs are able to penetrate biological membranes and as such trigger the movement of various biomolecules across cell membranes into the cytoplasm and to improve their intracellular routing, and hence facilitate interaction of the biomolecule with the target. Examples of CPP include amongst others: Tat, a nuclear transcriptional activator protein required for viral replication by HIV type1, penetratin, Kaposi fibroblast growth factor (FGF) signal peptide sequence, integrin p3 signal peptide sequence; polyarginine peptide Args sequence, Guanine rich-molecular transporters, sweet arrow peptide, etc.

Plant Cultures and Regeneration

In particular embodiments, plant cells which have a modified genome and that are produced or obtained by any of the methods described herein, can be cultured to regenerate a whole plant which possesses the transformed or modified genotype and thus the desired phenotype. Conventional regeneration techniques are well known to those skilled in the art. Particular examples of such regeneration techniques rely on manipulation of certain phytohormones in a tissue culture growth medium, and typically relying on a biocide and/or herbicide marker which has been introduced together with the desired nucleotide sequences. In further particular embodiments, plant regeneration is obtained from cultured protoplasts, plant callus, explants, organs, pollens, embryos or parts thereof (see e.g. Evans et al. (1983), Handbook of Plant Cell Culture, Klee et al (1987) Ann. Rev. of Plant Phys.).

In particular embodiments, transformed or improved plants as described herein can be self-pollinated to provide seed for homozygous improved plants of the invention (homozygous for the DNA modification) or crossed with non-transgenic plants or different improved plants to provide seed for heterozygous plants. Where a recombinant DNA was introduced into the plant cell, the resulting plant of such a crossing is a plant which is heterozygous for the recombinant DNA molecule. Both such homozygous and heterozygous plants obtained by crossing from the improved plants and comprising the genetic modification (which can be a recombinant DNA) are referred to herein as "progeny". Progeny plants are plants descended from the original transgenic plant and containing the genome modification or recombinant DNA molecule introduced by the methods provided herein. Alternatively, genetically modified plants can be obtained by one of the methods described supra using nucleic acid molecules encoding the targeting system components whereby no foreign DNA is incorporated into the genome. Progeny of such plants, obtained by further breeding may also contain the genetic modification. Breedings are performed by any breeding methods that are commonly used for different crops (e.g., Allard, Principles of Plant Breeding, John Wiley & Sons, NY, U. of CA, Davis, CA, 50-98 (1960).

Use of the Targeting System to Confer Desired Agronomic Traits.

In particular embodiments, the invention encompasses the use of the targeting system as described herein for detection and/or modification of macromolecule substrates of interest, including protein, polypeptide, DNA or RNA molecules including one or more plant expressible gene(s) or gene products. In further particular embodiments, the invention encompasses methods and tools using the targeting system as described herein modification, cleavage, activation or de-activation of one or more plant gene products such as proteins, or for partial or complete deletion of one or more plant expressed gene(s). In other further particular embodiments, the invention encompasses methods and tools using the targeting system as described herein to ensure modification of one or more plant-expressed genes by mutation, substitution, insertion of one of more nucleotides. In other particular embodiments, the invention encompasses the use of the targeting system as described herein to ensure modification of expression of one or more plant-expressed genes by specific modification of one or more of the regulatory elements directing expression of said genes.

In particular embodiments, the invention encompasses methods which involve the introduction of exogenous genes and/or the targeting of endogenous genes and their regulatory elements, such as listed below.

1. Genes that Confer Resistance to Pests or Diseases:

Plant disease resistance genes. A plant can be transformed with cloned resistance genes to engineer plants that are resistant to specific pathogen strains. See, e.g., Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis* may be RSP2 gene for resistance to *Pseudomonas syringae*). A plant gene that is upregulated or down regulated during pathogen infection can be engineered for pathogen resistance. See, e.g., Thomazella et al., bioRxiv 064824; doi: doi.org/10.1101/064824 Epub. Jul. 23, 2016 (tomato plants with deletions in the SlDMR6-1 which is normally upregulated during pathogen infection).

Genes conferring resistance to a pest, such as soybean cyst nematode. See e.g., PCT Application WO 96/30517; PCT Application WO 93/19181.

*Bacillus thuringiensis* proteins see, e.g., Geiser et al., Gene 48:109 (1986).

Lectins, see, for example, Van Damme et al., Plant Molec. Biol. 24:25 (1994).

Vitamin-binding protein, such as avidin, see PCT application US93/06487, teaching the use of avidin and avidin homologues as larvicides against insect pests.

Enzyme inhibitors such as protease or proteinase inhibitors or amylase inhibitors. See, e.g., Abe et al., J. Biol. Chem. 262:16793 (1987), Huub et al., Plant Molec. Biol. 21:985 (1993)), Sumitani et al., Biosci. Biotech. Biochem. 57:1243 (1993) and U.S. Pat. No. 5,494,813.

Insect-specific hormones or pheromones such as ecdysteroid or juvenile hormone, a variant thereof, a mimetic based thereon, or an antagonist or agonist thereof. See, for example Hammock et al., Nature 344:458 (1990).

Insect-specific peptides or neuropeptides which, upon expression, disrupts the physiology of the affected pest. For example, Regan, J. Biol. Chem. 269:9 (1994) and Pratt et al., Biochem. Biophys. Res. Comm. 163:1243 (1989). See also U.S. Pat. No. 5,266,317.

Insect-specific venom produced in nature by a snake, a wasp, or any other organism. For example, see Pang et al., Gene 116: 165 (1992).

Enzymes responsible for a hyperaccumulation of a monoterpene, a sesquiterpene, a steroid, hydroxamic acid, a phenylpropanoid derivative or another nonprotein molecule with insecticidal activity.

Enzymes involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO93/02197, Kramer et al., Insect Biochem. Molec. Biol. 23:691 (1993) and Kawalleck et al., Plant Molec. Biol. 21:673 (1993).

Molecules that stimulate signal transduction. For example, see Botella et al., Plant Molec. Biol. 24:757 (1994), and Griess et al., Plant Physiol. 104:1467 (1994).

Viral-invasive proteins or a complex toxin derived therefrom. See Beachy et al., Ann. rev. Phytopathol. 28:451 (1990).

Developmental-arrestive proteins produced in nature by a pathogen or a parasite. See Lamb et al., Bio/Technology 10:1436 (1992) and Toubart et al., Plant J. 2:367 (1992).

A developmental-arrestive protein produced in nature by a plant. For example, Logemann et al., Bio/Technology 10:305 (1992).

In plants, pathogens are often host-specific. For example, some *Fusarium* species will cause tomato wilt but attacks only tomato, and other *Fusarium* species attack only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible or there can be partial resistance against all races of a pathogen, typically controlled by many genes and/or also complete resistance to some races of a pathogen but not to other races. Such resistance is typically controlled by a few genes. Accordingly, one can analyze the genome of sources of resistance genes, and in plants having desired characteristics or traits, use the method and components of the targeting system to induce the rise of resistance genes. The present systems can do so with more precision than previous mutagenic agents and hence accelerate and improve plant breeding programs.

2. Genes involved in plant diseases, such as those listed in WO 2013046247:

Rice diseases: *Magnaporthe grisea, Cochliobolus miyabeanus, Rhizoctonia solani, Gibberella fujikuroi*; Wheat diseases: *Erysiphe graminis, Fusarium graminearum, F. avenaceum, F. culmorum, Microdochium nivale, Puccinia striiformis, P. graminis, P. recondita, Micronectriella nivale, Typhula* sp., *Ustilago tritici, Tilletia caries, Pseudocercosporella herpotrichoides, Mycosphaerella graminicola, Stagonospora nodorum, Pyrenophora tritici-repentis*; Barley diseases: *Erysiphe graminis, Fusarium graminearum, F. avenaceum, F. culmorum, Microdochium nivale, Puccinia striiformis, P. graminis, P. hordei, Ustilago nuda, Rhynchosporium secalis, Pyrenophora teres, Cochliobolus sativus, Pyrenophora graminea, Rhizoctonia solani*; Maize diseases: *Ustilago maydis, Cochliobolus heterostrophus, Gloeocercospora sorghi, Puccinia polysora, Cercospora zeae-maydis, Rhizoctonia solani*;

Citrus diseases: *Diaporthe citri, Elsinoe fawcettii, Penicillium digitatum, P. italicum, Phytophthora parasitica, Phytophthora citrophthora*; Apple diseases: *Monilinia mali, Valsa ceratosperma, Podosphaera leucotricha, Alternaria alternata* apple pathotype, *Venturia inaequalis, Colletotrichum acutatum, Phytophthora cactorum;*

Pear diseases: *Venturia nashicola, V. pirina, Alternaria alternata* Japanese pear pathotype, *Gymnosporangium haraeanum, Phytophtora cactorum;*

Peach diseases: *Monilinia fructicola, Cladosporium carpophilum, Phomopsis* sp.;

Grape diseases: *Elsinoe ampelina, Glomerella cingulata, Uncinula necator, Phakopsora ampelopsidis, Guignardia bidwellii, Plasmopara viticola;*

Persimmon diseases: *Gloeosporium kaki, Cercospora kaki, Mycosphaerella nawae;*

Gourd diseases: *Colletotrichum lagenarium, Sphaerotheca fuliginea, Mycosphaerella melonis, Fusarium oxysporum, Pseudoperonospora cubensis, Phytophthora* sp., *Pythium* sp.;

Tomato diseases: *Alternaria solani, Cladosporium fulvum, Phytophthora infestans; Pseudomonas syringae* pv. Tomato; *Phytophthora capsici; Xanthomonas*

Eggplant diseases: *Phomopsis vexans, Erysiphe cichoracearum;*

Brassicaceous vegetable diseases: *Alternaria japonica, Cercosporella brassicae, Plasmodiophora brassicae, Peronospora parasitica;*

Welsh onion diseases: *Puccinia allii, Peronospora destructor;*

Soybean diseases: *Cercospora kikuchii, Elsinoe glycines, Diaporthe phaseolorum* var. *sojae, Septoria glycines, Cercospora sojina, Phakopsora pachyrhizi, Phytophthora sojae, Rhizoctonia solani, Corynespora cassiicola, Sclerotinia sclerotiorum;*

Kidney bean diseases: *Colletotrichum lindemuthianum;*

Peanut diseases: *Cercospora personata, Cercospora arachidicola, Sclerotium rolfsii;*

Pea diseases pea: *Erysiphe pisi;*

Potato diseases: *Alternaria solani, Phytophthora infestans, Phytophthora erythroseptica, Spongospora subterranea, f.* sp. *Subterranea;*

Strawberry diseases: *Sphaerotheca humuli, Glomerella cingulata;*

Tea diseases: *Exobasidium reticulatum, Elsinoe leucospila, Pestalotiopsis* sp., *Colletotrichum theae-sinensis;*

Tobacco diseases: *Alternaria longipes, Erysiphe cichoracearum, Colletotrichum tabacum, Peronospora tabacina, Phytophthora nicotianae;*

Rapeseed diseases: *Sclerotinia sclerotiorum, Rhizoctonia solani;*

Cotton diseases: *Rhizoctonia solani;*

Beet diseases: *Cercospora beticola, Thanatephorus cucumeris, Aphanomyces cochlioides;*

Rose diseases: *Diplocarpon rosae, Sphaerotheca pannosa, Peronospora sparsa;*

Diseases of *chrysanthemum* and asteraceae: *Bremia lactucae, Septoria chrysanthemi-indici, Puccinia horiana;*

Diseases of various plants: *Pythium aphanidermatum, Pythium debaryanum, Pythium graminicola, Pythium irregulare, Pythium ultimum, Botrytis cinerea, Sclerotinia sclerotiorum;*

Radish diseases: *Alternaria brassicicola;*

Zoysia diseases: *Sclerotinia homoeocarpa, Rhizoctonia solani;*

Banana diseases: *Mycosphaerella fijiensis, Mycosphaerella musicola;*

Sunflower diseases: *Plasmopara halstedii;*

Seed diseases or diseases in the initial stage of growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Rhoma* spp., *Rhizoctonia* spp., *Diplodia* spp., or the like;

Virus diseases of various plants mediated by *Polymyxa* spp., *Olpidium* spp., or the like.

3. Examples of Genes that Confer Resistance to Herbicides:

Resistance to herbicides that inhibit the growing point or meristem, such as an imidazolinone or a sulfonylurea, for example, by Lee et al., EMBO J. 7:1241 (1988), and Miki et al., Theor. Appl. Genet. 80:449 (1990), respectively.

Glyphosate tolerance (resistance conferred by, e.g., mutant 5-enolpyruvylshikimate-3-phosphate synthase (EPSPs) genes, aroA genes and glyphosate acetyl transferase (GAT) genes, respectively), or resistance to other phosphono compounds such as by glufosinate (phosphinothricin acetyl transferase (PAT) genes from *Streptomyces* species, including *Streptomyces hygroscopicus* and *Streptomyces viridochromogenes*), and to pyridinoxy or phenoxy propionic acids and cyclohexones by ACCase inhibitor-encoding genes. See, for example, U.S. Pat. Nos. 4,940,835 and 6,248,876, 4,769,061, EP No. 0 333 033 and U.S. Pat. No. 4,975,374. See also EP No. 0242246, DeGreef et al., Bio/Technology 7:61 (1989), Marshall et al., Theor. Appl. Genet. 83:435 (1992), WO 2005012515 to Castle et. al. and WO 2005107437.

Resistance to herbicides that inhibit photosynthesis, such as a triazine (psbA and gs+ genes) or a benzonitrile (nitrilase gene), and glutathione S-transferase in Przibila et al., Plant Cell 3:169 (1991), U.S. Pat. No. 4,810,648, and Hayes et al., Biochem. J. 285: 173 (1992).

Genes encoding Enzymes detoxifying the herbicide or a mutant glutamine synthase enzyme that is resistant to inhibition, e.g. n U.S. patent application Ser. No. 11/760,602. Or a detoxifying enzyme is an enzyme encoding a phosphinothricin acetyltransferase (such as the bar or pat protein from *Streptomyces* species). Phosphinothricin acetyltransferases are for example described in U.S. Pat. Nos. 5,561,236; 5,648,477; 5,646,024; 5,273,894; 5,637,489; 5,276,268; 5,739,082; 5,908,810 and 7,112,665.

Hydroxyphenylpyruvatedioxygenases (HPPD) inhibitors, ie naturally occurring HPPD resistant enzymes, or genes encoding a mutated or chimeric HPPD enzyme as described in WO 96/38567, WO 99/24585, and WO 99/24586, WO 2009/144079, WO 2002/046387, or U.S. Pat. No. 6,768,044.

4. Examples of Genes Involved in Abiotic Stress Tolerance:

Transgene capable of reducing the expression and/or the activity of poly(ADP-ribose) polymerase (PARP) gene in the plant cells or plants as described in WO 00/04173 or, WO/2006/045633.

Transgenes capable of reducing the expression and/or the activity of the PARG encoding genes of the plants or plants cells, as described e.g. in WO 2004/090140.

Transgenes coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002433, EP 1999263, or WO 2007/107326.

Enzymes involved in carbohydrate biosynthesis include those described in e.g. EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026 or WO 97/20936 or enzymes involved in the production of polyfructose, especially of the inulin and levan-type, as disclosed in EP 0663956, WO 96/01904, WO 96/21023, WO 98/39460, and WO 99/24593, the production of alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, the production of alpha-1,6 branched alpha-1,4-glucans, as disclosed in WO 00/73422, the production of alternan, as disclosed in e.g. WO 00/47727, WO 00/73422, EP 06077301.7, U.S. Pat. No. 5,908,975 and EP 0728213, the production of hyaluronan, as for example disclosed in WO 2006/032538, WO 2007/039314, WO 2007/039315, WO 2007/039316, JP 2006304779, and WO 2005/012529.

Genes that improve drought resistance. For example, WO 2013122472 discloses that the absence or reduced level of functional Ubiquitin Protein Ligase protein (UPL) protein, more specifically, UPL3, leads to a decreased need for water or improved resistance to drought of said plant. Other examples of transgenic plants with increased drought tolerance are disclosed in, for example, US 2009/0144850, US 2007/0266453, and WO 2002/083911. US2009/0144850 describes a plant displaying a drought tolerance phenotype due to altered expression of a DR02 nucleic acid. US 2007/0266453 describes a plant displaying a drought tolerance phenotype due to altered expression of a DR03 nucleic acid and WO 2002/08391 1 describes a plant having an increased tolerance to drought stress due to a reduced activity of an ABC transporter which is expressed in guard cells. Another example is the work by Kasuga and co-authors (1999), who describe that overexpression of cDNA encoding DREB1 A in transgenic plants activated the expression of many stress tolerance genes under normal growing conditions and resulted in improved tolerance to drought, salt loading, and freezing. However, the expression of DREB1A also resulted in severe growth retardation under normal growing conditions (Kasuga (1999) Nat Biotechnol 17(3) 287-291).

In further particular embodiments, crop plants can be improved by influencing specific plant traits. For example, by developing pesticide-resistant plants, improving disease resistance in plants, improving plant insect and nematode resistance, improving plant resistance against parasitic weeds, improving plant drought tolerance, improving plant nutritional value, improving plant stress tolerance, avoiding self-pollination, plant forage digestibility biomass, grain yield etc. A few specific non-limiting examples are provided hereinbelow.

Use of the Targeting System to Affect Fruit-Ripening

Ripening is a normal phase in the maturation process of fruits and vegetables. Only a few days after it starts it renders a fruit or vegetable inedible. This process brings significant losses to both farmers and consumers. In particular embodiments, the methods of the present invention are used to reduce ethylene production. This is ensured by ensuring one or more of the following: a. Suppression of ACC synthase gene expression. ACC (1-aminocyclopropane-1-carboxylic acid) synthase is the enzyme responsible for the conversion of S-adenosylmethionine (SAM) to ACC; the second to the last step in ethylene biosynthesis. Enzyme expression is hindered when an antisense ("mirror-image") or truncated copy of the synthase gene is inserted into the plant's genome; b. Insertion of the ACC deaminase gene. The gene coding for the enzyme is obtained from *Pseudomonas chlororaphis*, a common nonpathogenic soil bacterium. It converts ACC to a different compound thereby reducing the amount of ACC available for ethylene production; c. Insertion of the SAM hydrolase gene. This approach is similar to ACC deaminase wherein ethylene production is hindered when the amount of its precursor metabolite is reduced; in this case SAM is converted to homoserine. The gene coding for the enzyme is obtained from *E. coli* T3 bacteriophage and d. Suppression of ACC oxidase gene expression. ACC oxidase is the enzyme which catalyzes the oxidation of ACC to ethylene, the last step in the ethylene biosynthetic pathway. Using the methods described herein, down regulation of the ACC oxidase gene results in the suppression of ethylene production, thereby delaying fruit ripening. In particular embodiments, additionally or alternatively to the modifications described above, the methods described herein are used to modify ethylene receptors, so as to interfere with ethylene signals obtained by the fruit. In particular embodiments, expression of the ETR1 gene, encoding an ethylene binding protein is modified, more particularly suppressed. In particular embodiments, additionally or alternatively to the modifications described above, the methods described herein are used to modify expression of the gene encoding Polygalacturonase (PG), which is the enzyme responsible for the breakdown of pectin, the substance that maintains the integrity of plant cell walls. Pectin breakdown occurs at the start of the ripening process resulting in the softening of the fruit. Accordingly, in particular embodiments, the methods described herein are used to introduce a mutation in the PG gene or to suppress activation of the PG gene in order to reduce the amount of PG enzyme produced thereby delaying pectin degradation.

Thus in particular embodiments, the methods comprise the use of the targeting system to ensure one or more modifications of the gene products of a plant cell such as described above, and regenerating a plant therefrom. In particular embodiments, the plant is a tomato plant. Increasing storage life of plants.

In particular embodiments, the methods of the present invention are used to modify genes involved in the production of compounds which affect storage life of the plant or plant part. More particularly, the modification is in a gene that prevents the accumulation of reducing sugars in potato tubers. Upon high-temperature processing, these reducing sugars react with free amino acids, resulting in brown, bitter-tasting products and elevated levels of acrylamide, which is a potential carcinogen. In particular embodiments, the methods provided herein are used to reduce or inhibit expression of the vacuolar invertase gene (VInv), which encodes a protein that breaks down sucrose to glucose and fructose (Clasen et al. DOI: 10.1111/pbi.12370).

The Use of the Targeting System to Ensure a Value Added Trait

In particular embodiments the targeting system is used to produce nutritionally improved agricultural crops. In particular embodiments, the methods provided herein are adapted to generate "functional foods", i.e. a modified food or food ingredient that may provide a health benefit beyond the traditional nutrients it contains and/or "nutraceutical", i.e. substances that may be considered a food or part of a food and provides health benefits, including the prevention and treatment of disease. In particular embodiments, the nutraceutical is useful in the prevention and/or treatment of one or more of cancer, diabetes, cardiovascular disease, and hypertension.

Examples of nutritionally improved crops include (Newell-McGloughlin, Plant Physiology, July 2008, Vol. 147, pp. 939-953):

Modified protein quality, content and/or amino acid composition, such as have been described for Bahiagrass (Luciani et al. 2005, Florida Genetics Conference Poster), Canola (Roesler et al., 1997, Plant Physiol 113 75-81), Maize (Cromwell et al, 1967, 1969 J Anim Sci 26 1325-1331, O'Quin et al. 2000 J Anim Sci 78 2144-2149, Yang et al. 2002, Transgenic Res 11 11-20, Young et al. 2004, Plant J 38 910-922), Potato (Yu J and Ao, 1997 Acta Bot Sin 39 329-334; Chakraborty et al. 2000, Proc Natl Acad Sci USA 97 3724-3729; Li et al. 2001) Chin Sci Bull 46 482-484, Rice (Katsube et al. 1999, Plant Physiol 120 1063-1074), Soybean (Dinkins et al. 2001, Rapp 2002, In Vitro Cell Dev Biol Plant 37 742-747), Sweet Potato (Egnin and Prakash 1997, In Vitro Cell Dev Biol 33 52A).

Essential amino acid content, such as has been described for Canola (Falco et al. 1995, Bio/Technology 13 577-582), Lupin (White et al. 2001, J Sci Food Agric 81 147-154), Maize (Lai and Messing, 2002, Agbios 2008 GM crop database (Mar. 11, 2008)), Potato (Zeh et al. 2001, Plant Physiol 127 792-802), Sorghum (Zhao et al. 2003, Kluwer Academic Publishers, Dordrecht, The Netherlands, pp 413-416), Soybean (Falco et al. 1995 Bio/Technology 13 577-582; Galili et al. 2002 Crit Rev Plant Sci 21 167-204).

Oils and Fatty acids such as for Canola (Dehesh et al. (1996) Plant J 9 167-172 [PubMed]; Del Vecchio (1996) INFORM International News on Fats, Oils and Related Materials 7 230-243; Roesler et al. (1997) Plant Physiol 113 75-81 [PMC free article] [PubMed]; Froman and Ursin (2002, 2003) Abstracts of Papers of the American Chemical Society 223 U35; James et al. (2003) Am J Clin Nutr 77 1140-1145 [PubMed]; Agbios (2008, above); cotton (Chapman et al. (2001). J Am Oil Chem Soc 78 941-947; Liu et al. (2002) J Am Coll Nutr 21 205S-211S [PubMed]; O'Neill (2007) Australian Life Scientist. (Jun. 17, 2008), Linseed (Abbadi et al., 2004, Plant Cell 16: 2734-2748), Maize (Young et al., 2004, Plant J 38 910-922), oil palm (Jalani et al. 1997, J Am Oil Chem Soc 74 1451-1455; Parveez, 2003, AgBiotechNet 113 1-8), Rice (Anai et al., 2003, Plant Cell Rep 21 988-992), Soybean (Reddy and Thomas, 1996, Nat Biotechnol 14 639-642; Kinney and Kwolton, 1998, Blackie Academic and Professional, London, pp 193-213), Sunflower (Arcadia, Biosciences 2008).

Carbohydrates, such as Fructans described for Chicory (Smeekens (1997) Trends Plant Sci 2 286-287, Sprenger et al. (1997) FEBS Lett 400 355-358, Sevenier et al. (1998) Nat Biotechnol 16 843-846), Maize (Caimi et al. (1996) Plant Physiol 110 355-363), Potato (Hellwege et al., 1997 Plant J 12 1057-1065), Sugar Beet (Smeekens et al. 1997, above), Inulin, such as described for Potato (Hellewege et al. 2000, Proc Natl Acad Sci USA 97 8699-8704), Starch, such as described for Rice (Schwall et al. (2000) Nat Biotechnol 18 551-554, Chiang et al. (2005) Mol Breed 15 125-143), Vitamins and carotenoids, such as described for Canola (Shintani and DellaPenna (1998) Science 282 2098-2100), Maize (Rocheford et al. (2002). J Am Coll Nutr 21 191S-198S, Cahoon et al. (2003) Nat Biotechnol 21 1082-1087, Chen et al. (2003) Proc Natl Acad Sci USA 100 3525-3530), Mustard seed (Shewmaker et al. (1999) Plant J 20 401-412, Potato (Ducreux et al., 2005, J Exp Bot 56 81-89), Rice (Ye et al. (2000) Science 287 303-305, Strawberry (Agius et al. (2003), Nat Biotechnol 21 177-181), Tomato (Rosati et al. (2000) Plant J 24 413-419, Fraser et al. (2001) J Sci Food Agric 81 822-827, Mehta et al. (2002) Nat Biotechnol 20 613-618, Diaz de la Garza et al. (2004) Proc Natl Acad Sci USA 101 13720-13725, Enfissi et al. (2005) Plant Biotechnol J 3 17-27, DellaPenna (2007) Proc Natl Acad Sci USA 104 3675-3676.

Functional secondary metabolites, such as described for Apple (stilbenes, Szankowski et al. (2003) Plant Cell Rep 22: 141-149), Alfalfa (resveratrol, Hipskind and Paiva (2000) Mol Plant Microbe Interact 13 551-562), Kiwi (resveratrol, Kobayashi et al. (2000) Plant Cell Rep 19 904-910), Maize and Soybean (flavonoids, Yu et al. (2000) Plant Physiol 124 781-794), Potato (anthocyanin and alkaloid glycoside, Lukaszewicz et al. (2004) J Agric Food Chem 52 1526-1533), Rice (flavonoids & resveratrol, Stark-Lorenzen et al. (1997) Plant Cell Rep 16 668-673, Shin et al. (2006) Plant Biotechnol J 4 303-315), Tomato (+resveratrol, chlorogenic acid, flavonoids, stilbene; Rosati et al. (2000) above, Muir et al. (2001) Nature 19 470-474, Niggeweg et al. (2004) Nat Biotechnol 22 746-754, Giovinazzo et al. (2005) Plant Biotechnol J 3 57-69), wheat (caffeic and ferulic acids, resveratrol; United Press International (2002)); and Mineral availabilities such as described for Alfalfa (phytase, Austin-Phillips et al. (1999)), Lettuce (iron, Goto et al. (2000) Theor Appl Genet 100 658-664), Rice (iron, Lucca et al. (2002) J Am Coll Nutr 21 184S-190S), Maize, Soybean and wheat (phytase, Drakakaki et al. (2005) Plant Mol Biol 59 869-880, Denbow et al. (1998) Poult Sci 77 878-881, Brinch-Pedersen et al. (2000) Mol Breed 6 195-206).

In particular embodiments, the value-added trait is related to the envisaged health benefits of the compounds present in the plant. For instance, in particular embodiments, the value-added crop is obtained by applying the methods of the invention to ensure the modification of or induce/increase the synthesis of one or more of the following compounds:

Carotenoids, such as α-Carotene present in carrots which Neutralizes free radicals that may cause damage to cells or β-Carotene present in various fruits and vegetables which neutralizes free radicals.

Lutein present in green vegetables which contributes to maintenance of healthy vision Lycopene present in tomato and tomato products, which is believed to reduce the risk of prostate cancer.

Zeaxanthin, present in citrus and maize, which contributes to maintenance of healthy vision Dietary fiber such as insoluble fiber present in wheat bran which may reduce the risk of breast and/or colon cancer and β-Glucan present in oat, soluble fiber present in Psyllium and whole cereal grains which may reduce the risk of cardiovascular disease (CVD).

Fatty acids, such as ω-3 fatty acids which may reduce the risk of CVD and improve mental and visual functions, Conjugated linoleic acid, which may improve body composition, may decrease risk of certain cancers and GLA which may reduce inflammation risk of cancer and CVD, may improve body composition.

Flavonoids such as Hydroxycinnamates, present in wheat which have Antioxidant-like activities, may reduce risk of degenerative diseases, flavonols, catechins and tannins present in fruits and vegetables which neutralize free radicals and may reduce risk of cancer.

Glucosinolates, indoles, isothiocyanates, such as Sulforaphane, present in Cruciferous vegetables (broccoli, kale), horseradish, which neutralize free radicals, may reduce risk of cancer Phenolics, such as stilbenes present in grape which May reduce risk of degenerative diseases, heart disease, and cancer, may have longevity effect and caffeic acid and ferulic acid present in vegetables and citrus which have Antioxidant-like activities, may reduce risk of degenerative diseases, heart disease, and eye disease, and epicatechin present in cacao which has Antioxidant-like activities, may reduce risk of degenerative diseases and heart disease.

Plant stanols/sterols present in maize, soy, wheat and wooden oils which May reduce risk of coronary heart disease by lowering blood cholesterol levels.

Fructans, inulins, fructo-oligosaccharides present in Jerusalem artichoke, shallot, onion powder which may improve gastrointestinal health.

Saponins present in soybean, which may lower LDL cholesterol.

Soybean protein present in soybean which may reduce risk of heart disease.

Phytoestrogens such as isoflavones present in soybean which May reduce menopause symptoms, such as hot flashes, may reduce osteoporosis and CVD and lignans present in flax, rye and vegetables, which May protect against heart disease and some cancers, may lower LDL cholesterol, total cholesterol.

Sulfides and thiols such as diallyl sulphide present in onion, garlic, olive, leek and scallion and Allyl methyl trisulfide, dithiolthiones present in cruciferous vegetables which may lower LDL cholesterol, helps to maintain healthy immune system Tannins, such as proanthocyanidins, present in cranberry, cocoa, which may improve urinary tract health, may reduce risk of CVD and high blood pressure.

In addition, the methods of the present invention also envisage modifying protein/starch functionality, shelf life, taste/aesthetics, fiber quality, and allergen, antinutrient, and toxin reduction traits.

Accordingly, the invention encompasses methods for producing plants with nutritional added value, said methods comprising introducing into a plant cell a gene encoding an enzyme involved in the production of a component of added nutritional value using the targeting system as described herein and regenerating a plant from said plant cell, said plant characterized in an increase expression of said component of added nutritional value. In particular embodiments, the targeting system is used to modify the endogenous synthesis of these compounds indirectly, e.g. by modifying one or more transcription factors that controls the metabolism of this compound. Methods for introducing a gene of interest into a plant cell and/or modifying an endogenous gene using the targeting system are described herein above.

Screening Methods for Endogenous Genes of Interest

The methods provided herein further allow the identification of genes of value encoding enzymes involved in the production of a component of added nutritional value or generally genes affecting agronomic traits of interest, across species, phyla, and plant kingdom. By selectively targeting e.g. enzymes of metabolic pathways in plants using the targeting system as described herein, the genes responsible for certain nutritional aspects of a plant can be identified. Similarly, by selectively targeting enzymes which may affect a desirable agronomic trait, the relevant genes can be identified. Accordingly, the present invention encompasses screening methods for genes encoding enzymes involved in the production of compounds with a particular nutritional value and/or agronomic traits.

Use of the Targeting System in Biofuel Production

The term "biofuel" as used herein is an alternative fuel made from plant and plant-derived resources. Renewable biofuels can be extracted from organic matter whose energy has been obtained through a process of carbon fixation or are made through the use or conversion of biomass. This biomass can be used directly for biofuels or can be converted to convenient energy containing substances by thermal conversion, chemical conversion, and biochemical conversion. This biomass conversion can result in fuel in solid, liquid, or gas form. There are two types of biofuels: bioethanol and biodiesel. Bioethanol is mainly produced by the sugar fermentation process of cellulose (starch), which is mostly derived from maize and sugar cane. Biodiesel on the other hand is mainly produced from oil crops such as rapeseed, palm, and soybean. Biofuels are used mainly for transportation.

In particular embodiments, the methods using the targeting system as described herein are used to alter the properties of the cell wall in order to facilitate access by key hydrolysing agents for a more efficient release of sugars for fermentation. In particular embodiments, the biosynthesis of cellulose and/or lignin are modified. Cellulose is the major component of the cell wall. The biosynthesis of cellulose and lignin are co-regulated. By reducing the proportion of lignin in a plant the proportion of cellulose can be increased. In particular embodiments, the methods described herein are used to downregulate lignin biosynthesis in the plant so as to increase fermentable carbohydrates. More particularly, the methods described herein are used to downregulate at least a first lignin biosynthesis gene selected from the group consisting of 4-coumarate 3-hydroxylase (C3H), phenylalanine ammonia-lyase (PAL), cinnamate 4-hydroxylase (C4H), hydroxycinnamoyl transferase (HCT), caffeic acid O-methyltransferase (COMT), caffeoyl CoA 3-O-methyltransferase (CCoAOMT), ferulate 5-hydroxylase (F5H), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH) as disclosed in WO 2008064289 A2.

Modifying Yeast for Biofuel Production

In particular embodiments, the engineered targeting protein provided herein is used for bioethanol production by recombinant micro-organisms. For instance, the engineered protein can be used to engineer micro-organisms, such as yeast, to generate biofuel or biopolymers from fermentable sugars and optionally to be able to degrade plant-derived lignocellulose derived from agricultural waste as a source of fermentable sugars.

Accordingly, in more particular embodiments, the methods described herein are used to modify a micro-organism as follows:
- to introduce at least one engineered protein or nucleic acid encoding thereof that modify the gene product or alter expression of at least one endogenous nucleic acid encoding a plant cell wall degrading enzyme, such that said micro-organism is capable of expressing said nucleic acid and of producing and secreting said plant cell wall degrading enzyme;
- to modify at least one nucleic acid encoding for an enzyme in a metabolic pathway in said host cell, wherein said pathway produces a metabolite other than acetaldehyde from pyruvate or ethanol from acetaldehyde, and wherein said modification results in a reduced production of said metabolite, or to introduce at least one nucleic acid encoding for an inhibitor of said enzyme.

The use of the targeting system in the generation of micro-organisms capable of organic acid production.

The methods provided herein are further used to engineer micro-organisms capable of organic acid production, more particularly from pentose or hexose sugars. In particular embodiments, the methods comprise introducing into a micro-organism an exogenous LDH gene. In particular embodiments, the organic acid production in said micro-organisms is additionally or alternatively increased by inactivating endogenous genes encoding proteins involved in an endogenous metabolic pathway which produces a metabolite other than the organic acid of interest and/or wherein the endogenous metabolic pathway consumes the organic acid. In particular embodiments, the modification ensures that the production of the metabolite other than the organic acid of interest is reduced. According to particular embodiments, the methods are used to introduce at least one engineered gene deletion and/or inactivation of an endogenous pathway in which the organic acid is consumed or a gene encoding a product involved in an endogenous pathway which produces a metabolite other than the organic acid of interest. In particular embodiments, the at least one engineered gene deletion or inactivation is in one or more gene encoding an enzyme selected from the group consisting of pyruvate decarboxylase (pdc), fumarate reductase, alcohol dehydrogenase (adh), acetaldehyde dehydrogenase, phosphoenolpyruvate carboxylase (ppc), D-lactate dehydrogenase (d-ldh), L-lactate dehydrogenase (l-ldh), lactate 2-monooxygenase.

In further embodiments the at least one engineered gene deletion and/or inactivation is in an endogenous gene encoding pyruvate decarboxylase (pdc).

In further embodiments, the micro-organism is engineered to produce lactic acid and the at least one engineered gene deletion and/or inactivation is in an endogenous gene encoding lactate dehydrogenase. Additionally or alternatively, the micro-organism comprises at least one engineered gene deletion or inactivation of an endogenous gene encoding a cytochrome-dependent lactate dehydrogenase, such as a cytochrome B2-dependent L-lactate dehydrogenase.

The use of the targeting system in the generation of improved xylose or cellobiose utilizing yeasts strains.

In particular embodiments, the targeting system may be applied to select for improved xylose or cellobiose utilizing yeast strains. Error-prone PCR can be used to amplify one (or more) genes involved in the xylose utilization or cellobiose utilization pathways. Examples of genes involved in xylose utilization pathways and cellobiose utilization pathways may include, without limitation, those described in Ha, S. J., et al. (2011) Proc. Natl. Acad. Sci. USA 108(2):504-9 and Galazka, J. M., et al. (2010) Science 330(6000):84-6.

Improved Plants and Yeast Cells

The present invention also provides plants and yeast cells obtainable and obtained by the methods provided herein. The improved plants obtained by the methods described herein may be useful in food or feed production through expression of genes which, for instance ensure tolerance to plant pests, herbicides, drought, low or high temperatures, excessive water, etc.

The improved plants obtained by the methods described herein, especially crops and algae may be useful in food or feed production through expression of, for instance, higher protein, carbohydrate, nutrient or vitamin levels than would normally be seen in the wildtype. In this regard, improved plants, especially pulses and tubers are preferred.

Improved algae or other plants such as rape may be particularly useful in the production of vegetable oils or biofuels such as alcohols (especially methanol and ethanol), for instance. These may be engineered to express or overexpress high levels of oil or alcohols for use in the oil or biofuel industries.

The invention also provides for improved parts of a plant. Plant parts include, but are not limited to, leaves, stems, roots, tubers, seeds, endosperm, ovule, and pollen. Plant parts as envisaged herein may be viable, nonviable, regeneratable, and/or non-regeneratable.

It is also encompassed herein to provide plant cells and plants generated according to the methods of the invention. Gametes, seeds, embryos, either zygotic or somatic, progeny or hybrids of plants comprising the genetic modification, which are produced by traditional breeding methods, are also included within the scope of the present invention. Such plants may contain a heterologous or foreign DNA sequence inserted at or instead of a target sequence. Alternatively, such plants may contain only an alteration (mutation, deletion, insertion, substitution) in one or more nucleotides. As such, such plants will only be different from their progenitor plants by the presence of the particular modification.

Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants.

The methods for genome editing using the targeting system as described herein can be used to confer desired traits on essentially any plant, algae, fungus, yeast, etc. A wide variety of plants, algae, fungus, yeast, etc and plant algae, fungus, yeast cell or tissue systems may be engineered for the desired physiological and agronomic characteristics described herein using the nucleic acid constructs of the present disclosure and the various transformation methods mentioned above.

In particular embodiments, the methods described herein are used to modify endogenous genes or to modify their expression without the permanent introduction into the genome of the plant, algae, fungus, yeast, etc of any foreign gene, including those encoding the targeting system components, so as to avoid the presence of foreign DNA in the genome of the plant. This can be of interest as the regulatory requirements for non-transgenic plants are less rigorous.

The targeting systems provided herein can be used to introduce targeted double-strand or single-strand breaks and/or to introduce gene activator and/or repressor systems and without being limitative, can be used for gene targeting, gene replacement, targeted mutagenesis, targeted deletions or insertions, targeted inversions and/or targeted translocations. By co-expression of multiple targeting RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

The methods described herein generally result in the generation of "improved plants, algae, fungi, yeast, etc" in that they have one or more desirable traits compared to the wildtype plant. In particular embodiments, the plants, algae, fungi, yeast, etc., cells or parts obtained are transgenic plants, comprising an exogenous DNA sequence incorporated into the genome of all or part of the cells. In particular embodiments, non-transgenic genetically modified plants, algae, fungi, yeast, etc., parts or cells are obtained, in that no exogenous DNA sequence is incorporated into the genome of any of the cells of the plant. In such embodiments, the improved plants, algae, fungi, yeast, etc. are non-transgenic. Where only the modification of a gene product is ensured and no foreign genes are introduced or maintained in the plant, algae, fungi, yeast, etc. genome, the resulting genetically modified crops contain no foreign genes and can thus basically be considered non-transgenic.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

106,000,000 unique proteins of the UniProt database were analyzed, revealing 283,489 unique proteins with repetitive domains, including domains repeated within proteins and domains repeated among different proteins.

Table 9 provides 38 amino acid sequences (SEQ ID NOS:128-165) representing a subset of proteins and orthologs comprising related repetitive sequences identified among *Photorhabdus* bacteria.

TABLE 9

| SEQ ID NO | Accession | |
|---|---|---|
| 128 | WP_0367 73878.1 | hypothetical protein [*Photorhabdus asymbiotica*] M |
| 129 | WP_0368 43789.1 | hypothetical protein [*Photorhabdus temperata*] |
| 130 | WP_0883 73187.1 | hypothetical protein [*Photorhabdus luminescens*] |
| 131 | WP0111 46190.1 | hypothetical protein [*Photorhabdus luminescens*] ASWEMGYDPNFKPKMDNIPFITGLPGM |
| 132 | WP_0401 52449.1 | hypothetical protein [*Photorhabdus luminescens*] |
| 133 | WP_0367 75722.1 | hypothetical protein, partial [*Photorhabdus luminescens*] |

TABLE 9-continued

| SEQ ID NO | Accession | |
|---|---|---|
| 134 | WP_105395755.1 | hypothetical protein [*Photorhabdus luminescens*] |
| 135 | OCA54061.1 | hypothetical protein Phpb_02502 [*Photorhabdus luminescens*] |
| 136 | WP_046397830.1 | hypothetical protein [*Photorhabdus luminescens*] |
| 137 | WP_036807456.1 | hypothetical protein [*Photorhabdus luminescens*] |
| 138 | WP_012776453.1 | hypothetical protein [*Photorhabdus asymbiotica*] |
| 139 | WP_065822736.1 | hypothetical protein [*Photorhabdus asymbiotica*] |
| 140 | WP_054478414.1 | hypothetical protein [*Photorhabdus heterorhabditis*] |
| 141 | WP_036775012.1 | hypothetical protein [*Photorhabdus asymbiotica*] |
| 142 | WP_012776450.1 | hypothetical protein [*Photorhabdus asymbiotica*] |
| 143 | WP_036773254.1 | hypothetical protein [*Photorhabdus asymbiotica*] |
| 144 | WP_036773948.1 | hypothetical protein [*Photorhabdus asymbiotica*] |
| 145 | WP_065822477.1 | hypothetical protein [*Photorhabdus asymbiotica*] |
| 146 | WP_041382200.1 | hypothetical protein [*Photorhabdus asymbiotica*] |
| 147 | WP_051691048.1 | hypothetical protein [*Photorhabdus asymbiotica*] |
| 148 | WP_036849041.1 | hypothetical protein [*Photorhabdus temperata*] |
| 149 | WP_046976484.1 | hypothetical protein [*Photorhabdus temperata*] |
| 150 | WP_046976473.1 | hypothetical protein [*Photorhabdus temperata*] |
| 151 | WP_046976477.1 | hypothetical protein [*Photorhabdus temperata*] |
| 152 | WP_046976475.1 | hypothetical protein [*Photorhabdus temperata*] |
| 153 | WP_046976479.1 | hypothetical protein [*Photorhabdus temperata*] |
| 154 | WP_046976480.1 | hypothetical protein [*Photorhabdus temperata*] |
| 155 | WP_046976482.1 | hypothetical protein [*Photorhabdus temperata*] |
| 156 | WP_082111283.1 | hypothetical protein [*Photorhabdus temperata*] |
| 157 | AKH65533.1 | hypothetical protein VY86_21375 [*Photorhabdus temperata* subsp. *thracensis*] |
| 158 | WP_054478108.1 | hypothetical protein [*Photorhabdus heterorhabditis*] |

TABLE 9-continued

| SEQ ID NO | Accession | |
|---|---|---|
| 159 | WP_054478110.1 | hypothetical protein [*Photorhabdus heterorhabditis*] |
| 160 | WP_015834765.1 | hypothetical protein [*Photorhabdus asymbiotica*] |
| 161 | WP_015834769.1 | hypothetical protein [*Photorhabdus asymbiotica*] |
| 162 | WP_015834771.1 | hypothetical protein [*Photorhabdus asymbiotica*] |
| 163 | WP_088371923.1 | hypothetical protein [*Photorhabdus luminescens*] |
| 164 | PQQ32646.1 | hypothetical protein C6H69_13130 [*Photorhabdus luminescens*] |
| 165 | PQQ36817.1 | hypothetical protein C6H68_17390 [*Photorhabdus luminescens*] |

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of engineering a protein or polypeptide to bind to a target of interest, which comprises:

inserting one or more engineered, heterologous *Photorhabdus* tandem repeat protein target recognition sequence (TRS) motif(s) in the protein or polypeptide, and modifying the one or more engineered, heterologous *Photorhabdus* TRS motif(s);

associating the one or more modified, engineered, heterologous *Photorhabdus* TRS motif(s) with a detectable marker; and detecting whether the engineered protein or polypeptide binds to the target; or detecting whether the engineered protein or polypeptide exhibits enzymatic activity against the target.

2. The method of claim 1, wherein the one or more modified, engineered, heterologous *Photorhabdus* TRS motif(s) comprises:

$X_1$(E/K)(N/D)$X_2$(S/T)$X_3$ (SEQ ID NO: 1) flanked by a hydrophobic region and a charged region;

wherein $X_1$ comprises 1 to 7 amino acid(s) in length and comprises any amino acid(s), wherein $X_2$ comprises 0 to 12 amino acid(s) in length and comprises any amino acid(s), and wherein $X_3$ comprises 1 to 7 amino acid(s) in length and comprises any amino acid(s), wherein the hydrophobic region comprises at least one hydrophobic amino acid residue, and wherein the charged region comprises at least one charged amino acid residue.

3. The method of claim 2, wherein the hydrophobic region is at the N-terminus and comprises G(V/A/L)G and the charged region is at the C-terminus and comprises K(K/E)Q.

4. The method of claim 1, wherein the protein or polypeptide comprises a functional domain.

5. The method of claim 1, wherein the protein comprises an insecticidal toxin or a component thereof.

6. The method of claim 1, wherein the one or more modified, engineered, heterologous *Photorhabdus* TRS motif(s) and the detectable marker are covalently linked.

7. The method of claim 1, wherein the target is a polypeptide or polynucleotide.

* * * * *